US012616649B2

(12) United States Patent
Lee et al.

(10) Patent No.: US 12,616,649 B2
(45) Date of Patent: May 5, 2026

(54) COMPOSITION CONTAINING PLANT EXTRACTS

(71) Applicant: LG HOUSEHOLD & HEALTH CARE LTD., Seoul (KR)

(72) Inventors: So Young Lee, Seoul (KR); Yun Hee Chang, Seoul (KR); Gil Nam Kim, Seoul (KR); Ji Hyun Seo, Seoul (KR); Young Je Ahn, Seoul (KR); Ji Hyung Kim, Seoul (KR); Mu Hyun Jin, Seoul (KR); Gwang Jin Lee, Seoul (KR); Jeong Eun Kim, Seoul (KR); Jung Ha Choo, Seoul (KR); Hong Gu Lee, Seoul (KR); Jun Hyeong Park, Seoul (KR); Jae Hee Kim, Seoul (KR)

(73) Assignee: LG HOUSEHOLD & HEALTH CARE LTD., Seoul (KR)

( * ) Notice: Subject to any disclaimer, the term of this patent is extended or adjusted under 35 U.S.C. 154(b) by 565 days.

(21) Appl. No.: 17/789,824

(22) PCT Filed: Jan. 4, 2021

(86) PCT No.: PCT/KR2021/000033
§ 371 (c)(1),
(2) Date: Jun. 29, 2022

(87) PCT Pub. No.: WO2021/137677
PCT Pub. Date: Jul. 8, 2021

(65) Prior Publication Data
US 2023/0075384 A1      Mar. 9, 2023

(30) Foreign Application Priority Data
Jan. 2, 2020      (KR) ........................ 10-2020-0000282

(51) Int. Cl.
*A61K 36/00*        (2006.01)
*A61K 8/9789*       (2017.01)
*A61K 8/9794*       (2017.01)
*A61Q 19/00*        (2006.01)

(52) U.S. Cl.
CPC .......... *A61K 8/9789* (2017.08); *A61K 8/9794* (2017.08); *A61Q 19/007* (2013.01)

(58) Field of Classification Search
CPC ................................ A61Q 19/00; A61Q 19/08
See application file for complete search history.

(56) References Cited

U.S. PATENT DOCUMENTS 5,698,199 A * 12/1997 Mori ...................... A61Q 19/06
424/734
2008/0124287 A1      5/2008 Kim et al.

FOREIGN PATENT DOCUMENTS

| BR | 102013005749 | A | * | 5/2017 |
|---|---|---|---|---|
| CN | 102686229 | A | | 9/2012 |
| CN | 103859276 | A | | 6/2014 |
| CN | 105520861 | A | | 4/2016 |
| CN | 105832624 | A | | 8/2016 |
| CN | 106039036 | A | | 10/2016 |
| CN | 106619323 | A | | 5/2017 |
| CN | 108813584 | A | | 11/2018 |
| FR | 3 011 181 | A1 | | 4/2015 |
| FR | 3 044 226 | A1 | | 6/2017 |
| JP | 2000-256123 | A | | 9/2000 |
| JP | 2006-52165 | A | | 2/2006 |
| JP | 2013-35801 | A | | 2/2013 |
| JP | 2015-86189 | A | | 5/2015 |
| JP | 2017-536803 | A | | 12/2017 |
| KR | 10-2004-033410 | A | | 4/2004 |
| KR | 10-2006-0012805 | A | | 2/2006 |
| KR | 10-2010-0037508 | A | | 4/2010 |
| KR | 20100037508 | A | * | 4/2010 |
| KR | 10-2014-0054618 | A | | 6/2014 |
| KR | 10-2014-0073784 | A | | 6/2014 |
| KR | 20140137557 | A | * | 12/2014 |
| KR | 2015145605 | A | * | 12/2015 |

(Continued)

OTHER PUBLICATIONS

Youn, "Evaluation of native plants in Ullung island for cosmeceutical activities and product development," Andong National University, Collection @ andong, Jun. 2011, 125 pages total, with partial English translation.

(Continued)

*Primary Examiner* — Qiuwen Mi

(74) *Attorney, Agent, or Firm* — Birch, Stewart, Kolasch & Birch, LLP

(57)        ABSTRACT

The present invention relates to a composition comprising plant extracts. The composition according to the present invention has a skin whitening effect by reducing the total amount of melanin and tyrosinase activity in melanocytes of the skin, promotes skin regeneration and increases skin elasticity or reduces skin wrinkles by promoting collagen synthesis and inhibiting collagenase activity in fibroblasts of the skin, has an anti-inflammatory effect or a skin soothing effect by inhibiting NO generation, increases the amount of moisture in the skin and has a moisturizing effect by promoting generation of hyaluronic acid in fibroblasts, and has an antioxidant effect by scavenging free radicals. In addition, since the composition of the present invention exhibits a broad antibacterial effect against various bacteria, the composition may be used as a cosmetic composition, a pharmaceutical composition, a skin external preparation, or a food composition.

9 Claims, No Drawings

(56)         References Cited

FOREIGN PATENT DOCUMENTS

KR     10-2017-0043095  A     4/2017
KR     10-2018-0000366  A     1/2018

OTHER PUBLICATIONS

Do et al.. "Isolation of Pectolinarin from the Aerial Parts of Cirsium nipponicum", Kor. J. Pharmacogn., 1994, vol. 25, No. 1, pp. 73-75.
International Search Report, issued in PCT/KR2021/000033, dated May 26, 2021.

* cited by examiner

COMPOSITION CONTAINING PLANT EXTRACTS

CROSS REFERENCE TO RELATED APPLICATIONS

This application is the National Phase of PCT International Application No. PCT/KR2021/000033, filed on Jan. 4, 2021, which claims priority under 35 U.S.C. 119(a) to Patent Application No. 10-2020-0000282, filed in the Republic of Korea on Jan. 2, 2020, all of which are hereby expressly incorporated by reference into the present application.

TECHNICAL FIELD

The present invention relates to a composition containing plant extracts, and more particularly, to a composition for skin whitening, skin regeneration, elasticity improvement, wrinkle suppression, inflammation suppression, skin soothing, skin moisturizing, oxidation inhibition, or bacterial inhibition.

BACKGROUND ART

Most people want to have fair skin. Skin color is genetically determined according to the concentration and distribution of melanin in the skin, but skin color is also affected by environmental factors such as ultraviolet rays and physiological factors such as fatigue and stress. Melanin is produced through a non-enzymatic oxidation reaction after tyrosine, a type of amino acid, is converted to dopa and dopaquinone by action of a tyrosinase enzyme. As such, the pathway by which melanin is produced is known, but the previous step of the step in which tyrosinase acts, that is, the mechanism of inducing melanin synthesis, is still unknown.

Examples of general whitening ingredients comprise substances that inhibit tyrosinase enzyme activity, such as kojic acid and arbutin, hydroquinone, vitamin-C (L-ascorbic acid) and derivatives thereof, and various plants extracts. The above-described whitening ingredients may lighten skin tone by inhibiting synthesis of a melanin pigment, thereby realizing skin whitening. In addition, the whitening ingredients may alleviate skin hyperpigmentation, such as melasma or freckles, caused by ultraviolet rays, hormones, or heredity. However, when the whitening ingredients are applied to the skin, usage thereof may be limited due to safety issues such as irritation and redness. In addition, in some cases, since the effect of the whitening ingredients is insignificant, a substantial effect may not be expected for the whitening ingredients.

Meanwhile, collagen is a major matrix protein produced by fibroblasts of the skin and is present in the extracellular matrix. Collagen is responsible for maintaining the mechanical strength of the skin, imparting resistance and bonding strength to the connective tissues, maintaining cell adhesion, and inducing cell division and differentiation (in growth of an organism or wound healing). Collagen decreases with age and photoaging caused by UV irradiation, which is known to be closely related to formation of wrinkles in the skin. Also, in recent years, as extensive research on skin aging progresses, new functions of collagen in the skin are being revealed.

Active ingredients that promote collagen synthesis and exhibit anti-wrinkle effects are known. For example, retinoic acid, a transforming growth factor (TGF) [Non-Patent Document 1], an animal placenta-derived protein [Patent Document 1], betulinic acid [Patent Document 2], and chlorella extracts [Patent Document 3, 4] are known as collagen synthesis promoting substances. However, when the active ingredients are applied to the skin, usage thereof may be limited due to safety issues such as irritation and redness. In addition, in some cases, since the effect of the active ingredients is insignificant, the effect of improving the skin function by promoting synthesis of collagen in the skin may be substantially insignificant.

Meanwhile, inflammation is an immune response of the human body in response to a wound or disease, and ultraviolet rays or oxidative stress due to reactive oxygen species or free radicals activates inflammatory factors to cause various diseases and aging of the skin. Vasoactive polypeptides such as kinin, plasmin, and complements play a role in vasodilation, vasoconstriction, and chemotaxis. In addition, lymphokines, such as interleukin-6 (IL-6), and arachidonic acid are responsible for inflammatory responses. Arachidonic acid is converted to prostaglandins and leukotrienes, which are inflammatory mediators, through two pathways associated with cyclooxygenase and lipooxygenase, and mediates various inflammatory responses.

Anti-inflammatory agents serve to eliminate inflammation by removing inflammatory sources and reducing biological responses and symptoms. To date, substances used for anti-inflammatory purposes comprise non-steroidal substances such as flufenamic acid, ibuprofen, benzydamine, and indomethacin and steroidal substances such as prednisolone and dexamethasone. In addition, allantoin, azene, hydrocortisone, and the like are known to have an anti-inflammatory effect. However, usage thereof may be limited due to skin safety issues, and the effect of alleviating inflammation by these substances may be insignificant.

Meanwhile, hyaluronic acid is a type of glycosaminoglycan and is a chain-shaped polymeric polysaccharide in which glucuronic acid and N-acetylglucosamine residues are repeatedly linked. Hyaluronic acid has high viscosity and elasticity and can form a gel by combining with a large amount of water. Hyaluronic acid is a major component of the extracellular matrix and is involved in water retention, maintenance of intercellular spacing, and storage and diffusion of cell growth factors and nutrients. In addition, hyaluronic acid is known to be involved in cell division and differentiation, cell migration, and the like.

According to previous reports, more than 50% of hyaluronic acid present in the body of a mammal is distributed in the skin, particularly between epidermal cells and in the connective tissues of the dermis. In addition, hyaluronic acid is mainly synthesized by keratinocytes and fibroblasts. It has been reported that the amount of hyaluronic acid in human skin decreases with aging and decrease in hyaluronic acid in the skin is considered to be one of the direct causes of decrease in skin elasticity and moisture content due to aging (BiochemBiophysActa 279, 265-275; Carbohydr Res 159, 127-136; Int J Dermatol 33, 119-122). In addition, hyaluronic acid is known to be involved in maintaining the structure of the stratum corneum and maintaining skin barrier function (J CosmetDermatol. 2007 Jun. 6(2), 75-82).

However, hyaluronic acid having the above effects is not effectively absorbed into the skin due to high molecular weight thereof. In addition, a method of injecting hyaluronic acid into the skin through injection is currently being implemented, but this method may cause great irritation. Compared to this method, a method that promotes synthesis of hyaluronic acid in skin cells is more effective. Therefore, research on a method for increasing production of hyaluronic acid in the human body is being actively conducted, but remarkable research results are not yet known.

Meanwhile, reactive oxygen species introduced into the human body from the outside or reactive oxygen species generated in the human body may accelerate aging of the human body or cause cancers. Accordingly, development and research on antioxidants that inhibit oxidation induced by reactive oxygen species are being actively conducted. Antioxidants are widely distributed in the animal and plant kingdoms, and many phenolic compounds, flavonoids, tocopherols, vitamin C, and selenium in fruits and vegetables are known as antioxidants. However, when naturally occurring antioxidants are applied to the skin, it is difficult to obtain sufficient antioxidant effects. Accordingly, although synthetic antioxidants with excellent antioxidant power and low price are widely used, use thereof is limited due to safety concerns such as side effects in the human body.

Meanwhile, with development of transportation, people around the world are moving actively. Accordingly, various infectious diseases and new diseases are rapidly spreading. In the past, the indiscriminate use of antibacterial substances has conferred resistance to various microorganisms, which threatens mankind. In particular, for preservation of perishable products (e.g., cosmetics, pharmaceuticals, or food), there is continuous demand for substances with antibacterial properties for direct cosmetic improvement or therapy against microorganisms that may adversely affect the body.

Pesticides may be broadly divided into fungicides, pesticides, herbicides, and growth regulators. To prevent damage to crops by viruses or microorganisms, fungicides are used. Excessive use of cheap and powerful synthetic antibacterial substances in agriculture has threatened our table. Various antibacterial substances are also used in household products that come into direct contact with the human body. In this case, most of these antibacterial substances are manufactured using inexpensive chemical components. Unfortunately, based on scientific evidence, long-term use of most of these antibacterial substances may be harmful to the human body.

Preservatives, antibacterial substances approved for human use, are added to many products such as food, pharmaceuticals, daily necessities, and cosmetics widely used in our daily life to prevent change in physical properties and preserve the products for a certain period of time. In particular, in the case of products that are in frequent contact with the hand or the human body, such as cosmetics, microorganisms may be introduced from the outside, and the quality of the product may be changed by these microorganisms. In particular, when products used around the eyes are contaminated, eye diseases may be induced. In the United States in the 1920s, there was a case in which a consumer went blind after using mascara contaminated with microorganisms. Accordingly, technologies for securing consumer safety and preserving product quality by preventing contamination of the products by microorganisms have been continuously developed.

Naturally produced substances are also used as the preservatives, but most of the preservatives are chemically synthesized artificial substances. Existing preservatives, such as parabens, are known to be safe and are widely used in household products, cosmetics, and pharmaceuticals. However, paraben preservatives also have problems such as skin allergies (Andrea Counti et al., Contact Dermatitis, 1997, 37; 35-36), potential as environmental hormones (Edwin et al., Toxicology and applied pharmacology, 1998, 153; 12-19), and generation of resistant bacteria.

Most of natural active substances used as preservatives have not been commercialized due to problems such as coloration, reduced stability, a narrow antibacterial spectrum, and formulation limitation. Only a few natural active substances are being commercialized, such as hinokitiol, which is a cypress extract, magnolol, which is a magnolia extract, and DF-100, which is a grapefruit extract. Accordingly, there is an increasing need for natural antibacterial substances that can replace existing synthetic chemical antibacterial substances. In particular, it is necessary to develop a natural antibacterial substance that reduces the side effects of antibacterial agents and has a wide antibacterial spectrum and formulation stability.

DISCLOSURE

Technical Problem

The present inventors confirmed that 109 plant extracts reduced the total amount of melanin and tyrosinase activity in melanocytes of the skin to obtain a skin whitening effect, promoted skin regeneration and improve skin elasticity or reduce skin wrinkles by promoting collagen synthesis and inhibiting collagenase activity in the fibroblasts of the skin, obtained an anti-inflammatory or a skin soothing effect by inhibiting NO generation, obtained a moisturizing effect by increasing the amount of moisture in the skin by promoting production of hyaluronic acid in fibroblasts, obtained an antioxidant effect by scavenging free radicals, and obtained a broad antibacterial effect against various bacteria. Based on these results, the present inventors conducted further studies to complete the present invention.

Therefore, the present invention has been made in view of the above problems, and it is one object of the present invention to provide a composition for skin whitening, skin regeneration, elasticity improvement, wrinkle suppression, inflammation suppression, skin soothing, skin moisturizing, oxidation inhibition, or bacterial inhibition comprising, as active ingredients, one or more plant extracts selected from the group consisting of Island thistle (scientific name: *Cirsium nipponicum* (Maxim.) Makino), Deodeok (scientific name: *Codonopsis lanceolata*), Ulleung goldenrod (scientific name: *Solidago virgaurea*), Ulleungdo *Aster* (scientific name: *Aster glehnii*), Myeongyi (scientific name: *Allium victorialis*), Aging chive (scientific name: *Allium senescens*), Silvery mountain ash (scientific name: *Sorbus commixta*), Wild chervil (scientific name: *Anthriscus sylvestris*), Giant Knotweed (scientific name: *Fallopia sachalinensis*), Mono maple (scientific name: *Acer pictum*), Ulleungdo ladyfern (scientific name: *Athyrium acutipinnulum*), Wild wasabi (scientific name: *Wasabia japonica*), Yellow Mongolian snakegourd (scientific name: *Trichosanthes kirilowii*), Pungdo solomon's seal (scientific name: *Polygonatum odoratum*), Songak (scientific name: *Hedera rhombea*), Ulleungdo sweet violet (scientific name: *Viola woosanensis*), Korean bellflower (scientific name: *Campanula takesimana*), Ulleungdo turk's-cap lily (scientific name: *Lilium hansonii*), Ulleungdo spike speedwell (scientific name: *Pseudolysimachion insulare*), Coastal moss-like stonecrop (scientific name: *Sedum oryzifolium*), Water chickweed (Giant chickweed) (scientific name: *Stellaria aquatica*), Heartleaf *Houttuynia* (scientific name: *Houttuynia cordata* Thunb.), Ulleungdo liverleaf (scientific name: *Hepatica maxima* (Nakai) Nakai), Chinese buttercup (scientific name: *Ranunculus quelpaertensis* (H. Lev.) Nakai), Tricuspidate falsenettle (scientific name: *Boehmeria tricuspis* (Hance) Makino), Long-calyx pink (scientific name: *Dianthus longicalyx* Miq.), Curled dock (scientific name: *Rumex crispus* L.), Erect St. Johnswort (scientific name:

*Hypericum erectum* Thunb.), Five-leaf *Gynostemma* (scientific name: *Gynostemma pentaphylla* (Thunb.) Makino), Bird's egg cucumber (scientific name: *Melothria japonica* (Thunb.) Maxim.), Ulleungdo rockcress (scientific name: *Arabis takesimana* Nakai), Hedge Mustard (scientific name: *Sisymbrium officinale* (L.) Scop.), Asian prince's pine (scientific name: *Chimaphila japonica* Miq.), Marlberry (scientific name: *Ardisia japonica* (Thunb.) Blume). Spoon-leaf yellow loosestrife (scientific name: *Lysimachia mauritiana* Lam.), Climbing *Hydrangea* (scientific name: *Hydrangea petiolaris* Siebold & Zucc.), Stringy stonecrop (scientific name: *Sedum sarmentosum* Bunge). Ulleungdo stonecrop (scientific name: *Sedum takesimense* Nakai), Foam flower (scientific name: *Tiarella polyphylla* D. Don.), East Asian cinquefoil (scientific name: *Potentilla chinensis* Ser.), Indigobush *Amorpha* (scientific name: *Amorpha fruticosa* L.), Sericea *Lespedeza* (scientific name: *Lespedeza cuneata* (Dum. Cours.) G. Don.), Alfalfa (scientific name: *Medicago sativa* L.), Amur vetch (scientific name: *Vicia amurensis* Oett.), Hairy purple loosestrife (scientific name: *Lythrum salicaria* L.), South enchanter's nightshade (scientific name: *Circaea mollis* Siebold & Zucc.), Long-seed willowherb (scientific name: *Epilobium pyrricholophum* Franch. & Sav.), Evening Primrose (scientific name: *Oenothera biennis* L.), Stolon golden saxifrage (scientific name: *Chrysosplenium flagelliferum* F. Schmidt), Serrate-petal rockfoil (scientific name: *Saxifraga fortunei* var. *incisolobata* (Engl. & Irmsch.) Nakai), Ulleungdo deadnettle (scientific name: *Lamium takesimense* NAKAI.), Island ninebark (scientific name: *Physocarpus insularis* (Nakai) Nakai), Island *Corydalis* (scientific name: *Corydalis ilistipes* Nakai), Ulleungdo raspberry; (scientific name: *Rubus takesimensis* Nakai), Korea *Dystaenia* (scientific name: *Dystaenia takeshimana* (Nakai) Kitag), Ulleungdo violet (scientific name: *Viola takeshimana* Nakai), Spindle Tree (scientific name: *Euonymus japonicus* Thunb.), Crimson grapevine (scientific name: *Vitis coignetiae* Pulliat ex Planch.), *Aralia continentalis* (scientific name: *Aralia cordata* var. *continentalis* (Kitag.) Y. C. Chu), Japanese Angelica (scientific name: *Aralia elata* (Miq.) Seem.), Glossy-leaf paper plant (scientific name: *Fatsia japonica* (Thunb.) Decne. & Planch.), Three-leaf *Clematis* (scientific name: *Clematis apiifolia* DC.). Lyre-leaf nightshade (scientific name: *Solanum lvratum* Thunb.), Ivy morning glory (scientific name: *Calystegia hederacea* Wall.), Beach morning glory (scientific name: *Calystegia soldanella* (L.) Roem. & Schult.), East Asian beautyberry (scientific name: *Callicarpa japonica* Thunb.), Korean mint (scientific name: *Agastache rugosa* (Fisch. & C. A. Mey.) Kuntze), Small-flower Asian calamint (scientific name: *Clinopodium chinense* var. *parviflorum* (Kudo) H. Hara), Henbit deadnettle (scientific name: *Lamium amplexicaule* L.), Oriental motherwort (scientific name: *Leonurus japonicus* Houtt.), Long-stalk low meadow-rue (scientific name: *Thalictrum kemense* Fr.), Korean spice *Viburnum* (scientific name: *Viburnum carlesii* Hemsl.), Asian greater celandine (scientific name: *Chelidonium majus* var. *asiaticum* (H. Hara) Ohwi), Seashore spatulate *Aster* (scientific name: *Aster spathulifolius* Maxim.), Leopard plant (scientific name: *Farfugium japonicum* (L.) Kitam.), Oriental yellowhead (scientific name: *Inula britannica* var. *japonica* (Thunb.) Franch. & Sav.), Giant butterbur (scientific name: *Petasites japonicus* (Siebold & Zucc.) Maxim.), Ciliated-fruit sedge (scientific name: *Carex blepharicarpa* Franch.), Short-stem sedge (scientific name: *Carex breviculmis* R. Br.), Purple maiden silvergrass (scientific name: *Miscanthus sinensis* var. *purpurascens* (Andersson) Rendle), Foxtail fountaingrass (scientific name: *Pennisetum alopecuroides*

(L.) Spreng.), Arrow bamboo (scientific name: *Pseudosasa japonica* (Siebold & Zucc. ex Steud.) Makino ex Nakai), Kuril bamboo (scientific name: *Sasa kurilensis* (Rupr.) Makino & Shibata), Shrubby *Sophora* (scientific name: *Sophora flavescens* Aiton), Orange Daylily (scientific name: *Hemerocallis fulva* (L.) L.), Tiger lily (scientific name: *Lilium lancifolium* Thunb.), Big blue lilyturf (scientific name: *Liriope platyphylla* F. T. Wang & T. Tang), False lily of the valley (scientific name: *Maianthemum dilatatum* (A. W. Wood) A. Nelson & J. F. Macbr.), Japanese Cedar (scientific name: *Cryptomeria japonica* (Thunb. ex L. f.) D. Don), Thunberg's bay-tree (scientific name: *Machilus thunbergii* Siebold & Zucc.), Ulleungdo white pine (scientific name: *Pinus parviflora* Siebold & Zucc.), Ulleungdo hemlock (scientific name: *Tsuga sieboldii* Carriere), Sericeous newlitsea (scientific name: *Neolitsea sericea* (Blume) Koidz.), Macropodous *Daphniphyllum* (scientific name: *Daphniphyllum macropodum* Miq.), Scabrous *Aphananthe* (scientific name: *Aphananthe aspera* (Thunb.) Planch.), Caudate-leaf hackberry (scientific name: *Celtis jessoensis* Koidz.), Manchurian Elm (scientific name: *Ulmus laciniata* (Trautv.) Mayr), Montane alder (scientific name: *Alnus maximowiczii* Callier), Ulleungdo linden (scientific name: *Tilia insularis* Nakai), Fragrant snowbell (scientific name: *Styrax obassia* Siebold & Zucc.), Ulleungdo flowering cherry (scientific name: *Prunus takesimensis* Nakai), Spotted laurel (scientific name: *Aucuba japonica* Thunb.), Ulleungdo maple (scientific name: *Acer takesimense* Nakai), Ulleungdo amur corktree (scientific name: *Phellodendron insulare* Nakai), Alianthus-like prickly-ash (scientific name: *Zanthoxylum ailanthoides* Siebold & Zucc.), Wax-leaf privet (scientific name: *Ligustrum japonicum* Thunb.), Ulleungdo honeysuckle (scientific name: *Lonicera insularis* Nakai), Silk tree (scientific name: *Albizia julibrissin*), and False daisy (scientific name: *Eclipta prostrata*).

Technical Solution

In accordance with one aspect of the present invention, provided is a composition for skin whitening, skin regeneration, elasticity improvement, wrinkle suppression, inflammation suppression, skin soothing, skin moisturizing, oxidation inhibition, or bacterial inhibition comprising, as active ingredients, one or more plant extracts selected from the group consisting of Island thistle (scientific name: *Cirsium nipponicum* (Maxim.) Makino), Deodeok (scientific name: *Codonopsis lanceolata*), Ulleung goldenrod (scientific name: *Solidago virgaurea*), Ulleungdo *Aster* (scientific name: *Aster glehnii*), Myeongyi (scientific name: *Allium victorialis*), Aging chive (scientific name: *Allium senescens*), Silvery mountain ash (scientific name: *Sorbus commixta*), Wild chervil (scientific name: *Anthriscus sylvestris*), Giant Knotweed (scientific name: *Fallopia sachalinensis*), Mono maple (scientific name: *Acer pictum*), Ulleungdo ladyfern (scientific name: *Athyrium acutipinnulum*), Wild wasabi (scientific name: *Wasabia japonica*), Yellow Mongolian snakegourd (scientific name: *Trichosanthes kirilowii*), Pungdo solomon's seal (scientific name: *Polygonatum odoratum*), Songak (scientific name: *Hedera rhombea*), Ulleungdo sweet violet (scientific name: *Viola woosanensis*), Korean bellflower (scientific name: *Campanula takesimana*). Ulleungdo turk's-cap lily (scientific name: *Lilium hansonii*), Ulleungdo spike speedwell (scientific name: *Pseudolysimachion insulare*), Coastal moss-like stonecrop (scientific name: *Sedum oryzifolium*), Water chickweed (Giant chickweed) (scientific name: *Stellaria aquatica*), Heartleaf *Houttuynia* (scientific name: *Houttuy-*

*nia cordata* Thunb.), Ulleungdo liverleaf (scientific name: *Hepatica maxima* (Nakai) Nakai), Chinese buttercup (scientific name: *Ranunculus quelpaertensis* (H. Lev.) Nakai), Tricuspidate falsenettle (scientific name: *Boehmeria tricuspis* (Hance) Makino), Long-calyx pink (scientific name: *Dianthus longicalyx* Miq.), Curled dock (scientific name: *Rumex crispus* L.), Erect St. Johnswort (scientific name: *Hypericum erectum* Thunb.), Five-leaf *Gynostemma* (scientific name: *Gynostemma pentaphylla* (Thunb.) Makino), Bird's egg cucumber (scientific name: *Melothria japonica* (Thunb.) Maxim.), Ulleungdo rockcress (scientific name: *Arabis takesimana* Nakai), Hedge Mustard (scientific name: *Sisymbrium officinale* (L.) Scop.), Asian prince's pine (scientific name: *Chimaphila japonica* Miq.), Marlberry (scientific name: *Ardisia japonica* (Thunb.) Blume), Spoon-leaf yellow loosestrife (scientific name: *Lysimachia mauritiana* Lam.), Climbing *Hydrangea* (scientific name: *Hydrangea petiolaris* Siebold & Zucc.), Stringy stonecrop (scientific name: *Sedum sarmentosum* Bunge), Ulleungdo stonecrop (scientific name: *Sedum takesimense* Nakai.). Foam flower (scientific name: *Tiarella polyphylla* D. Don), East Asian cinquefoil (scientific name: *Potentilla chinensis* Ser.), Indigobush *Amorpha* (scientific name: *Amorpha fruticosa* L.), Sericea *Lespedeza* (scientific name: *Lespedeza cuneata* (Dum. Lours.) G. Don.). Alfalfa (scientific name: *Medicago sativa* L.), Amur vetch (scientific name: *Vicia amurensis* Oett.), Hairy purple loosestrife (scientific name: *Lythrum salicaria* L.), South enchanter's nightshade (scientific name: *Circaea mollis* Siebold & Zucc.), Long-seed willowherb (scientific name: *Epilobium pyrricholophum* Franch. &. Sav.), Evening Primrose (scientific name: *Oenothera biennis* L.), Stolon golden saxifrage (scientific name: *Chrysosplenium flagelliferum* F. Schmidt), Serrate-petal rockfoil (scientific name: *Saxifraga fortunei* var. *incisolobata* (Engl. & Irmsch.) Nakai), Ulleungdo deadnettle (scientific name: *Lamium takesimense* NAKAI.), Island ninebark (scientific name: *Physocarpus insularis* (Nakai) Nakai), Island *Corydalis* (scientific name: *Corydalis ilistipes* Nakai), Ulleungdo raspberry (scientific name: *Rubus takesimensis* Nakai), Korea *Dystaenia* (scientific name: *Dystaenia takeshimana* (Nakai) Kitag), Ulleungdo violet (scientific name: *Viola takeshimana* Nakai), Spindle Tree (scientific name: *Euonymus japonicus* Thunb.), Crimson grapevine (scientific name: *Vitis coignetiae* Pulliat ex Planch.), *Aralia continentalis* (scientific name: *Aralia cordata* var. *continentalis* (Kitag.) Y. C. Chu), Japanese Angelica (scientific name: *Aralia elata* (Miq.) Seem.), Glossy-leaf paper plant (scientific name: *Fatsia japonica* (Thunb.) Decne. & Planch.), Three-leaf *Clematis* (scientific name: *Clematis apiifolia* DC.), Lyre-leaf nightshade (scientific name: *Solanum lyratum* Thunb.), Ivy morning glory (scientific name: *Calystegia hederacea* Wall.), Beach morning glory (scientific name: *Calystegia soldanella* (L.) Roem. & Schutt.), East Asian beautyberry (scientific name: *Callicarpa japonica* Thunb.), Korean mint (scientific name: *Agastache rugosa* (Fisch. & C. A. Mey.) Kuntze), Small-flower Asian calamint (scientific name: *Clinopodium chinense* var. *parviflorum* (Kudo) H. Hara), Henbit deadnettle (scientific name: *Lamium amplexicaule* L.), Oriental motherwort (scientific name: *Leonurus japonicus* Houtt.), Long-stalk low meadow-rue (scientific name: *Thalictrum kemense* Fr.), Korean spice *Viburnum* (scientific name: *Viburnum carlesii* Hemsl.), Asian greater celandine (scientific name: *Chelidonium majus* var. *asiaticum* (H. Hara) Ohwi), Seashore spatulate *Aster* (scientific name: *Aster spathulifolius* Maxim.), Leopard plant (scientific name: *Farfugium japonicum* (L.) Kitam.), Oriental yellowhead (scientific name: *Inula britannica* var, *japonica*

(Thunb.) Franch. & Sav.), Giant butterbur (scientific name: *Petasites japonicus* (Siebold & Zucc.) Maxim.), Ciliated-fruit sedge (scientific name: *Carex blepharicarpa* Franch.), Short-stem sedge (scientific name: *Carex breviculmis* R., Br.), Purple maiden silvergrass (scientific name: *Miscanthus sinensis* var. *purpurascens* (Andersson) Rendle). Foxtail fountaingrass (scientific name: *Pennisetum alopecuroides* (L.) Spreng.), Arrow bamboo (scientific name: *Pseudosasa japonica* (Siebold & Zucc. ex Steud.) Makino ex Nakai), Kuril bamboo (scientific name: *Sasa kurilensis* (Rupr.) Makino & Shibata), Shrubby *Sophora* (scientific name: *Sophora flavescens* Aiton), Orange Daylily (scientific name: *Hemerocallis fulva* (L.) L.), Tiger lily (scientific name: *Lilium lancifolium* Thunb.), Big blue lilyturf (scientific name: *Liriope platyphylla* F. T. Wang & T. Tang). False lily of the valley (scientific name: *Maianthemum dilatatum* (A. W Wood) A. Nelson & J. F. Macbr.), Japanese Cedar (scientific name: *Cryptomeria japonica* (Thunb. ex L. f) D. Don), Thunberg's bay-tree (scientific name: *Machilus thunbergii* Siebold & Zucc.), Ulleungdo white pine (scientific name: *Pinus parviflora* Siebold & Zucc.), Ulleungdo hemlock (scientific name: *Tsuga sieboldii* Carriere), Sericeous newlitsea (scientific name: *Neolitsea sericea* (Blume) Koidz.), Macropodous *Daphniphyllum* (scientific name: *Daphniphyllum macropodum* Miq.), Scabrous *Aphananthe* (scientific name: *Aphananthe aspera* (Thunb.) Planch.), Caudate-leaf hackberry (scientific name: *Celtis jessoensis* Koidz.), Manchurian Elm (scientific name: *Ulmus laciniata* (Trautv.) Mayr), Montane alder (scientific name: *Alnus maximowiczii* Callier), Ulleungdo linden (scientific name: *Tilia insularis* Nakai), Fragrant snowbell (scientific name: *Styrax obassia* Siebold & Zucc.), Ulleungdo flowering cherry (scientific name: *Prunus takesimensis* Nakai), Spotted laurel (scientific name: *Aucuba japonica* Thunb.). Ulleungdo maple (scientific name: *Acer takesimense* Nakai), Ulleungdo amur corktree (scientific name: *Phellodendron insulare* Nakai), Alianthus-like prickly-ash (scientific name: *Zanthoxylum ailanthoides* Siebold & Zucc.), Wax-leaf privet (scientific name: *Ligustrum japonicum* Thunb.), Ulleungdo honeysuckle (scientific name: *Lonicera insularis* Nakai), Silk tree (scientific name: *Albizia julibrissin*), and False daisy (scientific name: *Eclipta prostrata*).

Advantageous Effects

A composition comprising plant extracts according to the present invention has a skin whitening effect by reducing the total amount of melanin and tyrosinase activity in melanocytes of the skin, promotes skin regeneration and increases skin elasticity or reduces skin wrinkles by promoting collagen synthesis and inhibiting collagenase activity in fibroblasts of the skin, has an anti-inflammatory or a skin soothing effect by suppressing NO generation, increases the amount of moisture in the skin and has a moisturizing effect by promoting generation of hyaluronic acid in fibroblasts, and has an antioxidant effect by scavenging free radicals. In addition, since the composition of the present invention exhibits a broad antibacterial effect against various bacteria, the composition of the present invention can be used as a cosmetic composition, a pharmaceutical composition, a skin external preparation, or a food composition.

Best Mode

Hereinafter, the configuration of the present invention will be described in detail.

The present invention relates to a composition comprising, as active ingredients, one or more plant extracts selected from the group consisting of Island thistle (scientific name: *Cirsium nipponicum* (Maxim.) Makino), Deodeok (scientific name: *Codonopsis lanceolata*), Ulleung goldenrod (scientific name: *Solidago virgaurea*), Ulleungdo *Aster* (scientific name: *Aster glehnii*), Myeongyi (scientific name: *Allium victorialis*), Aging chive (scientific name: *Allium senescens*), Silvery mountain ash (scientific name: *Sorbus commixta*), Wild chervil (scientific name: *Anthriscus sylvestris*), Giant Knotweed (scientific name: *Fallopia sachalinensis*), Mono maple (scientific name: *Acer pictum*), Ulleungdo ladyfern (scientific name: *Athyrium acutipinnulum*), Wild wasabi (scientific name: *Wasabia japonica*), Yellow Mongolian snakegourd (scientific name: *Trichosanthes kirilowii*), Pungdo solomon's seal (scientific name: *Polygonatum odoratum*), Songak (scientific name: *Hedera rhombea*), Ulleungdo sweet violet (scientific name: *Viola woosanensis*), Korean bellflower (scientific name: *Campanula takesimana*), Ulleungdo turk's-cap lily (scientific name: *Lilium hansonii*), Ulleungdo spike speedwell (scientific name: *Pseudolysimachion insulare*), Coastal moss-like stonecrop (scientific name: *Sedum oryzifolium*), Water chickweed (Giant chickweed) (scientific name: *Stellaria aquatica*), Heartleaf *Houttuynia* (scientific name: *Houttuynia cordata* Thunb.), Ulleungdo liverleaf (scientific name: *Hepatica maxima* (Nakai) Nakai), Chinese buttercup (scientific name: *Ranunculus quelpaertensis* (H. Lev.) Nakai), Tricuspidate falsenettle (scientific name: *Boehmeria tricuspis* (Fiance) Makino), Long-calyx pink (scientific name: *Dianthus longicalyx* Miq.), Curled dock (scientific name: *Rumex crispus* L.), Erect St. Johnswort (scientific name: *Hypericum erectum* Thunb.), Five-leaf *Gynostemma* (scientific name: *Gynostemma pentaphylla* (Thunb.) Makino), Bird's egg cucumber (scientific name: *Melothria japonica* (Thunb.) Maxim.), Ulleungdo rockcress (scientific name: *Arabis takesimana* Nakai), Hedge Mustard (scientific name: *Sisymbrium officinale* (L.) Scop.), Asian prince's pine (scientific name: *Chimaphila japonica* Miq.), Mulberry (scientific name: *Ardisia japonica* (Thunb.) Blume), Spoon-leaf yellow loosestrife (scientific name: *Lysimachia mauritiana* Lam.), Climbing *Hydrangea* (scientific name: *Hydrangea petiolaris* Siebold & Zucc.), Stringy stonecrop (scientific name: *Sedum sarmentosum* Bunge), Ulleungdo stonecrop (scientific name: *Sedum takesimense* Nakai), Foam flower (scientific name: *Tiarella polyphylla* D. Don), East Asian cinquefoil (scientific name: *Potentilla chinensis* Ser.), Indigobush *Amorpha* (scientific name: *Amorpha fruticosa* L.), Sericea *Lespedeza* (scientific name: *Lespedeza cuneata* (Dum. Cours.) G. Don.), Alfalfa (scientific name: *Medicago sativa* L.), Amur vetch (scientific name: *Vicia amurensis* Oett.), Hairy purple loosestrife (scientific name: *Lythrum salicaria* L.), South enchanter's nightshade (scientific name: *Circaea mollis* Siebold & Zucc.), Long-seed willowherb (scientific name: *Epilobium pyrricholophum* Franch. & Sav.), Evening Primrose (scientific name: *Oenothera biennis* L.), Stolon golden saxifrage (scientific name: *Chrysosplenium flagelliferum* F. Schmidt), Serrate-petal rockfoil (scientific name: *Saxifraga fortunei* var. *incisolobata* (Engl. & Irmsch.) Nakai), Ulleungdo cleadnettle (scientific name: *Lamium takesimense* NAKAI.), Island ninebark (scientific name: *Physocarpus insularis* (Nakai) Nakai), Island *Corydalis* (scientific name: *Corydalis ilistipes* Nakai), Ulleungdo raspberry (scientific name: *Rubus takesimensis* Nakai), Korea *Dystaenia* (scientific name: *Dystaenia takeshimana* (Nakai) Kitag.), Ulleungdo violet (scientific name: *Viola takeshimana* Nakai), Spindle Tree (scientific name:

*Euonymus japonicus* Thunb.), Crimson grapevine (scientific name: *Vitis coignetiae* Pulliat ex Planch.), *Aralia continentalis* (scientific name: *Aralia cordata* var. *continentalis* (Kitag.) Y. C. Chu), Japanese Angelica (scientific name: *Aralia elata* (Miq.) Seem.), Glossy-leaf paper plant (scientific name: *Fatsia japonica* (Thunb.) Decne. & Planch.), Three-leaf *Clematis* scientific name: *Clematis apiifolia* DC.), Lyre-leaf nightshade (scientific name: *Solanum lyratum* Thunb.), Ivy morning glory (scientific name: *Calystegia hederacea* Wall.), Beach morning glory (scientific name: *Calystegia soldanella* (L.) Roem. & Schult.), East Asian beautyberry (scientific name: *Callicarpa japonica* Thunb.), Korean mint (scientific name: *Agastache rugosa* (Fisch: & C. A. Mey.) Kuntze), Small-flower Asian calamint (scientific name: *Clinopodium chinense* var. *parviflorum* (Kudo) H. Hara), Henbit deadnettle (scientific name: *Lamium amplexicaule* L.), Oriental motherwort (scientific name: *Leonurus japonicus* Houtt.), Long-stalk low meadow-rue (scientific name: *Thalictrum kemense* Fr), Korean spice *Viburnum* (scientific name: *Viburnum carlesii* Hemsl.), Asian greater celandine (scientific name: *Chelidonium majus* var. *asiaticum* (H. Hara) Ohwi), Seashore spatulate *Aster* (scientific name: *Aster spathulifolius* Maxim.), Leopard plant (scientific name: *Farfugium japonicum* (L.) Kitam.), Oriental yellow-head (scientific name: *Inula britannica* var. *japonica* (Thunb.) Franch. & Sav.), Giant butterbur (scientific name: *Petasites japonicus* (Siebold & Zucc.) Maxim.), Ciliated-fruit sedge scientific name: *Carex blepharicarpa* Franch.), Short-stem sedge (scientific name: *Carex breviculmis* R. Br.), Purple maiden silvergrass (scientific name: *Miscanthus sinensis* var. *purpurascens* (Andersson) Rendle), Foxtail fountaingrass (scientific name: *Pennisetum alopecuroides* (L.) Spreng.), Arrow bamboo (scientific name: *Pseudosasa japonica* (Siebold & Zucc. ex Steud.) Makino ex Nakai), Kuril bamboo (scientific name: *Sasa kurilensis* (Rupr.) Makino & Shibata), Shrubby *Sophora* (scientific name: *Sophora flavescens* Aiton), Orange Daylily (scientific name: *Hemerocallis fulva* (L.) L.). Tiger lily (scientific name: *Lilium lancifolium* Thunb.), Big blue lilyturf (scientific name: *Liriope platyphylla* F. T. Wang & T. Tang), False lily of the valley (scientific name: *Maianthemum dilatatum* (A. W. Wood) A. Nelson & J. F. Macbr.), Japanese Cedar (scientific name: *Cryptomeria japonica* (Thunb. ex L. f.) D. Don), Thunberg's bay-tree (scientific name: *Machilus thunbergii* Siebold & Zucc.), Ulleungdo white pine (scientific name: *Pinus parviflora* Siebold & Zucc.). Ulleungdo hemlock (scientific name: *Tsuga sieboldii*, Carriere), Sericeous newlitsea (scientific name: *Neolitsea sericea* (Blume) Koidz.), Macropodous *Daphniphyllum* (scientific name: *Daphniphyllum macropodum* Miq.), Scabrous *Aphananthe* (scientific name: *Aphananthe aspera* (Thunb.) Planch.), Caudate-leaf hackberry (scientific name: *Celtis jessoensis* Koidz.), Manchurian Elm (scientific name: *Ulmus laciniata* (Trautv.) Mayr), Montane alder (scientific name: *Alnus maximowiczii* Callier). Ulleungdo linden (scientific name: *Tilia insularis* Nakai), Fragrant snowbell (scientific name: *Styrax obassia* Siebold & Zucc.), Ulleungdo flowering cherry (scientific name: *Prunus takesimensis* Nakai), Spotted laurel (scientific name: *Aucuba japonica* Thunb.), Ulleungdo maple (scientific name: *Acer takesimense* Nakai). Ulleungdo amur corktree (scientific name: *Phellodendron insulare* Nakai), Alianthus-like prickly-ash (scientific name: *Zanthoxylum ailanthoides* Siebold & Zucc.), Wax-leaf privet (scientific name: *Ligustrum japonicum* Thunb.), Ulleungdo honeysuckle (scientific name: *Lonicera insularis* Nakai), Silk tree (scientific name: *Albizia julibrissin*), and False daisy (scientific name: *Eclipta prostrata*).

The composition comprising plant extracts as active ingredients according to the present invention may be used as a composition for skin whitening, skin regeneration, elasticity improvement, wrinkle suppression, inflammation suppression, skin soothing, skin moisturizing, oxidation inhibition, and/or bacterial inhibition. The antibacterial composition may be used as an oral antibacterial composition, an anti-cavity composition, a periodontal disease alleviation composition, and an anti-halitosis composition.

According to an embodiment of the present invention, since the composition comprising plant extracts as active ingredients according to the present invention clearly exhibits a skin whitening effect, a skin regeneration effect, a skin elasticity improvement effect, an anti-wrinkle effect, an anti-inflammatory effect, a skin soothing effect, a moisturizing effect, an antioxidant effect, and/or an antibacterial effect at a low concentration, the composition may be used as an active ingredient for a cosmetic composition, a pharmaceutical composition, a skin external preparation, and a food composition for skin whitening, skin regeneration, elasticity improvement, wrinkle suppression, inflammation suppression, skin soothing, skin moisturizing, oxidation inhibition, and/or bacterial inhibition.

In the present invention, the type of plant is not limited, and a cultivated plant may be used, or a commercially available plant may be used, and the source of the plant is not limited.

The plant extracts of the present invention may be extracted according to a method known in the art, and the method is not particularly limited. Alternatively, commercially available extracts may be used.

Regardless of regions in which plants are grown, the plant extracts according to the present invention may have a skin whitening, a skin regeneration effect, an elasticity improvement effect, an anti-wrinkle effect, an anti-inflammatory effect, a skin soothing effect, a skin moisturizing effect, an antioxidative effect, and/or an antibacterial effect. Preferably, plant extracts collected from Ulleungdo may have superior skin whitening, skin regeneration, elasticity improvement, anti-wrinkle, anti-inflammatory, skin soothing, skin moisturizing, anti oxidative, and/or antibacterial effects.

The plant extracts may be obtained using any part of a plant, and there is no limitation on extraction sites. Obtaining the plant extracts is not limited by the shape of a plant, and a process of obtaining the extracts comprises a process of drying the plant. For example, in the present invention, the plant may be the whole, roots, stems, leaves, fruits, flowers, shoots, branches, bark, sap, bulbils, and/or seeds of the above-described plant.

In the present invention, the term "extracts" comprise extracts and all formulations that may be formed using extracts, such as extracts obtained by extracting the above-described plants, a diluted or concentrated liquid of the extracts, a product obtained by drying the extracts, a substance prepared by adjusting or purifying the extracts, a fermented product of the extracts, or a mixture thereof. In addition, the extracts comprise juice obtained by filtrating the product obtained after directly pressing or pulverizing the plants. The plant may be extracted as it is or may be extracted by oriental medicine processing. The "oriental medicine processing (鋪制)" refers to a pharmaceutical technology that changes the original properties of medicines by processing the medicines based on oriental medicine theory. For example, the "oriental medicine processing" includes the "cho (炒)" method of roasting medicinal materials, the "ja (炙)" method in which a liquid auxiliary material is permeated into medicinal materials by roasting the medicinal materials with a certain amount of the liquid auxiliary material, and the "steam (蒸)" method in which liquid auxiliary materials according to the oriental medicine processing regulations for each medicinal material are added into an appropriate container, and the mixture is mixed, heated, and dried to an appropriate degree.

In the present invention, an extraction method is not particularly limited, and extraction may be performed according to a method commonly used in the art. Non-limiting examples of the extraction method comprise a solvent extraction method, a hot water extraction method, an ultrasonic extraction method, a filtration method, a reflux extraction method, and the like, and the methods may be performed alone, or two or more methods may be used in combination.

In the present invention, the type of extraction solvent used for extraction is not particularly limited, and any solvent known in the art may be used. In the present invention, the extracts may be obtained by performing extraction using water, a low-grade alcohol having 1 to 6 carbon atoms, or a mixture thereof. In addition, non-limiting examples of the extraction solvent comprise water; a low-grade alcohol having 1 to 6 carbon atoms, such as methanol, ethanol, propyl alcohol, and butyl alcohol; a polyhydric alcohol such as glycerin, butylene glycol, and propylene glycol; a hydrocarbon-based solvent such as methyl acetate, ethyl acetate, acetone, benzene, hexane, diethyl ether, and dichloromethane; or a mixture thereof. Specifically, as the extraction solvent, water, a low-grade alcohol, 1,3-butylene glycol, and ethyl acetate may be used alone, or two or more thereof may be used in combination. In this case, when two or more solvents are mixed and used, the mixing ratio between the solvents is not particularly limited.

In the present invention, extraction may be performed at an extraction temperature of 10 to 80° C., specifically 15 to 50° C. for an extraction time of 2 hours to 3 days, specifically 12 hours to 18 days using a solvent of 1 to 100 times by weight, specifically 1 to 50 times by weight, more specifically 2 to 20 times by weight based on the weight of the dry matter of the plants. The extraction method may comprise a process of obtaining a liquid crude extract by performing extraction 1 to 5 times consecutively for the dried material and the crushed material.

In the present invention, to remove solid particles suspended in the extracts, the solid particles may be filtered out from the extracts by filtration (e.g., using nylon or filter paper). In addition, the extracts may be used after performing filtration using freeze filtration or the like, or the filtered extracts may be used after drying using freeze drying, hot air drying, spray drying, or the like.

The liquid crude extract may be separated from the dried lysate of a plant by a method such as reduced pressure filtration and then subjected to a process of concentration or drying. For example, the liquid crude extract may be a concentrated solution obtained by perforating reduced pressure concentration at 20 to 100° C., preferably 30 to 70° C. using a vacuum rotary concentrator, and a powdered extract may be obtained by drying the liquid extract. When necessary, the concentrated or powdered extract may be used by dissolving the extract in water, alcohol, dimethyl sulfoxide (DMSO), or a mixed solvent thereof.

In the present invention, the active ingredient may be a fraction of a plant extract.

In the present invention, the term "fraction" refers to a specific component or a group consisting of specific components separated from a mixture comprising various components by performing fractionation.

In the present invention, the fractionation method for obtaining the fraction is not particularly limited, and fractionation may be performed according to a method commonly used in the art. Non-limiting examples of the fractionation method comprise a method of obtaining a fraction from extracts by treating a predetermined solvent to plant extracts obtained by extracting a plant.

In the present invention, the kind of solvent used to obtain the traction is not particularly limited, and any solvent known in the art may be used. Non-limiting examples of the fractionation solvent comprise polar solvents such as water and alcohols; and non-polar solvents, such as hexane, ethyl acetate, chloroform, dichloromethane, and butanol. These solvents may be used alone or two or more thereof may be used in combination. When an alcohol is used as the fractionation solvent, an alcohol having 1 to 6 carbon atoms may be used.

In the present invention, the term "whitening effect" refers to lightening skin tone by inhibiting synthesis of melanin, inhibiting or preventing melanin deposition (hyperpigmentation), and suppressing occurrence of melasma and freckles due to UV rays, hormones, or heredity.

In the present invention, the term "skin regeneration effect" refers to recovery of skin tissues against damage caused by external and internal causes as the activity of skin stem cells is promoted. In this case, the damage caused by the external cause comprises ultraviolet rays, external pollutants, wounds, and trauma, and the damage caused by the internal cause comprises stress and the like.

In the present invention, the term "elasticity improvement effect" refers to alleviating the degree of sagging of the skin. In addition, the elasticity means maintaining the elasticity of the skin in a state in which elastin and collagen are sufficiently present.

In the present invention, the term "anti-wrinkle effect" refers to suppressing or inhibiting formation of wrinkles on the skin or alleviating already formed wrinkles.

In the present invention, the term "anti-inflammatory effect" refers to suppressing inflammation. Inflammation is a kind of defense mechanism of a living tissue against a certain stimulus and refers to a complex lesion associated with three responses: tissue deterioration, circulatory disturbance and exudation, and tissue proliferation. More specifically, inflammation is part of innate immunity, and as in other animals, human innate immunity recognizes patterns on the surface of cells that are specific to pathogens. Phagocytes recognize cells having such a surface as foreign cells and attack pathogens. When pathogens break through the body's physical barriers, an inflammatory response occurs. The inflammatory response is a non-specific defense action that creates a hostile environment for microorganisms that invade a wound site. In the inflammatory response, when a wound is formed or an external infectious agent enters the body, white blood cells responsible for the initial stage of the immune response penetrate the site of infection and express cytokines. Accordingly, the expression level of intracellular cytokines is an indicator of inflammatory response activation. Examples of skin diseases related to inflammation include atopic dermatitis, psoriasis, erythematous diseases triggered by radiation, chemicals, burns, etc., acid burn, bullous dermatosis, lichenoid-type diseases, itching caused by allergies, seborrheic eczema, rosacea, pemphigus vulgaris, erythema multiforme, erythema nodosum, balanitis, inflammatory hair loss such as alopecia areata, and cutaneous T-cell lymphoma, but the present invention is not limited thereto. In addition to an anti-inflammatory effect, a cosmetic having an anti-inflammatory effect has a skin soothing effect.

In the present invention, the term "moisturizing effect" refers to increasing the moisture content of the skin, reducing the roughness of the skin, and keeping the skin moist. The "moisturizing effect" is related to maintaining the flexibility of the skin by supplying moisture to the skin or blocking evaporation of moisture from the skin and maintaining a smooth surface by inducing uniform exfoliation of dead skin cells. When the skin moisturizing effect is increased, skin elasticity may be increased, and skin wrinkles may be reduced.

In the present invention, the term "antioxidant effect" refers to inhibiting oxidation of cells by highly reactive free radicals or reactive oxygen species (ROS) that are generated by oxidative stress due to intracellular metabolism or ultraviolet rays. The "antioxidant effect" is associated with reducing cell damage by removing free radicals or reactive oxygen species.

In the present invention, the term "antibacterial effect" refers to ability to resist bacteria, and comprises all mechanisms performed to protect the human body from microorganisms such as bacteria, fungi, and yeast. In addition, in the present invention, the "antibacterial effect" may mean inhibiting growth of bacteria in the oral cavity, and the bacteria may be bacteria such as the *Streptococcus* genus and the *Porphyromonas* genus. Specifically, the bacteria may be selected from the group consisting of *Streptococcus mutans, Streptococcus sanguinis, Streptococcus sanguinis, Streptococcus salivarius* subsp. *thermophilus*, and *Porphyromonas gingivalis*.

In the present invention, the term "effective amount" or "comprising as an active ingredient" means an amount of extracts capable of exhibiting a whitening effect, promoting regeneration of damaged skin, reducing wrinkles, inhibiting inflammation, exhibiting a moisturizing effect, inhibiting or alleviating cell oxidation, or exhibiting a broad antibacterial effect against various bacteria. When the composition of the present invention comprises an effective amount of the plant extracts, the composition may have a skin whitening effect, a skin regeneration effect, an elasticity improvement effect, an anti-wrinkle effect, an anti-inflammatory effect, a skin soothing effect, a moisturizing effect, an anti-oxidative effect, and an antibacterial effect.

In a cosmetic composition, a pharmaceutical composition, a skin external preparation, or a food composition according to the present invention, based on a total weight of the cosmetic composition, the pharmaceutical composition, the skin external preparation, or the food composition, the plant extracts are preferably comprised in an amount of 0.0001 to 10 parts by weight.

The present invention provides a cosmetic composition for skin whitening, skin regeneration, elasticity improvement, wrinkle suppression, inflammation suppression, skin soothing, skin moisturizing, oxidation inhibition, and/or bacterial inhibition comprising the plant extracts as active ingredients.

When the composition is used as a cosmetic composition, the composition may be prepared in the form of a general emulsified or solubilized formulation. For example, the composition may be formulated as skin tonics such as softening skin tonics or nourishing skin tonics; emulsions such as facial lotions or body lotions; creams such as nourishing creams, moisturizing creams, and eye creams;

essences; makeup ointments; sprays; gels; packs; sunscreens; makeup bases; foundations such as liquid-type foundations, solid-type foundations, and spray-type foundations; powders; makeup removers such as cleansing creams, cleansing lotions, and cleansing oils; and detergents such as cleansing foams, soaps, and body washes.

In addition to the plant extracts, the cosmetic composition may comprise additives commonly used in the cosmetic field, such as fatty substances, organic solvents, solubilizers, thickeners, gelling agents, emollients, antioxidants, suspending agents, stabilizers, foaming agents, fragrances, surfactants, water, ionic emulsifiers, nonionic emulsifiers, fillers, sequestering agents, chelating agents, preservatives, vitamins, blocking agents, wetting agents, essential oils, dyes, pigments, hydrophilic active agents, lipophilic active agents, and lipid vesicles. The additives may comprise both natural additives and synthetic additives.

The natural additives refer to ingredients such as organic raw materials, plants and plant-derived raw materials, animals and animal-derived raw materials, minerals and mineral-derived raw materials, and water. For example, the natural additives comprise one or more additives selected from the group consisting of a moisturizer, a sunscreen, a neutralizer, a fragrance, a preservative, an antioxidant, a thickener, a viscosity modifier, a film former, and a colorant.

In the present invention, the natural additive may be obtained from a natural product, may be obtained by simply modifying a natural product or a component derived from a natural product, or may comprise a component synthesized from among components derived from nature, and excludes a synthetic component synthesized by an artificial method rather than a component derived from nature.

For example, the natural raw material may mean a cosmetic raw material derived from nature that conforms to organic standards and eco-friendly certification standards determined by the country.

The eco-friendly certification standard is a certification standard for a composition composed of ingredients grown and processed in an environment-friendly manner, excluding a synthetic process. Representative eco-friendly certifications include Ecocert in France, Cosmos in Europe, US Department of Agriculture (USDA) in the US, Association of German Industries and Trading Firms (BDIH) in Germany, and Japanese Association of Standard (JAS) in Japan, and the like. In response to the recent demands of consumers who prefer eco-friendly products, various eco-friendly certification systems are being implemented in each country to certify the safety of ingredients or products. In the category of environmental certification, each country shows partial differences in the detailed numerical values and ranges but shows unity in the primary composition of raw materials and ingredients. Natural ingredients derived from nature are included in the category of eco-friendly organic ingredients. Other semi-processed ingredients are classified into Physically Processed Agro Ingredient (PPAI) and Chemically Processed Agro Ingredient (CPAI), and only raw materials that meet these standards are certified by Ecocert, Cosmos, or USDA.

In the present invention, organic raw materials and eco-friendly certified raw materials and ingredients determined by the government refer to cosmetic raw materials and compositions composed only of ingredients that comply with the organic standards and eco-friendly certification standards set by the government. For example, organic and eco-certified raw materials and ingredients consist only of ingredients that comply with the standards set by the Chinese government or organic and eco-friendly certification standards recognized in China.

In the present invention, the synthetic additive refers to a raw material that has been chemically synthesized rather than naturally derived.

When the plant extracts are formulated as a cosmetic, wash-off type cosmetics such as a makeup remover and a cleanser, characterized in that active ingredients stays on the skin within a short period of time, may comprise a relatively high concentration of the plant extracts. On the other hand, leave-on type cosmetics such as lotions, emulsions, creams, and essences, characterized in that active ingredients stay on the skin for a long time, may comprise a lower concentration of the plant extracts than the wash-off type cosmetics, but the present invention is not limited thereto. In a specific example of the present invention, based on a total weight of the composition, the composition may comprise the plant extracts in an amount of 0.0001 parts by weight to 10 parts by weight, preferably 0.0001 parts by weight to 5 parts by weight. When the composition of the present invention comprise the plant extracts in an amount less than 0.0001 parts by weight, it is difficult to sufficiently express a skin whitening, a skin regeneration effect, an elasticity improvement effect, an anti-wrinkle effect, an anti-inflammatory effect, a skin soothing effect, a skin moisturizing effect, an antioxidative effect, and/or an antibacterial effect. When the composition comprise the plant extracts in an amount exceeding 10 parts by weight, unwanted reaction such as allergies may occur, or problems related with skin safety may occur.

Preferably, each component comprised in the cosmetic composition according to the present invention may be comprised in the cosmetic composition of the present invention within a range that does not exceed the maximum amount stipulated in the "Safety and Technical Standards for Cosmetics" set by the Chinese government.

In addition, the present invention provides a pharmaceutical composition for skin whitening, skin regeneration, elasticity improvement, wrinkle suppression, inflammation suppression, skin soothing, skin moisturizing, oxidation inhibition, and/or bacterial inhibition comprising the plant extracts as active ingredients.

In the present invention, "pharmaceutical composition" may be used as a concept comprising the meaning of "quasi-drugs" or "drugs".

In comprising embodiment, skin lightening may refer to prevention or treatment of skin hyperpigmentation, inflammation suppression or moisturizing may mean prevention or treatment of dry skin diseases comprising atopic dermatitis or psoriasis, and antioxidation may mean removal of reactive oxygen species.

The pharmaceutical composition may be prepared as a solution using an oil or aqueous medium as a solvent, may be prepared in the form of a suspension or emulsion, or may be prepared in the form of extracts, powder, granules, tablets, or capsules.

In addition, the composition may further comprise one or more active ingredients exhibiting the same or similar function. For example, the composition may comprisie known skin whitening, skin regeneration, elasticity improvement, anti-wrinkle, anti-inflammatory, skin soothing, skin moisturizing, antioxidant, and/or antibacterial ingredients. When the composition further comprise skin whitening, skin regeneration, elasticity improvement, anti-wrinkle, anti-inflammatory, skin soothing, skin moisturizing, antioxidant, and/or antibacterial ingredients, in the composition of the present invention, a skin whitening effect, a skin regeneration effect, an elasticity improvement effect, an anti-wrinkle effect, an anti-inflammatory effect, a skin soothing effect, a skin moisturizing effect, an antioxidative effect, and/or an antibacterial effect may be further improved. When adding the above ingredients, skin safety according to combined use, ease of formulation, and stability of active ingredients may be considered. In a specific example of the present invention, as skin whitening ingredients known in the art, the composition may further comprise one or more components selected from the group consisting of substances that inhibit tyrosinase enzyme activity, such as kojic acid and arbutin; hydroquinone, vitamin-C, and derivatives thereof; and various plant extracts. The additional components may be comprised in an amount of 0.0001 to 10 parts by weight based on a total weight of the composition. In this case, the content range may be adjusted according to requirements such as skin safety and ease of formulation of the plant extracts.

In addition, the composition of the present invention may further comprise pharmaceutically acceptable carriers.

The pharmaceutically acceptable carrier may contain various ingredients such as buffers, sterile water for injection, normal saline or phosphate buffered saline, sucrose, histidine, salts, and polysorbates.

The composition of the present invention may be administered via an oral or parenteral route. The composition may be administered in the form of a general pharmaceutical preparation. For example, in clinical administration, the composition may be administered in various oral and parenteral formulations. When the composition is formulated, the composition may be prepared using general diluents or excipients such as fillers, extenders, binders, wetting agents, disintegrants, and surfactants.

Solid preparations for oral administration comprise tablets, pills, powders, granules, capsules, and the like. The solid preparation may be prepared by mixing one or more excipients selected from starch, calcium carbonate, sucrose or lactose, and gelatin with the pharmaceutical composition of the present invention.

In addition to simple excipients, lubricants such as magnesium stearate talc are also used. Liquid formulations for oral administration comprise suspensions, oral solutions, emulsions, syrups, and the like. In addition to water and liquid paraffin, which are commonly used simple diluents, various excipients, for example, wetting agents, sweetening agents, fragrances, preservatives, and the like may be comprised.

Formulations for parenteral administration comprise sterile aqueous solutions, non-aqueous solutions, suspensions, emulsions, freeze-dried preparations, and suppositories. The non-aqueous solutions and the suspensions may comprise propylene glycol, polyethylene glycol, vegetable oils such as olive oil, and injectable esters such as ethyl oleate. As the bases of the suppositories, witepsol, macrogol, tween 61, cacao butter, laurin butter, glycerogelatin, and the like may be used.

The effective amount of the plant extracts comprised in the composition of the present invention may vary depending on formulation of the composition, a method of applying the compound to the skin, and a length of time the compound stays on the skin. For example, when the composition is formulated into a pharmaceutical formulation, the composition may comprise a higher concentration of the plant extracts than when formulated as a cosmetic that is routinely applied to the skin. Accordingly, based on the amount of the plant extracts, a daily dose may be 0.1 to 100 mg/kg, preferably 30 to 80 mg/kg, more preferably 50 to 60 mg/kg, and the pharmaceutical formulation may be administered at a frequency of 1 to 6 administrations per day.

The composition of the present invention may be used alone or in combination with surgery, radiation therapy, hormone therapy, chemotherapy, and methods using biological response modifiers.

In addition, the composition for skin whitening, skin regeneration, elasticity improvement, wrinkle suppression, inflammation suppression, skin soothing, skin moisturizing, oxidation inhibition, and/or bacterial inhibition comprising the plant extracts of the present invention as active ingredients may be provided as a quasi-drug.

In the present invention, the "quasi-drug" comprises the plant extracts as active ingredients. In addition, when necessary, the "quasi-drug" may comprise a pharmaceutically acceptable carrier, an excipient, or a diluent. As long as the effect of the present invention is not hindered, the pharmaceutically acceptable carrier, excipient, or diluent may be used without particular limitation. For example, a tiller, an extender, a binder, a wetting agent, a disintegrant, a surfactant, a lubricant, a sweetening agent, a perfuming agent, or a preservative may be comprised, but the present invention is not limited thereto.

For example, the quasi-drug may be a disinfectant cleaner, a shower foam, an ointment, a wet tissue, a coating agent, and the like. The quasi-drug is preferably prepared as a semi-solid preparation such as an ointment for external use and a lotion, without being limited thereto. A method of formulating the quasi-drug, a method of using the same, and the dose and components thereof may be appropriately selected from conventional techniques known in the art.

In addition, the present invention provides a skin external preparation for skin whitening, skin regeneration, elasticity improvement, wrinkle suppression, inflammation suppression, skin soothing, skin moisturizing, oxidation inhibition, and/or bacterial inhibition comprising the plant extracts as active ingredients.

When the plant extracts are used as a skin external preparation, the skin external preparation may further comprise fatty substances, organic solvents, solubilizers, thickening and gelling agents, emollients, antioxidants, suspending agents, stabilizers, foaming agents, fragrances, surfactants, water, ionic or non-ionic emulsifiers, fillers, sequestering agents and chelates agents, preservatives, vitamins, blockers, humectants, essential oils, dyes, pigments, hydrophilic or lipophilic active agents, lipid vesicles, or supplements commonly used for external preparations for skin in the field of dermatology. In addition, the above ingredients may be introduced in an amount generally used in the field of dermatology.

When the plant extracts are provided as a skin external preparation, the skin external preparation may be prepared in the form of an ointment, a patch, a gel, a cream, or a spray, without being limited thereto.

In addition, the present invention relates to a food composition for skin whitening, skin regeneration, elasticity improvement, wrinkle suppression, inflammation suppression, skin soothing, skin moisturizing, oxidation inhibition, and/or bacterial inhibition comprising the plant extracts.

When the plant extracts of the present invention are provided as a food composition, the composition may comprise food supplements in addition to active ingredients.

The food supplement means a component added to preserve food and is added to manufacture health functional food of each formulation. The food supplements may be appropriately selected and used by those skilled in the art. For example, the food supplements comprise various nutrients, vitamins, minerals (electrolytes), flavoring agents such as synthetic flavoring agents and natural flavoring agents, staining agents and fillers, pectic acid and salts thereof, alginic acid and salts thereof, organic acids, protective colloidal thickeners, pH regulators, stabilizers, preservatives, glycerin, alcohols, carbonating agent used in carbonated beverages, and the like, without being limited thereto.

In addition, the food composition may comprise a health functional food. In the present invention, the "health functional food" refers to a food group that allows the function of a food to be expressed to meet a specific purpose using a physical, biochemical, or bioengineering method, or a food designed and processed to sufficiently express body control functions related to biological defense rhythm control, disease prevention, and health recovery of the food composition. The health functional food has an active health maintenance or promotion effect compared to general food, and a health supplement food refers to a food intended for health supplement. In some cases, the terms functional food, health food, and dietary supplement are used interchangeably.

Specifically, the health functional food is a food prepared by adding the plant extracts of the present invention to food materials such as beverages, teas, spices, gum, and confectionery, or a food prepared by encapsulating, powdering, or suspension of the plant extracts of the present invention. When the health functional food is ingested, a specific health effect may be obtained. In particular, unlike general drugs, since the health functional food uses food as a raw material, there is an advantage in that there are no side effects that may occur when taking drugs for a long time.

The food may comprise food scientifically acceptable food supplement additives, and may further comprise carriers, excipients and diluents commonly used in manufacture of health functional foods.

Since the composition is commonly used in food compositions, the composition may comprise additional ingredients capable of improving odor, taste, visual, and the like. For example, the composition may comprise vitamins A, C, D, E, B1, B2, B6, and B12, niacin, biotin, folate, panthotenic acid, and the like. In addition, the composition may comprise minerals such as zinc (Zn), iron (Fe), calcium (Ca), chromium (Cr), magnesium (Mg), manganese (Mn), copper (Cu), and chromium (Cr). In addition, the composition may comprise amino acids such as lysine, tryptophan, cysteine, and valine. The health functional food of the present invention may be prepared in various forms without any particular limitation, may comprise all foods in a conventional sense, and may be used interchangeably with terms known in the art, such as functional food.

In addition, according to selection of those skilled in the art, the health functional food of the present invention may be prepared by mixing other auxiliary ingredients that may be comprised in food and known additives. Examples of foods to which the health functional food of the present invention may be added comprise meat, sausage, bread, chocolate, candy, snacks, confectionery, pizza, ramen, other noodles, gums, dairy products comprising ice cream, various soups, beverages, tea, drinks, alcoholic beverages, and vitamin complexes. The health functional food may be added to juice, tea, jelly, and juice prepared by using the plant extracts of the present invention as a main component. In addition, the health functional food may be added to animal feed.

Hereinafter, embodiments of the present invention will be described in detail. However, the following examples are only illustrative of the present invention, and the content of the present invention is not limited to the following examples.

MODES FOR CARRYING OUT THE INVENTION

Preparation Example 1

Preparation of Plant Extracts

A 70% aqueous ethanol solution was added to the whole plant, roots, stems, leaves, fruits, flowers, shoots, branches, bark, sap, bulbils, or seeds of each of plants 1 to 112. At this time, the 70% aqueous ethanol solution was added in a volume corresponding to 20 times the mass of each plant tissue. Then, extraction was performed at room temperature for 3 days, and then filtration under reduced pressure was performed. Then, the filtered extracts were concentrated and dried using a rotary evaporator (Buchi, Switzerland) to prepare plant extracts.

Experimental Example 1

Effect of Reducing Total Amount of Melanin

After a sample was added to the culture medium of B-16 mouse melanoma cells, a whitening effect was confirmed by measuring the total amount of melanin at the cellular level (Lotan R., Lotan D. Cancer Res. 40:3345-3350, 1980). Before the experiment, toxicity evaluation was performed on mouse melanoma cells to select a concentration without toxicity, and then whitening evaluation was performed at the concentration.

The sample was added to the culture medium so that the final concentration is the treatment concentration shown in the table below. As a control, arbutin was added to the culture medium at a concentration of 200 ppm. B-16 melanoma cells treated with the sample or arbutin were cultured for 3 days.

Thereafter, the cells were removed from a culture vessel and centrifuged, 1 ml of sodium hydroxide solution (1N concentration) was added to the centrifuged cell pellet, heating was performed at 80° C. for 10 minutes to dissolve melanin, and using a spectrophotometer, absorbance at 400 nm was measured to measure the amount of melanin produced.

The amount of melanin was determined according to absorbance per unit cell number ($1 \times 10^6$ cells). In addition, based on a non-addition control group, the relative total amount of melanin in the experimental group treated with each sample was calculated as inhibition rate (%), and the results are summarized in the table below.

Experimental Example 2

Effect of Promoting Synthesis of Type I Collagen in Human-Derived Fibroblasts Each sample was added to the culture medium of human-derived fibroblasts to confirm the effect of promoting synthesis of type I collagen at the cellular level. Measurement of synthesized collagen was quantified using a Procollagen Type I C-Peptide Enzyme Immuno Assay KIT (PICP ETA kit). To measure the amount of synthesized collagen, each sample was added to a fibroblast culture medium (DMEM culture medium). After cell culture for 48 hours, the culture medium was taken, and the degree of synthesis of type I collagen at each concentration was measured at 450 nm using a spectrophotometer using the PICP ETA kit.

For comparison of the effects, a collagen synthesis level was measured in the same manner for the culture medium of untreated fibroblasts (negative control) and a sample (positive control) to which TGFb was added to a final concentration of 10 ppb. A collagen production increase rate was calculated as the ratio of relative collagen production to the negative control group, and the results are shown in the table below.

Experimental Example 3

NO Generation Inhibitory Effect

To check the anti-inflammatory effect and skin trouble alleviation effect of each sample, an experiment was conducted to evaluate inhibition of nitric oxide (NO) formation by the GRIESS method using the RAW264.7 cell line (ATCC number: CRL-2278).

Specifically, RAW264.7 cells, which are macrophages of mice, were subcultured several times, and the cells were seeded at a cell density of $3\times10^5$ cells per well in a 24-well plate, followed by cell culture for 24 hours. Then, the final concentration was replaced with the diluted cell medium as shown in the table below. At this time, as a positive control, the cells were treated with L-NG-monomethylarginine (L-NMMA), a NO-production inhibitor, to a final concentration of 5 ppm and cultured for 30 minutes. Then, the cells were treated with lipopolysaccharide (LPS) as a stimulus at a concentration of 1 µg/ml and cultured for 24 hours. 100 µl of the supernatant was transferred to a 96-well plate, 100 µl of a GRIESS solution was added thereto, and then reaction was performed at room temperature for 10 minutes. Then, absorbance at 540 nm was measured, and the NO inhibitory effect of each sample was determined based on the absorbance, and the results are shown in the table below.

Experimental Example 4

Evaluation of Hyaluronic Acid Synthesis Enhancement

Human-derived fibroblasts (human dermal fibroblasts) cultured in a DMEM culture medium containing 10% fetal bovine serum at a cell density of $1\times10^5$ cells/mL, and 500 µl of the cell culture medium was added to each well of a 24-well plate. After incubation for 18 hours, the samples were diluted with a DMEM culture medium without fetal bovine serum, and each sample was added at the following concentrations. As a positive control, epidermal growth factor (EGF), which is known to promote hyaluronic acid production, was added at a concentration of 10 ppb. After incubation for 24 hours, the cell culture medium was recovered, and the concentration of hyaluronic acid was measured using a Hyaluronan ELISA kit (R&D Systems).

In addition, based on the hyaluronic acid concentration (100%) of a non-addition control group, the hyaluronic acid concentrations of the experimental groups treated with each sample were quantified, and the results are shown in the following table.

Experimental Example 5

Antioxidant Effect—Free Radical Scavenging Rate

To confirm antioxidant activity, free radical scavenging activity was measured using DPPH. DPPH was purchased from Sigma Co., Ltd. (USA). First, a standard DPPH ethanol solution with a concentration of 1.5 mM (0.06 mg/ml) was prepared. Then, ethanol was added to each extract and ascorbic acid as a reference material, which is known as an antioxidant, to prepare samples at a concentration of 0.1%, and serial dilution was performed. Then, the sample and the standard DPPH solution were added in the same ratio and stirred, followed by reaction at 37° C. for 30 minutes. Then, absorbance was measured at 517 nm. At this time, addition of ethanol instead of the sample was used as a control. Free radical scavenging ability was measured by calculating IC50, which is half maximal inhibitory concentration, and the results are shown in the following table. IC50 is a general method of expressing free radical scavenging ability as the concentration of ascorbic acid and extract required to remove 50% of free radicals of a non-addition control group.

Experimental Example 6

Antibacterial Effect—Minimum Inhibitory Concentration (MIC) Measurement Method MICs were measured for fermented cultures of *Staphylococcus aureus* and *Aspergillus niger.*

MIC measurement for *Staphylococcus aureus* was performed using Mueller Hinton broth, an optimal culture medium, at a bacterial concentration of $10^6$ CFU/mL at 37° C. for 24 hours. MIC measurement for *Aspergillus niger* was performed using potato dextrose broth at a bacterial concentration of $10^5$ CFU/mL at 30° C. for 48 hours. The serial dilution method was used for both bacteria, and the MIC of fermentation culture was confirmed by visually comparing the turbidity between wells after the incubation was completed.

The minimum inhibitory concentration of each extract was expressed as % (w/v), and MIC (%) in each table means % (w/v) unless otherwise stated.

Experimental Example 7

Antibacterial Effect Against Bacteria Causing Dental Caries and Periodontitis Antibacterial activity experiment was performed to confirm the preventive or therapeutic effect on dental caries and periodontitis of each sample. To confirm the effect of inhibiting the growth of oral pathogens, an antibacterial activity test was conducted by using the paper disc test method using *Streptococcus mutans*, a representative bacterium that causes dental caries, and *Porphyromonas gingivalis*, a representative bacterium that causes periodontal diseases.

After increasing the activity of each oral pathogen under the optimal culture conditions shown in the table below, each pathogen was cultured in an optimal medium for about 4 to 6 hours so that the turbidity of the culture medium was set to Macfarland turbidity No. 0.5 ($1.5\times10^8$), and then 0.1 ml of each oral pathogen was spread evenly on a plate medium. Thereafter, each sample was added at a concentration of 10 mg/disc and left for 1 hour for absorption drying. Then, each oral pathogen was cultured at the optimum temperature for 24 to 48 hours, and then the size (diameter, mm) of a growth inhibition ring was measured.

TABLE 1

| Strain | | Optimum conditions | | |
|---|---|---|---|---|
| Gram staining | Strain name | Temperature | Culture medium | Traits |
| Gram (+) | *Streptococcus mutans* | 37° C. | BHI | Facultative anaerobic |

TABLE 1-continued

| Strain | | Optimum conditions | | |
|---|---|---|---|---|
| Gram staining | Strain name | Temperature | Culture medium | Traits |
| Gram (−) | *Porphyromonas gingivalis* | 37° C. | TSA Hemin Menadione medium | Anaerobic |

Example 1

Island Thistle

TABLE 2

| No. | Sample | Conc. (ppm) | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|---|
| | Control group | | | | Vitamin C 7.5 ppm | Hexanediol Bacteria: *P. aeruginosa* 2% Fungi: *A. niger* 1% | Untreated 0 mm | Untreated 0 mm |
| 1 | Island thistle | | *Cirsium nipponicum* (Maxim) Makino | Island thistle | | | | |
| Comparative Example | Thistle | 50 | *Cirsium Japonicum* | | 4.23 | MIC (%) Bacteria: 2 MIC (%) Fungi: 2 | 8.5 | 8.1 |
| 1-1 | Whole plant | 2 10 50 | | | 0.88 | MIC (%) Bacteria: 0.5 MIC (%) Fungi: 0.5 | 21.9 | 15.1 |
| 1-2 | Roots | 2 10 50 | | | 0.96 | MIC (%) Bacteria: 0.25 MIC (%) Fungi: 0.25 | 13.9 | 19.5 |
| 1-3 | Stems | 2 10 50 | | | 0.77 | MIC (%) Bacteria: 0.5 MIC (%) Fungi: 0.5 | 24.1 | 16.1 |
| 1-4 | Leaves | 2 10 50 | | | 0.64 | MIC (%) Bacteria: 0.5 MIC (%) Fungi: 0.5 | 27.8 | 17.9 |
| 1-5 | Fruits | 2 10 50 | | | 0.13 | MIC (%) Bacteria: 0.125 MIC (%) Fungi: 0.125 | 22.8 | 19.0 |
| 1-6 | Flowers | 2 10 50 | | | 0.97 | MIC (%) Bacteria: 0.0625 MIC (%) Fungi: 0.0625 | 11.1 | 8.4 |

TABLE 3

| No. | Sample | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|
| | Control group | | | Vitamin C 7.5 ppm | Hexanediol Bacteria: *P. aeruginosa* 2% Fungi: *A. niger* 1% | Untreated 0 mm | Untreated 0 mm |
| 1 | Island thistle | *Cirsium nipponicum* (Maxim.) Makino | Island thistle | | | | |
| Comparative Example | Thistle | *Cirsium Japonicum* | | 4.23 | MIC (%) Bacteria: 2 MIC (%) Fungi: 2 | 8.5 | 8.1 |
| 1-1 | Whole plant | | | 0.88 | MIC (%) Bacteria: 0.5 MIC (%) Fungi: 0.5 | 21.9 | 15.1 |
| 1-2 | Roots | | | 0.96 | MIC (%) Bacteria: 0.25 MIC (%) Fungi: 0.25 | 13.9 | 19.5 |
| 1-3 | Stems | | | 0.77 | MIC (%) Bacteria: 0.5 MIC (%) Fungi: 0.5 | 24.1 | 16.1 |
| 1-4 | Leaves | | | 0.64 | MIC (%) Bacteria: 0.5 MIC (%) Fungi: 0.5 | 27.8 | 17.9 |
| 1-5 | Fruits | | | 0.13 | MIC (%) Bacteria: 0.125 MIC (%) Fungi: 0.125 | 22.8 | 19.0 |
| 1-6 | Flowers | | | 0.97 | MIC (%) Bacteria: 0.0625 MIC (%) Fungi: 0.0625 | 11.1 | 8.4 |

Example 2

Deodeok

TABLE 4

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 2 | Deodeok | | *Codonopsis lanceolata* | Deodeok | | | | |
| Comparative Example | Pilose asiabell | 50 | *Codonopsis Pilosula* | | 98.81 | 2.34 | 2.64 | 10.34 |
| 2-1 | Whole plant | 2 | | | 36.56 | 15.55 | 25.86 | 376.57 |
| | | 10 | | | 33.66 | 25.01 | 32.54 | 498.43 |
| | | 50 | | | 25.39 | 39.40 | 34.86 | 654.56 |
| 2-2 | Roots | 2 | | | 47.81 | 11.58 | 10.16 | 10.77 |
| | | 10 | | | 41.70 | 14.34 | 13.68 | 59.86 |
| | | 50 | | | 31.62 | 15.96 | 14.78 | 66.59 |
| 2-3 | Stems | 2 | | | 37.26 | 14.59 | 25.93 | 380.41 |
| | | 10 | | | 32.92 | 29.14 | 29.48 | 483.35 |
| | | 50 | | | 23.76 | 35.25 | 34.03 | 629.94 |
| 2-4 | Leaves | 2 | | | 35.40 | 19.24 | 26.68 | 298.83 |
| | | 10 | | | 27.43 | 29.68 | 27.53 | 557.21 |
| | | 50 | | | 22.63 | 35.74 | 35.11 | 763.79 |
| 2-5 | Fruits | 2 | | | 39.94 | 12.90 | 21.47 | 213.22 |
| | | 10 | | | 29.09 | 28.83 | 32.19 | 512.23 |
| | | 50 | | | 24.11 | 35.27 | 35.73 | 763.76 |
| 2-6 | Flowers | 2 | | | 34.37 | 13.44 | 20.36 | 287.30 |
| | | 10 | | | 27.81 | 20.40 | 31.74 | 557.13 |
| | | 50 | | | 20.01 | 30.11 | 38.08 | 642.15 |

TABLE 5

| No. | Sample | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|
| | Control group | | | Vitamin C 7.5 ppm | Hexanediol Bacteria: *P. aeruginosa* 2% Fungi: *A. niger* 1% | Untreated 0 mm | Untreated 0 mm |
| 2 | Deodeok | *Codonopsis lanceolata* | Deodeok | | | | |
| Comparative Example | Pilose asiabell | *Codonopsis Pilosula* | | 6.78 | MIC (%) Bacteria: 2 MIC (%) Fungi: 2 | 11.1 | 13.2 |
| 2-1 | Whole plant | | | 0.84 | MIC (%) Bacteria: 0.25 MIC (%) Fungi: 0.25 | 16.2 | 17.7 |
| 2-2 | Roots | | | 1.34 | MIC (%) Bacteria: 1 MIC (%) Fungi: 1 | 23.3 | 25.8 |
| 2-3 | Stems | | | 0.74 | MIC (%) Bacteria: 0.0625 MIC (%) Fungi: 0.0625 | 13.4 | 22.3 |
| 2-4 | Leaves | | | 0.47 | MIC (%) Bacteria: 0.5 MIC (%) Fungi: 0.5 | 10.6 | 13.4 |
| 2-5 | Fruits | | | 0.99 | MIC (%) Bacteria: 0.5 MIC (%) Fungi: 0.5 | 14.3 | 8.8 |
| 2-6 | Flowers | | | 0.85 | MIC (%) Bacteria: 0.5 MIC (%) Fungi: 0.5 | 21.6 | 21.1 |

Example 3

Ulleung Goldenrod

TABLE 6

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 3 | Ulleung goldenrod | | *Solidago virgaurea* subsp. *Gigantea* | Ulleung goldenrod | | | | |
| Comparative Example 1 | Canadian goldenrod | 50 | *Solidago Canadensis* | | 61.25 | 10.02 | 2.68 | 52.64 |
| Comparative Example 2 | European goldenrod (Whole plant) | 50 | *Solidago virgaurea* var. *leiocarpa* | | 45.27 | 8.11 | 10.77 | 150.44 |
| 3-1 | Whole plant | 2 | | | 34.61 | 10.91 | 20.78 | 207.09 |
| | | 10 | | | 32.89 | 20.92 | 30.81 | 595.19 |
| | | 50 | | | 23.81 | 37.93 | 36.47 | 722.54 |
| 3-2 | Roots | 2 | | | 37.54 | 18.92 | 25.58 | 276.27 |
| | | 10 | | | 28.83 | 28.31 | 29.70 | 503.07 |
| | | 50 | | | 22.82 | 33.63 | 34.58 | 645.75 |
| 3-3 | Stems | 2 | | | 34.86 | 11.15 | 26.42 | 275.04 |
| | | 10 | | | 33.33 | 26.25 | 30.85 | 425.87 |
| | | 50 | | | 25.32 | 37.04 | 36.02 | 697.23 |
| 3-4 | Leaves | 2 | | | 39.29 | 11.33 | 23.72 | 394.14 |
| | | 10 | | | 27.03 | 24.44 | 28.91 | 544.89 |
| | | 50 | | | 21.20 | 34.94 | 38.52 | 797.78 |
| 3-5 | Fruits | 2 | | | 37.20 | 11.05 | 25.04 | 200.97 |
| | | 10 | | | 32.63 | 24.53 | 28.92 | 580.65 |
| | | 50 | | | 20.88 | 35.86 | 35.27 | 665.67 |
| 3-6 | Flowers | 2 | | | 39.98 | 11.13 | 23.18 | 334.25 |
| | | 10 | | | 29.18 | 24.37 | 33.37 | 481.45 |
| | | 50 | | | 24.68 | 36.84 | 38.81 | 777.36 |

TABLE 7

| No. | Sample | Conc. (ppm) | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|---|
| | Control group | | | | Vitamin C 7.5 ppm | Hexanediol Bacteria: *P. aeruginosa* 2% Fungi: *A. niger* 1% | Untreated 0 mm | Untreated 0 mm |
| 3 | Ulleung goldenrod | | *Solidago virgaurea* subsp. *Gigantea* | Ulleung goldenrod | | | | |
| Comparative Example 1 | Canadian goldenrod | 50 | *Solidago Canadensis* | | 2.45 | MIC (%) Bacteria: 1 MIC (%) Fungi: 1 | 15.1 | 11.8 |
| Comparative Example 2 | European goldenrod (Whole plant) | 50 | *Solidago virgaurea* var. *leiocarpa* | | 2.11 | MIC (%) Bacteria: 1 MIC (%) Fungi: 1 | 11.8 | 8.7 |
| 3-1 | Whole plant | 2 10 50 | | | 0.48 | MIC (%) Bacteria: 0.5 MIC (%) Fungi: 0.25 | 22.5 | 19.0 |
| 3-2 | Roots | 2 10 50 | | | 0.58 | MIC (%) Bacteria: 0.5 MIC (%) Fungi: 0.25 | 25.0 | 19.4 |
| 3-3 | Stems | 2 10 50 | | | 0.88 | MIC (%) Bacteria: 0.5 MIC (%) Fungi: 0.25 | 10.3 | 9.4 |
| 3-4 | Leaves | 2 10 50 | | | 0.96 | MIC (%) Bacteria: 0.25 MIC (%) Fungi: 0.25 | 15.7 | 16.7 |
| 3-5 | Fruits | 2 10 50 | | | 0.85 | MIC (%) Bacteria: 0.5 MIC (%) Fungi: 0.25 | 9.3 | 10.4 |

TABLE 7-continued

| No. | Sample | Conc. (ppm) | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|---|
| 3-6 | Flowers | 2 10 50 | | | 0.87 | MIC (%) Bacteria: 0.25 MIC (%) Fungi: 0.125 | 24.7 | 24.6 |

Example 5

Ulleungdo *Aster*

TABLE 8

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 5 | Ulleungdo aster | | *Aster glehnii* | Ulleungdo aster | | | | |
| Comparative Example | Ulleungdo aster (other area) | 50 | *Aster glehnii* | | 62.23 | 10.42 | 15.02 | 100.64 |
| Comparative Example | Aster | 50 | *Aster Yomena* | | 80.76 | 4.98 | 5.25 | 34.82 |
| 5-1 | Whole plant | 2 10 50 | | | 37.51 33.86 24.66 | 17.34 20.38 33.77 | 25.80 32.44 35.69 | 205.45 491.79 707.09 |
| 5-2 | Roots | 2 10 50 | | | 34.29 28.36 21.69 | 11.39 20.40 38.01 | 25.14 33.28 34.59 | 259.24 593.29 789.90 |
| 5-3 | Stems | 2 10 50 | | | 37.98 30.32 26.82 | 15.13 28.50 38.84 | 26.97 27.89 37.02 | 270.31 595.08 641.95 |
| 5-4 | Leaves | 2 10 50 | | | 35.03 32.94 26.26 | 11.77 23.15 34.57 | 25.97 30.73 34.14 | 284.00 590.13 635.28 |
| 5-5 | Fruits | 2 10 50 | | | 36.86 28.05 20.93 | 10.66 29.31 37.37 | 24.47 31.71 39.03 | 367.08 445.51 706.53 |
| 5-6 | Flowers | 2 10 50 | | | 39.75 30.29 20.43 | 18.42 27.07 39.22 | 25.85 27.96 36.45 | 345.91 437.49 724.41 |
| 5-7 | Shoots | 2 10 50 | | | 38.47 33.77 22.20 | 12.97 24.93 31.37 | 25.43 33.53 36.67 | 210.57 424.05 696.15 |

TABLE 9

| No. | Sample | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|
| | Control group | | | Vitamin C 7.5 ppm | Hexanediol Bacteria: *P. aeruginosa* 2% Fungi: *A. niger* 1% | Untreated 0 mm | Untreated 0 mm |
| 5 | Ulleungdo aster | *Aster glehnii* | Ulleungdo aster | | | | |
| Comparative Example | Ulleungdo aster (other area) | *Aster glehnii* | | 2.52 | MIC (%) Bacteria: 1 MIC (%) Fungi: 1 | 16.7 | 16.0 |
| Comparative Example | Aster | *Aster Yomena* | | 3.93 | MIC (%) Bacteria: >2 MIC (%) Fungi: >2 | 13.1 | 19.0 |
| 5-1 | Whole plant | | | 0.12 | MIC (%) Bacteria: 0.25 MIC (%) Fungi: 0.25 | 22.6 | 27.5 |

TABLE 9-continued

| No. | Sample | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|
| 5-2 | Roots | | | 0.02 | MIC (%) Bacteria: 0.5 MIC (%) Fungi: 0.25 | 27.8 | 20.1 |
| 5-3 | Stems | | | 0.50 | MIC (%) Bacteria: 1 MIC (%) Fungi: 0.5 | 15.9 | 13.0 |
| 5-4 | Leaves | | | 0.52 | MIC (%) Bacteria: 1 MIC (%) Fungi: 1 | 13.1 | 13.5 |
| 5-5 | Fruits | | | 0.54 | MIC (%) Bacteria: 0.5 MIC (%) Fungi: 0.25 | 11.9 | 14.1 |
| 5-6 | Flowers | | | 0.69 | MIC (%) Bacteria: 0.25 MIC (%) Fungi: 0.25 | 8.7 | 9.0 |
| 5-7 | Shoots | | | 0.78 | MIC (%) Bacteria: 1 MIC (%) Fungi: 1 | 23.3 | 17.2 |

Example 6

Myeongyi

20

TABLE 10

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 6 Comparative Example | Myeongyi Garlic | 50 | *Allium victorialis* *Allium Sativum* | Myeongyi | 77.95 | 14.24 | 3.05 | 73.76 |
| 6-1 | Whole plant | 2 | | | 38.45 | 10.95 | 20.51 | 388.28 |
| | | 10 | | | 28.60 | 20.61 | 27.05 | 582.69 |
| | | 50 | | | 23.93 | 34.76 | 38.02 | 623.48 |
| 6-2 | Roots | 2 | | | 35.97 | 17.15 | 26.52 | 400.58 |
| | | 10 | | | 33.95 | 21.18 | 33.24 | 507.00 |
| | | 50 | | | 26.51 | 31.11 | 37.38 | 660.75 |
| 6-3 | Stems | 2 | | | 39.12 | 10.26 | 26.27 | 209.64 |
| | | 10 | | | 28.79 | 28.91 | 31.09 | 559.99 |
| | | 50 | | | 25.94 | 33.37 | 35.71 | 702.71 |
| 6-4 | Leaves | 2 | | | 36.64 | 17.53 | 23.66 | 219.80 |
| | | 10 | | | 33.92 | 25.20 | 31.66 | 543.26 |
| | | 50 | | | 25.64 | 30.77 | 35.10 | 626.32 |
| 6-5 | Fruits | 2 | | | 39.58 | 18.69 | 25.04 | 255.24 |
| | | 10 | | | 30.50 | 20.97 | 30.88 | 595.46 |
| | | 50 | | | 23.75 | 36.64 | 35.69 | 659.26 |
| 6-6 | Flowers | 2 | | | 34.07 | 13.61 | 22.05 | 296.84 |
| | | 10 | | | 30.33 | 27.69 | 31.21 | 419.24 |
| | | 50 | | | 26.90 | 36.98 | 37.68 | 689.02 |

TABLE 11

| No. | Sample | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|
| | Control group | | | Vitamin C 7.5 ppm | Hexanediol Bacteria: *P. aeruginosa* 2% Fungi: *A. niger* 1% | Untreated 0 mm | Untreated 0 mm |
| 6 Comparative Example | Myeongyi Garlic | *Allium victorialis* *Allium Sativum* | Myeongyi | 3.52 | MIC (%) Bacteria: 2 MIC (%) Fungi: 1 | 11.1 | 12.9 |
| 6-1 | Whole plant | | | 0.73 | MIC (%) Bacteria: 0.25 MIC (%) Fungi: 0.5 | 14.9 | 19.4 |
| 6-2 | Roots | | | 0.27 | MIC (%) Bacteria: 1 MIC (%) Fungi: 1 | 12.8 | 13.5 |

TABLE 11-continued

| No. | Sample | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|
| 6-3 | Stems | | | 0.18 | MIC (%) Bacteria: 1 MIC (%) Fungi: 0.5 | 10.0 | 14.4 |
| 6-4 | Leaves | | | 0.36 | MIC (%) Bacteria: 0.125 MIC (%) Fungi: 0.25 | 16.8 | 14.4 |
| 6-5 | Fruits | | | 0.27 | MIC (%) Bacteria: 0.5 MIC (%) Fungi: 0.5 | 21.3 | 24.1 |
| 6-6 | Flowers | | | 0.44 | MIC (%) Bacteria: 0.125 MIC (%) Fungi: 0.25 | 12.5 | 16.6 |

15

Example 7

Aging Chive

TABLE 12

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizng HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 7 Comparative Example | Aging chive Chive | 50 | *Allium senescens Allium Tuberosum* | Aging chive | 52.06 | 15.42 | 7.68 | 79.87 |
| 7-1 | Whole plant | 2 | | | 38.07 | 16.08 | 24.27 | 379.52 |
| | | 10 | | | 28.44 | 27.62 | 27.63 | 501.87 |
| | | 50 | | | 23.58 | 30.75 | 34.13 | 642.80 |
| 7-2 | Roots | 2 | | | 34.62 | 15.86 | 21.97 | 226.89 |
| | | 10 | | | 30.32 | 21.09 | 30.44 | 424.33 |
| | | 50 | | | 26.68 | 32.52 | 36.80 | 703.68 |
| 7-4 | Leaves | 2 | | | 35.78 | 11.69 | 31.38 | 181.63 |
| | | 10 | | | 28.40 | 15.26 | 41.36 | 274.64 |
| | | 50 | | | 25.55 | 19.15 | 56.99 | 487.67 |
| 7-5 | Fruits | 2 | | | 37.02 | 16.53 | 22.76 | 236.69 |
| | | 10 | | | 27.93 | 28.95 | 32.32 | 473.43 |
| | | 50 | | | 22.03 | 33.68 | 38.05 | 723.11 |
| 7-6 | Flowers | 2 | | | 27.84 | 13.05 | 21.47 | 300.18 |
| | | 10 | | | 18.26 | 20.55 | 31.58 | 514.97 |
| | | 50 | | | 12.01 | 36.51 | 39.51 | 800.56 |

TABLE 13

| No. | Sample | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|
| | Control group | | | Vitamin C 7.5 ppm | Hexanediol Bacteria: *P. aeruginosa* 2% Fungi: *A. niger* 1% | Untreated 0 mm | Untreated 0 mm |
| 7 Comparative Example | Aging chive Chive | *Allium senescens Allium Tuberosum* | Aging chive | 2.74 | MIC (%) Bacteria: 1 MIC (%) Fungi: 2 | 9.6 | 8.9 |
| 7-1 | Whole plant | | | 0.20 | MIC (%) Bacteria: 1 MIC (%) Fungi: 0.5 | 19.6 | 22.6 |
| 7-2 | Roots | | | 0.37 | MIC (%) Bacteria: 1 MIC (%) Fungi: 1 | 9.1 | 8.9 |
| 7-4 | Leaves | | | 0.51 | MIC (%) Bacteria: 0.5 MIC (%) Fungi: 0.5 | 22.1 | 22.6 |

TABLE 13-continued

| No. | Sample | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|
| 7-5 | Fruits | | | 0.34 | MIC (%) Bacteria: 0,5 MIC (%) Fungi: 0.25 | 10.6 | 8.8 |
| 7-6 | Flowers | | | 0.07 | MIC (%) Bacteria: 0.13 MIC (%) Fungi: 0.06 | 14.9 | 19.7 |

Example 8

Silvery Mountain Ash

15

TABLE 14

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 8 | Silvery mountain ash | | *Sorbus commixta* | Silvery mountain ash | | | | |
| Comparative Example | Wild pear tree | 50 | *Sorbus alnifolia* | | 61.11 | 9.55 | 4.08 | 95.25 |
| Comparative Example | Silvery mountain ash (other area) | 50 | *Sorbus commixta* | | 49.03 | 16.63 | 10.63 | 268.61 |
| 8-1 | Whole plant | 2 | | | 36.68 | 10.84 | 25.91 | 274.89 |
| | | 10 | | | 27.35 | 26.63 | 27.92 | 438.35 |
| | | 50 | | | 25.28 | 33.84 | 38.79 | 643.28 |
| 8-2 | Roots | 2 | | | 37.44 | 17.33 | 24.72 | 269.07 |
| | | 10 | | | 28.07 | 22.13 | 30.59 | 441.39 |
| | | 50 | | | 20.83 | 31.53 | 37.60 | 733.14 |
| 8-3 | Bark | 2 | | | 38.20 | 13.91 | 22.84 | 253.50 |
| | | 10 | | | 31.60 | 27.09 | 32.36 | 494.36 |
| | | 50 | | | 21.43 | 34.05 | 37.10 | 671.99 |
| 8-4 | Leaves | 2 | | | 39.72 | 10.26 | 24.92 | 400.91 |
| | | 10 | | | 29.63 | 22.21 | 33.55 | 424.09 |
| | | 50 | | | 25.41 | 34.91 | 36.93 | 691.17 |
| 8-5 | Fruits | 2 | | | 37.10 | 14.75 | 26.59 | 256.05 |
| | | 10 | | | 32.15 | 23.88 | 27.51 | 527.60 |
| | | 50 | | | 23.86 | 32.74 | 37.12 | 686.07 |
| 8-6 | Flowers | 2 | | | 39.86 | 13.29 | 25.14 | 235.83 |
| | | 10 | | | 28.03 | 29.53 | 28.17 | 427.91 |
| | | 50 | | | 20.48 | 34.30 | 37.28 | 796.52 |
| 8-7 | Branches | 2 | | | 38.43 | 15.83 | 25.15 | 244.29 |
| | | 10 | | | 28.89 | 28.37 | 30.50 | 578.10 |
| | | 50 | | | 23.06 | 35.87 | 37.94 | 764.41 |

TABLE 15

| No. | Sample | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|
| | Control group | | | Vitamin C 7.5 ppm | Hexanediol Bacteria: *P. aeruginosa* 2% Fungi: *A. niger* 1% | Untreated 0 mm | Untreated 0 mm |
| 8 | Silvery mountain ash | *Sorbus commixta* | Silvery mountain ash | | | | |
| Comparative Example | Wild pear tree | *Sorbus alnifolia* | | 3.87 | MIC (%) Bacteria: >2 MIC (%) Fungi: >2 | 0.0 | 0.0 |
| Comparative Example | Silvery mountain ash (other area) | *Sorbus commixta* | | 1.06 | MIC (%) Bacteria: 0.5 MIC (%) Fungi: 1 | 10.6 | 8.8 |
| 8-1 | Whole plant | | | 0.11 | MIC (%) Bacteria: 0.5 MIC (%) Fungi: 0.25 | 21.8 | 18.7 |

TABLE 15-continued

| No. | Sample | Scientific name | English name | Anti-oxidation IC50 (%) | Anti-bacteria MIC (%) | Anti-bacteria (S. mutans) Size of growth inhibition ring (mm) | Anti-bacteria (P. gingivalis) Size of growth inhibition ring (mm) |
|---|---|---|---|---|---|---|---|
| 8-2 | Roots | | | 0.14 | MIC (%) Bacteria: 0.25 MIC (%) Fungi: 0.13 | 9.0 | 11.2 |
| 8-3 | Bark | | | 0.30 | MIC (%) Bacteria: 0.13 MIC (%) Fungi: 0.25 | 21.8 | 21.3 |
| 8-4 | Leaves | | | 0.73 | MIC (%) Bacteria: 0.25 MIC (%) Fungi: 0.13 | 24.4 | 16.5 |
| 8-5 | Fruits | | | 0.70 | MIC (%) Bacteria: 0.5 MIC (%) Fungi: 1 | 26.3 | 27.0 |
| 8-6 | Flowers | | | 0.86 | MIC (%) Bacteria: 0.13 MIC (%) Fungi: 0.06 | 17.1 | 20.8 |
| 8-7 | Branches | | | 0.29 | MIC (%) Bacteria: 0.5 MIC (%) Fungi: 0.25 | 25.2 | 21.1 |

Example 10

Wild Chervil

TABLE 16

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 10 | Wild chervil | | *Anthriscus sylvestris* | Wild chervil | | | | |
| Comparative Example | Chervil | 50 | *Anthriscus Cerefolium* | | 65.80 | 5.45 | 6.44 | 45.59 |
| 10-1 | Whole plant | 2 | | | 37.81 | 17.65 | 23.37 | 394.44 |
| | | 10 | | | 27.02 | 21.45 | 27.51 | 553.58 |
| | | 50 | | | 23.67 | 34.67 | 35.97 | 632.62 |
| 10-2 | Roots | 2 | | | 31.87 | 11.64 | 22.77 | 241.74 |
| | | 10 | | | 27.06 | 22.16 | 33.74 | 402.96 |
| | | 50 | | | 21.94 | 39.19 | 35.10 | 644.03 |
| 10-3 | Stems | 2 | | | 34.76 | 18.48 | 26.38 | 399.00 |
| | | 10 | | | 30.08 | 28.90 | 28.71 | 600.83 |
| | | 50 | | | 22.10 | 38.32 | 37.78 | 613.72 |
| 10-4 | Leaves | 2 | | | 37.30 | 11.84 | 25.46 | 380.25 |
| | | 10 | | | 28.82 | 29.39 | 28.65 | 523.39 |
| | | 50 | | | 28.89 | 37.22 | 34.90 | 723.91 |
| 10-5 | Fruits | 2 | | | 34.52 | 12.18 | 23.94 | 360.97 |
| | | 10 | | | 29.50 | 28.36 | 30.47 | 409.65 |
| | | 50 | | | 23.11 | 31.53 | 39.49 | 718.16 |
| 10-6 | Flowers | 2 | | | 39.02 | 12.16 | 25.41 | 334.85 |
| | | 10 | | | 28.90 | 26.24 | 31.70 | 415.00 |
| | | 50 | | | 26.56 | 35.25 | 38.01 | 725.14 |

TABLE 17

| No. | Sample | Scientific name | English name | Anti-oxidation IC50 (%) | Anti-bacteria MIC (%) | Anti-bacteria (S. mutans) Size of growth inhibition ring (mm) | Anti-bacteria (P. gingivalis) Size of growth inhibition ring (mm) |
|---|---|---|---|---|---|---|---|
| | Control group | | | Vitamin C 7.5 ppm | Hexanediol Bacteria: *P. aeruginosa* 2% Fungi: *A. niger* 1% | Untreated 0 mm | Untreated 0 mm |
| 10 | Wild chervil | *Anthriscus sylvestris* | Wild chervil | | | | |
| Comparative Example | Chervil | *Anthriscus Cerefolium* | | 3.96 | MIC (%) Bacteria: 2, Fungi: 2 | 9.5 | 8.1 |
| 10-1 | Whole plant | | | 0.46 | MIC (%) Bacteria: 1, Fungi: 0.25 | 20.4 | 18.9 |
| 10-2 | Roots | | | 0.88 | MIC (%) Bacteria: 2, Fungi: 1 | 13.5 | 14.6 |

TABLE 17-continued

| No. | Sample | Scientific name | English name | Anti-oxidation IC50 (%) | Anti-bacteria MIC (%) | Anti-bacteria (S. mutans) Size of growth inhibition ring (mm) | Anti-bacteria (P. gingivalis) Size of growth inhibition ring (mm) |
|---|---|---|---|---|---|---|---|
| 10-3 | Stems | | | 0.77 | MIC (%) Bacteria: 1, Fungi: 0.5 | 27.9 | 25.6 |
| 10-4 | Leaves | | | 0.14 | MIC (%) Bacteria; 0.5, Fungi: 0.125 | 26.4 | 22.8 |
| 10-5 | Fruits | | | 0.21 | MIC (%) Bacteria: 1, Fungi: 0.5 | 8.1 | 13.5 |
| 10-6 | Flowers | | | 0.14 | MIC (%) Bacteria: 1, Fungi: 0.5 | 11.7 | 14.6 |

Example 11

Giant Knotweed

15

TABLE 18

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 11 | Giant Knotweed | | Fallopia sachalinensis | Giant Knotweed | | | | |
| 11-1 | Whole plant | 2 | | | 59.68 | 11.66 | 21.01 | 387.34 |
| | | 10 | | | 31.07 | 21.49 | 28.05 | 428.82 |
| | | 50 | | | 24.89 | 37.23 | 36.38 | 650.06 |
| 11-2 | Roots | 2 | | | 37.83 | 10.41 | 15.84 | 214.49 |
| | | 10 | | | 29.15 | 21.60 | 26.64 | 530.09 |
| | | 50 | | | 26.87 | 32.10 | 28.28 | 639.00 |
| 11-3 | Stems | 2 | | | 36.28 | 17.19 | 22.76 | 279.70 |
| | | 10 | | | 27.78 | 22.50 | 29.33 | 505.63 |
| | | 50 | | | 24.85 | 34.45 | 38.58 | 678.94 |
| 11-4 | Leaves | 2 | | | 34.94 | 18.84 | 17.72 | 341.25 |
| | | 10 | | | 30.33 | 20.37 | 27.18 | 576.23 |
| | | 50 | | | 25.03 | 32.53 | 30.71 | 668.77 |
| 11-5 | Fruits | 2 | | | 36.97 | 18.82 | 15.32 | 254.31 |
| | | 10 | | | 29.51 | 21.90 | 26.35 | 484.44 |
| | | 50 | | | 25.87 | 33.63 | 30.42 | 800.32 |
| 11-6 | Flowers | 2 | | | 36.34 | 13.90 | 23.72 | 315.29 |
| | | 10 | | | 30.06 | 29.19 | 32.24 | 488.00 |
| | | 50 | | | 20.16 | 35.56 | 36.27 | 712.56 |

TABLE 19

| No. | Sample | Scientific name | English name | Anti-oxidation IC50 (%) | Anti-bacteria MIC (%) | Anti-bacteria (S. mutans) Size of growth inhibition ring (mm) | Anti-bacteria (P. gingivalis) Size of growth inhibition ring (mm) |
|---|---|---|---|---|---|---|---|
| | Control group | | | Vitamin C 7.5 ppm | Hexanediol Bacteria: P. aeruginosa 2% Fungi: A. niger 1% | Untreated 0 mm | Untreated 0 mm |
| 11 | Giant Knotweed | Fallopia sachalinensis | Giant Knotweed | | | | |
| 11-1 | Whole plant | | | 0.46 | MIC (%) Bacteria: 1, Fungi: 0.25 | 14.4 | 12.2 |
| 11-2 | Roots | | | 0.98 | MIC (%) Bacteria: 2, Fungi: 1 | 9.8 | 9.2 |
| 11-3 | Stems | | | 0.70 | MIC (%) Bacteria: 1, Fungi: 0.5 | 12.3 | 11.3 |
| 11-4 | Leaves | | | 0.10 | MIC (%) Bacteria: 0.5, Fungi: 0.25 | 23.0 | 25.3 |
| 11-5 | Fruits | | | 0.74 | MIC (%) Bacteria: 0.5, Fungi: 0.5 | 11.3 | 8.8 |
| 11-6 | Flowers | | | 0.53 | MIC (%) Bacteria: 0.5, Fungi: 0.5 | 12.8 | 15.0 |

Example 12

Mono Maple

TABLE 20

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 12 Comparative Example | Mono maple Maple | 50 | *Acer pictum* *Acer Saccharum* | Mono maple Sugar Maple | 70.79 | 9.64 | 3.41 | 75.42 |
| 12-1 | Whole plant | 2 | | | 35.24 | 13.80 | 26.11 | 243.88 |
| | | 10 | | | 27.75 | 21.80 | 33.43 | 550.99 |
| | | 50 | | | 25.33 | 31.77 | 37.13 | 643.20 |
| 12-2 | Roots | 2 | | | 35.39 | 17.80 | 26.93 | 215.59 |
| | | 10 | | | 29.91 | 29.57 | 31.84 | 423.71 |
| | | 50 | | | 23.03 | 35.14 | 39.54 | 755.21 |
| 12-3 | Stems | 2 | | | 38.18 | 19.84 | 25.31 | 367.01 |
| | | 10 | | | 30.15 | 22.37 | 33.55 | 485.49 |
| | | 50 | | | 26.78 | 34.90 | 37.67 | 620.17 |
| 12-4 | Leaves | 2 | | | 36.31 | 14.39 | 21.89 | 327.34 |
| | | 10 | | | 33.74 | 22.68 | 30.11 | 458.76 |
| | | 50 | | | 24.72 | 32.20 | 37.51 | 642.40 |
| 12-5 | Fruits | 2 | | | 38.27 | 14.80 | 24.19 | 279.00 |
| | | 10 | | | 28.81 | 22.96 | 32.62 | 557.16 |
| | | 50 | | | 22.25 | 38.03 | 38.01 | 671.92 |
| 12-6 | Flowers | 2 | | | 37.68 | 13.94 | 26.62 | 226.58 |
| | | 10 | | | 28.40 | 20.88 | 33.40 | 434.92 |
| | | 50 | | | 21.51 | 38.30 | 38.72 | 722.56 |
| 12-7 | Sap | 2 | | | 38.21 | 10.94 | 25.49 | 395.96 |
| | | 10 | | | 30.70 | 27.21 | 32.47 | 540.47 |
| | | 50 | | | 26.28 | 34.24 | 37.18 | 662.98 |

TABLE 21

| No. | Sample | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|
| | Control group | | | Vitamin C 7.5 ppm | Hexanediol Bacteria: *P. aeruginosa* 2% Fungi: *A. niger* 1% | Untreated 0 mm | Untreated 0 mm |
| 12 Comparative Example | Mono maple Maple | *Acer pictum* *Acer Saccharum* | Mono maple Sugar Maple | 1.89 | MIC (%) Bacteria: >2 MIC (%) Fungi: 2 | 10.3 | 8.9 |
| 12-1 | Whole plant | | | 0.53 | MIC (%) Bacteria: 0,5 MIC (%) Fungi: 0.125 | 24.6 | 23.7 |
| 12-2 | Roots | | | 0.08 | MIC (%) Bacteria: 0.25 MIC (%) Fungi: 0.125 | 24.1 | 27.4 |
| 12-3 | Stems | | | 0.63 | MIC (%) Bacteria: 0.5 MIC (%) Fungi: 0.5 | 27.4 | 12.1 |
| 12-4 | Leaves | | | 0.34 | MIC (%) Bacteria: 1 MIC (%) Fungi: 0.25 | 23.1 | 27.0 |
| 12-5 | Fruits | | | 0.19 | MIC (%) Bacteria: 0.5 MIC (%) Fungi: 0.25 | 12.9 | 11.1 |
| 12-6 | Flowers | | | 0.31 | MIC (%) Bacteria: 0.25 MIC (%) Fungi: 0.125 | 23.1 | 12.3 |
| 12-7 | Sap | | | 0.40 | MIC (%) Bacteria: 0.5 MIC (%) Fungi: 0.5 | 24.4 | 26.5 |

Example 13

Ulleungdo Ladyfern

TABLE 22

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 13 | Ulleungdo ladyfern | | *Athyrium acutipinnulum* | Ulleungdo ladyfern | | | | |
| 13-1 | Whole plant | 2 | | | 35.20 | 10.14 | 23.14 | 361.62 |
| | | 10 | | | 28.32 | 23.20 | 29.45 | 563.53 |
| | | 50 | | | 26.99 | 31.14 | 34.98 | 639.02 |
| 13-2 | Roots | 2 | | | 38.10 | 16.81 | 25.76 | 366.29 |
| | | 10 | | | 30.22 | 20.33 | 28.06 | 526.26 |
| | | 50 | | | 20.81 | 35.25 | 35.77 | 698.90 |
| 13-3 | Stems | 2 | | | 38.42 | 18.18 | 23.02 | 242.99 |
| | | 10 | | | 33.26 | 26.68 | 30.38 | 512.00 |
| | | 50 | | | 21.47 | 34.54 | 39.37 | 726.00 |
| 13-4 | Leaves | 2 | | | 37.84 | 18.20 | 26.33 | 265.80 |
| | | 10 | | | 33.65 | 26.72 | 33.73 | 507.92 |
| | | 50 | | | 21.22 | 38.69 | 37.98 | 702.42 |

TABLE 23

| No. | Sample | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|
| | Control group | | | Vitamin C 7.5 ppm | Hexanediol Bacteria: *P. aeiuginosa* 2% Fungi: *A. niger* 1% | Untreated 0 mm | Untreated 0 mm |
| 13 | Ulleungdo ladyfern | *Athyrium acutipinnulum* | Ulleungdo ladyfern | | | | |
| 13-1 | Whole plant | | | 0.92 | MIC (%) Bacteria: 0.5 MIC (%) Fungi: 0.5 | 18.4 | 18.8 |
| 13-2 | Roots | | | 0.82 | MIC (%) Bacteria: 0.25 MIC (%) Fungi: 0.25 | 13.2 | 15.7 |
| 13-3 | Stems | | | 0.85 | MIC (%) Bacteria: 0.125 MIC (%) Fungi: 0.5 | 13.2 | 14.7 |
| 13-4 | Leaves | | | 0.13 | MIC (%) Bacteria: 0.125 MIC (%) Fungi: 0.25 | 12.7 | 14.6 |

Example 14

Wild Wasabi

TABLE 24

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 14 | Wild wasabi | | *Wasabia japonica* | Wild wasabi | | | | |
| 14-1 | Whole plant | 2 | | | 35.18 | 12.15 | 26.01 | 354.70 |
| | | 10 | | | 32.28 | 25.75 | 29.52 | 572.56 |
| | | 50 | | | 23.12 | 32.46 | 38.97 | 691.59 |
| 14-2 | Roots | 2 | | | 34.08 | 17.46 | 22.04 | 328.75 |
| | | 10 | | | 32.61 | 25.85 | 31.88 | 428.89 |
| | | 50 | | | 20.82 | 37.85 | 35.63 | 789.50 |

TABLE 24-continued

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| 14-3 | Stems | 2 | | | 39.68 | 19.43 | 22.97 | 314.61 |
| | | 10 | | | 33.77 | 28.64 | 31.00 | 487.16 |
| | | 50 | | | 26.86 | 34.38 | 35.05 | 636.91 |
| 14-4 | Leaves | 2 | | | 34.12 | 18.73 | 24.89 | 265.98 |
| | | 10 | | | 30.48 | 29.53 | 32.04 | 575.39 |
| | | 50 | | | 26.31 | 31.22 | 34.50 | 759.63 |
| 14-5 | Fruits | 2 | | | 34.30 | 14.83 | 25.50 | 230.84 |
| | | 10 | | | 33.86 | 22.03 | 32.66 | 449.33 |
| | | 50 | | | 22.44 | 37.72 | 37.47 | 768.96 |
| 14-6 | Flowers | 2 | | | 37.74 | 14.83 | 24.21 | 266.20 |
| | | 10 | | | 27.39 | 22.03 | 31.29 | 499.43 |
| | | 50 | | | 21.64 | 37.72 | 37.27 | 765.75 |

TABLE 25

| No. | Sample | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|
| | Control group | | | Vitamin C 7.5 ppm | Hexanediol Bacteria: *P. aeruginosa* 2% Fungi: *A. niger* 1% | Untreated 0 mm | Untreated 0 mm |
| 14 | Wild wasabi | *Wasabia japonica* | Wild wasabi | | | | |
| 14-1 | Whole plant | | | 0.89 | MIC (%) Bacteria: 0.25 MIC (%) Fungi: 0.125 | 18.8 | 8.1 |
| 14-2 | Roots | | | 0.27 | MIC (%) Bacteria: 0.0625 MIC (%) Fungi: 0.0625 | 12.8 | 14.0 |
| 14-3 | Stems | | | 0.51 | MIC (%) Bacteria: 0.25 MIC (%) Fungi: 0.125 | 25.1 | 13.4 |
| 14-4 | Leaves | | | 0.96 | MIC (%) Bacteria: 0.25 MIC (%) Fungi: 0.125 | 27.9 | 21.3 |
| 14-5 | Fruits | | | 0.02 | MIC (%) Bacteria: 0.125 MIC (%) Fungi: 0.125 | 15.5 | 8.1 |
| 14-6 | Flowers | | | 0.29 | MIC (%) Bacteria: 0.125 MIC (%) Fungi: 0.25 | 16.0 | 12.0 |

Example 15

Yellow Mongolian Snakegourd

TABLE 26

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 15 | Yellow Mongolian snakegourd | | *Trichosanthes kirilowii* | Yellow Mongolian snakegourd | | | | |
| Comparative Example | Snake gourd | 50 | *Trichosanthes Cucumerina* | Shake gourd | 66.95 | 4.44 | 2.14 | 53.86 |
| Comparative Example | Yellow Mongolian snakegourd (other area) | 50 | | | 45.93 | 9.03 | 13.82 | 194.00 |
| 15-1 | Whole plant | 2 | | | 35.80 | 17.08 | 22.73 | 267.84 |
| | | 10 | | | 30.80 | 21.87 | 29.58 | 511.44 |
| | | 50 | | | 23.06 | 35.88 | 37.35 | 638.89 |

TABLE 26-continued

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| 15-2 | Roots | 2 | | | 36.13 | 11.89 | 26.42 | 360.15 |
| | | 10 | | | 31.31 | 26.10 | 29.76 | 408.58 |
| | | 50 | | | 25.67 | 33.81 | 37.26 | 607.40 |
| 15-3 | Stems | 2 | | | 35.44 | 10.74 | 22.17 | 275.00 |
| | | 10 | | | 32.51 | 20.34 | 27.22 | 452.01 |
| | | 50 | | | 20.11 | 36.15 | 36.19 | 643.27 |
| 15-4 | Leaves | 2 | | | 37.49 | 14.50 | 26.48 | 373.49 |
| | | 10 | | | 27.21 | 28.93 | 33.56 | 576.12 |
| | | 50 | | | 25.29 | 37.16 | 38.71 | 696.96 |
| 15-5 | Fruits | 2 | | | 34.58 | 19.98 | 21.13 | 245.22 |
| | | 10 | | | 33.69 | 29.38 | 31.64 | 547.50 |
| | | 50 | | | 22.01 | 39.65 | 36.13 | 741.23 |
| 15-6 | Flowers | 2 | | | 39.06 | 15.76 | 23.17 | 212.73 |
| | | 10 | | | 32.26 | 28.48 | 29.66 | 508.65 |
| | | 50 | | | 23.44 | 37.03 | 37.41 | 622.40 |

TABLE 27

| No. | Sample | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|
| | Control group | | | Vitamin C 7.5 ppm | Hexanediol Bacteria: *P. aeruginosa* 2% Fungi: *A. niger* 1% | Untreated 0 mm | Untreated 0 mm |
| 15 | Yellow Mongolian snakegourd | *Trichosanthes kirilowii* | Yellow Mongolian snakegourd | | | | |
| Comparative Example | Snake gourd | *Trichosanthes Cucumerina* | Shake gourd | 3.24 | MIC (%) Bacteria: 0.5, Fungi: 1 | 8.9 | 9.6 |
| Comparative Example | Yellow Mongolian snakegourd (other area) | | | 2.94 | MIC (%) Bacteria: 2, Fungi: 1 | 12.1 | 11.8 |
| 15-1 | Whole plant | | | 0.82 | MIC (%) Bacteria: 0.25, Fungi: 0.125 | 19.0 | 18.9 |
| 15-2 | Roots | | | 0.32 | MIC (%) Bacteria: 1, Fungi: 0.125 | 12.1 | 13.1 |
| 15-3 | Stems | | | 0.51 | MIC (%) Bacteria: 1, Fungi: 0.5 | 21.5 | 10.8 |
| 15-4 | Leaves | | | 0.89 | MIC (%) Bacteria: 1, Fungi: 1 | 12.9 | 20.0 |
| 15-5 | Fruits | | | 0.23 | MIC (%) Bacteria: 2, Fungi: 0.5 | 16.4 | 9.2 |
| 15-6 | Flowers | | | 0.48 | MIC (%) Bacteria: 1, Fungi: 0.25 | 24.3 | 24.5 |

Example 16

Pungdo Solomon's Seal

TABLE 28

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |

TABLE 28-continued

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| 16 | Pungdo solomon's seal | | *Polygonatum odoratum* | Pungdo solomon's seal | | | | |
| Comparative Example | Solomon's seal | 50 | *Polygonatum Officinale* | | 67.65 | 15.62 | 2.18 | 38.60 |
| 16-1 | Whole plant | 2 | | | 37.85 | 16.85 | 20.23 | 322.89 |
| | | 10 | | | 28.02 | 25.19 | 28.22 | 583.88 |
| | | 50 | | | 24.42 | 38.61 | 37.58 | 700.87 |
| 16-2 | Roots | 2 | | | 38.18 | 15.81 | 20.55 | 264.71 |
| | | 10 | | | 33.87 | 15.14 | 24.42 | 326.80 |
| | | 50 | | | 31.39 | 27.59 | 27.62 | 493.86 |
| 16-3 | Stems | 2 | | | 35.94 | 18.27 | 23.63 | 211.64 |
| | | 10 | | | 31.14 | 25.63 | 30.87 | 555.83 |
| | | 50 | | | 20.29 | 33.29 | 37.47 | 792.53 |
| 16-4 | Leaves | 2 | | | 35.15 | 15.01 | 20.87 | 391.90 |
| | | 10 | | | 28.15 | 20.87 | 32.69 | 446.94 |
| | | 50 | | | 21.57 | 31.25 | 36.47 | 606.81 |
| 16-5 | Fruits | 2 | | | 36.65 | 10.37 | 26.18 | 237.45 |
| | | 10 | | | 29.90 | 28.16 | 30.74 | 537.46 |
| | | 50 | | | 20.10 | 35.81 | 36.98 | 609.72 |
| 16-6 | Flowers | 2 | | | 38.80 | 12.43 | 20.13 | 235.88 |
| | | 10 | | | 36.17 | 18.65 | 26.23 | 384.95 |
| | | 50 | | | 28.88 | 29.62 | 30.19 | 432.12 |

TABLE 29

| No. | Sample | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|
| | Control group | | | Vitamin C 7.5 ppm | Hexanediol Bacteria: *P. aeruginosa* 2% Fungi: *A. niger* 1% | Untreated 0 mm | Untreated 0 mm |
| 16 | Pungdo solomon's seal | *Polygonatum odoratum* | Pungdo solomon's seal | | | | |
| Comparative Example | Solomon's seal | *Polygonatum Officinale* | | 2.55 | MIC (%) Bacteria: 2, Fungi: >2 | 9.5 | 9.5 |
| 16-1 | Whole plant | | | 0.05 | MIC (%) Bacteria: 0.5, Fungi: 0.25 | 19.6 | 21.6 |
| 16-2 | Roots | | | 0.62 | MIC (%) Bacteria: 2, Fungi: 0.5 | 9.8 | 10.2 |
| 16-3 | Stems | | | 0.08 | MIC (%) Bacteria: 1, Fungi: 0.25 | 17.0 | 14.6 |
| 16-4 | Leaves | | | 0.68 | MIC (%) Bacteria: 0.25, Fungi: 0.5 | 19.3 | 25.7 |
| 16-5 | Fruits | | | 0.88 | MIC (%) Bacteria: 2, Fungi: 0.25 | 9.2 | 9.8 |
| 16-6 | Flowers | | | 1.15 | MIC (%) Bacteria: 0.5, Fungi: 0.25 | 12.3 | 11.5 |

Example 17

Songak

TABLE 30

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 17 | Songak | | *Hedera rhombea* | Songak | | | | |
| Comparative Example | Ivy | 50 | *Hedera Helix* | IVY | 75.07 | 12.30 | 5.61 | 69.05 |
| 17-1 | Whole plant | 2 | | | 39.70 | 13.18 | 25.95 | 384.76 |
| | | 10 | | | 34.03 | 16.74 | 33.68 | 533.11 |
| | | 50 | | | 30.20 | 26.66 | 35.29 | 630.99 |
| 17-2 | Roots | 2 | | | 34.73 | 14.66 | 26.78 | 363.91 |
| | | 10 | | | 27.47 | 26.35 | 33.73 | 557.23 |
| | | 50 | | | 22.11 | 39.47 | 38.77 | 747.46 |
| 17-3 | Stems | 2 | | | 35.28 | 19.96 | 23.79 | 292.85 |
| | | 10 | | | 33.57 | 21.59 | 26.44 | 451.96 |
| | | 50 | | | 21.01 | 36.37 | 27.76 | 675.93 |
| 17-4 | Leaves | 2 | | | 37.81 | 10.90 | 20.04 | 327.85 |
| | | 10 | | | 27.26 | 23.01 | 24.58 | 453.75 |
| | | 50 | | | 21.00 | 34.21 | 28.03 | 652.23 |
| 17-5 | Fruits | 2 | | | 34.71 | 18.38 | 25.58 | 340.23 |
| | | 10 | | | 33.71 | 27.23 | 32.03 | 432.18 |
| | | 50 | | | 20.61 | 36.10 | 36.33 | 755.89 |
| 17-6 | Flowers | 2 | | | 39.56 | 10.48 | 25.40 | 295.11 |
| | | 10 | | | 32.14 | 27.90 | 31.89 | 547.33 |
| | | 50 | | | 22.92 | 37.56 | 36.88 | 756.04 |

TABLE 31

| No. | Sample | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|
| | Control group | | | Vitamin C 7.5 ppm | Hexanediol Bacteria: *P. aeruginosa* 2% Fungi: *A. niger* 1% | Untreated 0 mm | Untreated 0 mm |
| 17 | Songak | *Hedera rhombea* | Songak | | | | |
| Comparative Example | Ivy | *Hedera Helix* | IVY | 3.14 | MIC (%) Bacteria: >2, Fungi: >2 | 0.0 | 0.0 |
| 17-1 | Whole plant | | | 1.25 | MIC (%) Bacteria: 1, Fungi: 0.25 | 9.7 | 8.6 |
| 17-2 | Roots | | | 0.53 | MIC (%) Bacteria: 0.25, Fungi: 0.5 | 8.7 | 8.7 |
| 17-3 | Stems | | | 1.42 | MIC (%) Bacteria: 1, Fungi: 0.25 | 7.2 | 10.6 |
| 17-4 | Leaves | | | 1.06 | MIC (%) Bacteria: 0.25, Fungi: 0.5 | 12.2 | 12.7 |
| 17-5 | Fruits | | | 0.22 | MIC (%) Bacteria: 1, Fungi: 1 | 9.3 | 11.0 |
| 17-6 | Flowers | | | 0.95 | MIC (%) Bacteria: 0.0625, Fungi: | 8.2 | 9.9 |

Example 18

Ulleungdo Sweet Violet

TABLE 32

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 18 | Ulleungdo sweet violet | | *Viola woosanensis* | Ulleungdo sweet violet | | | | |
| Comparative Example | Violet | 50 | *Viola Mandshurica* | | 69.26 | 8.30 | 3.84 | 50.72 |
| 18-1 | Whole plant | 2 | | | 34.87 | 10.56 | 26.39 | 212.88 |
| | | 10 | | | 33.86 | 24.79 | 28.63 | 508.12 |
| | | 50 | | | 24.44 | 34.91 | 38.68 | 749.46 |
| 18-2 | Roots | 2 | | | 37.62 | 18.59 | 24.06 | 323.53 |
| | | 10 | | | 31.95 | 20.58 | 27.71 | 568.50 |
| | | 50 | | | 24.77 | 38.02 | 38.25 | 721.49 |
| 18-3 | Stems | 2 | | | 35.35 | 18.71 | 26.57 | 390.60 |
| | | 10 | | | 30.90 | 29.76 | 32.70 | 547.48 |
| | | 50 | | | 22.54 | 31.26 | 38.74 | 742.86 |
| 18-4 | Leaves | 2 | | | 38.50 | 17.40 | 21.87 | 357.39 |
| | | 10 | | | 29.13 | 29.08 | 29.15 | 416.77 |
| | | 50 | | | 21.22 | 35.01 | 39.57 | 707.45 |
| 18-5 | Fruits | 2 | | | 39.87 | 10.46 | 23.24 | 365.58 |
| | | 10 | | | 28.73 | 26.11 | 29.69 | 505.28 |
| | | 50 | | | 22.21 | 38.83 | 34.40 | 611.69 |
| 18-6 | Flowers | 2 | | | 35.79 | 19.49 | 22.75 | 248.41 |
| | | 10 | | | 29.87 | 25.59 | 27.75 | 403.78 |
| | | 50 | | | 22.64 | 35.81 | 37.27 | 756.55 |

TABLE 33

| No. | Sample | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|
| | Control group | | | Vitamin C 7.5 ppm | Hexanediol Bacteria: *P. aeruginosa* 2% Fungi: *A. niger* 1% | Untreated 0 mm | Untreated 0 mm |
| 18 | Ulleungdo sweet violet | *Viola woosanensis* | Ulleungdo sweet violet | | | | |
| Comparative Example | Violet | *Viola Mandshurica* | | 5.56 | MIC (%) Bacteria: 2, Fungi: 2 | 11.5 | 9.3 |
| 18-1 | Whole plant | | | 0.35 | MIC (%) Bacteria: 1, Fungi: 0.25 | 21.5 | 17.5 |
| 18-2 | Roots | | | 0.25 | MIC (%) Bacteria: 1, Fungi: 1 | 13.9 | 13.6 |
| 18-3 | Stems | | | 0.71 | MIC (%) Bacteria: 0.5, Fungi: 0.5 | 21.5 | 14.9 |
| 18-4 | Leaves | | | 0.37 | MIC (%) Bacteria: 0.5, Fungi: 0.25 | 13.6 | 24.0 |
| 18-5 | Fruits | | | 0.82 | MIC (%) Bacteria: 0.5, Fungi: 0.5 | 18.2 | 14.1 |
| 18-6 | Flowers | | | 0.55 | MIC (%) Bacteria: 1, Fungi: 0.5 | 17.3 | 11.6 |

Example 19

Korean Bellflower

TABLE 34

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 19 | Korean bellflower | | *Campanula takesimana* | Korean bellflower | | | | |
| Comparative Example | Bellflower | 50 | *Campanula punctata* | | 57.17 | 10.93 | 2.02 | 81.77 |
| 19-1 | Whole plant | 2 | | | 36.28 | 14.05 | 24.36 | 372.27 |
| | | 10 | | | 29.14 | 27.50 | 32.48 | 566.92 |
| | | 50 | | | 20.91 | 33.70 | 37.44 | 671.09 |
| 19-2 | Roots | 2 | | | 38.31 | 18.87 | 24.89 | 298.71 |
| | | 10 | | | 28.06 | 26.72 | 29.80 | 413.73 |
| | | 50 | | | 24.92 | 38.86 | 39.07 | 715.15 |
| 19-3 | Stems | 2 | | | 39.06 | 14.19 | 25.57 | 373.82 |
| | | 10 | | | 28.25 | 23.81 | 33.04 | 403.43 |
| | | 50 | | | 23.95 | 31.38 | 36.25 | 758.71 |
| 19-4 | Leaves | 2 | | | 36.07 | 12.77 | 22.81 | 305.58 |
| | | 10 | | | 29.29 | 27.83 | 29.52 | 470.42 |
| | | 50 | | | 23.15 | 35.33 | 34.43 | 763.66 |
| 19-5 | Fruits | 2 | | | 35.03 | 12.93 | 21.38 | 326.18 |
| | | 10 | | | 32.89 | 24.26 | 32.29 | 506.96 |
| | | 50 | | | 24.04 | 32.28 | 34.07 | 625.68 |
| 19-6 | Flowers | 2 | | | 35.53 | 16.85 | 21.71 | 257.53 |
| | | 10 | | | 32.44 | 21.94 | 29.23 | 533.07 |
| | | 50 | | | 23.25 | 38.09 | 37.03 | 752.50 |

TABLE 35

| No. | Sample | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|
| | Control group | | | Vitamin C 7.5 ppm | Hexanediol Bacteria: *P. aeruginosa* 2% Fungi: *A. niger* 1% | Untreated 0 mm | Untreated 0 mm |
| 19 | Korean bellflower | *Campanula takesimana* | Korean bellflower | | | | |
| Comparative Example | Bellflower | *Campanula punctata* | | 9.87 | MIC (%) Bacteria: >2/ Fungi: 2 | 10.9 | 11.3 |
| 19-1 | Whole plant | | | 0.21 | MIC (%) Bacteria: 2/ Fungi: 1 | 26.2 | 16.3 |
| 19-2 | Roots | | | 0.43 | MIC (%) Bacteria: 0.5, Fungi: 0.5 | 9.2 | 20.7 |
| 19-3 | Stems | | | 0.17 | MIC (%) Bacteria: 1, Fungi: 0.5 | 15.1 | 12.8 |
| 19-4 | Leaves | | | 0.1 | MIC (%) Bacteria: 1, Fungi: 0.5 | 19.9 | 22.2 |
| 19-5 | Fruits | | | 0.42 | MIC (%) Bacteria: 1, Fungi: 1 | 9.9 | 22.0 |
| 19-6 | Flowers | | | 0.94 | MIC (%) Bacteria: 0.25, Fungi: 0.25 | 26.9 | 26.0 |

Example 20

Ulleungdo Turk's-Cap Lily

TABLE 36

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 20 | Ulleungdo turk's-cap lily | | *Lilium hansonii* | Ulleungdo turk's-cap lily | | | | |
| Comparative Example | Lily | 50 | *Lilium Candidum* | | 86.37 | 12.59 | 3.10 | 46.18 |
| 20-1 | Whole plant | 2 | | | 39.78 | 14.51 | 20.75 | 307.30 |
| | | 10 | | | 30.75 | 27.01 | 33.36 | 445.02 |
| | | 50 | | | 24.62 | 35.30 | 38.39 | 686.19 |
| 20-2 | Roots | 2 | | | 34.17 | 14.40 | 21.72 | 263.94 |
| | | 10 | | | 30.82 | 23.13 | 29.24 | 435.95 |
| | | 50 | | | 22.66 | 37.10 | 38.03 | 715.89 |
| 20-3 | Stems | 2 | | | 36.90 | 18.14 | 21.35 | 304.03 |
| | | 10 | | | 33.77 | 23.81 | 27.20 | 461.21 |
| | | 50 | | | 23.27 | 39.45 | 34.39 | 708.43 |
| 20-4 | Leaves | 2 | | | 36.53 | 14.41 | 23.56 | 226.56 |
| | | 10 | | | 32.88 | 24.26 | 30.21 | 597.01 |
| | | 50 | | | 24.22 | 37.57 | 34.91 | 771.58 |
| 20-5 | Fruits | 2 | | | 39.07 | 17.29 | 21.08 | 336.13 |
| | | 10 | | | 29.90 | 20.74 | 31.04 | 591.19 |
| | | 50 | | | 23.92 | 37.42 | 35.28 | 767.52 |
| 20-6 | Flowers | 2 | | | 34.70 | 18.76 | 25.64 | 356.83 |
| | | 10 | | | 33.45 | 22.78 | 28.46 | 449.21 |
| | | 50 | | | 24.08 | 36.69 | 38.14 | 735.30 |

TABLE 37

| No. | Sample | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|
| | Control group | | | Vitamin C 7.5 ppm | Hexanediol Bacteria: *P. aeruginosa* 2% Fungi: *A. niger* 1% | Untreated 0 mm | Untreated 0 mm |
| 20 | Ulleungdo turk's-cap lily | *Lilium hansonii* | Ulleungdo turk's-cap lily | | | | |
| Comparative Example | Lily | *Lilium Candidum* | | 6.87 | MIC (%) Bacteria: >2/ Fungi: 2 | 12.3 | 9.4 |
| 20-1 | Whole plant | | | 0.39 | MIC (%) Bacteria: 0.5/ Fungi: 0.5 | 18.4 | 21.5 |
| 20-2 | Roots | | | 0.37 | MIC (%) Bacteria: 1, Fungi: 0.25 | 12.7 | 25.5 |
| 20-3 | Stems | | | 0.91 | MIC (%) Bacteria: 1, Fungi: 0.5 | 13.8 | 20.3 |
| 20-4 | Leaves | | | 0.27 | MIC (%) Bacteria: 1, Fungi: 1 | 13.7 | 21.1 |
| 20-5 | Fruits | | | 0.88 | MIC (%) Bacteria: 0.5, Fungi: 0.5 | 10.9 | 12.0 |
| 20-6 | Flowers | | | 0.74 | MIC (%) Bacteria: 0.25, Fungi: 1 | 17.4 | 25.5 |

Example 21

Ulleungdo Spike Speedwell

TABLE 38

| No. | Sample | Conc. (ppm) | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|---|
| | Control group | | | | Vitamin C 7.5 ppm | Hexanediol Bacteria: *P. aeruginosa* 2% Fungi: *A. niger* 1% | Untreated 0 mm | Untreated 0 mm |
| 21 | Ulleungdo spike speedwell | | *Pseudolysimachion insulare* | Ulleungdo spike speedwell | | | | |
| Comparative Example | Speedwell | 50 | *Veronica Officinalis* | | 3.17 | MIC (%) Bacteria, Fungi: 2 | 13.8 | 11.5 |
| 21-1 | Whole plant | 2 10 50 | | | 0.73 | MIC (%) Bacteria: 1 MIC (%) Fungi: 0.5 | 8.3 17.8 | 9.0 19.7 |
| 21-2 | Roots | 2 10 50 | | | 0.9 | MIC (%) Bacteria, Fungi: 1 | 13.2 | 11.5 |
| 21-3 | Stems | 2 10 50 | | | 0.47 | MIC (%) Bacteria, Fungi: 1 | 23.4 | 13.7 |
| 21-4 | Leaves | 2 10 50 | | | 0.22 | MIC (%) Bacteria: 0.25 MIC (%) Fungi: 0.5 | 23.6 | 22.0 |
| 21-5 | Fruits | 2 10 50 | | | 0.8 | MIC (%) Bacteria: 0.25 MIC (%) Fungi: 0.25 | 10.3 | 11.8 |
| 21-6 | Flowers | 2 10 50 | | | 0.93 | MIC (%) Bacteria: 0.25 MIC (%) Fungi: 1 | 14.2 | 15.1 |

TABLE 39

| No. | Sample | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|
| 21 | Ulleungdo spike speedwell | *Pseudolysimachion insulare* | Ulleungdo spike speedwell | | | | |
| Comparative Example | Speedwell | *Veronica Officinalis* | | 3.17 | MIC (%) Bacteria, Fungi: 2 | 13.8 | 11.5 |
| 21-1 | Whole plant | | | 0.73 | MIC (%) Bacteria: 1 MIC (%) Fungi: 0.5 | 8.3 17.8 | 9.0 19.7 |
| 21-2 | Roots | | | 0.9 | MIC (%) Bacteria, Fungi: 1 | 13.2 | 11.5 |
| 21-3 | Stems | | | 0.47 | MIC (%) Bacteria, Fungi: 1 | 23.4 | 13.7 |
| 21-4 | Leaves | | | 0.22 | MIC (%) Bacteria: 0.25 MIC (%) Fungi: 0.5 | 23.6 | 22.0 |
| 21-5 | Fruits | | | 0.8 | MIC (%) Bacteria: 0.25 MIC (%) Fungi: 0.25 | 10.3 | 11.8 |
| 21-6 | Flowers | | | 0.93 | MIC (%) Bacteria: 0.25 MIC (%) Fungi: 1 | 14.2 | 15.1 |

Example 22

Coastal Moss-Like Stonecrop

TABLE 40

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 22 | Coastal moss-like stonecrop | | *Sedum oryzifolium* | Coastal moss-like stonecrop | | | | |
| Comparative Example | Orange stonecrop | 50 | *Sedum Kamtschaticum* | | 80.19 | 6.04 | 3.98 | 13.00 |
| 22-1 | Whole plant | 2 | | | 45.74 | 3.60 | 11.19 | 298.50 |
| | | 10 | | | 38.34 | 17.52 | 19.66 | 598.40 |
| | | 50 | | | 35.36 | 26.37 | 26.84 | 785.92 |
| 22-2 | Roots | 2 | | | 37.34 | 13.83 | 20.45 | 312.88 |
| | | 10 | | | 33.85 | 28.34 | 29.29 | 403.47 |
| | | 50 | | | 22.45 | 37.74 | 39.25 | 735.40 |
| 22-3 | Stems | 2 | | | 34.48 | 15.30 | 26.40 | 315.03 |
| | | 10 | | | 31.12 | 24.10 | 29.97 | 495.51 |
| | | 50 | | | 25.25 | 38.15 | 34.96 | 719.30 |
| 22-4 | Leaves | 2 | | | 37.06 | 18.16 | 26.70 | 333.50 |
| | | 10 | | | 29.18 | 21.75 | 30.14 | 599.29 |
| | | 50 | | | 26.08 | 38.90 | 32.91 | 757.00 |
| 22-5 | Fruits | 2 | | | 38.07 | 18.34 | 21.39 | 248.33 |
| | | 10 | | | 33.40 | 29.93 | 30.26 | 560.51 |
| | | 50 | | | 23.70 | 34.97 | 31.63 | 708.07 |
| 22-6 | Flowers | 2 | | | 35.09 | 10.80 | 21.62 | 215.01 |
| | | 10 | | | 28.93 | 21.05 | 33.29 | 531.83 |
| | | 50 | | | 25.49 | 34.20 | 35.62 | 648.15 |

TABLE 41

| No. | Sample | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|
| | Control group | | | Vitamin C 7.5 ppm | Hexanediol Bacteria: *P. aeruginosa* 2% Fungi: *A. niger* 1% | Untreated 0 mm | Untreated 0 mm |
| 22 | Coastal moss-like stonecrop | *Sedum oryzifolium* | Coastal moss-like stonecrop | | | | |
| Comparative Example | Orange stonecrop | *Sedum Kamtschaticum* | | 9.25 | MIC (%) Bacteria2, Fungi: 2 | 9.7 | 10.0 |
| 22-1 | Whole plant | | | 0.9 | MIC (%) Bacteria, Fungi: 1 | 18.6 | 16.6 |
| 22-2 | Roots | | | 0.66 | MIC (%) Bacteria, Fungi: 0.5 | 19.6 | 23.3 |
| 22-3 | Stems | | | 0.77 | MIC (%) Bacteria, Fungi: 0.0625 | 15.3 | 20.1 |
| 22-4 | Leaves | | | 0.63 | MIC (%) Bacteria: 0.125 MIC (%) Fungi: 0.25 | 26.7 | 14.9 |
| 22-5 | Fruits | | | 0.29 | MIC (%) Bacteria: 0.25 MIC (%) Fungi: 0.5 | 17.2 | 12.0 |
| 22-6 | Flowers | | | 0.49 | MIC (%) Bacteria: 0.25 MIC (%) Fungi: 0.125 | 16.0 | 16.1 |

Example 23

Water Chickweed (Giant Chickweed)

TABLE 42

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 23 | Water chickweed (Giant chickweed) | | *Stellaria aquatica* | Water chickweed (Giant chickweed) | | | | |
| Comparative Example | Chickweed | 50 | *Stellaria Media* | | 72.34 | 3.29 | 7.25 | 97.51 |
| 23-1 | Whole plant | 2 | | | 39.14 | 15.12 | 24.37 | 261.94 |
| | | 10 | | | 28.86 | 25.28 | 30.96 | 455.93 |
| | | 50 | | | 24.18 | 32.21 | 34.75 | 659.55 |
| 23-2 | Roots | 2 | | | 35.91 | 17.10 | 22.57 | 218.92 |
| | | 10 | | | 29.12 | 29.98 | 28.85 | 450.38 |
| | | 50 | | | 20.51 | 43.46 | 39.79 | 733.82 |
| 23-3 | Stems | 2 | | | 36.96 | 13.61 | 24.24 | 261.55 |
| | | 10 | | | 32.40 | 21.65 | 33.21 | 593.68 |
| | | 50 | | | 25.25 | 31.46 | 37.75 | 674.45 |
| 23-4 | Leaves | 2 | | | 36.68 | 17.32 | 20.14 | 382.63 |
| | | 10 | | | 28.01 | 27.89 | 31.61 | 532.62 |
| | | 50 | | | 25.08 | 30.10 | 36.61 | 723.84 |
| 23-5 | Fruits | 2 | | | 39.55 | 10.55 | 26.03 | 371.93 |
| | | 10 | | | 28.84 | 27.40 | 31.11 | 553.71 |
| | | 50 | | | 20.67 | 33.06 | 37.01 | 726.98 |
| 23-6 | Flowers | 2 | | | 39.55 | 10.95 | 20.66 | 208.33 |
| | | 10 | | | 30.93 | 21.37 | 28.01 | 581.25 |
| | | 50 | | | 23.79 | 36.43 | 33.56 | 625.44 |

TABLE 43

| No. | Sample | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|
| | Control group | | | Vitamin C 7.5 ppm | Hexanediol Bacteria: *P. aeruginosa* 2% Fungi: *A. niger* 1% | Untreated 0 mm | Untreated 0 mm |
| 23 | Water chickweed (Giant chickweed) | *Stellaria aquatica* | Water chickweed (Giant chickweed) | | | | |
| Comparative Example | Chickweed | *Stellaria Media* | | 8.7 | MIC (%) Bacteria, Fungi: >2 | 12.5 | 10.9 |
| 23-1 | Whole plant | | | 0.9 | MIC (%) Bacteria, Fungi: 1 | 24.4 | 25.2 |
| 23-2 | Roots | | | 0.45 | MIC (%) Bacteria, Fungi: 0.5 | 17.0 | 11.0 |
| 23-3 | Stems | | | 0.51 | MIC (%) Bacteria, Fungi: 1 | 13.7 | 12.7 |
| 23-4 | Leaves | | | 0.71 | MIC (%) Bacteria: 0.25 MIC (%) Fungi: 0.125 | 27.5 | 25.0 |
| 23-5 | Fruits | | | 0.86 | MIC (%) Bacteria: 0.25 MIC (%) Fungi: 0.25 | 17.0 | 17.4 |
| 23-6 | Flowers | | | 0.39 | MIC (%) Bacteria: 0.0625 MIC (%) Fungi: 0.125 | 27.3 | 26.9 |

Example 24

Heartleaf *Houttuynia*

TABLE 44

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 24 | Heartleaf Houttuynia | | *Houttuynia cordata* Thunb. | Heartleaf Houttuynia | | | | |
| Comparative Example | Heartleaf Houttuynia (other area) | 50 | | | 89.15 | 17.24 | 1.12 | 45.73 |
| 24-1 | Whole plant | 2 | | | 39.15 | 13.24 | 23.12 | 273.73 |
| | | 10 | | | 28.76 | 23.82 | 31.95 | 407.75 |
| | | 50 | | | 21.14 | 38.76 | 35.87 | 630.10 |
| 24-2 | Roots | 2 | | | 38.13 | 17.61 | 20.65 | 261.26 |
| | | 10 | | | 27.26 | 24.89 | 33.97 | 442.32 |
| | | 50 | | | 25.62 | 38.01 | 35.23 | 726.65 |
| 24-3 | Stems | 2 | | | 38.63 | 19.91 | 24.71 | 305.14 |
| | | 10 | | | 31.19 | 24.56 | 28.93 | 536.67 |
| | | 50 | | | 21.69 | 33.70 | 38.60 | 628.47 |
| 24-4 | Leaves | 2 | | | 34.76 | 10.56 | 25.91 | 229.14 |
| | | 10 | | | 28.32 | 23.51 | 30.92 | 517.19 |
| | | 50 | | | 21.28 | 30.14 | 34.25 | 728.73 |
| 24-5 | Fruits | 2 | | | 37.70 | 18.08 | 24.11 | 327.46 |
| | | 10 | | | 32.78 | 28.75 | 33.37 | 464.74 |
| | | 50 | | | 22.64 | 32.24 | 34.27 | 687.35 |
| 24-6 | Flowers | 2 | | | 36.56 | 13.44 | 22.74 | 294.42 |
| | | 10 | | | 33.66 | 20.40 | 32.96 | 406.96 |
| | | 50 | | | 25.39 | 30.11 | 39.43 | 614.75 |

TABLE 45

| No. | Sample | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|
| | Control group | | | Vitamin C 7.5 ppm | Hexanediol Bacteria: *P. aeruginosa* 2% Fungi: *A. niger* 1% | Untreated 0 mm | Untreated 0 mm |
| 24 | Heartleaf Houttuynia | *Houttuynia cordata* Thunb. | Heartleaf Houttuynia | | | | |
| Comparative Example | Heartleaf Houttuynia (other area) | | | 3.23 | MIC (%) Bacteria: 1 MIC (%) Fungi: 1 | 8.7 | 12.4 |
| 24-1 | Whole plant | | | 0.76 | MIC (%) Bacteria: 0.0625 MIC (%) Fungi: 0.0625 | 18.8 | 20.3 |
| 24-2 | Roots | | | 0.81 | MIC (%) Bacteria: 0.125 MIC (%) Fungi: 0.125 | 24.4 | 23.1 |
| 24-3 | Stems | | | 0.12 | MIC (%) Bacteria: 0.5 MIC (%) Fungi: 0.5 | 10.9 | 16.7 |
| 24-4 | Leaves | | | 0.86 | MIC (%) Bacteria: 0.5 MIC (%) Fungi: 0.5 | 17.2 | 10.4 |
| 24-5 | Fruits | | | 0.59 | MIC (%) Bacteria: 0.5 MIC (%) Fungi: 0.5 | 18.8 | 17.2 |
| 24-6 | Flowers | | | 0.12 | MIC (%) Bacteria: 0.5 MIC (%) Fungi: 0.5 | 17.4 | 17.8 |

Example 25

Ulleungdo Liverleaf

TABLE 46

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 25 | Ulleungdo liverleaf | | *Hepatica maxima* (Nakai) Nakai | Ulleungdo liverleaf | | | | |
| 25-1 | Whole plant | 2 | | | 76.56 | 11.72 | 21.32 | 272.64 |
| | | 10 | | | 33.66 | 21.74 | 31.40 | 562.62 |
| | | 50 | | | 25.39 | 39.73 | 37.68 | 603.06 |
| 25-2 | Roots | 2 | | | 39.84 | 13.44 | 23.91 | 230.66 |
| | | 10 | | | 31.46 | 20.68 | 32.24 | 538.29 |
| | | 50 | | | 24.46 | 33.78 | 35.45 | 618.18 |
| 25-3 | Stems | 2 | | | 39.24 | 15.10 | 22.02 | 242.11 |
| | | 10 | | | 31.34 | 24.90 | 30.86 | 400.26 |
| | | 50 | | | 24.14 | 32.37 | 39.08 | 639.19 |
| 25-4 | Leaves | 2 | | | 34.09 | 15.35 | 25.02 | 287.66 |
| | | 10 | | | 31.67 | 25.97 | 33.55 | 484.59 |
| | | 50 | | | 23.61 | 32.33 | 34.12 | 652.27 |
| 25-5 | Fruits | 2 | | | 35.72 | 19.53 | 23.99 | 381.86 |
| | | 10 | | | 30.08 | 29.73 | 28.61 | 470.18 |
| | | 50 | | | 23.09 | 33.26 | 39.13 | 770.08 |
| 25-6 | Flowers | 2 | | | 39.83 | 13.44 | 20.51 | 308.72 |
| | | 10 | | | 27.62 | 20.40 | 32.72 | 443.95 |
| | | 50 | | | 20.16 | 30.11 | 37.02 | 706.41 |

TABLE 47

| No. | Sample | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|
| | Control group | | | Vitamin C 7.5 ppm | Hexanediol Bacteria: *P. aeruginosa* 2% Fungi: *A. niger* 1% | Untreated 0 mm | Untreated 0 mm |
| 25 | Ulleungdo liverleaf | *Hepatica maxima* (Nakai) Nakai | Ulleungdo liverleaf | | | | |
| 25-1 | Whole plant | | | 0.45 | MIC (%) Bacteria: 0.25 MIC (%) Fungi: 0.25 | 24.5 | 24.4 |
| 25-2 | Roots | | | 0.76 | MIC (%) Bacteria: 0.0625 MIC (%) Fungi: 0.0625 | 17.5 | 13.0 |
| 25-3 | Stems | | | 0.42 | MIC (%) Bacteria: 0.5 MIC (%) Fungi: 0.5 | 14.0 | 13.7 |
| 25-4 | Leaves | | | 0.21 | MIC (%) Bacteria: 0.5 MIC (%) Fungi: 0.5 | 21.6 | 26.7 |
| 25-5 | Fruits | | | 0.84 | MIC (%) Bacteria: 0.5 MIC (%) Fungi: 0.5 | 16.1 | 8.8 |
| 25-6 | Flowers | | | 0.53 | MIC (%) Bacteria: 0.125 MIC (%) Fungi: 0.125 | 21.3 | 12.8 |

Example 26

Chinese Buttercup

TABLE 48

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 26 | Chinese buttercup | | *Ranunculus quelpaertensis* (H. Lév.) Nakai | Chinese buttercup | | | | |
| Comparative Example | Ranunculus ficaria | 50 | *Ranunculus Ficaria* | | 89.24 | 1.34 | 1.54 | 22.34 |
| 26-1 | Whole plant | 2 | | | 39.57 | 15.51 | 22.72 | 395.30 |
| | | 10 | | | 32.67 | 29.69 | 29.50 | 575.83 |
| | | 50 | | | 24.86 | 33.60 | 39.40 | 650.79 |
| 26-2 | Roots | 2 | | | 39.86 | 11.34 | 22.72 | 312.22 |
| | | 10 | | | 29.07 | 22.16 | 29.50 | 451.69 |
| | | 50 | | | 24.83 | 35.64 | 39.40 | 738.08 |
| 26-3 | Stems | 2 | | | 38.29 | 18.13 | 22.72 | 213.87 |
| | | 10 | | | 28.34 | 29.98 | 29.50 | 493.07 |
| | | 50 | | | 22.42 | 30.93 | 39.40 | 799.14 |
| 26-4 | Leaves | 2 | | | 34.45 | 12.48 | 22.72 | 355.20 |
| | | 10 | | | 28.78 | 23.10 | 29.50 | 470.04 |
| | | 50 | | | 23.43 | 35.94 | 39.40 | 771.73 |
| 26-5 | Fruits | 2 | | | 35.91 | 18.09 | 22.72 | 256.23 |
| | | 10 | | | 28.13 | 22.78 | 29.50 | 579.79 |
| | | 50 | | | 21.52 | 34.15 | 39.40 | 667.50 |
| 26-6 | Flowers | 2 | | | 34.37 | 13.44 | 22.72 | 317.22 |
| | | 10 | | | 27.81 | 20.40 | 29.50 | 498.77 |
| | | 50 | | | 20.01 | 30.11 | 39.40 | 663.17 |

TABLE 49

| No. | Sample | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|
| | Control group | | | Vitamin C 7.5 ppm | Hexanediol Bacteria: *P. aeruginosa* 2% Fungi: *A. niger* 1% | Untreated 0 mm | Untreated 0 mm |
| 26 | Chinese buttercup | *Ranunculus quelpaertensis* (H. Lév.) Nakai | Chinese buttercup | | | | |
| Comparative Example | Ranunculus ficaria | *Ranunculus Ficaria* | | 6.67 | MIC (%) Bacteria: 1 MIC (%) Fungi: 1 | 8.0 | 8.0 |
| 26-1 | Whole plant | | | 0.46 | MIC (%) Bacteria: 0.125 MIC (%) Fungi: 0.125 | 19.0 | 27.1 |
| 26-2 | Roots | | | 0.23 | MIC (%) Bacteria: 0.5 MIC (%) Fungi: 0.5 | 10.2 | 15.9 |
| 26-3 | Stems | | | 0.34 | MIC (%) Bacteria: 0.125 MIC (%) Fungi: 0.125 | 11.3 | 11.4 |
| 26-4 | Leaves | | | 0.67 | MIC (%) Bacteria: 0.0625 MIC (%) Fungi: 0.0625 | 15.3 | 13.0 |
| 26-5 | Fruits | | | 0.46 | MIC (%) Bacteria: 0.5 MIC (%) Fungi: 0.5 | 16.7 | 16.6 |
| 26-6 | Flowers | | | 0.45 | MIC (%) Bacteria: 0.5 MIC (%) Fungi: 0.5 | 12.7 | 12.5 |

Example 27

Tricuspidate Falsenettle

TABLE 50

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 27 | Tricuspidate falsenettle | | *Boehmeria tricuspis* (Hance) Makino | Tricuspidate falsenettle | | | | |
| Comparative Example | Ramie | 50 | *Boehmeria nivea* | | 99.86 | 2.34 | 1.72 | 87.22 |
| Comparative Example | Tricuspidate falsenettle (other area) | 50 | | | 85.86 | 16.34 | 5.72 | 127.22 |
| 27-1 | Whole plant | 2 | | | 37.03 | 17.40 | 22.84 | 349.46 |
| | | 10 | | | 27.05 | 20.29 | 29.06 | 409.35 |
| | | 50 | | | 24.39 | 37.06 | 38.80 | 603.30 |
| 27-2 | Roots | 2 | | | 35.50 | 12.20 | 22.91 | 288.20 |
| | | 10 | | | 28.28 | 28.55 | 33.37 | 431.21 |
| | | 50 | | | 22.70 | 36.57 | 36.45 | 707.65 |
| 27-3 | Stems | 2 | | | 36.83 | 14.82 | 25.39 | 361.73 |
| | | 10 | | | 32.39 | 22.83 | 29.25 | 550.31 |
| | | 50 | | | 26.48 | 38.93 | 34.90 | 656.87 |
| 27-4 | Leaves | 2 | | | 39.50 | 18.49 | 23.84 | 255.08 |
| | | 10 | | | 32.30 | 27.16 | 32.21 | 532.98 |
| | | 50 | | | 20.05 | 34.72 | 36.47 | 727.63 |
| 27-5 | Fruits | 2 | | | 39.35 | 17.12 | 23.57 | 262.11 |
| | | 10 | | | 28.64 | 21.57 | 32.62 | 424.16 |
| | | 50 | | | 24.78 | 30.22 | 34.07 | 749.64 |
| 27-6 | Flowers | 2 | | | 34.37 | 13.44 | 26.04 | 394.81 |
| | | 10 | | | 27.81 | 20.40 | 30.38 | 459.42 |
| | | 50 | | | 20.01 | 30.11 | 34.82 | 651.09 |

TABLE 51

| No. | Sample | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|
| | Control group | | | Vitamin C 7.5 ppm | Hexanediol Bacteria: *P. aeruginosa* 2% Fungi: *A. niger* 1% | Untreated 0 mm | Untreated 0 mm |
| 27 | Tricuspidate falsenettle | *Boehmeria tricuspis* (Hance) Makino | Tricuspidate falsenettle | | | | |
| Comparative Example | Ramie | *Boehmeria nivea* | | 2.78 | MIC (%) Bacteria: 1 MIC (%) Fungi: 1 | 8.4 | 9.4 |
| Comparative Example | Tricuspidate falsenettle (other area) | | | 3.56 | MIC (%) Bacteria: 1 MIC (%) Fungi: 1 | 11.6 | 11.7 |
| 27-1 | Whole plant | | | 0.1 | MIC (%) Bacteria: 0.125 MIC (%) Fungi: 0.125 | 18.6 | 22.1 |
| 27-2 | Roots | | | 0.63 | MIC (%) Bacteria: 0.5 MIC (%) Fungi: 0.5 | 10.5 | 17.3 |
| 27-3 | Stems | | | 0.48 | MIC (%) Bacteria: 0.0625 MIC (%) Fungi: 0.0625 | 18.4 | 10.9 |
| 27-4 | Leaves | | | 0.5 | MIC (%) Bacteria: 0.5 MIC (%) Fungi: 0.5 | 26.8 | 22.6 |
| 27-5 | Fruits | | | 0.87 | MIC (%) Bacteria: 0.125 MIC (%) Fungi: 0.125 | 16.2 | 12.1 |
| 27-6 | Flowers | | | 0.72 | MIC (%) Bacteria: 0.125 MIC (%) Fungi: 0.125 | 10.3 | 17.3 |

Example 28

Long-Calyx Pink

TABLE 52

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 28 | Long-calyx pink | | *Dianthus longicalyx* Miq. | Long-calyx pink | | | | |
| Comparative Example | Carnation | 50 | *Dianthus Caryophyllus* | | 76.48 | 13.66 | 2.65 | 50.69 |
| 28-1 | Whole plant | 2 | | | 39.25 | 23.43 | 23.55 | 283.74 |
| | | 10 | | | 32.46 | 28.42 | 33.89 | 414.73 |
| | | 50 | | | 25.16 | 35.96 | 36.66 | 745.27 |
| 28-2 | Roots | 2 | | | 38.91 | 20.24 | 25.92 | 360.57 |
| | | 10 | | | 27.38 | 27.00 | 33.90 | 484.73 |
| | | 50 | | | 24.09 | 35.56 | 37.56 | 604.21 |
| 28-3 | Stems | 2 | | | 35.70 | 22.44 | 22.02 | 256.20 |
| | | 10 | | | 30.77 | 33.18 | 28.90 | 425.05 |
| | | 50 | | | 23.59 | 39.52 | 35.28 | 675.27 |
| 28-4 | Leaves | 2 | | | 38.34 | 21.36 | 25.74 | 315.51 |
| | | 10 | | | 33.13 | 27.54 | 30.19 | 427.62 |
| | | 50 | | | 20.49 | 38.78 | 39.55 | 630.51 |
| 28-5 | Fruits | 2 | | | 34.49 | 25.21 | 22.53 | 324.59 |
| | | 10 | | | 30.00 | 32.59 | 28.47 | 436.64 |
| | | 50 | | | 23.30 | 37.99 | 39.61 | 700.96 |
| 28-6 | Flowers | 2 | | | 36.16 | 26.95 | 25.10 | 346.90 |
| | | 10 | | | 30.59 | 33.44 | 27.52 | 524.21 |
| | | 50 | | | 23.26 | 39.34 | 39.55 | 734.88 |

TABLE 53

| No. | Sample | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|
| | Control group | | | Vitamin C 7.5 ppm | Hexanediol Bacteria: *P. aeruginosa* 2% Fungi: *A. niger* 1% | Untreated 0 mm | Untreated 0 mm |
| 28 | Long-calyx pink | *Dianthus longicalyx* Miq. | Long-calyx pink | | | | |
| Comparative Example | Carnation | *Dianthus Caryophyllus* | | 7.56 | MIC (%) Bacteria, Fungi: >2 | 10.9 | 10.2 |
| 28-1 | Whole plant | | | 0.49 | MIC (%) Bacteria: 0.5 MIC (%) Fungi: 0.25 | 19.3 | 22.2 |
| 28-2 | Roots | | | 0.55 | MIC (%) Bacteria: 1 MIC (%) Fungi: 0.5 | 27.7 | 19.5 |
| 28-3 | Stems | | | 0.69 | MIC (%) Bacteria: 0.5 MIC (%) Fungi: 0.5 | 13.3 | 17.0 |
| 28-4 | Leaves | | | 0.63 | MIC (%) Bacteria: 0.5 MIC (%) Fungi: 0.25 | 15.3 | 15.4 |
| 28-5 | Fruits | | | 0.78 | MIC (%) Bacteria: 0.25 MIC (%) Fungi: 0.125 | 14.0 | 12.9 |
| 28-6 | Flowers | | | 0.79 | MIC (%) Bacteria: 0.25 MIC (%) Fungi: 0.125 | 13.5 | 13.5 |

Example 29

Curled Dock

TABLE 54

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 29 | Curled dock | | *Rumex crispus* L. | Curled dock | | | | |
| Comparative Example | Garden dock | 50 | *Rumex acetosa* L. | | 86.74 | 3.84 | 2.15 | 35.42 |
| Comparative Example | Curled dock (other area) | 50 | *Rumex crispus* L. | | 60.55 | 15.47 | 12.49 | 153.98 |
| 29-1 | Whole plant | 2 | | | 37.45 | 15.86 | 25.10 | 321.94 |
| | | 10 | | | 33.55 | 23.61 | 33.98 | 483.24 |
| | | 50 | | | 24.29 | 30.23 | 37.25 | 656.65 |
| 29-2 | Roots | 2 | | | 36.74 | 15.25 | 25.12 | 234.55 |
| | | 10 | | | 32.48 | 27.74 | 27.30 | 579.17 |
| | | 50 | | | 22.68 | 36.49 | 38.45 | 751.93 |
| 29-3 | Stems | 2 | | | 34.40 | 17.75 | 26.93 | 383.95 |
| | | 10 | | | 32.06 | 30.00 | 30.27 | 510.16 |
| | | 50 | | | 21.16 | 32.61 | 34.28 | 753.61 |
| 29-4 | Leaves | 2 | | | 35.96 | 14.81 | 26.55 | 223.18 |
| | | 10 | | | 28.51 | 22.56 | 30.86 | 474.09 |
| | | 50 | | | 21.58 | 37.25 | 34.04 | 723.59 |
| 29-5 | Fruits | 2 | | | 39.99 | 19.39 | 24.67 | 352.93 |
| | | 10 | | | 29.56 | 22.41 | 32.61 | 584.88 |
| | | 50 | | | 25.52 | 35.89 | 34.73 | 771.51 |
| 29-6 | Flowers | 2 | | | 39.30 | 18.83 | 25.07 | 339.29 |
| | | 10 | | | 27.17 | 28.19 | 32.38 | 418.58 |
| | | 50 | | | 23.67 | 36.36 | 36.15 | 729.03 |

TABLE 55

| No. | Sample | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|
| | Control group | | | Vitamin C 7.5 ppm | Hexanediol Bacteria: *P. aeruginosa* 2% Fungi: *A. niger* 1% | Untreated 0 mm | Untreated 0 mm |
| 29 | Curled dock | *Rumex crispus* L. | Curled dock | | | | |
| Comparative Example | Garden dock | *Rumex acetosa* L. | | 9.93 | MIC (%) Bacteria: 1 MIC (%) Fungi: 1 | 13.5 | 10.5 |
| Comparative Example | Curled dock (other area) | *Rumex crispus* L. | | 3.14 | MIC (%) Bacteria: 0.5 MIC (%) Fungi: 0.5 | 13.3 | 14.1 |
| 29-1 | Whole plant | | | 0.07 | MIC (%) Bacteria: 0.125 MIC (%) Fungi: 0.125 | 27.5 | 20.2 |
| 29-2 | Roots | | | 0.1 | MIC (%) Bacteria: 0.25 MIC (%) Fungi: 0.125 | 18.7 | 12.5 |
| 29-3 | Stems | | | 0.12 | MIC (%) Bacteria: 0.125 MIC (%) Fungi: 0.0625 | 13.1 | 9.3 |
| 29-4 | Leaves | | | 0.07 | MIC (%) Bacteria: 0.25 MIC (%) Fungi: 0.125 | 20.2 | 26.3 |
| 29-5 | Fruits | | | 0.24 | MIC (%) Bacteria: 0.25 MIC (%) Fungi: 0.125 | 10.8 | 13.1 |
| 29-6 | Flowers | | | 0.05 | MIC (%) Bacteria: 0.0625 MIC (%) Fungi: 0.0625 | 14.0 | 10.8 |

Example 30

Erect St. Johnswort

TABLE 56

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 30 | Erect St. Johnswort | | *Hypericum erectum* Thunb. | Erect St. Johnswort | | | | |
| Comparative Example | St John's Wort | 50 | *Hypericum Perforatum* | | 75.66 | 9.56 | 2.45 | 41.52 |
| Comparative Example | Erect St. Johnswort (other area) | 50 | *Hypericum erectum* Thunb. | | 40.54 | 17.14 | 9.66 | 267.21 |
| 30-1 | Whole plant | 2 | | | 38.07 | 14.81 | 20.41 | 231.71 |
| | | 10 | | | 29.29 | 28.36 | 28.65 | 469.39 |
| | | 50 | | | 26.78 | 34.65 | 35.31 | 700.48 |
| 30-2 | Roots | 2 | | | 38.55 | 17.03 | 26.18 | 209.85 |
| | | 10 | | | 31.05 | 27.88 | 27.00 | 571.33 |
| | | 50 | | | 26.78 | 39.28 | 39.29 | 783.75 |
| 30-3 | Stems | 2 | | | 39.48 | 17.09 | 24.47 | 325.93 |
| | | 10 | | | 31.96 | 29.13 | 33.27 | 447.72 |
| | | 50 | | | 23.61 | 30.86 | 37.62 | 687.97 |
| 30-4 | Leaves | 2 | | | 35.92 | 18.17 | 24.59 | 292.75 |
| | | 10 | | | 29.46 | 27.46 | 29.57 | 462.78 |
| | | 50 | | | 22.99 | 35.11 | 34.57 | 638.97 |
| 30-5 | Fruits | 2 | | | 34.79 | 11.00 | 25.79 | 318.17 |
| | | 10 | | | 33.65 | 21.53 | 27.37 | 470.88 |
| | | 50 | | | 22.84 | 30.29 | 35.55 | 604.30 |
| 30-6 | Flowers | 2 | | | 35.12 | 15.09 | 21.85 | 241.03 |
| | | 10 | | | 28.48 | 25.98 | 29.90 | 538.52 |
| | | 50 | | | 21.89 | 34.36 | 39.29 | 666.36 |

TABLE 57

| No. | Sample | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|
| | Control group | | | Vitamin C 7.5 ppm | Hexanediol Bacteria: *P. aeruginosa* 2% Fungi: *A. niger* 1% | Untreated 0 mm | Untreated 0 mm |
| 30 | Erect St. Johnswort | *Hypericum erectum* Thunb. | Erect St. Johnswort | | | | |
| Comparative Example | St John's Wort | *Hypericum Perforatum* | | 4.65 | MIC (%) Bacteria: 1 MIC (%) Fungi: 1 | 11.2 | 9.2 |
| Comparative Example | Erect St. Johnswort (other area) | *Hypericum erectum* Thunb. | | 1.23 | MIC (%) Bacteria: 1 MIC (%) Fungi: 1 | 17.7 | 16.5 |
| 30-1 | Whole plant | | | 0.15 | MIC (%) Bacteria: 0.25 MIC (%) Fungi: 0.125 | 26.4 | 22.9 |
| 30-2 | Roots | | | 0.07 | MIC (%) Bacteria: 0.25 MIC (%) Fungi: 0.25 | 27.3 | 24.2 |
| 30-3 | Stems | | | 0.14 | MIC (%) Bacteria: 0.125 MIC (%) Fungi: 0.0625 | 13.0 | 9.8 |
| 30-4 | Leaves | | | 0.04 | MIC (%) Bacteria: 0.125 MIC (%) Fungi: 0.0625 | 15.7 | 19.1 |
| 30-5 | Fruits | | | 0.21 | MIC (%) Bacteria: 0.25 MIC (%) Fungi: 0.25 | 21.1 | 19.3 |
| 30-6 | Flowers | | | 0.11 | MIC (%) Bacteria: 0.125 MIC (%) Fungi: 0.125 | 22.6 | 15.6 |

Example 31

Five-Leaf *Gynostemma*

TABLE 58

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 31 | Five-leaf gynostemma | | *Gynostemma pentaphylla* (Thunb.) Makino | Five-leaf gynostemma | | | | |
| Comparative Example | Five-leaf gynostemma (other area) | 50 | *Gynostemma pentaphylla* (Thunb.) Makino | | 87.21 | 17.45 | 12.14 | 214.55 |
| 31-1 | Whole plant | 2 | | | 35.80 | 11.06 | 24.25 | 274.50 |
| | | 10 | | | 27.39 | 24.54 | 28.71 | 439.60 |
| | | 50 | | | 25.00 | 30.42 | 38.95 | 698.74 |
| 31-2 | Roots | 2 | | | 38.47 | 11.34 | 24.85 | 378.08 |
| | | 10 | | | 27.92 | 23.92 | 31.52 | 596.78 |
| | | 50 | | | 26.27 | 38.88 | 38.95 | 654.92 |
| 31-3 | Stems | 2 | | | 34.24 | 14.05 | 20.83 | 324.60 |
| | | 10 | | | 28.03 | 22.57 | 33.80 | 507.38 |
| | | 50 | | | 23.41 | 36.12 | 39.31 | 673.64 |
| 31-4 | Leaves | 2 | | | 38.58 | 13.41 | 25.71 | 353.19 |
| | | 10 | | | 27.00 | 27.69 | 27.25 | 427.32 |
| | | 50 | | | 21.56 | 36.22 | 36.09 | 669.94 |
| 31-5 | Fruits | 2 | | | 36.30 | 16.31 | 25.21 | 310.69 |
| | | 10 | | | 32.13 | 23.49 | 31.08 | 432.14 |
| | | 50 | | | 24.46 | 37.41 | 37.61 | 650.81 |
| 31-6 | Flowers | 2 | | | 34.46 | 11.13 | 22.81 | 368.00 |
| | | 10 | | | 28.37 | 26.57 | 33.88 | 491.92 |
| | | 50 | | | 21.31 | 34.72 | 35.19 | 705.71 |

TABLE 59

| No. | Sample | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|
| | Control group | | | Vitamin C 7.5 ppm | Hexanediol Bacteria: *P. aeruginosa* 2% Fungi: *A. niger* 1% | Untreated 0 mm | Untreated 0 mm |
| 31 | Five-leaf gynostemma | *Gynostemma pentaphylla* (Thunb.) Makino | Five-leaf gynostemma | | | | |
| Comparative Example | Five-leaf gynostemma (other area) | *Gynostemma pentaphylla* (Thunb.) Makino | | 6.58 | MIC (%) Bacteria: 1 MIC (%) Fungi: 1 | 15.7 | 14.1 |
| 31-1 | Whole plant | | | 0.25 | MIC (%) Bacteria: 0.25 MIC (%) Fungi: 0.25 | 24.7 | 25.9 |
| 31-2 | Roots | | | 0.12 | MIC (%) Bacteria: 0.125 MIC (%) Fungi: 0.25 | 9.6 | 10.0 |
| 31-3 | Stems | | | 0.28 | MIC (%) Bacteria: 0.25 MIC (%) Fungi: 0.25 | 11.3 | 15.7 |
| 31-4 | Leaves | | | 0.20 | MIC (%) Bacteria: 0.25 MIC (%) Fungi: 0.25 | 13.3 | 17.7 |
| 31-5 | Fruits | | | 0.15 | MIC (%) Bacteria: 0.125 MIC (%) Fungi: 0.0625 | 25.2 | 25.8 |
| 31-6 | Flowers | | | 0.18 | MIC (%) Bacteria: 0.0625 MIC (%) Fungi: 0.125 | 10.6 | 13.0 |

Example 32

Bird's Egg Cucumber

TABLE 60

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 32 | Bird's egg cucumber | | Melothria japonica (Thunb.) Maxim. | Bird's egg cucumber | | | | |
| Comparative Example | Melothria | 50 | Melothria Heterophylla | Solena | 97.29 | 12.18 | 4.48 | 98.05 |
| 32-1 | Whole plant | 2 | | | 35.22 | 17.75 | 23.05 | 301.04 |
| | | 10 | | | 31.77 | 22.83 | 28.32 | 512.22 |
| | | 50 | | | 22.04 | 34.98 | 39.30 | 711.80 |
| 32-2 | Roots | 2 | | | 36.97 | 18.04 | 26.07 | 341.54 |
| | | 10 | | | 30.34 | 27.19 | 33.34 | 447.46 |
| | | 50 | | | 24.10 | 30.40 | 39.20 | 718.95 |
| 32-3 | Stems | 2 | | | 35.67 | 13.82 | 25.71 | 315.42 |
| | | 10 | | | 27.26 | 23.31 | 27.54 | 525.52 |
| | | 50 | | | 21.62 | 32.95 | 36.30 | 662.05 |
| 32-4 | Leaves | 2 | | | 34.24 | 12.78 | 24.73 | 204.89 |
| | | 10 | | | 27.69 | 22.64 | 33.27 | 446.93 |
| | | 50 | | | 20.96 | 33.17 | 38.47 | 767.15 |
| 32-5 | Fruits | 2 | | | 38.43 | 12.62 | 25.20 | 255.15 |
| | | 10 | | | | | | |
| | | 50 | | | 24.11 | 30.13 | 38.19 | 651.54 |
| 32-6 | Flowers | 2 | | | 38.31 | 12.76 | 22.73 | 372.09 |
| | | 10 | | | 33.55 | 24.13 | 29.82 | 471.65 |
| | | 50 | | | 22.33 | 31.38 | 39.57 | 735.96 |

TABLE 61

| No. | Sample | Scientific name | English name | Anti-oxidation IC50 (%) | Anti-bacteria MIC (%) | Anti-bacteria (S. mutans) Size of growth inhibition ring (mm) | Anti-bacteria (P. gingivalis) Size of growth inhibition ring (mm) |
|---|---|---|---|---|---|---|---|
| | Control group | | | Vitamin C 7.5 ppm | Hexanediol Bacteria: P. aeruginosa 2% Fungi: A. niger 1% | Untreated 0 mm | Untreated 0 mm |
| 32 | Bird's egg cucumber | Melothria japonica (Thunb.) Maxim | Bird's egg cucumber | | | | |
| Comparative Example | Melothria | Melothria Heterophylla | Solena | 8.01 | MIC (%) Bacteria: >2 MIC (%) Fungi: >2 | 0.0 | 0.0 |
| 32-1 | Whole plant | | | 0.45 | MIC (%) Bacteria: 0.25 MIC (%) Fungi: 0.125 | 12.8 | 17.0 |
| 32-2 | Roots | | | 0.96 | MIC (%) Bacteria: 0.25 MIC (%) Fungi: 0.5 | 9.4 | 8.7 |
| 32-3 | Stems | | | 0.30 | MIC (%) Bacteria: 0.25 MIC (%) Fungi: 0.25 | 17.2 | 18.2 |
| 32-4 | Leaves | | | 0.65 | MIC (%) Bacteria: 0.125 MIC (%) Fungi: 0.25 | 10.5 | 13.6 |
| 32-5 | Fruits | | | 0.38 | MIC (%) Bacteria: 0.5 MIC (%) Fungi: 1 | 18.9 | 13.3 |
| 32-6 | Flowers | | | 0.14 | MIC (%) Bacteria: 1 MIC (%) Fungi: 1 | 13.9 | 9.5 |

Example 33

Ulleungdo Rockcress

TABLE 62

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|-----|--------|-------------|-----------------|--------------|-------------------------------|------------------------------------------------|---------------------------------------------------|-------------------------------|
| | Control group | | | | Arbutin (200 ppm) 35% | TGFb (10 ppb) 25% | L-NMMA (5 ppm) 28% | EGF (10 ppb) 320% |
| 33 | Ulleungdo rockcress | | *Arabis takesimana* Nakai | Ulleungdo rockcress | | | | |
| 33-1 | Whole plant | 2 | | | 37.72 | 13.67 | 21.77 | 278.76 |
| | | 10 | | | 31.23 | 26.76 | 33.86 | 514.61 |
| | | 50 | | | 22.29 | 30.87 | 36.51 | 708.03 |
| 33-2 | Roots | 2 | | | 39.47 | 16.47 | 23.64 | 370.23 |
| | | 10 | | | 32.97 | 27.30 | 32.13 | 553.07 |
| | | 50 | | | 25.75 | 35.29 | 37.43 | 768.17 |
| 33-3 | Stems | 2 | | | 34.64 | 16.00 | 24.31 | 352.19 |
| | | 10 | | | 33.96 | 21.11 | 32.72 | 462.20 |
| | | 50 | | | 25.46 | 32.06 | 35.53 | 773.27 |
| 33-4 | Leaves | 2 | | | 36.91 | 12.32 | 22.72 | 353.17 |
| | | 10 | | | 29.84 | 20.27 | 30.87 | 545.48 |
| | | 50 | | | 21.70 | 33.57 | 37.70 | 715.68 |
| 33-5 | Fruits | 2 | | | 37.95 | 18.60 | 24.64 | 323.92 |
| | | 10 | | | 33.61 | 25.03 | 28.92 | 455.97 |
| | | 50 | | | 22.34 | 31.34 | 36.77 | 787.93 |
| 33-6 | Flowers | 2 | | | 36.28 | 10.35 | 24.60 | 317.34 |
| | | 10 | | | 29.18 | 24.08 | 29.08 | 549.16 |
| | | 50 | | | 25.34 | 39.51 | 34.56 | 682.67 |

TABLE 63

| No. | Sample | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|-----|--------|-----------------|--------------|-------------------------|-----------------------|----------------------------------------------------------------|---------------------------------------------------------------------|
| | Control group | | | Vitamin C 7.5 ppm | Hexanediol Bacteria: *P. aeruginosa* 2% Fungi: *A. niger* 1% | Untreated 0 mm | Untreated 0 mm |
| 33 | Ulleungdo rockcress | *Arabis takesimana* Nakai | Ulleungdo rockcress | | | | |
| 33-1 | Whole plant | | | 0.82 | MIC (%) Bacteria: 1 MIC (%) Fungi: 0.5 | 13.8 | 19.5 |
| 33-2 | Roots | | | 0.64 | MIC (%) Bacteria: 0.5 MIC (%) Fungi: 0.5 | 24.3 | 20.9 |
| 33-3 | Stems | | | 0.58 | MIC (%) Bacteria: 0.25 MIC (%) Fungi: 0.5 | 9.4 | 11.6 |
| 33-4 | Leaves | | | 0.51 | MIC (%) Bacteria: 0.125 MIC (%) Fungi: 0.25 | 26.8 | 24.7 |
| 33-5 | Fruits | | | 0.88 | MIC (%) Bacteria: 1 MIC (%) Fungi: 0.5 | 8.3 | 9.6 |
| 33-6 | Flowers | | | 0.39 | MIC (%) Bacteria: 0.25 MIC (%) Fungi: 0.25 | 10.2 | 11.6 |

Example 34

Hedge Mustard

TABLE 64

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 34 | Hedge Mustard | | *Sisymbrium officinale* (L.) Scop. | Hedge Mustard | | | | |
| Comparative Example | London rocket | 50 | *Sisymbrium Irio* | | 89.81 | 9.46 | 5.06 | 32.25 |
| 34-1 | Whole plant | 2 | | | 38.49 | 10.86 | 25.18 | 292.14 |
| | | 10 | | | 32.11 | 25.67 | 27.04 | 517.63 |
| | | 50 | | | 23.22 | 32.02 | 37.38 | 676.68 |
| 34-2 | Roots | 2 | | | 37.61 | 19.84 | 20.59 | 254.44 |
| | | 10 | | | 30.49 | 23.52 | 32.49 | 466.11 |
| | | 50 | | | 21.30 | 38.86 | 39.81 | 751.79 |
| 34-3 | Stems | 2 | | | 35.49 | 10.10 | 22.45 | 303.26 |
| | | 10 | | | 27.41 | 29.96 | 31.77 | 461.07 |
| | | 50 | | | 26.31 | 32.69 | 34.05 | 658.52 |
| 34-4 | Leaves | 2 | | | 37.26 | 18.89 | 24.40 | 327.53 |
| | | 10 | | | 28.76 | 22.54 | 32.46 | 553.91 |
| | | 50 | | | 23.38 | 35.16 | 36.40 | 726.03 |
| 34-5 | Fruits | 2 | | | 34.66 | 12.44 | 22.45 | 260.84 |
| | | 10 | | | 32.71 | 29.56 | 30.57 | 578.41 |
| | | 50 | | | 20.47 | 35.81 | 36.02 | 666.84 |
| 34-6 | Flowers | 2 | | | 39.76 | 18.39 | 22.61 | 253.08 |
| | | 10 | | | 27.26 | 29.26 | 31.64 | 600.38 |
| | | 50 | | | 23.06 | 34.22 | 37.73 | 735.66 |

TABLE 65

| No. | Sample | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|
| | Control group | | | Vitamin C 7.5 ppm | Hexanediol Bacteria: *P. aeruginosa* 2% Fungi: *A. niger* 1% | Untreated 0 mm | Untreated 0 mm |
| 34 | Hedge Mustard | *Sisymbrium officinale* (L.) Scop. | Hedge Mustard | | | | |
| Comparative Example | London rocket | *Sisymbrium Irio* | | 4.90 | MIC (%) Bacteria: >2 MIC (%) Fungi: 1 | 8.8 | 8.5 |
| 34-1 | Whole plant | | | 0.38 | MIC (%) Bacteria: 1 MIC (%) Fungi: 1 | 14.4 | 19.0 |
| 34-2 | Roots | | | 0.22 | MIC (%) Bacteria: 0.125 MIC (%) Fungi: 0.125 | 8.8 | 10.2 |
| 34-3 | Stems | | | 0.41 | MIC (%) Bacteria: 0.5 MIC (%) Fungi: 1 | 26.0 | 24.8 |
| 34-4 | Leaves | | | 0.62 | MIC (%) Bacteria: 1 MIC (%) Fungi: 1 | 25.7 | 20.1 |
| 34-5 | Fruits | | | 0.87 | MIC (%) Bacteria: 0.5 MIC (%) Fungi: 0.5 | 11.7 | 13.0 |
| 34-6 | Flowers | | | 0.99 | MIC (%) Bacteria: 1 MIC (%) Fungi: 0.5 | 15.7 | 9.6 |

Example 36

Asian Prince's Pine

TABLE 66

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 36 | Asian prince's pine | | *Chimaphila japonica* Miq. | Asian prince's pine | | | | |
| Comparative Example | Prince's pine | 50 | *Chimaphila Umbellata* | | 67.74 | 8.83 | 4.97 | 158.68 |
| 36-1 | Whole plant | 2 | | | 37.36 | 11.97 | 24.91 | 292.59 |
| | | 10 | | | 30.31 | 23.27 | 31.53 | 531.91 |
| | | 50 | | | 24.54 | 37.43 | 35.40 | 622.84 |
| 36-2 | Roots | 2 | | | 37.97 | 13.36 | 25.79 | 277.44 |
| | | 10 | | | 27.85 | 21.89 | 31.51 | 484.73 |
| | | 50 | | | 24.31 | 31.15 | 35.40 | 762.40 |
| 36-3 | Stems | 2 | | | 37.73 | 17.93 | 25.37 | 315.14 |
| | | 10 | | | 32.14 | 28.00 | 27.79 | 500.91 |
| | | 50 | | | 22.25 | 37.06 | 34.13 | 786.79 |
| 36-4 | Leaves | 2 | | | 36.80 | 11.10 | 21.58 | 226.74 |
| | | 10 | | | 27.02 | 24.99 | 33.79 | 577.91 |
| | | 50 | | | 21.58 | 39.31 | 39.12 | 603.85 |
| 36-5 | Fruits | 2 | | | 36.29 | 17.93 | 23.20 | 388.08 |
| | | 10 | | | 32.33 | 28.00 | 33.77 | 504.97 |
| | | 50 | | | 23.42 | 37.06 | 35.22 | 683.52 |
| 36-6 | Flowers | 2 | | | 39.54 | 19.93 | 21.80 | 233.90 |
| | | 10 | | | 29.28 | 21.51 | 30.81 | 471.50 |
| | | 50 | | | 20.52 | 39.96 | 39.91 | 788.63 |

TABLE 67

| No. | Sample | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|
| | Control group | | | Vitamin C 7.5 ppm | Hexanediol Bacteria: *P. aeruginosa* 2% Fungi: *A. niger* 1% | Untreated 0 mm | Untreated 0 mm |
| 36 | Asian prince's pine | *Chimaphila japonica* Miq. | Asian prince's pine | | | | |
| Comparative Example | Prince's pine | *Chimaphila Umbellata* | | 1.57 | MIC (%) Bacteria: 1 MIC (%) Fungi: 2 | 10.0 | 9.4 |
| 36-1 | Whole plant | | | 0.23 | MIC (%) Bacteria: 0.13 MIC (%) Fungi: 0.06 | 23.2 | 21.3 |
| 36-2 | Roots | | | 0.46 | MIC (%) Bacteria: 0.13 MIC (%) Fungi: 0.25 | 17.9 | 14.8 |
| 36-3 | Stems | | | 0.37 | MIC (%) Bacteria: 0.5 MIC (%) Fungi: 0.25 | 10.4 | 17.1 |
| 36-4 | Leaves | | | 0.12 | MIC (%) Bacteria: 0.25 MIC (%) Fungi: 0.13 | 13.0 | 14.9 |
| 36-5 | Fruits | | | 0.32 | MIC (%) Bacteria: 0.5 MIC (%) Fungi: 1 | 11.1 | 15.7 |
| 36-6 | Flowers | | | 0.91 | MIC (%) Bacteria: 0.06 MIC (%) Fungi: 0.13 | 24.0 | 23.7 |

Example 37

Marlberry

TABLE 68

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 37 | Marlberry | | *Ardisia japonica* (Thunb.) Blume | Marlberry | | | | |
| Comparative Example | Christmas berry | 50 | *Ardisia Crenata* | | 80.02 | 4.89 | 3.54 | 77.70 |
| Comparative Example | Marlberry (other area) | 50 | *Ardisia japonica* (Thunb.) Blume | | 52.96 | 13.58 | 9.48 | 286.38 |
| 37-1 | Whole plant | 2 | | | 37.79 | 12.10 | 21.69 | 245.22 |
| | | 10 | | | 29.02 | 23.20 | 31.43 | 498.31 |
| | | 50 | | | 20.60 | 31.19 | 38.29 | 721.29 |
| 37-2 | Roots | 2 | | | 37.02 | 19.20 | 23.88 | 306.75 |
| | | 10 | | | 32.02 | 21.99 | 31.12 | 476.21 |
| | | 50 | | | 20.68 | 37.64 | 34.32 | 660.18 |
| 37-3 | Stems | 2 | | | 34.12 | 14.23 | 25.90 | 349.78 |
| | | 10 | | | 27.97 | 29.99 | 27.83 | 571.61 |
| | | 50 | | | 22.81 | 37.74 | 37.63 | 717.21 |
| 37-4 | Leaves | 2 | | | 38.89 | 19.43 | 23.36 | 234.02 |
| | | 10 | | | 29.01 | 27.26 | 32.39 | 494.80 |
| | | 50 | | | 26.81 | 36.19 | 38.48 | 761.34 |
| 37-5 | Fruits | 2 | | | 39.24 | 13.08 | 21.27 | 206.40 |
| | | 10 | | | 32.42 | 23.46 | 32.25 | 573.25 |
| | | 50 | | | 21.03 | 38.66 | 36.56 | 767.58 |
| 37-6 | Flowers | 2 | | | 34.71 | 14.29 | 23.82 | 359.34 |
| | | 10 | | | 28.87 | 27.26 | 30.99 | 498.80 |
| | | 50 | | | 21.47 | 37.75 | 38.00 | 734.55 |

TABLE 69

| No. | Sample | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|
| | Control group | | | Vitamin C 7.5 ppm | Hexanediol Bacteria: *P. aeruginosa* 2% Fungi: *A. niger* 1% | Untreated 0 mm | Untreated 0 mm |
| 37 | Marlberry | *Ardisia japonica* (Thunb.) Blume | Marlberry | | | | |
| Comparative Example | Christmas berry | *Ardisia Crenata* | | 2.25 | MIC (%) Bacteria: 2 MIC (%) Fungi: >2 | 12.5 | 10.0 |
| Comparative Example | Marlberry (other area) | *Ardisia japonica* (Thunb.) Blume | | 1.31 | MIC (%) Bacteria: 1 MIC (%) Fungi: 1 | 11.2 | 13.4 |
| 37-1 | Whole plant | | | 0.20 | MIC (%) Bacteria: 0.5 MIC (%) Fungi: 0.25 | 27.0 | 21.1 |
| 37-2 | Roots | | | 0.15 | MIC (%) Bacteria: 0.13 MIC (%) Fungi: 0.25 | 16.3 | 10.0 |
| 37-3 | Stems | | | 0.99 | MIC (%) Bacteria: 0.5 MIC (%) Fungi: 1 | 12.3 | 10.9 |
| 37-4 | Leaves | | | 0.69 | MIC (%) Bacteria: 0.13 MIC (%) Fungi: 0.06 | 14.2 | 9.5 |
| 37-5 | Fruits | | | 0.17 | MIC (%) Bacteria: 0.25 MIC (%) Fungi: 0.5 | 27.7 | 20.8 |
| 37-6 | Flowers | | | 0.70 | MIC (%) Bacteria: 0.5 MIC (%) Fungi: 0.25 | 12.1 | 10.3 |

Example 38

Spoon-Leaf Yellow Loosestrife

TABLE 70

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 38 | Spoon-leaf yellow loosestrife | | *Lysimachia mauritiana Lam.* | Spoon-leaf yellow loosestrife | | | | |
| Comparative Example | Bog loosestrife | 50 | *Lysimachia Foenum-graecum* | | 71.24 | 8.82 | 1.52 | 181.01 |
| 38-1 | Whole plant | 2 | | | 34.92 | 17.76 | 25.41 | 196.21 |
| | | 10 | | | 27.95 | 26.79 | 31.42 | 370.62 |
| | | 50 | | | 24.82 | 30.19 | 35.02 | 511.53 |
| 38-2 | Roots | 2 | | | 37.18 | 11.23 | 21.17 | 296.61 |
| | | 10 | | | 29.67 | 25.75 | 32.66 | 472.30 |
| | | 50 | | | 23.60 | 33.75 | 36.67 | 558.49 |
| 38-3 | Stems | 2 | | | 39.65 | 12.57 | 23.12 | 377.75 |
| | | 10 | | | 27.22 | 27.86 | 31.84 | 430.19 |
| | | 50 | | | 20.06 | 30.39 | 39.72 | 690.04 |
| 38-4 | Leaves | 2 | | | 39.38 | 12.42 | 23.77 | 170.49 |
| | | 10 | | | 29.01 | 21.94 | 29.04 | 421.56 |
| | | 50 | | | 14.30 | 38.24 | 39.74 | 588.19 |
| 38-5 | Fruits | 2 | | | 37.80 | 13.48 | 25.34 | 276.49 |
| | | 10 | | | 32.12 | 25.31 | 33.37 | 463.56 |
| | | 50 | | | 23.87 | 36.57 | 34.27 | 657.79 |
| 38-6 | Flowers | 2 | | | 26.54 | 19.89 | 24.85 | 397.78 |
| | | 10 | | | 18.88 | 29.42 | 29.17 | 523.38 |
| | | 50 | | | 8.91 | 39.16 | 39.73 | 780.79 |

TABLE 71

| No. | Sample | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|
| | Control group | | | Vitamin C 7.5 ppm | Hexanediol Bacteria: *P. aeruginosa* 2% Fungi: *A. niger* 1% | Untreated 0 mm | Untreated 0 mm |
| 38 | Spoon-leaf yellow loosestrife | *Lysimachia mauritiana Lam.* | Spoon-leaf yellow loosestrife | | | | |
| Comparative Example | Bog loosestrife | *Lysimachia Foenum-graecum* | | 9.98 | MIC (%) Bacteria: 2 MIC (%) Fungi: >2 | 11.2 | 15.8 |
| 38-1 | Whole plant | | | 0.17 | MIC (%) Bacteria: 0.5 MIC (%) Fungi: 0.25 | 26.5 | 23.9 |
| 38-2 | Roots | | | 0.74 | MIC (%) Bacteria: 0.5 MIC (%) Fungi: 0.5 | 16.5 | 11.2 |
| 38-3 | Stems | | | 0.03 | MIC (%) Bacteria: 1 MIC (%) Fungi: 1 | 13.4 | 10.2 |
| 38-4 | Leaves | | | 0.72 | MIC (%) Bacteria: 0.06 MIC (%) Fungi: 0.13 | 23.2 | 24.0 |
| 38-5 | Fruits | | | 0.83 | MIC (%) Bacteria: 0.5 MIC (%) Fungi: 1 | 14.3 | 10.9 |
| 38-6 | Flowers | | | 0.34 | MIC (%) Bacteria: 0.13 MIC (%) Fungi: 0.06 | 9.6 | 8.3 |

Example 39

Climbing *Hydrangea*

TABLE 72

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 39 | Climbing hydrangea | | *Hydrangea petiolaris* Siebold & Zucc. | Climbing hydrangea | | | | |
| Comparative Example | Bigleaf hydrangea | 50 | *Hydrangea Macrophylla* | | 89.97 | 7.11 | 2.87 | 117.39 |
| 39-1 | Whole plant | 2 | | | 38.79 | 17.95 | 23.27 | 210.48 |
| | | 10 | | | 29.62 | 26.39 | 31.23 | 418.43 |
| | | 50 | | | 26.34 | 30.09 | 38.78 | 621.31 |
| 39-2 | Roots | 2 | | | 38.22 | 10.58 | 21.30 | 283.26 |
| | | 10 | | | 29.21 | 27.19 | 32.91 | 542.12 |
| | | 50 | | | 22.36 | 33.35 | 34.26 | 675.65 |
| 39-3 | Stems | 2 | | | 34.64 | 16.51 | 23.88 | 365.81 |
| | | 10 | | | 29.55 | 29.73 | 31.87 | 402.38 |
| | | 50 | | | 22.22 | 34.20 | 35.28 | 673.77 |
| 39-4 | Leaves | 2 | | | 39.53 | 12.38 | 26.32 | 343.01 |
| | | 10 | | | 22.33 | 25.77 | 31.37 | 436.24 |
| | | 50 | | | 13.11 | 38.75 | 44.01 | 703.27 |
| 39-6 | Flowers | 2 | | | 39.71 | 15.10 | 25.51 | 357.64 |
| | | 10 | | | 33.43 | 25.50 | 29.19 | 587.88 |
| | | 50 | | | 21.86 | 39.02 | 39.31 | 701.80 |

30

TABLE 73

| No. | Sample | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|
| | Control group | | | Vitamin C 7.5 ppm | Hexanediol Bacteria: *P. aeruginosa* 2% Fungi: *A. niger* 1% | Untreated 0 mm | Untreated 0 mm |
| 39 | Climbing hydrangea | *Hydrangea petiolaris* Siebold & Zucc. | Climbing hydrangea | | | | |
| Comparative Example | Bigleaf hydrangea | *Hydrangea Macrophylla* | | 3.95 | MIC (%) Bacteria: 2 MIC (%) Fungi: >2 | 11.1 | 11.0 |
| 39-1 | Whole plant | | | 0.13 | MIC (%) Bacteria: 0.5 MIC (%) Fungi: 0.5 | 19.5 | 18.0 |
| 39-2 | Roots | | | 0.54 | MIC (%) Bacteria: 1 MIC (%) Fungi: 0.5 | 9.9 | 10.0 |
| 39-3 | Stems | | | 0.61 | MIC (%) Bacteria: 0.06 MIC (%) Fungi: 0.13 | 11.1 | 13.9 |
| 39-4 | Leaves | | | 0.90 | MIC (%) Bacteria: 0.13 MIC (%) Fungi: 0.25 | 23.7 | 23.1 |
| 39-6 | Flowers | | | 0.37 | MIC (%) Bacteria: 0.5 MIC (%) Fungi: 0.25 | 26.9 | 24.2 |

Example 40

Stringy Stonecrop

TABLE 74

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 40 | Stringy stonecrop | | *Sedum sarmentosum* Bunge | Stringy stonecrop | | | | |
| Comparative Example | Purple stonecrop | 50 | *Sedum Purpureum* | | 76.08 | 13.10 | 2.38 | 23.78 |
| 40-1 | Whole plant | 2 | | | 35.39 | 10.57 | 16.54 | 253.81 |
| | | 10 | | | 31.83 | 23.48 | 28.53 | 329.93 |
| | | 50 | | | 33.75 | 26.13 | 29.54 | 584.07 |
| 40-2 | Roots | 2 | | | 37.72 | 14.22 | 26.29 | 229.26 |
| | | 10 | | | 31.98 | 23.42 | 27.48 | 600.32 |
| | | 50 | | | 26.74 | 30.35 | 34.39 | 743.58 |
| 40-3 | Stems | 2 | | | 34.77 | 8.52 | 15.43 | 214.85 |
| | | 10 | | | 33.20 | 19.09 | 22.27 | 467.36 |
| | | 50 | | | 32.38 | 25.45 | 28.18 | 527.02 |
| 40-4 | Leaves | 2 | | | 37.56 | 13.01 | 15.82 | 180.44 |
| | | 10 | | | 37.73 | 21.17 | 28.38 | 349.50 |
| | | 50 | | | 29.88 | 26.09 | 27.09 | 547.23 |
| 40-6 | Flowers | 2 | | | 38.53 | 15.35 | 24.01 | 311.16 |
| | | 10 | | | 31.46 | 28.33 | 32.01 | 518.92 |
| | | 50 | | | 26.18 | 35.04 | 35.48 | 645.94 |

30

TABLE 75

| No. | Sample | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|
| | Control group | | | Vitamin C 7.5 ppm | Hexanediol Bacteria: *P. aeruginosa* 2% Fungi: *A. niger* 1% | Untreated 0 mm | Untreated 0 mm |
| 40 | Stringy stonecrop | *Sedum sarmentosum* Bunge | Stringy stonecrop | | | | |
| Comparative Example | Purple stonecrop | *Sedum Purpureum* | | 6.94 | MIC (%) Bacteria: >2, Fungi: >2 | 10.4 | 12.1 |
| 40-1 | Whole plant | | | 0.78 | MIC (%) Bacteria: 1, Fungi: 2 | 21.7 | 21.7 |
| 40-2 | Roots | | | 0.21 | MIC (%) Bacteria: 0.5, Fungi: 1 | 19.1 | 17.2 |
| 40-3 | Stems | | | 0.83 | MIC (%) Bacteria: 1, Fungi: 2 | 13.3 | 12.1 |
| 40-4 | Leaves | | | 0.87 | MIC (%) Bacteria: 1, Fungi: 2 | 11.8 | 12.1 |
| 40-6 | Flowers | | | 0.75 | MIC (%) Bacteria: 0.5, Fungi: 0.5 | 27.3 | 21.6 |

50

Example 41

Ulleungdo Stonecrop

TABLE 76

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 41 | Ulleungdo stonecrop | | *Sedum takesimense* Nakai | Ulleungdo stonecrop | | | | |

TABLE 76-continued

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| Comparative Example | Purple stonecrop | 50 | *Sedum Purpureum* | | 76.08 | 13.10 | 2.38 | 23.78 |
| 41-1 | Whole plant | 2 | | | 33.73 | 11.80 | 20.36 | 253.41 |
| | | 10 | | | 31.83 | 23.25 | 22.52 | 469.56 |
| | | 50 | | | 29.27 | 29.39 | 29.28 | 580.53 |
| 41-2 | Roots | 2 | | | 35.86 | 13.83 | 24.41 | 238.58 |
| | | 10 | | | 29.79 | 23.23 | 27.70 | 524.91 |
| | | 50 | | | 23.36 | 35.49 | 36.60 | 619.40 |
| 41-3 | Stems | 2 | | | 35.95 | 18.89 | 24.77 | 253.27 |
| | | 10 | | | 31.13 | 22.43 | 33.45 | 415.51 |
| | | 50 | | | 22.66 | 33.46 | 39.79 | 742.65 |
| 41-4 | Leaves | 2 | | | 36.38 | 18.06 | 22.51 | 398.73 |
| | | 10 | | | 28.52 | 22.01 | 29.15 | 452.69 |
| | | 50 | | | 21.34 | 36.67 | 37.86 | 618.56 |
| 41-5 | Fruits | 2 | | | 37.60 | 13.45 | 26.81 | 334.49 |
| | | 10 | | | 29.85 | 27.09 | 32.93 | 426.94 |
| | | 50 | | | 25.50 | 35.10 | 37.42 | 780,63 |
| 41-6 | Flowers | 2 | | | 34.03 | 10.42 | 26.28 | 361.76 |
| | | 10 | | | 30.38 | 22.05 | 27.69 | 494.13 |
| | | 50 | | | 24.25 | 31.70 | 34.29 | 701.39 |

TABLE 77

| No. | Sample | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|
| | Control group | | | Vitamin C 7.5 ppm | Hexanediol Bacteria: *P. aeruginosa* 2% Fungi: *A. niger* 1% | Untreated 0 mm | Untreated 0 mm |
| 41 | Ulleungdo stonecrop | *Sedum takesimense* Nakai | Ulleungdo stonecrop | | | | |
| Comparative Example | Purple stonecrop | *Sedum Purpureum* | | 6.94 | MIC (%) Bacteria: >2, Fungi: >2 | 8.2 | 9.1 |
| 41-1 | Whole plant | | | 0.99 | MIC (%) Bacteria: 2, Fungi: 1 | 15.3 | 15.3 |
| 41-2 | Roots | | | 0.51 | MIC (%) Bacteria: 0.5, Fungi: 0.25 | 10.4 | 12.1 |
| 41-3 | Stems | | | 0.17 | MIC (%) Bacteria: 0.5, Fungi: 0.25 | 10.0 | 9.2 |
| 41-4 | Leaves | | | 0.53 | MIC (%) Bacteria: 0.5, Fungi: 0.25 | 12.9 | 13.6 |
| 41-5 | Fruits | | | 0.40 | MIC (%) Bacteria: 1, Fungi: 0.5 | 11.1 | 9.9 |
| 41-6 | Flowers | | | 0.77 | MIC (%) Bacteria: 1, Fungi: 0.5 | 23.3 | 22.9 |

45

Example 42

Foam Flower

TABLE 78

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 42 | Foam flower | | *Tiarella polyphylla* D. Don | Foam flower | | | | |
| 42-1 | Whole plant | 2 | | | 32.92 | 10.33 | 17.50 | 281.20 |
| | | 10 | | | 32.25 | 17.53 | 23.93 | 361.49 |
| | | 50 | | | 33.53 | 24.49 | 31.33 | 581.22 |
| 42-2 | Roots | 2 | | | 40.72 | 11.87 | 20.72 | 283.04 |
| | | 10 | | | 32.08 | 26.27 | 31.65 | 442.89 |
| | | 50 | | | 29.20 | 32.84 | 36.40 | 649.06 |

TABLE 78-continued

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| 42-3 | Stems | 2 | | | 40.52 | 11.95 | 25.70 | 344.61 |
| | | 10 | | | 36.44 | 22.98 | 27.56 | 476.99 |
| | | 50 | | | 32.09 | 33.52 | 38.77 | 684.26 |
| 42-4 | Leaves | 2 | | | 37.82 | 16.05 | 21.78 | 271.75 |
| | | 10 | | | 36.76 | 25.01 | 27.79 | 464.01 |
| | | 50 | | | 30.30 | 36.17 | 38.76 | 626.38 |
| 42-5 | Fruits | 2 | | | 41.19 | 18.76 | 21.46 | 350.48 |
| | | 10 | | | 33.53 | 27.78 | 27.73 | 403.43 |
| | | 50 | | | 29.19 | 36.53 | 36.44 | 695.07 |
| 42-6 | Flowers | 2 | | | 38.58 | 16.61 | 24.09 | 295.04 |
| | | 10 | | | 30.01 | 26.57 | 32.72 | 548.47 |
| | | 50 | | | 21.04 | 37.12 | 35.87 | 638.35 |

TABLE 79

| No. | Sample | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|
| | Control group | | | Vitamin C 7.5 ppm | Hexanediol Bacteria: *P. aeruginosa* 2% Fungi: *A. niger* 1% | Untreated 0 mm | Untreated 0 mm |
| 42 | Foam flower | *Tiarella polyphylla* D. Don | Foam flower | | | | |
| 42-1 | Whole plant | | | 0.94 | MIC (%) Bacteria: 0.5, Fungi: 1 | 9.8 | 11.8 |
| 42-2 | Roots | | | 0.85 | MIC (%) Bacteria: 0.125, Fungi: 0.25 | 7.7 | 9.1 |
| 42-3 | Stems | | | 0.56 | MIC (%) Bacteria: 0.125, Fungi: 0.25 | 10.1 | 11.0 |
| 42-4 | Leaves | | | 0.60 | MIC (%) Bacteria: 0.125, Fungi: 0.25 | 8.2 | 8.7 |
| 42-5 | Fruits | | | 0.70 | MIC (%) Bacteria: 0.25, Fungi: 0.5 | 8.6 | 8.8 |
| 42-6 | Flowers | | | 0.34 | MIC (%) Bacteria: 0.25, Fungi: 0.5 | 10.5 | 8.2 |

Example 43

East Asian Cinquefoil

TABLE 80

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Aibutin (200 ppm) 35% | TGFb (10 ppb) 25% | L-NMMA (5 ppm) 28% | EGF (10 ppb) 320% |
| 43 | East Asian cinquefoil | *Potentilla chinensis* Ser. | East Asian cinquefoil | | | | | |
| Comparative Example | Cinquefoil | 50 | *Potentilla Fragarioides* | | 88.07 | 16.32 | 6.56 | 27.58 |
| 43-1 | Whole plant | 2 | | | 35.27 | 13.65 | 21.34 | 364.57 |
| | | 10 | | | 28.24 | 24.98 | 30.42 | 599.09 |
| | | 50 | | | 25.83 | 39.02 | 39.00 | 745.04 |
| 43-2 | Roots | 2 | | | 39.63 | 12.91 | 16.55 | 300.91 |
| | | 10 | | | 32.51 | 23.78 | 24.91 | 356.73 |
| | | 50 | | | 29.51 | 30.30 | 30.13 | 550.44 |
| 43-3 | Stems | 2 | | | 39.83 | 12.41 | 17.59 | 272.21 |
| | | 10 | | | 36.83 | 16.29 | 26.94 | 478.27 |
| | | 50 | | | 31.45 | 30.02 | 27.35 | 544.84 |
| 43-4 | Leaves | 2 | | | 39.98 | 10.47 | 20.57 | 155.81 |
| | | 10 | | | 36.24 | 18.67 | 23.16 | 323.39 |
| | | 50 | | | 29.05 | 26.30 | 32.57 | 603.21 |
| 43-5 | Fruits | 2 | | | 36.28 | 13.61 | 20.54 | 217.19 |
| | | 10 | | | 30.69 | 21.80 | 28.68 | 448.88 |
| | | 50 | | | 21.74 | 35.27 | 35.40 | 647.89 |

TABLE 80-continued

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| 43-6 | Flowers | 2 | | | 39.95 | 11.70 | 18.58 | 268.01 |
| | | 10 | | | 32.13 | 21.05 | 26.12 | 362.91 |
| | | 50 | | | 32.13 | 30.29 | 28.11 | 574.09 |

TABLE 81

| No. | Sample | Conc. (ppm) | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|---|
| | Control group | | | | Vitamin C 7.5 ppm | Hexanediol Bacteria: *P. aeruginosa* 2% Fungi: *A. niger* 1% | Untreated 0 mm | Untreated 0 mm |
| 43 | East Asian cinquefoil | | *Potentilla chinensis* Ser. | East Asian cinquefoil | | | | |
| Comparative Example | Cinquefoil | 50 | *Potentilla Fragarioides* | | 8.99 | MIC (%) Bacteria: 2, Fungi: >2 | 10.7 | 9.1 |
| 43-1 | Whole plant | 2 | | | 0.43 | MIC (%) Bacteria: 0.5, Fungi: 1 | 27.4 | 22.0 |
| | | 10 | | | | | | |
| | | 50 | | | | | | |
| 43-2 | Roots | 2 | | | 0.48 | MIC (%) Bacteria: 1, Fungi: 2 | 12.3 | 14.3 |
| | | 10 | | | | | | |
| | | 50 | | | | | | |
| 43-3 | Stems | 2 | | | 0.71 | MIC (%) Bacteria: 1, Fungi: 2 | 10.4 | 12.0 |
| | | 10 | | | | | | |
| | | 50 | | | | | | |
| 43-4 | Leaves | 2 | | | 0.84 | MIC (%) Bacteria: 1, Fungi: 2 | 16.3 | 11.1 |
| | | 10 | | | | | | |
| | | 50 | | | | | | |
| 43-5 | Fruits | 2 | | | 0.33 | MIC (%) Bacteria: 0.5, Fungi: 1 | 26.5 | 27.2 |
| | | 10 | | | | | | |
| | | 50 | | | | | | |
| 43-6 | Flowers | 2 | | | 0.93 | MIC (%) Bacteria; 1, Fungi: 2 | 23.2 | 26.5 |
| | | 10 | | | | | | |
| | | 50 | | | | | | |

Example 44

Indigobush *Amorpha*

TABLE 82

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 44 | Indigobush Amorpha | | *Amorpha fruticosa* L. | Indigobnsh Amorpha | | | | |
| Comparative Example | Indigobush Amorpha (other area) | 50 | | | 68.12 | 10.71 | 12.24 | 98.27 |
| 44-1 | Whole plant | 2 | | | 38.07 | 13.33 | 22.43 | 374.92 |
| | | 10 | | | 32.00 | 24.16 | 31.54 | 472.24 |
| | | 50 | | | 23.50 | 39.80 | 39.92 | 777.80 |
| 44-2 | Roots | 2 | | | 39.58 | 10.22 | 26.46 | 385.24 |
| | | 10 | | | 30.90 | 29.26 | 27.46 | 506.11 |
| | | 50 | | | 20.89 | 38.05 | 39.67 | 779.60 |
| 44-3 | Stems | 2 | | | 34.50 | 16.37 | 25.79 | 284.40 |
| | | 10 | | | 27.46 | 23.20 | 27.90 | 574.37 |
| | | 50 | | | 25.70 | 37.89 | 36.57 | 678.03 |

TABLE 82-continued

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| 44-4 | Leaves | 2 | | | 36.70 | 16.06 | 23.06 | 277.22 |
| | | 10 | | | 33.04 | 23.51 | 28.60 | 503.70 |
| | | 50 | | | 24.81 | 38.61 | 35.74 | 672.03 |
| 44-5 | Fruits | 2 | | | 37.14 | 10.13 | 22.82 | 269.86 |
| | | 10 | | | 29.98 | 23.29 | 29.47 | 504.28 |
| | | 50 | | | 21.54 | 31.80 | 37.19 | 693.12 |
| 44-6 | Flowers | 2 | | | 35.01 | 17.34 | 20.36 | 326.61 |
| | | 10 | | | 29.38 | 21.63 | 27.86 | 458.33 |
| | | 50 | | | 23.27 | 34.98 | 37.99 | 716.50 |

15

TABLE 83

| No. | Sample | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|
| | Control group | | | Vitamin C 7.5 ppm | Hexanediol Bacteria: *P. aeruginosa* 2% Fungi: *A. niger* 1% | Untreated 0 mm | Untreated 0 mm |
| 44 | Indigobush Amorpha | *Amorpha fruticosa* L. | Indigobush Amorpha | | | | |
| Comparative Example | Indigobush Amorpha (other area) | | | 2.45 | MIC (%) Bacteria: 1 MIC (%) Fungi: 2 | 15.8 | 14.0 |
| 44-1 | Whole plant | | | 0.74 | MIC (%) Bacteria: 0.25 MIC (%) Fungi: 0.5 | 26.6 | 24.6 |
| 44-2 | Roots | | | 0.03 | MIC (%) Bacteria: 0.25 MIC (%) Fungi: 0.5 | 9.3 | 8.5 |
| 44-3 | Stems | | | 0.50 | MIC (%) Bacteria: 0.5 MIC (%) Fungi: 0.5 | 13.5 | 14.0 |
| 44-4 | Leaves | | | 0.16 | MIC (%) Bacteria: 0.5 MIC (%) Fungi: 0.5 | 23.1 | 25.9 |
| 44-5 | Fruits | | | 0.32 | MIC (%) Bacteria: 1 MIC (%) Fungi: 0.5 | 14.1 | 13.1 |
| 44-6 | Flowers | | | 0.35 | MIC (%) Bacteria: 1 MIC (%) Fungi: 0.5 | 26.6 | 27.6 |

Example 45

Sericea *Lespedeza*

TABLE 84

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 45 | Sericea lespedeza | *Lespedeza cuneata* (Dum. Cours.) G. Don | Sericea lespedeza | | | | | |
| Comparative Example | Leafy lespedeza | 50 | *Lespedeza Cyrtobotrya* | | 90.93 | 10.72 | 4.67 | 74.92 |
| 45-1 | Whole plant | 2 | | | 36.68 | 15.09 | 21.51 | 352.11 |
| | | 10 | | | 33.46 | 29.94 | 27.22 | 437.21 |
| | | 50 | | | 23.34 | 30.60 | 36.63 | 602.02 |
| 45-2 | Roots | 2 | | | 39.64 | 19.22 | 23.59 | 278.18 |
| | | 10 | | | 27.50 | 23.80 | 31.62 | 488.76 |
| | | 50 | | | 21.68 | 32.52 | 36.64 | 622.98 |

TABLE 84-continued

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| 45-3 | Stems | 2 | | | 37.77 | 14.84 | 24.66 | 361.91 |
| | | 10 | | | 28.94 | 23.27 | 30.43 | 406.33 |
| | | 50 | | | 20.17 | 36.76 | 37.81 | 609.27 |
| 45-4 | Leaves | 2 | | | 39.24 | 12.55 | 25.39 | 376.56 |
| | | 10 | | | 31.04 | 26.94 | 27.48 | 504.51 |
| | | 50 | | | 24.28 | 31.41 | 36.77 | 675.53 |
| 45-5 | Fruits | 2 | | | 37.34 | 19.97 | 22.68 | 307.41 |
| | | 10 | | | 31.81 | 29.49 | 29.60 | 402.24 |
| | | 50 | | | 22.30 | 32.23 | 37.52 | 735.82 |
| 45-6 | Flowers | 2 | | | 34.63 | 11.42 | 24,05 | 339.02 |
| | | 10 | | | 31.11 | 27.68 | 31.53 | 516.40 |
| | | 50 | | | 22.49 | 39.90 | 37.70 | 761.92 |

TABLE 85

| No. | Sample | Conc. (ppm) | Scientific name | English name | Anti-oxidation IC50 (%) | Anti-bacteria MIC (%) |
|---|---|---|---|---|---|---|
| | Control group | | | | Vitamin C 7.5 ppm | Hexanediol Bacteria: P.aeruginosa 2% Fungi: A.niger 1% |
| 45 | *Sericea lespedeza* | *Lespedeza cuneata* (Dum. Cours.) G. Don. | *Sericea lespedeza* | | | |
| Comparative Example | Leafy lespedeza | *Lespedeza Cyrtobotrya* | | | 4.93 | MIC (%) Bacteria: >2 MIC (%) Fungi: >2 |
| 45-1 | Whole plant | 2 | | | 0.90 | MIC (%) Bacteria: 0.5 MIC (%) Fungi: 0.5 |
| | | 10 | | | | |
| | | 50 | | | | |
| 45-2 | Roots | 2 | | | 0.89 | MIC (%) Bacteria: 0.125 MIC (%) Fungi: 0.5 |
| | | 10 | | | | |
| | | 50 | | | | |
| 45-3 | Stems | 2 | | | 0.68 | MIC (%) Bacteria: 0.25 MIC (%) Fungi: 0.25 |
| | | 10 | | | | |
| | | 50 | | | | |
| 45-4 | Leaves | 2 | | | 0.22 | MIC (%) Bacteria: 0.125 MIC (%) Fungi: 0.25 |
| | | 10 | | | | |
| | | 50 | | | | |
| 45-5 | Fruits | 2 | | | 0.78 | MIC (%) Bacteria: 0.5 MIC (%) Fungi: 0.5 |
| | | 10 | | | | |
| | | 50 | | | | |
| 45-6 | Flowers | 2 | | | 0.03 | MIC (%) Bacteria: 0.25 MIC (%) Fungi: 0.5 |
| | | 10 | | | | |
| | | 50 | | | | |

| No. | Sample | Anti-bacteria (S. mutans) Size of growth inhibition ring (mm) | Anti-bacteria (P. gingivalis) Size of growth inhibition ring (mm) |
|---|---|---|---|
| | Control group | Untreated 0 mm | Untreated 0 mm |
| 45 | *Sericea lespedeza* | | |
| Comparative Example | Leafy lespedeza | 0.0 | 0.0 |
| 45-1 | Whole plant | 8.8 | 9.4 |
| 45-2 | Roots | 13.6 | 12.0 |
| 45-3 | Stems | 11.9 | 14.9 |
| 45-4 | Leaves | 9.1 | 10.0 |
| 45-5 | Fruits | 12.5 | 12.4 |
| 45-6 | Flowers | 8.6 | 9.4 |

Example 46

Alfalfa

TABLE 86

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 46 | Alfalfa | | *Medicago sativa* L. | Alfalfa | | | | |
| 46-1 | Whole plant | 2 | | | 38.32 | 13.70 | 23.48 | 265.24 |
| | | 10 | | | 31.97 | 21.20 | 28.33 | 595.91 |
| | | 50 | | | 24.28 | 30.18 | 35.78 | 701.01 |
| 46-2 | Roots | 2 | | | 36.65 | 18.39 | 23.94 | 337.91 |
| | | 10 | | | 29.15 | 27.16 | 33.82 | 498.90 |
| | | 50 | | | 20.35 | 34.26 | 36.27 | 731.25 |
| 46-3 | Stems | 2 | | | 39.90 | 15.39 | 24.36 | 385.97 |
| | | 10 | | | 27.33 | 22.35 | 31.45 | 538.06 |
| | | 50 | | | 23.61 | 33.40 | 35.94 | 611.31 |
| 46-4 | Leaves | 2 | | | 37.26 | 19.83 | 22.65 | 262.66 |
| | | 10 | | | 31.85 | 27.25 | 29.45 | 525.95 |
| | | 50 | | | 26.42 | 39.98 | 37.97 | 720.95 |
| 46-5 | Fruits | 2 | | | 36.02 | 15.79 | 25.60 | 310.30 |
| | | 10 | | | 32.92 | 28.89 | 32.42 | 559.89 |
| | | 50 | | | 23.11 | 39.98 | 36.37 | 789.47 |
| 46-6 | Flowers | 2 | | | 38.02 | 10.08 | 23.91 | 371.58 |
| | | 10 | | | 27.35 | 25.91 | 28.98 | 500.28 |
| | | 50 | | | 21.51 | 34.78 | 36.66 | 770.21 |

TABLE 87

| No. | Sample | Scientific name | English name | Anti-oxidation IC50 (%) | Anti-bacteria MIC (%) | Anti-bacteria (S. mutans) Size of growth inhibition ring (mm) | Anti-bacteria (P. gingivalis) Size of growth inhibition ring (mm) |
|---|---|---|---|---|---|---|---|
| | Control group | | | Vitamin C 7.5 ppm | Hexanediol Bacteria: P.aeruginosa 2% Fungi: A.niger 1% | Untreated 0 mm | Untreated 0 mm |
| 46 | Alfalfa | *Medicago sativa* L. | Alfalfa | | | | |
| 46-1 | Whole plant | | | 0.72 | MIC (%) Bacteria: 1 MIC (%) Fungi: 1 | 14.5 | 23.6 |
| 46-2 | Roots | | | 0.62 | MIC (%) Bacteria: 0.25 MIC (%) Fungi: 1 | 18.2 | 12.1 |
| 46-3 | Stems | | | 1.00 | MIC (%) Bacteria: 1 MIC (%) Fungi: 0.5 | 18.0 | 15.5 |
| 46-4 | Leaves | | | 0.62 | MIC (%) Bacteria: 0.25 MIC (%) Fungi: 0.25 | 18.8 | 19.5 |
| 46-5 | Fruits | | | 0.61 | MIC (%) Bacteria: 0.25 MIC (%) Fungi: 0.5 | 9.6 | 9.1 |
| 46-6 | Flowers | | | 0.39 | MIC (%) Bacteria: 0.25 MIC (%) Fungi: 0.25 | 21.5 | 23.3 |

50

Example 47

Amur Vetch

TABLE 88

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 47 | Amur vetch | | *Vicia amurensis* Oett. | Amur vetch | | | 2.33 | 48.67 |

TABLE 88-continued

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| Comparative Example | Broad bean | 50 | Vicia Faba | | 99.44 | 4.07 | 26.68 | 270.24 |
| 47-1 | Whole plant | 2 | | | 39.97 | 17.99 | 33.37 | 420.30 |
| | | 10 | | | 30.18 | 21.04 | 34.06 | 658.79 |
| | | 50 | | | 22.69 | 33.43 | 24.72 | 352.08 |
| 47-2 | Roots | 2 | | | 39.26 | 12.69 | 29.46 | 579.68 |
| | | 10 | | | 30.17 | 20.13 | 35.13 | 613.79 |
| | | 50 | | | 21.97 | 38.61 | 22.23 | 300.87 |
| 47-3 | Stems | 2 | | | 38.08 | 17.51 | 32.11 | 524.86 |
| | | 10 | | | 33.66 | 26.64 | 37.94 | 678.84 |
| | | 50 | | | 20.74 | 37.72 | 26.05 | 350.85 |
| 47-4 | Leaves | 2 | | | 37.90 | 11.37 | 31.08 | 515.02 |
| | | 10 | | | 30.76 | 20.91 | 34.10 | 789.15 |
| | | 50 | | | 22.69 | 33.04 | 21.96 | 291.96 |
| 47-5 | Fruits | 2 | | | 37.86 | 13.37 | 27.05 | 535.22 |
| | | 10 | | | 27.59 | 25.76 | 37.24 | 773.53 |
| | | 50 | | | 24.21 | 36.96 | 23.17 | 382.55 |
| 47-6 | Flowers | 2 | | | 34.62 | 19.57 | 32.58 | 497.85 |
| | | 10 | | | 32.38 | 25.45 | 35.98 | 624.42 |
| | | 50 | | | 24.05 | 36.86 | Anti-inflammation | Moisturizing |

TABLE 89

| No. | Sample | Scientific name | English name | Anti-oxidation IC50 (%) | Anti-bacteria MIC (%) | Anti-bacteria (S. mutans) Size of growth inhibition ring (mm) | Anti-bacteria (P. gingivalis) Size of growth inhibition ring (mm) |
|---|---|---|---|---|---|---|---|
| | Control group | | | Vitamin C 7.5 ppm | Hexanediol Bacteria: P.aeruginosa 2% Fungi: A.niger 1% | Untreated 0 mm | Untreated 0 mm |
| 47 | Amur vetch | Vicia amurensis Oett. | Amur vetch | | | | |
| Comparative Example | Broad bean | Vicia Faba | | 5.01 | MIC (%) Bacteria: >2 MIC (%) Fungi: 2 | 8.6 | 9.2 |
| 47-1 | Whole plant | | | 0.63 | MIC (%) Bacteria: 1 MIC (%) Fungi: 0.5 | 23.7 | 21.7 |
| 47-2 | Roots | | | 0.86 | MIC (%) Bacteria: 0.25 MIC (%) Fungi: 0.5 | 26.6 | 21.4 |
| 47-3 | Stems | | | 0.57 | MIC (%) Bacteria: 1 MIC (%) Fungi: 0.5 | 27.2 | 17.3 |
| 47-4 | Leaves | | | 0.40 | MIC (%) Bacteria: 0.5 MIC (%) Fungi: 0.5 | 23.7 | 21.8 |
| 47-5 | Fruits | | | 0.28 | MIC (%) Bacteria: 1 MIC (%) Fungi: 0.5 | 15.1 | 9.7 |
| 47-6 | Flowers | | | 0.30 | MIC (%) Bacteria: 1 MIC (%) Fungi: 0.5 | 18.0 | 18.9 |

Example 48

Hairy Purple Loosestrife

TABLE 90

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF(10 ppb) 320% |
| 48 | Hairy purple loosestrife | | Lythrum salicaria L. | Hairy purple loosestrife | | | | |
| 48-1 | Whole plant | 2 | | | 37.35 | 17.25 | 22.56 | 349.99 |
| | | 10 | | | 35.58 | 26.34 | 24.34 | 559.12 |
| | | 50 | | | 30.49 | 31.64 | 28.61 | 687.02 |

TABLE 90-continued

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| 48-2 | Roots | 2 | | | 35.02 | 13.53 | 22.55 | 307.92 |
| | | 10 | | | 30.53 | 25.75 | 27.19 | 468.32 |
| | | 50 | | | 21.03 | 38.59 | 37.53 | 662.99 |
| 48-3 | Stems | 2 | | | 35.39 | 12.59 | 26.40 | 266.77 |
| | | 10 | | | 32.88 | 22.87 | 27.52 | 495.52 |
| | | 50 | | | 23.41 | 39.46 | 35.09 | 620.57 |
| 48-4 | Leaves | 2 | | | 38.33 | 12.92 | 24.19 | 252.16 |
| | | 10 | | | 27.28 | 27.70 | 32.91 | 511.41 |
| | | 50 | | | 21.09 | 33.61 | 38.26 | 708.37 |
| 48-5 | Fruits | 2 | | | 34.37 | 10.52 | 22.03 | 381.00 |
| | | 10 | | | 31.72 | 28.95 | 29.90 | 476.07 |
| | | 50 | | | 21.29 | 38.03 | 39.07 | 740.05 |
| 48-6 | Flowers | 2 | | | 38.25 | 15.18 | 20.83 | 309.53 |
| | | 10 | | | 30.12 | 19.22 | 30.31 | 404.98 |
| | | 50 | | | 20.58 | 29.24 | 37.94 | 763.26 |
| 48-7 | Shoots | 2 | | | 39.93 | 11.12 | 20.26 | 306.27 |
| | | 10 | | | 33.81 | 23.68 | 33.16 | 534.68 |
| | | 50 | | | 24.16 | 32.23 | 39.67 | 722.82 |

TABLE 91

| No. | Sample | Scientific name | English name | Anti-oxidation IC50 (%) | Anti-bacteria MIC (%) | Anti-bacteria (S. mutans) Size of growth inhibition ring (mm) | Anti-bacteria (P. gingivalis) Size of growth inhibition ring (mm) |
|---|---|---|---|---|---|---|---|
| | Control group | | | Vitamin C 7.5 ppm | Hexanediol Bacteria: P.aeruginosa 2% Fungi: A.niger 1% | Untreated 0 mm | Untreated 0 mm |
| 48 | Hairy purple loosestrife | Lythrum salicaria L. | Hairy purple loosestrife | | | | |
| 48-1 | Whole plant | | | 1.95 | MIC (%) Bacteria: 0.25, Fungi:0.25 | 16.2 | 8.9 |
| 48-2 | Roots | | | 0.21 | MIC (%) Bacteria: 1, Fungi: 0.125 | 24.8 | 18.7 |
| 48-3 | Stems | | | 0.75 | MIC (%) Bacteria: 2, Fungi: 0.5 | 21.2 | 8.9 |
| 48-4 | Leaves | | | 0.95 | MIC (%) Bacteria: 0.5, Fungi: 1 | 15.2 | 26.1 |
| 48-5 | Fruits | | | 0.56 | MIC (%) Bacteria: 2, Fungi: 0.5 | 14.6 | 15.3 |
| 48-6 | Flowers | | | 0.59 | MIC (%) Bacteria: 1, Fungi: 0.25 | 27.2 | 26.3 |
| 48-7 | Shoots | | | 0.80 | MIC (%) Bacteria: 2, Fungi: 1 | 11.6 | 13.5 |

Example 49

South Enchanter's Nightshade

TABLE 92

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25 | L-NMMA (5 ppm) 28% | EGF (10 ppb) 320% |
| 49 | South enchanter's nightshade | | Circaea mollis Siebold & Zucc. | South enchanter's nightshade | | | | |
| Comparative Example | Cordata enchanter's nightshade | 50 | Circaea Cordata | Cordata | 84.92 | 15.76 | 2.11 | 82.40 |
| 49-1 | Whole plant | 2 | | | 37.51 | 16.04 | 21.59 | 400.02 |
| | | 10 | | | 33.85 | 22.68 | 25.26 | 478.55 |
| | | 50 | | | 21.52 | 31.88 | 27.96 | 767.34 |
| 49-2 | Roots | 2 | | | 35.69 | 19.75 | 25.72 | 355.34 |
| | | 10 | | | 31.89 | 24.22 | 28.16 | 447.18 |
| | | 50 | | | 20.58 | 34.35 | 34.60 | 654.97 |
| 49-3 | Stems | 2 | | | 39.27 | 11.89 | 21.43 | 363.29 |
| | | 10 | | | 29.58 | 21.06 | 31.27 | 409.44 |
| | | 50 | | | 20.88 | 34.70 | 36.11 | 737.06 |

TABLE 92-continued

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| 49-4 | Leaves | 2 | | | 34.92 | 17.84 | 26.40 | 357.85 |
| | | 10 | | | 30.89 | 21.26 | 29.24 | 484.90 |
| | | 50 | | | 24.75 | 31.58 | 38.05 | 621.21 |
| 49-5 | Fruits | 2 | | | 37.92 | 17.63 | 22.60 | 280.84 |
| | | 10 | | | 30.21 | 25.50 | 33.99 | 529.37 |
| | | 50 | | | 20.77 | 33.25 | 38.86 | 789.95 |
| 49-6 | Flowers | 2 | | | 38.52 | 17.02 | 22.50 | 384.53 |
| | | 10 | | | 32.44 | 38.82 | 27.66 | 468.93 |
| | | 50 | | | 20.91 | 33.14 | 37.28 | 614.21 |

TABLE 93

| No. | Sample | Scientific name | English name | Anti-oxidation IC50 (%) |
|---|---|---|---|---|
| | Control group | | | Vitamin C 7.5 ppm |
| 49 | South enchanter's nightshade | *Circaea mollis* Siebold & Zucc. | South enchanter's nightshade | |
| Comparative Example | Cordata enchanter's nightshade | *Circaea Cordata* | Cordata | 3.81 |
| 49-1 | Whole plant | | | 0.22 |
| 49-2 | Roots | | | 0.67 |
| 49-3 | Stems | | | 0.03 |
| 49-4 | Leaves | | | 0.03 |
| 49-5 | Fruits | | | 0.93 |
| 49-6 | Flowers | | | 0.21 |

| No. | Sample | Anti-bacteria MIC (%) | Anti-bacteria (S. mutans) Size of growth inhibition ring (mm) | Anti-bacteria (P. gingivalis) Size of growth inhibition ring (mm) |
|---|---|---|---|---|
| | Control group | Hexanediol Bacteria: P.aeruginosa 2% Fungi: A.niger 1% | Untreated 0 mm | Untreated 0 mm |
| 49 | South enchanter's nightshade | | | |
| Comparative Example | Cordata enchanter's nightshade | MIC (%) Bacteria: 2, Fungi: 2 | 11.4 | 8.2 |
| 49-1 | Whole plant | MIC (%) Bacteria: 0.25, Fungi: 0.125 | 25.2 | 20.8 |
| 49-2 | Roots | MIC (%) Bacteria: 1, Fungi: 0.125 | 14.8 | 13.9 |
| 49-3 | Stems | MIC (%) Bacteria: 0.5, Fungi: 1 | 27.5 | 19.6 |
| 49-4 | Leaves | MIC (%) Bacteria: 1, Fungi: 1 | 9.4 | 14.9 |
| 49-5 | Fruits | MIC (%) Bacteria: 2, Fungi: 0.5 | 12.6 | 26.4 |
| 49-6 | Flowers | MIC (%) Bacteria: 0.5, Fungi: 0.125 | 15.2 | 19.8 |

Example 50

Long-Seed Willowherb

TABLE 94

| No. | Sample | Conc. (ppm) | Scientific name | English name | Whitening Melanin content (%) |
|---|---|---|---|---|---|
| | Control group | | | | Arbutin (200 ppm) 35% |
| 50 | Long-seed willowherb | | *Epilobium pyrricholophum* Franch. & Sav. | Long-seed willowherb | |

TABLE 94-continued

| | | | | | |
|---|---|---|---|---|---|
| Comparative Example | Willow herb | 50 | *Epilobium Angustifolium* | | 77.09 |
| 50-1 | Whole plant | 2 | | | 37.44 |
| | | 10 | | | 36.73 |
| | | 50 | | | 30.18 |
| 50-2 | Roots | 2 | | | 36.95 |
| | | 10 | | | 27.26 |
| | | 50 | | | 23.37 |
| 50-3 | Stems | 2 | | | 37.70 |
| | | 10 | | | 28.71 |
| | | 50 | | | 20.98 |
| 50-4 | Leaves | 2 | | | 34.31 |
| | | 10 | | | 29.40 |
| | | 50 | | | 22.55 |
| 50-5 | Fruits | 2 | | | 36.94 |
| | | 10 | | | 31.57 |
| | | 50 | | | 21.68 |
| 50-6 | Flowers | 2 | | | 37.73 |
| | | 10 | | | 31.02 |
| | | 50 | | | 21.89 |

| No. | Sample | Anti-wrinkle Collagen synthesis (% of control) | Anti-inflammation Inhibition of NO production (%) | Moisturizing HA synthesis (%) |
|---|---|---|---|---|
| 50 | Control group Long-seed willowherb | TGFb (10 ppb) 25% | L-NMMA (5 ppm) 28% | EGF (10 ppb) 320% |
| Comparative Example | Willow herb | 4.19 | 3.89 | 83.23 |
| 50-1 | Whole plant | 10.27 | 20.52 | 294.93 |
| | | 16.25 | 24.97 | 337.84 |
| | | 25.92 | 30.19 | 440.70 |
| 50-2 | Roots | 16.83 | 22.42 | 252.06 |
| | | 28.23 | 28.55 | 577.26 |
| | | 36.60 | 39.95 | 602.36 |
| 50-3 | Stems | 10.49 | 22.70 | 356.82 |
| | | 29.58 | 27.27 | 419.73 |
| | | 32.44 | 36.82 | 656.87 |
| 50-4 | Leaves | 13.21 | 23.28 | 309.86 |
| | | 22.99 | 31.42 | 497.72 |
| | | 36.94 | 38.17 | 608.79 |
| 50-5 | Fruits | 10.39 | 21.86 | 292.71 |
| | | 29.84 | 30.92 | 408.55 |
| | | 31.70 | 35.24 | 759.80 |
| 50-6 | Flowers | 18.51 | 26.27 | 272.12 |
| | | 27.36 | 31.85 | 523.59 |
| | | 35.72 | 37.51 | 779.15 |

TABLE 95

| No. | Sample | Scientific name | English name | Anti-oxidation IC50 (%) | Anti-bacteria MIC (%) |
|---|---|---|---|---|---|
| | Control group | | | Vitamin C 7.5 ppm | Hexanediol Bacteria: P.aeruginosa 2% Fungi: A.niger 1% |
| 50 | Long-seed willowherb | *Epilobium pyrricholophum* Franch. & Sav. | Long-seed willowherb | | |
| Comparative Example | Willow herb | *Epilobium Angustifolium* | | 3.34 | MIC (%) Bacteria, Fungi: >2 |
| 50-1 | Whole plant | | | 1.76 | MIC (%) Bacteria: 2, Fungi: 0.5 |
| 50-2 | Roots | | | 0.61 | MIC (%) Bacteria: 1, Fungi: 0.125 |
| 50-3 | Stems | | | 0.76 | MIC (%) Bacteria: 1, Fungi: 0.5 |
| 50-4 | Leaves | | | 0.91 | MIC (%) Bacteria: 1, Fungi: 1 |
| 50-5 | Fruits | | | 0.95 | MIC (%) Bacteria: 2, Fungi: 0.5 |
| 50-6 | Flowers | | | 0.49 | MIC (%) Bacteria: 1, Fungi: 0.25 |

TABLE 95-continued

| No. | Sample | Anti-bacteria (S. mutans) Size of growth inhibition ring (mm) | Anti-bacteria (P. gingivalis) Size of growth inhibition ring (mm) |
|---|---|---|---|
| 50 | Control group Long-seed willowherb | Untreated 0 mm | Untreated 0 mm |
| Comparative Example | Willow herb | 8.4 | 9.6 |
| 50-1 | Whole plant | 18.7 | 18.0 |
| 50-2 | Roots | 27.2 | 26.2 |
| 50-3 | Stems | 14.8 | 21.7 |
| 50-4 | Leaves | 18.7 | 16.9 |
| 50-5 | Fruits | 20.9 | 14.4 |
| 50-6 | Flowers | 23.3 | 14.4 |

Example 51

Evening Primrose

20

TABLE 96

| No. | Sample | Conc. (ppm) | Scientific name | English name | Whitening Melanin content (%) |
|---|---|---|---|---|---|
| | Control group | | | | Arbutin (200 ppm) 35% |
| 51 | Evening Primrose | | *Oenothera biennis L* | Evening Primrose | |
| Comparative Example | Baby Evening Primrose | 50 | *Oenothera Laciniata* | | 94.61 |
| Comparative Example | Evening Primrose (other area) | 50 | | | 57.79 |
| 51-1 | Whole plant | 2 | | | 39.09 |
| | | 10 | | | 32.01 |
| | | 50 | | | 25.30 |
| 51-2 | Roots | 2 | | | 36.95 |
| | | 10 | | | 30.69 |
| | | 50 | | | 23.42 |
| 51-3 | Stems | 2 | | | 36.29 |
| | | 10 | | | 28.25 |
| | | 50 | | | 26.83 |
| 51-4 | Leaves | 2 | | | 39.62 |
| | | 10 | | | 31.30 |
| | | 50 | | | 22.36 |
| 51-5 | Fruits | 2 | | | 38.13 |
| | | 10 | | | 34.15 |
| | | 50 | | | 31.67 |
| 51-6 | Flowers | 2 | | | 37.11 |
| | | 10 | | | 36.75 |
| | | 50 | | | 33.18 |

| No. | Sample | Anti-wrinkle Collagen synthesis (% of control) | Anti-inflammation Inhibition of NO production (%) | Moisturizing HA synthesis (%) |
|---|---|---|---|---|
| | Control group | TGFb (10 ppb) 25% | L-NMMA (5 ppm) 28% | EGF (10 ppb) 320% |
| 51 | Evening Primrose | | | |
| Comparative Example | Baby Evening Primrose | 11.04 | 1.55 | 38.49 |
| Comparative Example | Evening Primrose (other area) | 19.76 | 13.57 | 223.99 |
| 51-1 | Whole plant | 13.95 | 25.50 | 326.64 |
| | | 29.55 | 29.67 | 429.82 |
| | | 39.57 | 34.21 | 640.63 |
| 51-2 | Roots | 18.88 | 22.30 | 251.32 |
| | | 27.94 | 30.80 | 541.90 |
| | | 39.36 | 34.68 | 688.18 |

TABLE 96-continued

| 51-3 | Stems | 14.69 | 21.01 | 339.07 |
|---|---|---|---|---|
| | | 23.22 | 31.45 | 492.49 |
| | | 36.18 | 37.45 | 788.18 |
| 51-4 | Leaves | 12.94 | 23.12 | 354.45 |
| | | 20.50 | 32.29 | 516.72 |
| | | 28.41 | 35.01 | 712.28 |
| 51-5 | Fruits | 14.06 | 23.22 | 330.97 |
| | | 20.56 | 31.46 | 539.64 |
| | | 27.26 | 35.17 | 630.25 |
| 51-6 | Flowers | 14.74 | 20.89 | 236.47 |
| | | 16.42 | 25.16 | 361.37 |
| | | 30.24 | 30.64 | 437.40 |

TABLE 97

| No. | Sample | Scientific name | English name | Anti-oxidation IC50 (%) | Anti-bacteria MIC (%) |
|---|---|---|---|---|---|
| | Control group | | | Vitamin C 7.5 ppm | Hexanediol 2% |
| 51 | Evening Primrose | *Oenothera biennis* L. | Evening Primrose | | Bacteria: P.aeruginosa |
| Comparative Example | Baby Evening Primrose | *Oenothera Laciniata* | | 5.14 | Fungi: A.niger 1% |
| Comparative Example | Evening Primrose (other area) | | | 2.21 | |
| 51-1 | Whole plant | | | 0.44 | MIC (%) Bacteria: 2, Fungi: >2 |
| 51-2 | Roots | | | 0.55 | MIC (%) Bacteria: 2, Fungi: 1 |
| 51-3 | Stems | | | 0.66 | MIC (%) Bacteria: 0.25, Fungi: 0.125 |
| 51-4 | Leaves | | | 0.62 | MIC (%) Bacteria: 1, Fungi: 0.125 |
| 51-5 | Fruits | | | 0.86 | MIC (%) Bacteria: 1, Fungi: 0.5 |
| 51-6 | Flowers | | | 0.37 | MIC (%) Bacteria: 1, Fungi: 1 |
| | | | | | MIC (%) Bacteria: 2, Fungi: 0.5 |
| | | | | | MIC (%) Bacteria: 1, Fungi: 0.25 |

| No. | Sample | Anti-bacteria (S. mutans) Size of growth inhibition ring (mm) | Anti-bacteria (P. gingivalis) Size of growth inhibition ring (mm) |
|---|---|---|---|
| | Control group | Untreated 0 mm | Untreated 0 mm |
| 51 | Evening Primrose | | |
| Comparative Example | Baby Evening Primrose | 8.6 | 8.5 |
| Comparative Example | Evening Primrose (other area) | 14.8 | 15.3 |
| 51-1 | Whole plant | 25.1 | 24.6 |
| 51-2 | Roots | 14.4 | 14.6 |
| 51-3 | Stems | 17.5 | 11.3 |
| 51-4 | Leaves | 24.6 | 22.5 |
| 51-5 | Fruits | 17.4 | 10.2 |
| 51-6 | Flowers | 19.5 | 26.2 |

Example 52

Stolon Golden Saxifrage

55

TABLE 98

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 52 | Stolon golden saxifrage | | *Chrysosplenium flagelliferum* F. Schmidt | Stolon golden saxifrage | | | | |

TABLE 98-continued

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| 52-1 | Whole plant | 2 | | | 36.59 | 14.26 | 21.63 | 231.94 |
| | | 10 | | | 32.17 | 20.06 | 29.07 | 540.11 |
| | | 50 | | | 21.60 | 31.87 | 35.53 | 658.17 |
| 52-2 | Roots | 2 | | | 36.59 | 19.79 | 23.84 | 386.69 |
| | | 10 | | | 29.86 | 22.99 | 29.34 | 565.77 |
| | | 50 | | | 20.02 | 39.37 | 35.88 | 712.63 |
| 52-3 | Stems | 2 | | | 36.03 | 17.00 | 20.24 | 350.77 |
| | | 10 | | | 30.24 | 22.42 | 27.65 | 585.34 |
| | | 50 | | | 24.79 | 37.40 | 35.59 | 732.85 |
| 52-4 | Leaves | 2 | | | 36.75 | 17.43 | 24.32 | 284.59 |
| | | 10 | | | 30.74 | 27.82 | 30.61 | 438.64 |
| | | 50 | | | 25.97 | 36.92 | 38.66 | 781.17 |
| 52-5 | Fruits | 2 | | | 36.98 | 12.00 | 24.68 | 244.28 |
| | | 10 | | | 29.57 | 20.62 | 32.56 | 471.22 |
| | | 50 | | | 20.64 | 33.33 | 36.77 | 727.23 |
| 52-6 | Flowers | 2 | | | 37.74 | 19.59 | 24.68 | 309.36 |
| | | 10 | | | 31.52 | 29.23 | 33.48 | 474.74 |
| | | 50 | | | 24.28 | 34.00 | 39.22 | 607.46 |

TABLE 99

| No. | Sample | Scientific name | English name | Anti-oxidation IC50 (%) | Anti-bacteria MIC (%) | Anti-bacteria (S. mutans) Size of growth inhibition ring (mm) | Anti-bacteria (P. gingivalis) Size of growth inhibition ring (mm) |
|---|---|---|---|---|---|---|---|
| | Control group | | | Vitamin C 7.5 ppm | Hexanediol Bacteria: P.aeruginosa 2% Fungi: A.niger 1% | Untreated 0 mm | Untreated 0 mm |
| 52 | Stolon golden saxifrage | *Chrysosplenium flagelliferum* F. Schmidt | Stolon golden saxifrage | | | | |
| 52-1 | Whole plant | | | 0.80 | MIC (%) Bacteria: 2, Fungi: 0.5 | 16.9 | 18.5 |
| 52-2 | Roots | | | 0.02 | MIC (%) Bacteria: 0.25, Fungi: 1 | 24.2 | 21.3 |
| 52-3 | Stems | | | 0.22 | MIC (%) Bacteria: 1, Fungi: 1 | 12.2 | 17.2 |
| 52-4 | Leaves | | | 0.34 | MIC (%) Bacteria: 0.5, Fungi: 0.25 | 17.8 | 10.9 |
| 52-5 | Fruits | | | 0.01 | MIC (%) Bacteria: 2, Fungi: 2 | 11.0 | 14.2 |
| 52-6 | Flowers | | | 0.89 | MIC (%) Bacteria: 0.5, Fungi: 0.5 | 24.5 | 25.0 |

Example 53

Serrate-Petal Rockfoil

TABLE 100

| No. | Sample | Conc. (ppm) | Scientific name | English name | Whitening Melanin content (%) |
|---|---|---|---|---|---|
| | Control group | | | | Arbutin (200 ppm) 35% |
| 53 | Serrate-petal rockfoil | | *Saxifraga fortunei var. incisolobata (Engl. & Irmsch.) Nakai* | Serrate-petal rockfoil | |
| Comparative Example | Saxifrage | 50 | *Saxifraga Sarmentosa* | | 75.71 |
| 53-1 | Whole plant | 2 | | | 36.24 |
| | | 10 | | | 31.41 |
| | | 50 | | | 21.94 |
| 53-2 | Roots | 2 | | | 37.48 |
| | | 10 | | | 33.12 |
| | | 50 | | | 24.52 |
| 53-3 | Stems | 2 | | | 37.19 |
| | | 10 | | | 32.02 |
| | | 50 | | | 22.65 |
| 53-4 | Leaves | 2 | | | 35.51 |
| | | 10 | | | 33.45 |
| | | 50 | | | 20.29 |

TABLE 100-continued

| 53-5 | Fruits | 2 | | 37.26 |
|---|---|---|---|---|
| | | 10 | | 29.18 |
| | | 50 | | 23.17 |
| 53-6 | Flowers | 2 | | 36.25 |
| | | 10 | | 33.27 |
| | | 50 | | 25.30 |

| No. | Sample | Anti-wrinkle Collagen synthesis (% of control) | Anti-inflammation Inhibition of NO production (%) | Moisturizing HA synthesis (%) |
|---|---|---|---|---|
| 53 | Control group Serrate-petal rockfoil | TGFb (10 ppb) 25% | L-NMMA (5 ppm) 28% | EGF(10 ppb) 320% |
| Comparative Example | Saxifrage | 2.97 | 2.30 | 81.06 |
| 53-1 | Whole plant | 14.99 | 24.26 | 304.59 |
| | | 29.39 | 29.47 | 432.81 |
| | | 36.98 | 36.25 | 722.55 |
| 53-2 | Roots | 14.15 | 21.98 | 391.12 |
| | | 24.91 | 33.02 | 485.04 |
| | | 36.48 | 36.27 | 718.62 |
| 53-3 | Stems | 16.78 | 21.00 | 348.27 |
| | | 25.75 | 31.39 | 535.01 |
| | | 32.13 | 34.94 | 680.48 |
| 53-4 | Leaves | 11.60 | 26.25 | 221.32 |
| | | 26.97 | 30.95 | 538.37 |
| | | 38.26 | 37.93 | 789.68 |
| 53-5 | Fruits | 11.61 | 26.72 | 389.54 |
| | | 22.17 | 29.96 | 524.36 |
| | | 33.69 | 35.59 | 600.26 |
| 53-6 | Flowers | 15.69 | 21.10 | 319.30 |
| | | 22.89 | 32.94 | 501.22 |
| | | 31.21 | 34.93 | 739.52 |

TABLE 101

| No. | Sample | Scientific name | English name | Anti-oxidation IC50 (%) |
|---|---|---|---|---|
| 53 | Control group Serrate-petal rockfoil | *Saxifraga fortunei* var. *incisolobata* (Engl. & Irmsch.) Nakai | Serrate-petal rockfoil | Vitamin C 7.5 ppm |
| Comparative Example | Saxifrage | *Saxifraga Sarmentosa* | | 4.65 |
| 53-1 | Whole plant | | | 0.18 |
| 53-2 | Roots | | | 0.25 |
| 53-3 | Stems | | | 0.69 |
| 53-4 | Leaves | | | 0.07 |
| 53-5 | Fruits | | | 0.12 |
| 53-6 | Flowers | | | 0.12 |

| No. | Sample | Anti-bacteria MIC (%) | Anti-bacteria (S. mutans) Size of growth inhibition ring (mm) | Anti-bacteria (P. gingivalis) Size of growth inhibition ring (mm) |
|---|---|---|---|---|
| 53 | Control group Serrate-petal rockfoil | Hexanediol Bacteria: P.aeruginosa 2% Fungi: A.niger 1% | Untreated 0 mm | Untreated 0 mm |
| Comparative Example | Saxifrage | MIC (%) Bacteria: 2/Fungi: >2 | 10.5 | 10.8 |
| 53-1 | Whole plant | MIC (%) Bacteria: 1/Fungi: 1 | 26.1 | 23.1 |
| 53-2 | Roots | MIC (%) Bacteria: 2, Fungi: 1 | 8.8 | 10.9 |
| 53-3 | Stems | MIC (%) Bacteria: 1, Fungi: 1 | 18.0 | 23.1 |
| 53-4 | Leaves | MIC (%) Bacteria: 0.25, Fungi: 0.25 | 11.5 | 9.7 |
| 53-5 | Fruits | MIC (%) Bacteria: 2, Fungi: 1 | 25.6 | 18.3 |
| 53-6 | Flowers | MIC (%) Bacteria: 0.5, Fungi: 0.5 | 16.1 | 16.3 |

Example 54

Ulleungdo Deadnettle

TABLE 102

| No. | Sample | Conc. (ppm) | Scientific name | English name | Whitening Melanin content (%) |
|---|---|---|---|---|---|
| | | | | | Arbutin (200 ppm) 35% |
| 54 | Control Group Ulleungdo deadnettle | | *Lamium takesimense* NAKAI. | Ulleungdo deadnettle | |
| Comparative Example | Deadnettle | 50 | *Lamium Album* | | 78.41 |
| 54-1 | Whole plant | 2 | | | 35.02 |
| | | 10 | | | 28.57 |
| | | 50 | | | 23.28 |
| 54-2 | Roots | 2 | | | 37.32 |
| | | 10 | | | 27.09 |
| | | 50 | | | 25.40 |
| 54-3 | Stems | 2 | | | 37.23 |
| | | 10 | | | 33.64 |
| | | 50 | | | 26.37 |
| 54-4 | Leaves | 2 | | | 34.00 |
| | | 10 | | | 30.87 |
| | | 50 | | | 26.75 |
| 54-5 | Fruits | 2 | | | 34.98 |
| | | 10 | | | 27.73 |
| | | 50 | | | 20.69 |
| 54-6 | Flowers | 2 | | | 34.02 |
| | | 10 | | | 29.85 |
| | | 50 | | | 26.21 |

| No. | Sample | Anti-wrinkle Collagen synthesis (% of control) | Anti-inflammation Inhibition of NO production (%) | Moisturizing HA synthesis (%) |
|---|---|---|---|---|
| 54 | Control Group Ulleungdo deadnettle | TGFb (10 ppb) 25% | L-NMMA (5 ppm) 28% | EGF (10 ppb) 320% |
| Comparative Example | Deadnettle | 10.29 | 3.06 | 54.28 |
| 54-1 | Whole plant | 11.63 | 26.42 | 384.50 |
| | | 29.08 | 32.93 | 501.69 |
| | | 38.86 | 37.60 | 687.74 |
| 54-2 | Roots | 13.70 | 20.03 | 377.20 |
| | | 24.49 | 38.40 | 537.75 |
| | | 33.48 | 39.61 | 703.10 |
| 54-3 | Stems | 17.90 | 21.52 | 348.69 |
| | | 22.15 | 31.40 | 452.58 |
| | | 36.21 | 37.74 | 696.56 |
| 54-4 | Leaves | 13.25 | 20.88 | 270.20 |
| | | 25.66 | 31.85 | 459.14 |
| | | 32.55 | 35.21 | 794.73 |
| 54-5 | Fruits | 12.86 | 22.31 | 288.52 |
| | | 25.92 | 30.60 | 541.29 |
| | | 37.78 | 38.43 | 683.72 |
| 54-6 | Flowers | 11.57 | 24.33 | 364.82 |
| | | 26.66 | 29.10 | 590.29 |
| | | 38.76 | 34.26 | 793.67 |

TABLE 103

| No. | Sample | Scientific name | English name | Anti-oxidation IC50 (%) |
|---|---|---|---|---|
| | | | | Vitamin C 7.5 ppm |
| 54 | Control group Ulleungdo deadnettle | *Lamium takesimense* NAKAI. | Ulleungdo deadnettle | |
| Comparative Example | Deadnettle | *Lamium Album* | | 5.58 |
| 54-1 | Whole plant | | | 0.25 |
| 54-2 | Roots | | | 0.30 |
| 54-3 | Stems | | | 0.97 |

TABLE 103-continued

| | | | | |
|---|---|---|---|---|
| 54-4 | Leaves | | | 0.50 |
| 54-5 | Fruits | | | 0.52 |
| 54-6 | Flowers | | | 0.70 |

| No. | Sample | Anti-bacteria MIC (%) | Anti-bacteria (S. mutans) Size of growth inhibition ring (mm) | Anti-bacteria (P. gingivalis) Size of growth inhibition ring (mm) |
|---|---|---|---|---|
| | Control group | Hexanediol Bacteria: P.aeruginosa 2% Fungi: A.niger 1% | Untreated 0 mm | Untreated 0 mm |
| 54 | Ulleungdo deadnettle | | | |
| Comparative Example | Deadnettle | MIC (%) Bacteria: 2/Fungi: 2 | 9.2 | 8.7 |
| 54-1 | Whole plant | MIC (%) Bacteria: 0.5/Fungi: 0.25 | 18.7 | 18.9 |
| 54-2 | Roots | MIC (%) Bacteria: 2, Fungi: 1 | 23.6 | 20.8 |
| 54-3 | Stems | MIC (%) Bacteria: 1, Fungi: 1 | 13.3 | 15.2 |
| 54-4 | Leaves | MIC (%) Bacteria: 0.125, Fungi: 0.5 | 15.3 | 14.2 |
| 54-5 | Fruits | MIC (%) Bacteria: 1, Fungi: 0.25 | 8.3 | 15.5 |
| 54-6 | Flowers | MIC (%) Bacteria: 1, Fungi: 0.5 | 17.8 | 21.1 |

Example 55

Island Ninebark

25

TABLE 104

| No. | Sample | Conc. (ppm) | Scientific name | English name | Whitening Melanin content (%) |
|---|---|---|---|---|---|
| | Control group | | | | Arbutin (200 ppm) 35% |
| 55 | Island ninebark | | Physocarpus insularis | Island ninebark | |
| Comparative Example | Amur ninebark | 50 | Physocarpus Amurensis | | 84.95 |
| 55-1 | Whole plant | 2 | | | 39.08 |
| | | 10 | | | 31.54 |
| | | 50 | | | 21.39 |
| 55-2 | Roots | 2 | | | 35.36 |
| | | 10 | | | 27.67 |
| | | 50 | | | 25.98 |
| 55-3 | Bark | 2 | | | 37.40 |
| | | 10 | | | 31.43 |
| | | 50 | | | 22.56 |
| 55-4 | Leaves | 2 | | | 38.97 |
| | | 10 | | | 32.73 |
| | | 50 | | | 26.73 |
| 55-5 | Fruits | 2 | | | 34.72 |
| | | 10 | | | 31.37 |
| | | 50 | | | 26.66 |
| 55-6 | Flowers | 2 | | | 39.69 |
| | | 10 | | | 30.86 |
| | | 50 | | | 24.56 |

| No. | Sample | Anti-wrinkle Collagen synthesis (% of control) | Anti-inflammation Inhibition of NO production (%) | Moisturizing HA synthesis (%) |
|---|---|---|---|---|
| | Control group | TGFb (10 ppb) 25% | L-NMMA (5 ppm) 28% | EGF (10 ppb) 320% |
| 55 | Island ninebark | | | |
| Comparative Example | Amur ninebark | 12.40 | 1.37 | 37.94 |
| 55-1 | Whole plant | 19.41 | 24.50 | 209.87 |
| | | 21.11 | 29.82 | 530.10 |
| | | 38.46 | 38.03 | 737.07 |
| 55-2 | Roots | 11.77 | 23.29 | 279.45 |
| | | 22.89 | 28.21 | 431.74 |
| | | 37.91 | 34.96 | 720.19 |
| 55-3 | Bark | 16.95 | 21.42 | 206.82 |
| | | 20.25 | 31.85 | 443.81 |
| | | 35.96 | 38.13 | 661.64 |

TABLE 104-continued

| | | | | |
|---|---|---|---|---|
| 55-4 | Leaves | 17.15 | 23.07 | 300.42 |
| | | 21.55 | 30.40 | 570.62 |
| | | 35.28 | 38.69 | 755.51 |
| 55-5 | Fruits | 11.53 | 24.42 | 349.79 |
| | | 25.60 | 29.22 | 591.94 |
| | | 35.49 | 39.44 | 653.78 |
| 55-6 | Flowers | 17.90 | 20.14 | 396.18 |
| | | 28.70 | 28.45 | 504.18 |
| | | 30.21 | 35.02 | 747.26 |

TABLE 105

| No. | Sample | Scientific name | English name | Anti-oxidation IC50 (%) | Anti-bacteria MIC (%) |
|---|---|---|---|---|---|
| | Control group | | | Vitamin C 7.5 ppm | Hexanediol Bacteria: P.aeruginosa 2% Fungi: A.niger 1% |
| 55 | Island ninebark | *Physocarpus insularis* | Island ninebark | | |
| Comparative Example | Amur ninebark | *Physocarpus Amurensis* | | 3.94 | MIC (%) Bacteria: >2/Fungi: >2 |
| 55-1 | Whole plant | | | 0.84 | MIC (%) Bacteria: 0.5/Fungi: 0.25 |
| 55-2 | Roots | | | 0.42 | MIC (%) Bacteria: 2, Fungi: 2 |
| 55-3 | Bark | | | 0.03 | MIC (%) Bacteria: 0.25, Fungi: 0.125 |
| 55-4 | Leaves | | | 0.98 | MIC (%) Bacteria: 1, Fungi: 0.5 |
| 55-5 | Fruits | | | 0.59 | MIC (%) Bacteria: 1, Fungi: 1 |
| 55-6 | Flowers | | | 0.43 | MIC (%) Bacteria: 2, Fungi: 2 |

| No. | Sample | Anti-bacteria (S. mutans) Size of growth inhibition ring (mm) | Anti-bacteria (P. gingivalis) Size of growth inhibition ring (mm) |
|---|---|---|---|
| | Control group | Untreated 0 mm | Untreated 0 mm |
| 55 | Island ninebark | | |
| Comparative Example | Amur ninebark | 9.2 | 8.1 |
| 55-1 | Whole plant | 21.6 | 24.7 |
| 55-2 | Roots | 13.9 | 16.8 |
| 55-3 | Bark | 17.9 | 23.3 |
| 55-4 | Leaves | 15.7 | 13.3 |
| 55-5 | Fruits | 8.6 | 22.7 |
| 55-6 | Flowers | 25.4 | 27.8 |

Example 56

Island *Corydalis*

45

TABLE 106

| No. | Sample | Conc. (ppm) | Scientific name | English name | Whitening Melanin content (%) |
|---|---|---|---|---|---|
| | Control group | | | | Arbutin (200 ppm) 35% |
| 56 | Island corydalis | | *Corydalis ilistipes* Nakai | Island corydalis | |
| Comparative Example | Korean corydalis | 50 | *Corydalis Turtschaninovii* | | 91.92 |
| 56-1 | Whole plant | 2 | | | 39.64 |
| | | 10 | | | 28.94 |
| | | 50 | | | 25.48 |
| 56-2 | Roots | 2 | | | 39.12 |
| | | 10 | | | 33.27 |
| | | 50 | | | 20.60 |
| 56-3 | Stems | 2 | | | 34.76 |
| | | 10 | | | 33.94 |
| | | 50 | | | 26.66 |
| 56-4 | Leaves | 2 | | | 38.58 |
| | | 10 | | | 27.73 |
| | | 50 | | | 21.32 |

TABLE 106-continued

| 56-5 | Fruits | 2 | | | 35.26 |
| | | 10 | | | 33.45 |
| | | 50 | | | 25.50 |
| 56-6 | Flowers | 2 | | | 38.37 |
| | | 10 | | | 28.41 |
| | | 50 | | | 25.38 |

| No. | Sample | Anti-wrinkle Collagen synthesis (% of control) | Anti-inflammation Inhibition of NO production (%) | Moisturizing HA synthesis (%) |
|---|---|---|---|---|
| | Control group | TGFb (10 ppb) 25% | L-NMMA (5 ppm) 28% | EGF (10 ppb) 320% |
| 56 | Island corydalis | | | |
| Comparative Example | Korean corydalis | 3.18 | 5.62 | 25.64 |
| 56-1 | Whole plant | 15.87 | 20.04 | 356.83 |
| | | 20.92 | 30.49 | 412.62 |
| | | 32.77 | 39.74 | 772.97 |
| 56-2 | Roots | 13.74 | 24.42 | 328.98 |
| | | 25.94 | 29.40 | 583.96 |
| | | 30.62 | 38.45 | 674.76 |
| 56-3 | Stems | 12.57 | 21.91 | 331.05 |
| | | 27.51 | 31.72 | 545.46 |
| | | 31.17 | 25.08 | 604.62 |
| 56-4 | Leaves | 13.76 | 23.35 | 258.94 |
| | | 23.44 | 33.96 | 560.31 |
| | | 31.11 | 34.68 | 717.89 |
| 56-5 | Fruits | 17.70 | 23.70 | 327.70 |
| | | 28.79 | 33.41 | 449.69 |
| | | 30.96 | 37.80 | 784.95 |
| 56-6 | Flowers | 13.41 | 23.30 | 302.66 |
| | | 29.21 | 32.15 | 479.57 |
| | | 39.24 | 36.54 | 658.20 |

TABLE 107

| No. | Sample | Scientific name | English name | Anti-oxidation IC50 (%) |
|---|---|---|---|---|
| | Control group | | | Vitamin C 7.5 ppm |
| 56 | Island corydalis | *Corydalis ilistipes* Nakai | Island corydalis | |
| Comparative Example | Korean corydalis | *Corydalis Turtschaninovii* | | 8.47 |
| 56-1 | Whole plant | | | 0.97 |
| 56-2 | Roots | | | 0.44 |
| 56-3 | Stems | | | 0.38 |
| 56-4 | Leaves | | | 0.21 |
| 56-5 | Fruits | | | 0.91 |
| 56-6 | Flowers | | | 0.98 |

| No. | Sample | Anti-bacteria MIC (%) | Anti-bacteria (S. mutans) Size of growth inhibition ring (mm) | Anti-bacteria (P .gingivalis) Size of growth inhibition ring (mm) |
|---|---|---|---|---|
| | Control group | Hexanediol Bacteria: P.aeruginosa 2% Fungi: A.niger 1% | Untreated 0 mm | Untreated 0 mm |
| 56 | Island corydalis | | | |
| Comparative Example | Korean corydalis | MIC (%) Bacteria, Fungi: >2 | 9.0 | 11.9 |
| 56-1 | Whole plant | MIC (%) Bacteria, Fungi: 1 | 25.9 | 27.1 |
| 56-2 | Roots | MIC (%) Bacteria, Fungi: 0.25 | 13.4 | 18.6 |
| 56-3 | Stems | MIC (%) Bacteria, Fungi: 1 | 22.5 | 22.5 |
| 56-4 | Leaves | MIC (%) Bacteria: 0.125 MIC (%)Fungi: 1 | 11.9 | 13.0 |
| 56-5 | Fruits | MIC (%) Bacteria: 0.25 MIC (%)Fungi: 1 | 14.4 | 15.0 |
| 56-6 | Flowers | MIC (%) Bacteria: 0.0625 MIC (%)Fungi: 0.125 | 22.6 | 20.1 |

Example 57

Ulleungdo Raspberry

TABLE 108

| No. | Sample | Conc. (ppm) | Scientific name | English name | Whitening Melanin content (%) |
|---|---|---|---|---|---|
| | Control group | | | | Arbutin (200 ppm) |
| 57 | Ulleungdo raspberry | | *Rubus takesimensis* Nakai | Ulleungdo raspberry | |
| Comparative Example | Red raspberry | 50 | *Rubus Idaeus* | | 88.26 |
| 57-1 | Whole plant | 2 | | | 35.52 |
| | | 10 | | | 29.30 |
| | | 50 | | | 24.59 |
| 57-2 | Roots | 2 | | | 36.20 |
| | | 10 | | | 29.89 |
| | | 50 | | | 21.49 |
| 57-3 | Stems | 2 | | | 38.43 |
| | | 10 | | | 27.47 |
| | | 50 | | | 24.59 |
| 57-4 | Leaves | 2 | | | 34.68 |
| | | 10 | | | 30.08 |
| | | 50 | | | 26.54 |
| 57-5 | Fruits | 2 | | | 36.61 |
| | | 10 | | | 29.00 |
| | | 50 | | | 24.52 |
| 57-6 | Flowers | 2 | | | 34.33 |
| | | 10 | | | 32.63 |
| | | 50 | | | 26.10 |

| No. | Sample | Anti-wrinkle Collagen synthesis (% of control) | Anti-inflammation Inhibition of NO production (%) | Moisturizing HA synthesis (%) |
|---|---|---|---|---|
| | Control group | TGFb (10 ppb) 25% | L-NMMA (5 ppm) 28% | EGF (10 ppb) 320% |
| 57 | Ulleungdo raspberry | | | |
| Comparative Example | Red raspberry | 7.23 | 5.12 | 190.56 |
| 57-1 | Whole plant | 18.45 | 21.88 | 212.06 |
| | | 20.35 | 31.14 | 599.34 |
| | | 35.92 | 37.45 | 799.77 |
| 57-2 | Roots | 15.02 | 25.11 | 269.16 |
| | | 20.18 | 30.97 | 533.24 |
| | | 32.12 | 38.29 | 618.28 |
| 57-3 | Stems | 19.94 | 21.47 | 325.60 |
| | | 28.81 | 29.09 | 593.48 |
| | | 37.81 | 35.85 | 749.63 |
| 57-4 | Leaves | 10.77 | 25.35 | 332.91 |
| | | 23.47 | 29.94 | 534.11 |
| | | 30.48 | 39.26 | 755.38 |
| 57-5 | Fruits | 18.20 | 24.11 | 305.69 |
| | | 28.90 | 30.69 | 402.85 |
| | | 34.50 | 34.28 | 650.34 |
| 57-6 | Flowers | 10.21 | 26.64 | 302.50 |
| | | 26.70 | 32.16 | 432.22 |
| | | 34.64 | 39.21 | 600.75 |

50

TABLE 109

| No. | Sample | Scientific name | English name | Anti-oxidation IC50 (%) |
|---|---|---|---|---|
| | Control group | | | Vitamin C 7.5 ppm |
| 57 | Ulleungdo raspberry | *Rubus takesimensis* Nakai | Ulleungdo raspberry | |
| Comparative Example | Red raspberry | *Rubus Idaeus* | | 6.27 |
| 57-1 | Whole plant | | | 0.56 |
| 57-2 | Roots | | | 0.19 |
| 57-3 | Stems | | | 0.76 |
| 57-4 | Leaves | | | 0.12 |
| 57-5 | Fruits | | | 0.67 |
| 57-6 | Flowers | | | 0.54 |

TABLE 109-continued

| No. | Sample | Anti-bacteria MIC (%) | Anti-bacteria (S. mutans) Size of growth inhibition ring (mm) | Anti-bacteria (P. gingivalis) Size of growth inhibition ring (mm) |
|---|---|---|---|---|
| | Control group | Hexanediol Bacteria: P.aeruginosa 2% Fungi: A.niger 1% | Untreated 0 mm | Untreated 0 mm |
| 57 Comparative Example | Ulleungdo raspberry Red raspberry | MIC (%) Bacteria: 2, Fungi: >2 | 10.2 | 11.8 |
| 57-1 | Whole plant | MIC (%) Bacteria, Fungi: 0.125 | 24.5 | 27.2 |
| 57-2 | Roots | MIC (%) Bacteria, Fungi: 0.5 | 15.9 | 14.6 |
| 57-3 | Stems | MIC (%) Bacteria, Fungi: 1 | 25.7 | 20.1 |
| 57-4 | Leaves | MIC (%) Bacteria: 0.125 MIC (%)Fungi: 0.25 | 8.7 | 14.9 |
| 57-5 | Fruits | MIC (%) Bacteria: 0.25 MIC (%)Fungi: 0.5 | 21.4 | 10.9 |
| 57-6 | Flowers | MIC (%) Bacteria: 0.25 MIC (%)Fungi: 0.125 | 26.7 | 16.6 |

Example 58

Korea *Dystaenia*

TABLE 110

| No. | Sample | Conc. (ppm) | Scientific name | English name | Whitening Melanin content (%) |
|---|---|---|---|---|---|
| | Control group | | | | Arbutin (200 ppm) 35% |
| 58 | Korea Dystaenia | | *Dystaenia takeshimana* (Nakai) Kitag | Korea Dystaenia | |
| 58-1 | Whole plant | 2 | | | 35.79 |
| | | 10 | | | 32.36 |
| | | 50 | | | 22.51 |
| 58-2 | Roots | 2 | | | 35.98 |
| | | 10 | | | 27.66 |
| | | 50 | | | 26.02 |
| 58-3 | Stems | 2 | | | 39.54 |
| | | 10 | | | 27.23 |
| | | 50 | | | 25.44 |
| 58-4 | Leaves | 2 | | | 34.93 |
| | | 10 | | | 33.42 |
| | | 50 | | | 28.82 |
| 58-5 | Fruits | 2 | | | 39.71 |
| | | 10 | | | 28.30 |
| | | 50 | | | 23.78 |
| 58-6 | Flowers | 2 | | | 38.83 |
| | | 10 | | | 33.66 |
| | | 50 | | | 21.78 |

| No. | Sample | Anti-wrinkle Collagen synthesis (% of control) | Anti-inflammation Inhibition of NO production (%) | Moisturizing HA synthesis (%) |
|---|---|---|---|---|
| 58 | Control group Korea Dystaenia | TGFb (10 ppb) 25% | L-NMMA (5 ppm) 28% | EGF(10 ppb) 320% |
| 58-1 | Whole plant | 16.06 | 21.05 | 275.71 |
| | | 23.15 | 29.41 | 498.69 |
| | | 35.58 | 38.15 | 664.44 |
| 58-2 | Roots | 10.72 | 21.58 | 351.33 |
| | | 20.10 | 31.30 | 500.37 |
| | | 30.30 | 33.63 | 679.52 |
| 58-3 | Stems | 15.38 | 20.69 | 279.07 |
| | | 20.58 | 29.96 | 541.11 |
| | | 32.18 | 32.74 | 764.16 |
| 58-4 | Leaves | 17.47 | 24.88 | 363.53 |
| | | 27.98 | 28.56 | 526.76 |
| | | 31.77 | 33.08 | 731.21 |
| 58-5 | Fruits | 15.34 | 23.59 | 241.39 |
| | | 21.95 | 32.68 | 462.67 |
| | | 36.43 | 37.84 | 727.07 |
| 58-6 | Flowers | 15.88 | 23.60 | 267.02 |
| | | 23.59 | 31.40 | 469.70 |
| | | 34.97 | 37.17 | 758.76 |

TABLE 111

| No. | Sample | Scientific name | English name | Anti-oxidation IC50 (%) |
|---|---|---|---|---|
|  | Control group Korea Dystaenia | *Dystaenia takeshimana* (Nakai) Kitag | Korea Dystaenia | Vitamin C 7.5 ppm |
| 58 |  |  |  |  |
| 58-1 | Whole plant |  |  | 0.43 |
| 58-2 | Roots |  |  | 0.55 |
| 58-3 | Stems |  |  | 0.87 |
| 58-4 | Leaves |  |  | 0.20 |
| 58-5 | Fruits |  |  | 0.89 |
| 58-6 | Flowers |  |  | 0.99 |

| No. | Sample | Anti-bacteria MIC (%) | Anti-bacteria (S. mutans) Size of growth inhibition ring (mm) | Anti-bacteria (P. gingivalis) Size of growth inhibition ring (mm) |
|---|---|---|---|---|
|  | Control group | Hexanediol Bacteria: P.aeruginosa 2% | Untreated 0 mm | Untreated 0 mm |
| 58 | Korea Dystaenia | Fungi: A.niger 1% |  |  |
| 58-1 | Whole plant | MIC (%) Bacteria, Fungi: 1 | 24.1 | 21.3 |
| 58-2 | Roots | MIC (%) Bacteria, Fungi: 2 | 10.9 | 14.5 |
| 58-3 | Stems | MIC (%) Bacteria, Fungi: 1 | 9.2 | 14.2 |
| 58-4 | Leaves | MIC (%) Bacteria: 0.5 MIC (%)Fungi: 0.25 | 18.7 | 22.7 |
| 58-5 | Fruits | MIC (%) Bacteria: 0.5 MIC (%)Fungi: 0.5 | 10.2 | 20.4 |
| 58-6 | Flowers | MIC (%) Bacteria: 0.25 MIC (%)Fungi: 0.5 | 20.7 | 25.7 |

Example 59

30

Ulleungdo Violet

TABLE 112

| No. | Sample | Conc. (ppm) | Scientific name | English name | Whitening Melanin content (%) |
|---|---|---|---|---|---|
|  | Control group Ulleungdo violet |  |  |  | Arbutin (200 ppm) 35% |
| 59 |  |  | *Viola takeshimana* Nakai | Ulleungdo violet |  |
| Comparative Example | Sweet violet | 50 | *Viola Odorata* |  | 72.36 |
| 59-1 | Whole plant | 2 |  |  | 36.20 |
|  |  | 10 |  |  | 27.81 |
|  |  | 50 |  |  | 20.44 |
| 59-2 | Roots | 2 |  |  | 35.90 |
|  |  | 10 |  |  | 27.60 |
|  |  | 50 |  |  | 20.85 |
| 59-3 | Stems | 2 |  |  | 38.00 |
|  |  | 10 |  |  | 29.56 |
|  |  | 50 |  |  | 23.42 |
| 59-4 | Leaves | 2 |  |  | 36.74 |
|  |  | 10 |  |  | 29.59 |
|  |  | 50 |  |  | 23.06 |
| 59-5 | Fruits | 2 |  |  | 37.12 |
|  |  | 10 |  |  | 32.95 |
|  |  | 50 |  |  | 23.64 |
| 59-6 | Flowers | 2 |  |  | 36.73 |
|  |  | 10 |  |  | 29.50 |
|  |  | 50 |  |  | 23.17 |

| No. | Sample | Anti-wrinkle Collagen synthesis (% of control) | Anti-inflammation Inhibition of NO production (%) | Moisturizing HA synthesis (%) |
|---|---|---|---|---|
|  | Control group Ulleungdo violet | TGFb (10 ppb) 25% | L-NMMA (5 ppm) 28% | EGF (10 ppb) 320% |
| 59 |  |  |  |  |
| Comparative Example | Sweet violet | 3.74 | 1.27 | 120.35 |
| 59-1 | Whole plant | 18.78 | 20.81 | 238.64 |
|  |  | 22.90 | 29.75 | 466.01 |
|  |  | 34.29 | 37.07 | 645.23 |

TABLE 112-continued

|  |  |  |  |  |
|---|---|---|---|---|
| 59-2 | Roots | 12.12 | 24.70 | 252.05 |
|  |  | 22.60 | 31.00 | 515.36 |
|  |  | 30.47 | 39.79 | 705.18 |
| 59-3 | Stems | 19.02 | 24.47 | 277.01 |
|  |  | 20.95 | 27.13 | 575.38 |
|  |  | 33.36 | 37.89 | 658.51 |
| 59-4 | Leaves | 17.43 | 24.13 | 363.57 |
|  |  | 21.49 | 31.24 | 562.86 |
|  |  | 33.71 | 38.37 | 758.61 |
| 59-5 | Fruits | 17.33 | 25.50 | 231.00 |
|  |  | 29.72 | 28.22 | 463.26 |
|  |  | 38.03 | 37.08 | 611.11 |
| 59-6 | Flowers | 17.77 | 26.96 | 398.74 |
|  |  | 24.68 | 33.30 | 410.85 |
|  |  | 30.30 | 38.10 | 675.69 |

TABLE 113

| No. | Sample | Scientific name | English name | Anti-oxidation IC50 (%) |
|---|---|---|---|---|
|  | Control group |  |  | Vitamin C 7.5 ppm |
| 59 | Ulleungdo violet | *Viola takeshimana* Nakai | Ulleungdo violet |  |
| Comparative Example | Sweet violet | *Viola Odorata* |  | 9.21 |
| 59-1 | Whole plant |  |  | 0.25 |
| 59-2 | Roots |  |  | 0.84 |
| 59-3 | Stems |  |  | 0.87 |
| 59-4 | Leaves |  |  | 0.51 |
| 59-5 | Fruits |  |  | 0.49 |
| 59-6 | Flowers |  |  | 0.21 |

| No. | Sample | Anti-bacteria MIC (%) | Anti-bacteria (S. mutans) Size of growth inhibition ring (mm) | Anti-bacteria (P. gingivalis) Size of growth inhibition ring (mm) |
|---|---|---|---|---|
|  | Control group | Hexanediol Bacteria: P.aeruginosa 2% Fungi: A.niger 1% | Untreated 0 mm | Untreated 0 mm |
| 59 | Ulleungdo violet |  |  |  |
| Comparative Example | Sweet violet | MIC (%) Bacteria, Fungi: 2 | 17.5 | 19.8 |
| 59-1 | Whole plant | MIC (%) Bacteria, Fungi: 1 | 21.0 | 23.7 |
| 59-2 | Roots | MIC (%) Bacteria, Fungi: 2 | 20.2 | 18.4 |
| 59-3 | Stems | MIC (%) Bacteria, Fungi: 1 | 25.3 | 20.4 |
| 59-4 | Leaves | MIC (%) Bacteria: 0.125 MIC (%)Fungi: 0.25 | 14.6 | 11.7 |
| 59-5 | Fruits | MIC (%) Bacteria: 0.25 MIC (%)Fungi: 0.5 | 20.2 | 10.1 |
| 59-6 | Flowers | MIC (%) Bacteria: 0.25 MIC (%)Fungi: 0.125 | 12.7 | 9.0 |

Example 60

Spindle Tree

TABLE 114

| No. | Sample | Conc. (ppm) | Scientific name | English name | Whitening Melanin content (%) |
|---|---|---|---|---|---|
|  | Control group |  |  |  | Arbutin (200 ppm) 35% |
| 60 | Spindle Tree |  | *Euonymus japonicus* Thunb. | Spindle Tree |  |
| Comparative | Korean spindle tree | 50 | *Euonymus sachalinensis* |  | 82.34 |
| Example |  |  |  |  |  |
| 60-1 | Whole plant | 2 |  |  | 39.32 |
|  |  | 10 |  |  | 29.75 |
|  |  | 50 |  |  | 22.60 |
| 60-2 | Roots | 2 |  |  | 36.51 |
|  |  | 10 |  |  | 30.47 |
|  |  | 50 |  |  | 22.95 |

TABLE 114-continued

| | | | |
|---|---|---|---|
| 60-3 | Stems | 2 | 37.09 |
| | | 10 | 29.16 |
| | | 50 | 20.86 |
| 60-4 | Leaves | 2 | 35.66 |
| | | 10 | 31.48 |
| | | 50 | 24.43 |
| 60-5 | Fruits | 2 | 37.26 |
| | | 10 | 29.84 |
| | | 50 | 25.04 |
| 60-6 | Flowers | 2 | 34.37 |
| | | 10 | 27.81 |
| | | 50 | 20.01 |

| No. | Sample | Anti-wrinkle Collagen synthesis (% of control) | Anti-inflammation Inhibition of NO production (%) | Moisturizing HA synthesis (%) |
|---|---|---|---|---|
| 60 | Control group Spindle Tree | TGFb (10 ppb) 25% | L-NMMA (5 ppm) 28% | EGF (10 ppb) 320% |
| Comparative Example | Korean spindle tree | 1.12 | 2.54 | 56.34 |
| 60-1 | Whole plant | 16.61 | 23.11 | 380.72 |
| | | 20.02 | 27.40 | 505.95 |
| | | 34.72 | 36.75 | 604.95 |
| 60-2 | Roots | 11.00 | 26.36 | 392.74 |
| | | 29.61 | 29.51 | 600.41 |
| | | 34.27 | 35.80 | 730.26 |
| 60-3 | Stems | 19.05 | 23.14 | 202.93 |
| | | 20.25 | 27.84 | 414.03 |
| | | 37.18 | 37.54 | 648.42 |
| 60-4 | Leaves | 16.85 | 24.69 | 282.19 |
| | | 29.43 | 27.19 | 453.32 |
| | | 38.83 | 37.66 | 642.30 |
| 60-5 | Fruits | 11.81 | 23.89 | 208.93 |
| | | 22.01 | 28.10 | 533.39 |
| | | 31.57 | 38.76 | 629.87 |
| 60-6 | Flowers | 13.44 | 23.24 | 325.66 |
| | | 20.40 | 29.56 | 483.29 |
| | | 30.11 | 38.91 | 793.18 |

35

TABLE 115

| No. | Sample | Scientific name | English name | Anti-oxidation IC50 (%) | Anti-bacteria MIC (%) | Anti-bacteria (S. mutans) Size of growth inhibition ring (mm) | Anti-bacteria (P. gingivalis) Size of growth inhibition ring (mm) |
|---|---|---|---|---|---|---|---|
| | Control group | | | Vitamin C 7.5 ppm | Hexanediol Bacteria: P. aeruginosa 2% Fungi: A. niger 1% | Untreated 0 mm | Untreated 0 mm |
| 60 | Spindle Tree | Euonymus japonicus Thunb. | Spindle Tree | | | | |
| Comparative Example | Korean spindle tree | Euonymus sachalinensis | | 2.98 | MIC (%) Bacteria: 1 MIC (%) Fungi: 1 | 9.7 | 9.1 |
| 60-1 | Whole plant | | | 0.13 | MIC (%) Bacteria: 0.0625 MIC (%) Fungi: 0.0625 | 18.2 | 20.2 |
| 60-2 | Roots | | | 0.43 | MIC (%) Bacteria: 0.125 MIC (%) Fungi: 0.125 | 10.5 | 12.1 |
| 60-3 | Stems | | | 0.50 | MIC (%) Bacteria: 0.5 MIC (%) Fungi: 0.5 | 11.9 | 13.1 |
| 60-4 | Leaves | | | 0.75 | MIC (%) Bacteria: 0.5 MIC (%) Fungi: 0.5 | 25.8 | 20.8 |
| 60-5 | Fruits | | | 0.81 | MIC (%) Bacteria: 0.5 MIC (%) Fungi: 0.5 | 11.0 | 10.8 |
| 60-6 | Flowers | | | 0.40 | MIC (%) Bacteria: 0.5 MIC (%) Fungi: 0.5 | 26.8 | 19.8 |

Example 61

Crimson Grapevine

TABLE 116

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 61 | Crimson grapevine | | *Vitis coignetiae* Pulliat ex Planch. | Crimson grapevine | | | | |
| Comparative Example | Grape | 50 | *Vitis Vinifera* (Grape) Fruit Water | | 95.32 | 3.34 | 2.56 | 76.43 |
| Comparative Example | Crimson grapevine (other area) | 50 | | | 57.82 | 15.36 | 14.45 | 165.33 |
| 61-1 | Whole plant | 2 | | | 32.22 | 15.88 | 25.98 | 408.55 |
| | | 10 | | | 25.14 | 20.19 | 41.07 | 683.78 |
| | | 50 | | | 14.44 | 42.33 | 55.90 | 849.00 |
| 61-2 | Roots | 2 | | | 32.08 | 18.83 | 21.04 | 344.14 |
| | | 10 | | | 23.78 | 25.79 | 28.65 | 415.52 |
| | | 50 | | | 35.87 | 30.71 | 35.03 | 682.84 |
| 61-3 | Stems | 2 | | | 32.50 | 12.01 | 22.60 | 291.68 |
| | | 10 | | | 23.71 | 23.88 | 27.88 | 574.32 |
| | | 50 | | | 39.42 | 36.04 | 34.97 | 750.46 |
| 61-4 | Leaves | 2 | | | 30.02 | 15.03 | 23.12 | 248.58 |
| | | 10 | | | 21.78 | 28.06 | 27.60 | 495.36 |
| | | 50 | | | 37.37 | 30.68 | 38.63 | 613.55 |
| 61-5 | Fruits | 2 | | | 31.99 | 14.81 | 24.60 | 221.57 |
| | | 10 | | | 24.21 | 27.48 | 31.27 | 400.96 |
| | | 50 | | | 34.37 | 38.59 | 38.41 | 760.87 |
| 61-6 | Flowers | 2 | | | 27.81 | 13.44 | 25.49 | 331.35 |
| | | 10 | | | 20.01 | 20.40 | 28.11 | 454.63 |
| | | 50 | | | | 30.11 | 35.49 | 794.05 |

TABLE 117

| No. | Sample | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|
| | Control group | | | Vitamin C 7.5 ppm | Hexanediol Bacteria: *P. aeruginosa* 2% Fungi: *A. niger* 1% | Untreated 0 mm | Untreated 0 mm |
| 61 | Crimson grapevine | *Vitis coignetiae* Pulliat ex Planch. | Crimson grapevine | | | | |
| Comparative Example | Grape | *Vitis Vinifera* (Grape) Fruit Water | | 2.98 | MIC (%) Bacteria: >2 MIC (%) Fungi: >2 | 0.0 | 0.0 |
| Comparative Example | Crimson grapevine (other area) | | | 3.77 | MIC (%) Bacteria: 2 MIC (%) Fungi: 1 | 8.2 | 9.4 |
| 61-1 | Whole plant | | | 0.65 | MIC (%) Bacteria: 0.125 MIC (%) Fungi: 0.125 | 17.3 | 16.4 |
| 61-2 | Roots | | | 0.30 | MIC (%) Bacteria: 0.5 MIC (%) Fungi: 0.5 | 13.4 | 17.6 |
| 61-3 | Stems | | | 0.74 | MIC (%) Bacteria: 0.125 MIC (%) Fungi: 0.125 | 23.4 | 21.0 |
| 61-4 | Leaves | | | 0.59 | MIC (%) Bacteria: 0.5 MIC (%) Fungi: 0.5 | 17.2 | 17.3 |
| 61-5 | Fruits | | | 0.41 | MIC (%) Bacteria: 0.5 MIC (%) Fungi: 0.5 | 11.8 | 16.0 |
| 61-6 | Flowers | | | 0.28 | MIC (%) Bacteria: 0.0625 MIC (%) Fungi: 0.0625 | 17.1 | 21.7 |

Example 62

*Aralia continentalis*

TABLE 118

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 62 | *Aralia continentalis* | | *Aralia cordata* var. *continentalis* (Kitag.) Y. C. Chu | *Aralia continentalis* | | | | |
| Comparative Example | American spikenard | 50 | *Aralia Racemosa* | | 89.23 | 5.23 | 5.34 | 66.87 |
| Comparative Example | *Aralia continentalis* (other area) | 50 | | | 66.58 | 12.61 | 12.60 | 105.41 |
| 62-1 | Whole plant | 2 | | | 39.28 | 14.41 | 25.98 | 317.84 |
| | | 10 | | | 31.42 | 26.00 | 31.07 | 507.23 |
| | | 50 | | | 23.10 | 38.66 | 35.90 | 626.10 |
| 62-2 | Roots | 2 | | | 37.60 | 19.53 | 21.04 | 214.14 |
| | | 10 | | | 28.26 | 24.36 | 28.65 | 590.21 |
| | | 50 | | | 23.13 | 36.31 | 35.03 | 608.17 |
| 62-3 | Stems | 2 | | | 36.58 | 11.61 | 22.60 | 245.41 |
| | | 10 | | | 31.58 | 29.45 | 27.88 | 452.94 |
| | | 50 | | | 26.32 | 35.33 | 34.97 | 761.80 |
| 62-4 | Leaves | 2 | | | 37.43 | 14.78 | 23.12 | 394.75 |
| | | 10 | | | 28.61 | 20.46 | 27.60 | 426.68 |
| | | 50 | | | 21.28 | 30.12 | 38.63 | 650.68 |
| 62-5 | Fruits | 2 | | | 39.19 | 17.14 | 24.60 | 259.10 |
| | | 10 | | | 28.96 | 20.59 | 31.27 | 492.63 |
| | | 50 | | | 24.77 | 32.77 | 38.41 | 625.32 |
| 62-6 | Flowers | 2 | | | 34.37 | 13.44 | 20.43 | 276.09 |
| | | 10 | | | 27.81 | 20.40 | 32.34 | 455.01 |
| | | 50 | | | 20.01 | 30.11 | 35.96 | 627.68 |

TABLE 119

| No. | Sample | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|
| | Control group | | | Vitamin C 7.5 ppm | Hexanediol Bacteria: *P. aeruginosa* 2% Fungi: *A. niger* 1% | Untreated 0 mm | Untreated 0 mm |
| 62 | *Aralia continentalis* | *Aralia cordata* var. *continentalis* (Kitag.) Y. C. Chu | *Aralia continentalis* | | | | |
| Comparative Example | American spikenard | *Aralia Racemosa* | | 3.23 | MIC (%) Bacteria: 2 MIC (%) Fungi: >2 | 9.6 | 9.6 |
| Comparative Example | *Aralia continentalis* (other area) | | | 3.42 | MIC (%) Bacteria: 1 MIC (%) Fungi: 2 | 10.2 | 11.5 |
| 62-1 | Whole plant | | | 0.45 | MIC (%) Bacteria: 0.5 MIC (%) Fungi: 0.5 | 19.3 | 24.9 |
| 62-2 | Roots | | | 0.46 | MIC (%) Bacteria: 0.5 MIC (%) Fungi: 0.5 | 8.5 | 8.2 |
| 62-3 | Stems | | | 0.11 | MIC (%) Bacteria: 0.5 MIC (%) Fungi: 0.5 | 11.9 | 13.6 |
| 62-4 | Leaves | | | 0.79 | MIC (%) Bacteria: 0.5 MIC (%) Fungi: 0.5 | 25.4 | 24.2 |
| 62-5 | Fruits | | | 0.46 | MIC (%) Bacteria: 0.0625 MIC (%) Fungi: 0.0625 | 11.5 | 9.9 |
| 62-6 | Flowers | | | 0.13 | MIC (%) Bacteria: 0.5 MIC (%) Fungi: 0.5 | 18.8 | 8.7 |

Example 63

Japanese Angelica

TABLE 120

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 Ppm) 35% | TGFb (10 ppb) 25% | L-NMMA (5 ppm) 28% | EGF (10 ppb) 320% |
| 63 | Japanese Angelica | | *Aralia elata* (Miq.) Seem. | Japanese Angelica | | | | |
| Comparative Example | American spikenard | 50 | *Aralia Racemosa* | | 89.23 | 5.23 | 5.34 | 66.87 |
| Comparative Example | Japanese Angelica (other area) | 50 | | | 76.58 | 16.85 | 11.60 | 244.41 |
| 63-1 | Whole plant | 2 | | | 39.81 | 19.60 | 23.91 | 296.54 |
| | | 10 | | | 33.97 | 22.11 | 32.00 | 454.69 |
| | | 50 | | | 26.10 | 37.22 | 37.55 | 769.13 |
| 63-2 | Roots | 2 | | | 34.90 | 13.86 | 20.55 | 290.93 |
| | | 10 | | | 32.78 | 24.54 | 32.39 | 455.13 |
| | | 50 | | | 25.51 | 31.82 | 34.95 | 779.22 |
| 63-3 | Stems | 2 | | | 36.66 | 18.28 | 21.70 | 205.08 |
| | | 10 | | | 30.99 | 29.99 | 30.41 | 465.64 |
| | | 50 | | | 20.28 | 34.15 | 37.03 | 635.56 |
| 63-4 | Leaves | 2 | | | 38.92 | 12.68 | 24.53 | 255.20 |
| | | 10 | | | 29.01 | 26.37 | 33.64 | 544.83 |
| | | 50 | | | 20.79 | 38.33 | 34.47 | 610.78 |
| 63-5 | Fruits | 2 | | | 37.27 | 16.63 | 25.55 | 361.49 |
| | | 10 | | | 33.82 | 28.20 | 32.69 | 519.50 |
| | | 50 | | | 24.26 | 39.00 | 39.16 | 602.39 |
| 63-6 | Flowers | 2 | | | 34.37 | 13.44 | 25.97 | 296.88 |
| | | 10 | | | 27.81 | 20.40 | 29.67 | 516.40 |
| | | 50 | | | 20.01 | 30.11 | 39.88 | 750.27 |
| 63-7 | Shoots | 2 | | | 39.07 | 15.89 | 22.17 | 352.19 |
| | | 10 | | | 33.76 | 22.69 | 28.37 | 549.85 |
| | | 50 | | | 22.00 | 35.56 | 38.97 | 666.01 |

TABLE 121

| No. | Sample | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|
| | Control group | | | Vitamin C 7.5 ppm | Hexanediol Bacteria: *P. aeruginosa* 2% Fungi: *A. niger* 1% | Untreated 0 mm | Untreated 0 mm |
| 63 | Japanese Angelica | *Aralia elata* (Miq.) Seem. | Japanese Angelica | | | | |
| Comparative Example | American spikenard | *Aralia Racemosa* | | 3.23 | MIC (%) Bacteria: 2 MIC (%) Fungi: >2 | 8.0 | 9.9 |
| Comparative Example | Japanese Angelica (other area) | | | 2.31 | MIC (%) Bacteria: 1 MIC (%) Fungi: 1 | 8.8 | 9.7 |
| 63-1 | Whole plant | | | 0.89 | MIC (%) Bacteria: 0.125 MIC (%) Fungi: 0.125 | 17.9 | 19.3 |
| 63-2 | Roots | | | 0.73 | MIC (%) Bacteria: 0.5 MIC (%) Fungi: 0.5 | 16.4 | 19.0 |
| 63-3 | Stems | | | 0.39 | MIC (%) Bacteria: 0.5 MIC (%) Fungi: 0.5 | 22.3 | 23.7 |
| 63-4 | Leaves | | | 0.67 | MIC (%) Bacteria: 0.5 MIC (%) Fungi: 0.5 | 12.5 | 14.0 |
| 63-5 | Fruits | | | 0.52 | MIC (%) Bacteria: 0.0625 MIC (%) Fungi: 0.0625 | 22.6 | 21.6 |
| 63-6 | Flowers | | | 0.65 | MIC (%) Bacteria: 0.125 MIC (%) Fungi: 0.125 | 15.7 | 11.7 |
| 63-7 | Shoots | | | 0.75 | MIC (%) Bacteria: 0.25 MIC (%) Fungi: 0.125 | 11.4 | 8.5 |

Example 64

Glossy-Leaf Paper Plant

TABLE 122

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 64 | Glossy-leaf paper plant | | Fatsia japonica (Thunb.) Decne. & Planch. | Glossy-leaf paper plant | | | | |
| Comparative Example | Glossy-leaf paper plant (other area) | 50 | | | 86.58 | 2.42 | 11.60 | 114.41 |
| 64-1 | Whole plant | 2 | | | 37.45 | 18.61 | 20.13 | 245.46 |
| | | 10 | | | 32.44 | 24.19 | 28.16 | 540.61 |
| | | 50 | | | 24.25 | 36.65 | 35.63 | 666.75 |
| 64-2 | Roots | 2 | | | 38.41 | 15.81 | 23.24 | 279.07 |
| | | 10 | | | 28.06 | 27.97 | 28.95 | 495.20 |
| | | 50 | | | 20.21 | 30.82 | 36.33 | 723.24 |
| 64-3 | Stems | 2 | | | 36.77 | 12.06 | 20.47 | 348.86 |
| | | 10 | | | 31.45 | 22.99 | 33.78 | 408.25 |
| | | 50 | | | 26.52 | 34.91 | 34.35 | 636.95 |
| 64-4 | Leaves | 2 | | | 37.25 | 16.73 | 24.24 | 225.89 |
| | | 10 | | | 32.73 | 27.21 | 28.14 | 458.51 |
| | | 50 | | | 26.18 | 32.93 | 38.26 | 642.56 |
| 64-5 | Fruits | 2 | | | 34.35 | 19.97 | 25.27 | 253.57 |
| | | 10 | | | 28.91 | 24.20 | 33.72 | 469.64 |
| | | 50 | | | 26.77 | 34.82 | 38.94 | 686.57 |
| 64-6 | Flowers | 2 | | | 34.37 | 13.44 | 25.79 | 292.97 |
| | | 10 | | | 27.81 | 20.40 | 32.55 | 469.32 |
| | | 50 | | | 20.01 | 30.11 | 36.38 | 708.80 |

TABLE 123

| No. | Sample | Scientific name | English name | Anti-oxidation IC50 (%) | Anti-bacteria MIC (%) | Anti-bacteria (S. mutans) Size of growth inhibition ring (mm) | Anti-bacteria (P. gingivalis) Size of growth inhibition ring (mm) |
|---|---|---|---|---|---|---|---|
| | Control group | | | Vitamin C 7.5 ppm | Hexanediol Bacteria: P. aeruginosa 2% Fungi: A. niger 1% | Untreated 0 mm | Untreated 0 mm |
| 64 | Glossy-leaf paper plant | Fatsia japonica (Thunb.) Decne. & Planch. | Glossy-leaf paper plant | | | | |
| Comparative Example | Glossy-leaf paper plant (other area) | | | 1.56 | MIC (%) Bacteria: 2 MIC (%) Fungi: 1 | 10.4 | 8.5 |
| 64-1 | Whole plant | | | 0.71 | MIC (%) Bacteria: 0.125 MIC (%) Fungi: 0.125 | 22.0 | 25.8 |
| 64-2 | Roots | | | 0.38 | MIC (%) Bacteria: 0.125 MIC (%) Fungi: 0.125 | 18.4 | 14.7 |
| 64-3 | Stems | | | 0.76 | MIC (%) Bacteria: 0.0625 MIC (%) Fungi: 0.0625 | 18.4 | 16.0 |
| 64-4 | Leaves | | | 0.72 | MIC (%) Bacteria: 0.5 MIC (%) Fungi: 0.5 | 24.0 | 23.0 |
| 64-5 | Fruits | | | 0.87 | MIC (%) Bacteria: 0.5 MIC (%) Fungi: 0.5 | 11.9 | 12.0 |
| 64-6 | Flowers | | | 0.23 | MIC (%) Bacteria: 0.5 MIC (%) Fungi: 0.5 | 10.0 | 15.7 |

Example 65

Three-Leaf *Clematis*

TABLE 124

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 65 | Three-leaf clematis | | *Clematis apiifolia* DC. | Three-leaf clematis | | | | |
| Comparative Example | *Clematis* | 50 | *Clematis Vitalba* | | 85.54 | 10.47 | 2.38 | 65.47 |
| 65-1 | Whole plant | 2 | | | 37.52 | 13.96 | 24.37 | 259.29 |
| | | 10 | | | 28.36 | 23.80 | 30.85 | 517.54 |
| | | 50 | | | 25.35 | 39.09 | 39.71 | 610.96 |
| 65-2 | Roots | 2 | | | 37.84 | 14.46 | 22.23 | 346.50 |
| | | 10 | | | 29.96 | 21.33 | 27.40 | 481.97 |
| | | 50 | | | 26.52 | 33.97 | 34.78 | 666.78 |
| 65-3 | Stems | 2 | | | 37.03 | 12.60 | 24.12 | 247.92 |
| | | 10 | | | 33.98 | 23.25 | 32.15 | 524.23 |
| | | 50 | | | 26.87 | 35.49 | 36.74 | 605.86 |
| 65-4 | Leaves | 2 | | | 34.16 | 13.84 | 22.63 | 233.90 |
| | | 10 | | | 31.93 | 20.54 | 32.12 | 411.84 |
| | | 50 | | | 21.90 | 39.60 | 35.02 | 612.26 |
| 65-5 | Fruits | 2 | | | 37.95 | 11.39 | 26.47 | 302.07 |
| | | 10 | | | 31.47 | 20.52 | 32.26 | 574.17 |
| | | 50 | | | 23.59 | 33.71 | 36.38 | 710.86 |
| 65-6 | Flowers | 2 | | | 36.25 | 16.47 | 26.71 | 386.59 |
| | | 10 | | | 32.25 | 29.84 | 28.47 | 557.17 |
| | | 50 | | | 25.58 | 35.29 | 35.98 | 734.71 |

TABLE 125

| No. | Sample | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|
| | Control group | | | Vitamin C 7.5 ppm | Hexanediol Bacteria: *P. aeruginosa* 2% Fungi: *A. niger* 1% | Untreated 0 mm | Untreated 0 mm |
| 65 | Three-leaf clematis | *Clematis apiifolia* DC. | Three-leaf clematis | | | | |
| Comparative Example | *Clematis* | *Clematis Vitalba* | | 7.48 | MIC (%) Bacteria, Fungi: >2 | 9.2 | 8.8 |
| 65-1 | Whole plant | | | 0.07 | MIC (%) Bacteria: 0.25 MIC (%) Fungi: 0.25 | 21.6 | 24.6 |
| 65-2 | Roots | | | 0.26 | MIC (%) Bacteria: 0.125 MIC (%) Fungi: 0.25 | 21.6 | 11.4 |
| 65-3 | Stems | | | 0.17 | MIC (%) Bacteria: 0.25 MIC (%) Fungi: 0.125 | 14.9 | 15.8 |
| 65-4 | Leaves | | | 0.08 | MIC (%) Bacteria: 0.0625 MIC (%) Fungi: 0.125 | 21.3 | 9.7 |
| 65-5 | Fruits | | | 0.13 | MIC (%) Bacteria: 0.125 MIC (%) Fungi: 0.125 | 26.2 | 14.0 |
| 65-6 | Flowers | | | 0.05 | MIC (%) Bacteria: 0.0625 MIC (%) Fungi: 0.0625 | 17.1 | 15.9 |

Example 66

Lyre-Leaf Nightshade

TABLE 126

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 66 | Lyre-leaf nightshade | | *Solanum lyratum* Thunb. | Lyre-leaf nightshade | | | | |
| Comparative Example | Tomato | 50 | *Solanum Lycopersicum* | | 93.21 | 7.28 | 2.14 | 84.19 |
| 66-1 | Whole plant | 2 | | | 36.68 | 16.83 | 20.25 | 239.79 |
| | | 10 | | | 32.11 | 27.46 | 30.93 | 423.49 |
| | | 50 | | | 23.19 | 37.75 | 35.93 | 777.92 |
| 66-2 | Roots | 2 | | | 36.65 | 15.33 | 20.40 | 314.55 |
| | | 10 | | | 28.42 | 28.98 | 28.38 | 598.91 |
| | | 50 | | | 23.93 | 31.59 | 39.09 | 750.34 |
| 66-3 | Stems | 2 | | | 34.70 | 19.09 | 26.61 | 245.91 |
| | | 10 | | | 31.98 | 23.39 | 33.86 | 458.53 |
| | | 50 | | | 22.20 | 31.38 | 34.41 | 685.22 |
| 66-4 | Leaves | 2 | | | 38.13 | 11.21 | 22.50 | 284.06 |
| | | 10 | | | 32.90 | 27.05 | 29.51 | 519.30 |
| | | 50 | | | 24.98 | 38.60 | 39.10 | 753.34 |
| 66-5 | Fruits | 2 | | | 34.68 | 17.96 | 24.33 | 400.53 |
| | | 10 | | | 27.49 | 23.68 | 31.23 | 443.47 |
| | | 50 | | | 24.80 | 34.55 | 37.69 | 606.11 |
| 66-6 | Flowers | 2 | | | 34.98 | 11.31 | 21.80 | 341.11 |
| | | 10 | | | 28.55 | 27.01 | 29.28 | 576.44 |
| | | 50 | | | 25.17 | 33.24 | 36.70 | 794.68 |

TABLE 127

| No. | Sample | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|
| | Control group | | | Vitamin C 7.5 ppm | Hexanediol Bacteria: *P. aeruginosa* 2% Fungi: *A. niger* 1% | Untreated 0 mm | Untreated 0 mm |
| 66 | Lyre-leaf nightshade | *Solanum lyratum* Thunb. | Lyre-leaf nightshade | | | | |
| Comparative Example | Tomato | *Solanum Lycopersicum* | | 3.29 | MIC (%) Bacteria, Fungi: >2 | 0.0 | 0.0 |
| 66-1 | Whole plant | | | 0.11 | MIC (%) Bacteria: 0.125 MIC (%) Fungi: 0.125 | 20.5 | 15.6 |
| 66-2 | Roots | | | 0.13 | MIC (%) Bacteria: 0.125 MIC (%) Fungi: 0.25 | 10.0 | 14.1 |
| 66-3 | Stems | | | 0.17 | MIC (%) Bacteria: 0.25 MIC (%) Fungi: 0.25 | 16.1 | 22.1 |
| 66-4 | Leaves | | | 0.09 | MIC (%) Bacteria: 0.0625 MIC (%) Fungi: 0.125 | 26.4 | 14.3 |
| 66-5 | Fruits | | | 0.14 | MIC (%) Bacteria: 0.125 MIC (%) Fungi: 0.125 | 23.5 | 25.7 |
| 66-6 | Flowers | | | 0.07 | MIC (%) Bacteria: 0.0625 MIC (%) Fungi: 0.0625 | 12.7 | 20.8 |

Example 67

Ivy Morning Glory

TABLE 128

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 67 | Ivy morning glory | | *Calystegia hederacea* Wall. | Ivy morning glory | | | | |
| Comparative Example | Convolvulus | 50 | *Calystegia Sepium* | | 85.14 | 15.56 | 5.33 | 64.52 |
| 67-1 | Whole plant | 2 | | | 38.64 | 16.33 | 25.11 | 235.21 |
| | | 10 | | | 32.30 | 24.08 | 32.94 | 406.90 |
| | | 50 | | | 21.02 | 36.03 | 38.04 | 627.45 |
| 67-2 | Roots | 2 | | | 34.06 | 10.35 | 23.95 | 329.07 |
| | | 10 | | | 33.40 | 24.23 | 32.64 | 583.00 |
| | | 50 | | | 21.07 | 31.04 | 39.75 | 714.13 |
| 67-3 | Stems | 2 | | | 35.55 | 18.48 | 25.12 | 349.26 |
| | | 10 | | | 28.21 | 28.01 | 32.23 | 405.88 |
| | | 50 | | | 24.42 | 30.25 | 39.96 | 669.08 |
| 67-4 | Leaves | 2 | | | 39.22 | 15.54 | 21.55 | 348.95 |
| | | 10 | | | 32.63 | 25.59 | 32.70 | 526.26 |
| | | 50 | | | 23.85 | 39.02 | 37.20 | 650.78 |
| 67-5 | Fruits | 2 | | | 35.41 | 15.59 | 20.04 | 300.06 |
| | | 10 | | | 32.56 | 28.31 | 32.67 | 416.83 |
| | | 50 | | | 26.07 | 32.69 | 36.37 | 794.47 |
| 67-6 | Flowers | 2 | | | 36.27 | 19.81 | 23.38 | 276.47 |
| | | 10 | | | 28.45 | 20.56 | 31.48 | 586.01 |
| | | 50 | | | 20.28 | 36.45 | 37.17 | 662.34 |
| 67-7 | Shoots | 2 | | | 36.98 | 12.58 | 23.24 | 242.25 |
| | | 10 | | | 30.33 | 22.60 | 31.52 | 589.80 |
| | | 50 | | | 23.23 | 31.32 | 37.31 | 695.08 |
| 67-8 | Underground stems | 2 | | | 36.20 | 11.17 | 25.75 | 355.04 |
| | | 10 | | | 31.55 | 22.27 | 31.74 | 536.31 |
| | | 50 | | | 26.13 | 33.26 | 37.62 | 705.69 |

TABLE 129

| No. | Sample | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|
| | Control group | | | Vitamin C 7.5 ppm | Hexanediol Bacteria: *P. aeruginosa* 2% Fungi: *A. niger* 1% | Untreated 0 mm | Untreated 0 mm |
| 67 | Ivy morning glory | *Calystegia hederacea* Wall. | Ivy morning glory | | | | |
| Comparative Example | Convolvulus | *Calystegia Sepium* | | 7.69 | MIC (%) Bacteria: 1, Fungi: 1 | 8.1 | 11.1 |
| 67-1 | Whole plant | | | 0.25 | MIC (%) Bacteria: 0.5 MIC (%) Fungi: 0.25 | 26.1 | 27.4 |
| 67-2 | Roots | | | 0.27 | MIC (%) Bacteria: 0.125 MIC (%) Fungi: 0.125 | 18.5 | 20.7 |
| 67-3 | Stems | | | 0.32 | MIC (%) Bacteria: 0.5 MIC (%) Fungi: 0.25 | 12.7 | 24.7 |
| 67-4 | Leaves | | | 0.24 | MIC (%) Bacteria: 0.25 MIC (%) Fungi: 0.25 | 14.3 | 25.6 |
| 67-5 | Fruits | | | 0.19 | MIC (%) Bacteria: 0.125 MIC (%) Fungi: 0.125 | 22.0 | 15.7 |
| 67-6 | Flowers | | | 0.26 | MIC (%) Bacteria: 0.125 MIC (%) Fungi: 0.125 | 21.5 | 17.3 |

TABLE 129-continued

| No. | Sample | Scientific name | English name | Anti-oxidation IC50 (%) | Anti-bacteria MIC (%) | Anti-bacteria (S. mutans) Size of growth inhibition ring (mm) | Anti-bacteria (P. gingivalis) Size of growth inhibition ring (mm) |
|---|---|---|---|---|---|---|---|
| 67-7 | Shoots | | | 0.27 | MIC (%) Bacteria: 0.5 MIC (%) Fungi: 0.5 | 21.0 | 20.5 |
| 67-8 | Underground stems | | | 0.89 | MIC (%) Bacteria: 0.25 MIC (%) Fungi: 0.5 | 9.0 | 22.9 |

Example 68

Beach Morning Glory

15

TABLE 130

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 68 | Beach morning glory | | Calystegia soldanella (L.) Roem & Schult. | Beach morning glory | | | | |
| Comparative Example | Convolvulus | 50 | Calystegia Sepium | | 85.14 | 15.56 | 5.33 | 64.52 |
| 68-1 | Whole plant | 2 | | | 38.02 | 17.78 | 25.89 | 276.45 |
| | | 10 | | | 31.51 | 26.14 | 33.55 | 429.08 |
| | | 50 | | | 23.85 | 32.15 | 37.39 | 746.07 |
| 68-2 | Roots | 2 | | | 39.44 | 11.12 | 22.08 | 231.29 |
| | | 10 | | | 28.06 | 29.12 | 33.41 | 581.52 |
| | | 50 | | | 24.66 | 31.50 | 34.77 | 760.42 |
| 68-3 | Stems | 2 | | | 37.85 | 16.50 | 22.92 | 399.08 |
| | | 10 | | | 31.67 | 24.51 | 30.99 | 578.28 |
| | | 50 | | | 21.36 | 32.89 | 38.80 | 708.35 |
| 68-4 | Leaves | 2 | | | 37.60 | 10.55 | 25.30 | 321.80 |
| | | 10 | | | 28.42 | 27.50 | 31.05 | 592.86 |
| | | 50 | | | 26.17 | 35.64 | 36.35 | 645.27 |
| 68-5 | Fruits | 2 | | | 34.78 | 17.61 | 21.45 | 389.10 |
| | | 10 | | | 27.14 | 28.27 | 32.01 | 401.26 |
| | | 50 | | | 21.73 | 32.35 | 39.56 | 606.85 |
| 68-6 | Flowers | 2 | | | 39.99 | 11.60 | 24.37 | 396.05 |
| | | 10 | | | 30.69 | 28.93 | 28.78 | 553.19 |
| | | 50 | | | 26.96 | 35.80 | 37.03 | 692.82 |
| 68-7 | Shoots | 2 | | | 37.02 | 17.85 | 24.52 | 267.00 |
| | | 10 | | | 33.34 | 27.70 | 33.75 | 541.63 |
| | | 50 | | | 22.71 | 31.02 | 34.83 | 793.25 |
| 68-8 | Underground stems | 2 | | | 38.57 | 14.04 | 23.21 | 244.39 |
| | | 10 | | | 32.36 | 28.32 | 31.65 | 589.79 |
| | | 50 | | | 23.13 | 31.38 | 36.58 | 786.22 |

TABLE 131

| No. | Sample | Scientific name | English name | Anti-oxidation IC50 (%) | Anti-bacteria MIC (%) | Anti-bacteria (S. mutans) Size of growth inhibition ring (mm) | Anti-bacteria (P. gingivalis) Size of growth inhibition ring (mm) |
|---|---|---|---|---|---|---|---|
| | Control group | | | Vitamin C 7.5 ppm | Hexanediol Bacteria: P. aeruginosa 2% Fungi: A. niger 1% | Untreated 0 mm | Untreated 0 mm |
| 68 | Beach morning glory | Calystegia soldanella (L.) Roem. & Schult. | Beach morning glory | | | | |

TABLE 131-continued

| No. | Sample | Scientific name | English name | Anti-oxidation IC50 (%) | Anti-bacteria MIC (%) | Anti-bacteria (S. mutans) Size of growth inhibition ring (mm) | Anti-bacteria (P. gingivalis) Size of growth inhibition ring (mm) |
|---|---|---|---|---|---|---|---|
| Comparative Example | Convolvulus | *Calystegia Sepium* | | 7.69 | MIC (%) Bacteria: 1, Fungi: 1 | 8.9 | 9.4 |
| 68-1 | Whole plant | | | 0.14 | MIC (%) Bacteria: 0.125 MIC (%) Fungi: 0.25 | 19.8 | 16.4 |
| 68-2 | Roots | | | 0.29 | MIC (%) Bacteria: 0.25 MIC (%) Fungi: 0.25 | 26.3 | 14.1 |
| 68-3 | Stems | | | 0.16 | MIC (%) Bacteria: 0.125 MIC (%) Fungi: 0.125 | 17.6 | 13.2 |
| 68-4 | Leaves | | | 0.21 | MIC (%) Bacteria: 0.25 MIC (%) Fungi: 0.125 | 22.0 | 9.8 |
| 68-5 | Fruits | | | 0.09 | MIC (%) Bacteria: 0.0625 MIC (%) Fungi: 0.0625 | 14.9 | 10.2 |
| 68-6 | Flowers | | | 0.07 | MIC (%) Bacteria: 0.0625 MIC (%) Fungi: 0.0625 | 16.3 | 26.6 |
| 68-7 | Shoots | | | 0.21 | MIC (%) Bacteria: 0.5 MIC (%) Fungi: 0.25 | 21.5 | 12.3 |
| 68-8 | Underground stems | | | 0.85 | MIC (%) Bacteria: 0.5 MIC (%) Fungi: 0.5 | 15.4 | 10.7 |

Example 69

East Asian Beautyberry

25

TABLE 132

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 69 | East Asian beautyberry | | *Callicarpa japonica* Thunb. | East Asian beautyberry | | | | |
| Comparative Example | Purple beautyberry | 50 | *Callicarpa Dichotoma* | | 74.64 | 15.12 | 2.41 | 54.26 |
| 69-1 | Whole plant | 2 | | | 39.15 | 15.22 | 26.94 | 400.97 |
| | | 10 | | | 31.26 | 20.91 | 28.04 | 577.41 |
| | | 50 | | | 21.32 | 36.26 | 36.46 | 695.41 |
| 69-2 | Roots | 2 | | | 38.49 | 17.26 | 21.19 | 209.06 |
| | | 10 | | | 27.03 | 28.92 | 30.16 | 480.34 |
| | | 50 | | | 24.94 | 36.82 | 39.89 | 672.78 |
| 69-3 | Stems | 2 | | | 35.78 | 11.06 | 21.65 | 273.62 |
| | | 10 | | | 27.98 | 27.69 | 31.54 | 451.81 |
| | | 50 | | | 21.62 | 36.69 | 35.57 | 742.09 |
| 69-4 | Leaves | 2 | | | 36.83 | 12.80 | 20.45 | 275.43 |
| | | 10 | | | 27.38 | 27.16 | 25.17 | 498.65 |
| | | 50 | | | 26.57 | 30.10 | 30.51 | 661.64 |
| 69-5 | Fruits | 2 | | | 34.78 | 12.00 | 20.71 | 244.98 |
| | | 10 | | | 29.89 | 21.03 | 32.88 | 466.34 |
| | | 50 | | | 20.89 | 32.39 | 39.78 | 775.51 |
| 69-6 | Flowers | 2 | | | 34.53 | 12.54 | 24.08 | 356.14 |
| | | 10 | | | 29.80 | 29.54 | 27.48 | 559.12 |
| | | 50 | | | 21.53 | 36.73 | 37.04 | 727.81 |

TABLE 133

| No. | Sample | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|
| | Control group | | | Vitamin C 7.5 ppm | Hexanediol Bacteria: *P. aeruginosa* 2% Fungi: *A. niger* 1% | Untreated 0 mm | Untreated 0 mm |
| 69 | East Asian beautyberry | *Callicarpa japonica* Thunb. | East Asian beautyberry | | | | |
| Comparative Example | Purple beautyberry | *Callicarpa Dichotoma* | | 3.22 | MIC (%) Bacteria: 1, Fungi: 2 | 11.5 | 11.0 |
| 69-1 | Whole plant | | | 0.14 | MIC (%) Bacteria: 0.5 MIC (%) Fungi: 0.5 | 25.5 | 20.6 |
| 69-2 | Roots | | | 0.19 | MIC (%) Bacteria: 0.25 MIC (%) Fungi: 0.25 | 17.3 | 14.5 |
| 69-3 | Stems | | | 0.15 | MIC (%) Bacteria: 0.125 MIC (%) Fungi: 0.25 | 13.6 | 12.6 |
| 69-4 | Leaves | | | 0.21 | MIC (%) Bacteria: 0.25 MIC (%) Fungi: 0.25 | 11.5 | 12.6 |
| 69-5 | Fruits | | | 0.08 | MIC (%) Bacteria: 0.0625 MIC (%) Fungi: 0.0625 | 25.3 | 25.8 |
| 69-6 | Flowers | | | 0.04 | MIC (%) Bacteria: 0.0625 MIC (%) Fungi: 0.0625 | 9.1 | 19.4 |

Example 70

Korean Mint

TABLE 134

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 70 | Korean mint | | *Agastache rugosa* (Fisch. & C. A. Mev) Kuntze | Korean mint | | | | |
| Comparative Example | Anise hyssop | 50 | *Agastache Foeniculum* | | 93.66 | 8.54 | 3.15 | 32.80 |
| 70-1 | Whole plant | 2 | | | 37.70 | 12.32 | 20.50 | 348.18 |
| | | 10 | | | 29.90 | 29.00 | 33.30 | 473.40 |
| | | 50 | | | 25.29 | 37.87 | 34.03 | 719.57 |
| 70-2 | Roots | 2 | | | 37.78 | 10.19 | 26.81 | 281.13 |
| | | 10 | | | 30.20 | 29.57 | 31.81 | 411.91 |
| | | 50 | | | 21.84 | 39.06 | 39.55 | 788.31 |
| 70-3 | Stems | 2 | | | 37.46 | 19.38 | 24.92 | 368.86 |
| | | 10 | | | 29.99 | 25.20 | 33.96 | 549.40 |
| | | 50 | | | 24.99 | 30.60 | 35.82 | 763.35 |
| 70-4 | Leaves | 2 | | | 36.23 | 17.25 | 24.54 | 218.66 |
| | | 10 | | | 30.26 | 29.65 | 30.89 | 542.20 |
| | | 50 | | | 25.01 | 31.94 | 34.40 | 754.76 |
| 70-5 | Fruits | 2 | | | 35.27 | 13.94 | 26.74 | 272.11 |
| | | 10 | | | 30.59 | 28.81 | 29.95 | 405.97 |
| | | 50 | | | 26.97 | 33.09 | 36.94 | 693.34 |
| 70-6 | Flowers | 2 | | | 36.66 | 19.88 | 21.38 | 261.56 |
| | | 10 | | | 29.81 | 26.47 | 28.47 | 418.52 |
| | | 50 | | | 25.43 | 35.27 | 36.54 | 622.59 |

TABLE 135

| No. | Sample | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|
| | Control group | | | Vitamin C 7.5 ppm | Hexanediol Bacteria: *P. aeruginosa* 2% Fungi: *A. niger* 1% | Untreated 0 mm | Untreated 0 mm |
| 70 | Korean mint | *Agastache rugosa* (Fisch. & C. A. Mey) Kuntze | Korean mint | | | | |
| Comparative Example | Anise hyssop | *Agastache Foeniculum* | | 6.34 | MIC (%) Bacteria: 2 MIC (%) Fungi: 2 | 9.6 | 8.4 |
| 70-1 | Whole plant | | | 0.31 | MIC (%) Bacteria: 0.25 MIC (%) Fungi: 0.25 | 15.5 | 16.8 |
| 70-2 | Roots | | | 0.90 | MIC (%) Bacteria: 0.25 MIC (%) Fungi: 0.125 | 14.9 | 16.1 |
| 70-3 | Stems | | | 0.85 | MIC (%) Bacteria: 0.5 MIC (%) Fungi: 0.5 | 13.4 | 10.8 |
| 70-4 | Leaves | | | 0.72 | MIC (%) Bacteria: 0.5 MIC (%) Fungi: 1 | 10.4 | 11.3 |
| 70-5 | Fruits | | | 0.59 | MIC (%) Bacteria: 0.25 MIC (%) Fungi: 0.5 | 12.5 | 12.2 |
| 70-6 | Flowers | | | 0.35 | MIC (%) Bacteria: 0.5 MIC (%) Fungi: 0.5 | 27.1 | 24.6 |

25

Example 71

Small-Flower Asian Calamint

TABLE 136

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 71 | Small-flower Asian calamint | | *Clinopodium chinense* var. *parviflorum* (Kudo) H. Hara | Small-flower Asian calamint | | | | |
| 71-1 | Whole plant | 2 | | | 39.05 | 19.09 | 25.67 | 212.59 |
| | | 10 | | | 27.46 | 21.25 | 31.95 | 405.11 |
| | | 50 | | | 25.13 | 34.77 | 35.04 | 691.93 |
| 71-2 | Roots | 2 | | | 38.04 | 16.00 | 22.54 | 221.35 |
| | | 10 | | | 32.20 | 25.27 | 30.65 | 403.43 |
| | | 50 | | | 20.89 | 36.83 | 34.01 | 779.37 |
| 71-3 | Stems | 2 | | | 36.15 | 13.73 | 26.33 | 260.07 |
| | | 10 | | | 29.72 | 21.66 | 32.13 | 541.45 |
| | | 50 | | | 26.33 | 32.25 | 35.65 | 776.96 |
| 71-4 | Leaves | 2 | | | 34.47 | 15.37 | 26.86 | 342.94 |
| | | 10 | | | 28.65 | 28.42 | 33.18 | 507.66 |
| | | 50 | | | 23.97 | 33.54 | 34.53 | 691.76 |
| 71-5 | Fruits | 2 | | | 36.79 | 16.97 | 26.91 | 271.18 |
| | | 10 | | | 31.14 | 20.86 | 31.09 | 549.19 |
| | | 50 | | | 25.16 | 34.43 | 35.50 | 647.63 |
| 71-6 | Flowers | 2 | | | 34.71 | 17.31 | 21.22 | 220.91 |
| | | 10 | | | 31.93 | 26.59 | 29.99 | 497.80 |
| | | 50 | | | 25.02 | 31.59 | 38.60 | 634.77 |

TABLE 137

| No. | Sample | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|
| | Control group | | | Vitamin C 7.5 ppm | Hexanediol Bacteria: *P. aeruginosa* 2% Fungi: *A. niger* 1% | Untreated 0 mm | Untreated 0 mm |
| 71 | Small-flower Asian calamint | *Clinopodium chinense* var. *parviflorum* (Kudo) H. Hara | Small-flower Asian calamint | | | | |
| 71-1 | Whole plant | | | 0.65 | MIC (%) Bacteria: 1 MIC (%) Fungi: 1 | 25.3 | 23.2 |
| 71-2 | Roots | | | 0.79 | MIC (%) Bacteria: 1 MIC (%) Fungi: 0.5 | 8.3 | 23.0 |
| 71-3 | Stems | | | 0.23 | MIC (%) Bacteria: 0.25 MIC (%) Fungi: 0.5 | 20.9 | 13.0 |
| 71-4 | Leaves | | | 0.70 | MIC (%) Bacteria: 1 MIC (%) Fungi: 0.5 | 19.9 | 27.3 |
| 71-5 | Fruits | | | 0.60 | MIC (%) Bacteria: 0.5 MIC (%) Fungi: 0.25 | 8.5 | 9.8 |
| 71-6 | Flowers | | | 0.16 | MIC (%) Bacteria: 0.25 MIC (%) Fungi: 0.125 | 13.4 | 23.3 |

Example 72

25

Henbit Deadnettle

TABLE 138

| No. | Sample | Cone, (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 72 | Henbit deadnettle | | *Lamium amplexicaule* L. | Henbit deadnettle | | | | |
| Comparative Example | Deadnettle | 50 | *Lamium Album* | | 95.57 | 11.23 | 4.43 | 31.32 |
| 72-1 | Whole plant | 2 | | | 39.53 | 12.69 | 15.50 | 278.63 |
| | | 10 | | | 28.06 | 29.35 | 21.55 | 517.60 |
| | | 50 | | | 24.19 | 32.10 | 30.14 | 734.73 |
| 72-2 | Roots | 2 | | | 35.97 | 12.89 | 11.93 | 299.85 |
| | | 10 | | | 32.27 | 26.50 | 25.34 | 577.49 |
| | | 50 | | | 21.49 | 38.06 | 37.34 | 734.88 |
| 72-3 | Stems | 2 | | | 36.30 | 17.87 | 19.63 | 262.37 |
| | | 10 | | | 32.30 | 23.96 | 24.25 | 543.84 |
| | | 50 | | | 25.60 | 35.49 | 39.23 | 611.56 |
| 72-4 | Leaves | 2 | | | 36.90 | 10.45 | 10.39 | 238.11 |
| | | 10 | | | 31.07 | 27.41 | 25.75 | 475.57 |
| | | 50 | | | 26.92 | 31.72 | 36.24 | 776.24 |
| 72-5 | Fruits | 2 | | | 37.88 | 15.96 | 11.79 | 309.45 |
| | | 10 | | | 28.68 | 21.05 | 24.78 | 478.81 |
| | | 50 | | | 23.60 | 34.57 | 36.22 | 764.62 |
| 72-6 | Flowers | 2 | | | 38.78 | 14.63 | 16.55 | 382.92 |
| | | 10 | | | 31.88 | 25.75 | 27.35 | 514.77 |
| | | 50 | | | 26.62 | 30.18 | 36.64 | 778.50 |

TABLE 139

| No. | Sample | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|
| | Control group | | | Vitamin C 7.5 ppm | Hexanediol Bacteria: *P. aeruginosa* 2% Fungi: *A. niger* 1% | Untreated 0 mm | Untreated 0 mm |
| 72 | Henbit deadnettle | *Lamium amplexicaule* L. | Henbit deadnettle | | | | |
| Comparative Example | Deadnettle | *Lamium Album* | | 5.56 | MIC (%) Bacteria: 0.5 MIC (%) Fungi: 1 | 8.5 | 8.1 |
| 72-1 | Whole plant | | | 0.58 | MIC (%) Bacteria: 0.5 MIC (%) Fungi: 1 | 17.3 | 15.0 |
| 72-2 | Roots | | | 0.82 | MIC (%) Bacteria: 0.5 MIC (%) Fungi: 0.5 | 17.6 | 9.0 |
| 72-3 | Stems | | | 0.81 | MIC (%) Bacteria: 0.25 MIC (%) Fungi: 0.5 | 13.0 | 16.0 |
| 72-4 | Leaves | | | 0.43 | MIC (%) Bacteria: 0.125 MIC (%) Fungi: 0.125 | 26.7 | 21.4 |
| 72-5 | Fruits | | | 0.79 | MIC (%) Bacteria: 0.25 MIC (%) Fungi: 0.125 | 25.6 | 22.5 |
| 72-6 | Flowers | | | 0.92 | MIC (%) Bacteria: 0.25 MIC (%) Fungi: 0.5 | 24.2 | 23.3 |

Example 73

Oriental Motherwort

TABLE 140

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 73 | Oriental motherwort | | *Leonurus japonicus* Houtt. | Oriental motherwort | | | | |
| Comparative Example | *Leonurus cardiaca* | 50 | *Leonurus Cardiaca* | motherwort | 77.38 | 11.28 | 2.17 | 98.89 |
| 73-1 | Whole plant | 2 | | | 38.56 | 13.52 | 22.63 | 270.14 |
| | | 10 | | | 30.27 | 26.46 | 30.90 | 460.52 |
| | | 50 | | | 21.34 | 31.55 | 39.50 | 672.99 |
| 73-2 | Roots | 2 | | | 37.08 | 12.90 | 23.40 | 306.15 |
| | | 10 | | | 32.84 | 21.09 | 31.02 | 509.48 |
| | | 50 | | | 26.79 | 38.51 | 34.98 | 721.68 |
| 73-3 | Stems | 2 | | | 38.83 | 11.63 | 22.59 | 250.02 |
| | | 10 | | | 27.96 | 28.21 | 32.41 | 408.30 |
| | | 50 | | | 20.10 | 34.73 | 36.43 | 794.16 |
| 73-4 | Leaves | 2 | | | 34.19 | 16.99 | 21.10 | 367.30 |
| | | 10 | | | 28.67 | 29.49 | 28.95 | 436.15 |
| | | 50 | | | 20.15 | 36.68 | 35.28 | 653.08 |
| 73-5 | Fruits | 2 | | | 37.41 | 12.48 | 25.19 | 305.01 |
| | | 10 | | | 28.36 | 27.03 | 32.82 | 512.05 |
| | | 50 | | | 25.09 | 31.77 | 36.93 | 632.87 |
| 73-6 | Flowers | 2 | | | 34.89 | 19.74 | 23.81 | 285.12 |
| | | 10 | | | 29.61 | 29.34 | 27.81 | 576.37 |
| | | 50 | | | 20.20 | 37.44 | 34.72 | 795.79 |

TABLE 141

| No. | Sample | Scientific name | English name | Anti-oxidation IC50 (%) | Anti-bacteria MIC (%) | Anti-bacteria (S. mutans) Size of growth inhibition ring (mm) | Anti-bacteria (P. gingivalis) Size of growth inhibition ring (mm) |
|---|---|---|---|---|---|---|---|
| | Control group | | | Vitamin C 7.5 ppm | Hexanediol Bacteria: *P. aeruginosa* 2% Fungi: *A. niger* 1% | Untreated 0 mm | Untreated 0 mm |
| 73 | Oriental motherwort | *Leonurus japonicus* Houtt. | Oriental motherwort | | | | |
| Comparative Example | *Leonurus cardiaca* | *Leonurus Cardiaca* | motherwort | 4.90 | MIC (%) Bacteria: 2 MIC (%) Fungi: 2 | 8.6 | 12.6 |
| 73-1 | Whole plant | | | 0.35 | MIC (%) Bacteria: 1 MIC (%) Fungi: 0.5 | 26.2 | 22.3 |
| 73-2 | Roots | | | 0.49 | MIC (%) Bacteria: 0.5 MIC (%) Fungi: 0.25 | 26.5 | 20.8 |
| 73-3 | Stems | | | 0.64 | MIC (%) Bacteria: 0.25 MIC (%) Fungi: 0.5 | 10.0 | 11.0 |
| 73-4 | Leaves | | | 0.88 | MIC (%) Bacteria: 0.5 MIC (%) Fungi: 0.5 | 24.5 | 15.5 |
| 73-5 | Fruits | | | 0.21 | MIC (%) Bacteria: 0.125 MIC (%) Fungi: 0.25 | 11.7 | 19.1 |
| 73-6 | Flowers | | | 0.19 | MIC (%) Bacteria: 0.0625 MIC (%) Fungi: 0.0625 | 18.3 | 17.0 |

Example 74

Long-Stalk Low Meadow-Rue

TABLE 142

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 74 | Long-stalk low meadow-rue | | *Thalictrum kemense* Fr. | Long-stalk low meadow-rue | | | | |
| Comparative Example | Columbine meadow rue | 50 | *Thalictrum aquilegiifolium* | | 78.25 | 1.82 | 2.71 | 56.01 |
| 74-1 | Whole plant | 2 | | | 39.94 | 12.01 | 23.53 | 361.89 |
| | | 10 | | | 32.57 | 27.73 | 32.27 | 476.94 |
| | | 50 | | | 22.49 | 33.51 | 35.39 | 732.35 |
| 74-2 | Roots | 2 | | | 34.83 | 16.83 | 24.21 | 285.43 |
| | | 10 | | | 27.15 | 20.55 | 32.11 | 573.31 |
| | | 50 | | | 21.28 | 31.86 | 35.82 | 767.85 |
| 74-3 | Stems | 2 | | | 38.94 | 12.99 | 23.32 | 212.01 |
| | | 10 | | | 31.35 | 28.30 | 32.13 | 404.86 |
| | | 50 | | | 20.81 | 38.94 | 34.33 | 675.30 |
| 74-4 | Leaves | 2 | | | 39.63 | 19.63 | 26.34 | 358.95 |
| | | 10 | | | 29.32 | 20.42 | 31.61 | 489.81 |
| | | 50 | | | 26.18 | 31.66 | 38.66 | 663.75 |
| 74-5 | Fruits | 2 | | | 38.84 | 10.71 | 21.99 | 269.70 |
| | | 10 | | | 27.25 | 27.49 | 30.64 | 519.83 |
| | | 50 | | | 25.00 | 39.33 | 34.38 | 606.34 |
| 74-6 | Flowers | 2 | | | 36.99 | 10.91 | 20.25 | 204.87 |
| | | 10 | | | 32.22 | 22.45 | 29.59 | 477.59 |
| | | 50 | | | 25.36 | 38.40 | 36.91 | 759.73 |

TABLE 143

| No. | Sample | Scientific name | English name | Anti-oxidation IC50 (%) | Anti-bacteria MIC (%) | Anti-bacteria (S. mutans) Size of growth inhibition ring (mm) | Anti-bacteria (P. gingivalis) Size of growth inhibition ring (mm) |
|---|---|---|---|---|---|---|---|
| | Control group | | | Vitamin C 7.5 ppm | Hexanediol Bacteria: P. aeruginosa 2% Fungi: A. niger 1% | Untreated 0 mm | Untreated 0 mm |
| 74 | Long-stalk low meadow-rue | Thalictrum kemense Fr. | Long-stalk low meadow-rue | | | | |
| Comparative Example | Columbine meadow rue | Thalictrum aquilegiifolium | | 3.29 | MIC (%) Bacteria: 1 MIC (%) Fungi: 1 | 8.2 | 13.3 |
| 74-1 | Whole plant | | | 0.31 | MIC (%) Bacteria: 0.125 MIC (%) Fungi: 0.125 | 15.1 | 21.5 |
| 74-2 | Roots | | | 0.71 | MIC (%) Bacteria: 0.25 MIC (%) Fungi: 0.5 | 14.9 | 18.1 |
| 74-3 | Stems | | | 0.46 | MIC (%) Bacteria: 0.125 MIC (%) Fungi: 0.0625 | 9.0 | 9.5 |
| 74-4 | Leaves | | | 0.06 | MIC (%) Bacteria: 0.0625 MIC (%) Fungi: 0.125 | 18.6 | 26.1 |
| 74-5 | Fruits | | | 0.93 | MIC (%) Bacteria: 0.25 MIC (%) Fungi: 0.5 | 11.3 | 11.8 |
| 74-6 | Flowers | | | 0.81 | MIC (%) Bacteria: 0.5 MIC (%) Fungi: 0.5 | 26.3 | 9.4 |

Example 75

Korean Spice *Viburnum*

TABLE 144

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 75 | Korean spice viburnum | | Viburnum carlesii Hemsl. | Korean spice viburnum | | | | |
| Comparative Example | Linden viburnum | 50 | Viburnum Dilatatum | | 84.07 | 12.94 | 6.22 | 61.57 |
| 75-1 | Whole plant | 2 | | | 34.82 | 11.78 | 26.91 | 210.15 |
| | | 10 | | | 27.05 | 28.23 | 30.44 | 542.08 |
| | | 50 | | | 21.00 | 34.30 | 38.98 | 662.25 |
| 75-2 | Roots | 2 | | | 35.93 | 11.98 | 20.09 | 375.86 |
| | | 10 | | | 31.12 | 25.74 | 31.19 | 598.44 |
| | | 50 | | | 22.62 | 30.83 | 39.49 | 758.04 |
| 75-3 | Stems | 2 | | | 36.85 | 18.80 | 22.62 | 261.05 |
| | | 10 | | | 31.59 | 28.02 | 31.42 | 525.80 |
| | | 50 | | | 22.87 | 36.08 | 39.55 | 662.72 |
| 75-4 | Leaves | 2 | | | 37.64 | 16.33 | 24.71 | 389.70 |
| | | 10 | | | 30.85 | 25.78 | 33.59 | 553.58 |
| | | 50 | | | 22.67 | 34.75 | 34.38 | 793.82 |
| 75-5 | Fruits | 2 | | | 38.79 | 15.15 | 20.85 | 336.66 |
| | | 10 | | | 27.83 | 20.80 | 28.28 | 575.45 |
| | | 50 | | | 25.71 | 32.51 | 35.56 | 792.88 |
| 75-6 | Flowers | 2 | | | 39.50 | 19.04 | 25.03 | 225.12 |
| | | 10 | | | 31.42 | 20.95 | 29.95 | 580.31 |
| | | 50 | | | 23.38 | 31.04 | 39.93 | 669.19 |

TABLE 145

| No. | Sample | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|
| | Control group | | | Vitamin C 7.5 ppm | Hexanediol Bacteria: *P. aeruginosa* 2% Fungi: *A. niger* 1% | Untreated 0 mm | Untreated 0 mm |
| 75 | Korean spice viburnum | *Viburnum carlesii* Hemsl. | Korean spice viburnum | | | | |
| Comparative Example | Linden viburnum | *Viburnum Dilatatum* | | 5.95 | MIC (%) Bacteria: 2 MIC (%) Fungi: 1 | 9.1 | 8.5 |
| 75-1 | Whole plant | | | 0.51 | MIC (%) Bacteria: 0.5 MIC (%) Fungi: 1 | 17.8 | 18.2 |
| 75-2 | Roots | | | 0.13 | MIC (%) Bacteria: 0.125 MIC (%) Fungi: 0.0625 | 14.6 | 20.0 |
| 75-3 | Stems | | | 0.40 | MIC (%) Bacteria: 1 MIC (%) Fungi: 1 | 9.0 | 8.6 |
| 75-4 | Leaves | | | 0.07 | MIC (%) Bacteria: 0.125 MIC (%) Fungi: 0.125 | 18.0 | 15.6 |
| 75-5 | Fruits | | | 0.21 | MIC (%) Bacteria: 0.25 MIC (%) Fungi: 0.125 | 8.6 | 18.1 |
| 75-6 | Flowers | | | 0.29 | MIC (%) Bacteria: 0.25 MIC (%) Fungi: 0.5 | 20.7 | 16.7 |

Example 76

Asian Greater Celandine

TABLE 146

| No. | Sample | Conc. (ppm) | Scientific name | English name | Whitening Melanin content (%) | Anti-wrinkle Collagen synthesis (% of control) | Anti-nflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 76 | Asian greater celandine | | *Chelidonium majus* var. *asiaticum* (H. Hara) Ohwi | Asian greater celandine | | | | |
| 76-1 | Whole plant | 2 | | | 39.13 | 15.19 | 23.36 | 312.25 |
| | | 10 | | | 32.88 | 19.55 | 33.44 | 439.24 |
| | | 50 | | | 25.55 | 25.23 | 38.57 | 687.41 |
| 76-2 | Roots | 2 | | | 36.37 | 17.69 | 23.81 | 320.67 |
| | | 10 | | | 30.79 | 20.97 | 33.09 | 467.14 |
| | | 50 | | | 23.25 | 38.50 | 37.65 | 600.48 |
| 76-3 | Stems | 2 | | | 37.22 | 7.57 | 11.82 | 299.32 |
| | | 10 | | | 32.82 | 14.19 | 14.78 | 347.45 |
| | | 50 | | | 23.42 | 18.46 | 24.50 | 422.77 |
| 76-4 | Leaves | 2 | | | 35.35 | 7.31 | 10.46 | 296.07 |
| | | 10 | | | 30.59 | 19.35 | 18.97 | 529.14 |
| | | 50 | | | 22.15 | 28.31 | 28.18 | 695.56 |
| 76-5 | Fruits | 2 | | | 37.67 | 9.85 | 9.20 | 370.18 |
| | | 10 | | | 29.00 | 13.51 | 18.96 | 440.31 |
| | | 50 | | | 26.18 | 26.63 | 25.44 | 736.00 |
| 76-6 | Flowers | 2 | | | 36.92 | 7.69 | 23.57 | 317.83 |
| | | 10 | | | 28.86 | 10.97 | 28.82 | 535.06 |
| | | 50 | | | 24.30 | 18.50 | 39.20 | 757.37 |

TABLE 147

| No. | Sample | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|
| | Control group | | | Vitamin C 7.5 ppm | Hexanediol Bacteria: *P. aeruginosa* 2% Fungi: *A. niger* 1% | Untreated 0 mm | Untreated 0 mm |
| 76 | Asian greater celandine | *Chelidonium majus* var. *asiaticum* (H. Hara) Ohwi | Asian greater celandine | | | | |
| 76-1 | Whole plant | | | 1.23 | MIC (%) Bacteria: 1 MIC (%) Fungi: 1 | 26.7 | 25.9 |
| 76-2 | Roots | | | 0.66 | MIC (%) Bacteria: 0.5 MIC (%) Fungi: 1 | 21.2 | 26.1 |
| 76-3 | Stems | | | 0.96 | MIC (%) Bacteria: 0.5 MIC (%) Fungi: 1 | 12.2 | 14.5 |
| 76-4 | Leaves | | | 0.53 | MIC (%) Bacteria: 0.5 MIC (%) Fungi: 0.5 | 18.6 | 18.9 |
| 76-5 | Fruits | | | 0.38 | MIC (%) Bacteria: 1 MIC (%) Fungi: 0.5 | 10.3 | 14.1 |
| 76-6 | Flowers | | | 0.13 | MIC (%) Bacteria: 0.13 MIC (%) Fungi: 0.06 | 22.9 | 24.3 |

Example 77

25

Seashore Spatulate *Aster*

TABLE 148

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 77 | Seashore spatulate aster | | *Aster spathulifolius* Maxim. | Seashore spatulate aster | | | | |
| Comparative Example | Edible aster | 50 | *Aster Scaber* | | 98.28 | 14.55 | 1.65 | 224.15 |
| 77-1 | Whole plant | 2 | | | 48.29 | 8.37 | 25.85 | 223.26 |
| | | 10 | | | 33.34 | 15.53 | 29.34 | 567.40 |
| | | 50 | | | 28.71 | 29.88 | 34.47 | 687.82 |
| 77-2 | Roots | 2 | | | 39.11 | 14.86 | 23.83 | 177.39 |
| | | 10 | | | 30.82 | 25.72 | 27.77 | 320.56 |
| | | 50 | | | 25.02 | 37.92 | 35.11 | 552.69 |
| 77-3 | Stems | 2 | | | 34.69 | 10.71 | 26.48 | 160.79 |
| | | 10 | | | 30.62 | 21.81 | 30.43 | 240.30 |
| | | 50 | | | 20.66 | 31.94 | 36.47 | 400.56 |
| 77-4 | Leaves | 2 | | | 36.76 | 10.31 | 23.93 | 155.15 |
| | | 10 | | | 27.20 | 24.88 | 28.24 | 265.59 |
| | | 50 | | | 21.94 | 31.69 | 39.13 | 415.56 |
| 77-5 | Fruits | 2 | | | 39.15 | 13.67 | 24.16 | 343.58 |
| | | 10 | | | 30.46 | 29.49 | 28.57 | 557.15 |
| | | 50 | | | 23.01 | 37.04 | 34.91 | 768.94 |
| 77-6 | Flowers | 2 | | | 24.92 | 19.52 | 24.58 | 201.60 |
| | | 10 | | | 20.86 | 24.74 | 31.07 | 566.81 |
| | | 50 | | | 16.09 | 39.88 | 37.98 | 731.69 |

TABLE 149

| No. | Sample | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|
| | Control group | | | Vitamin C 7.5 ppm | Hexanediol Bacteria: *P. aeruginosa* 2% Fungi: *A. niger* 1% | Untreated 0 mm | Untreated 0 mm |
| 77 | Seashore spatulate aster | *Aster spathulifolius* Maxim. | Seashore spatulate aster | | | | |
| Comparative Example | Edible aster | *Aster Scaber* | | 4.99 | MIC (%) Bacteria: >2 MIC (%) Fungi: 2 | 8.5 | 9.5 |
| 77-1 | Whole plant | | | 0.63 | MIC (%) Bacteria: 1 MIC (%) Fungi: 0.5 | 19.7 | 23.4 |
| 77-2 | Roots | | | 0.62 | MIC (%) Bacteria: 0.25 MIC (%) Fungi: 0.5 | 11.0 | 19.4 |
| 77-3 | Stems | | | 0.92 | MIC (%) Bacteria: 0.25 MIC (%) Fungi: 0.5 | 12.1 | 13.4 |
| 77-4 | Leaves | | | 0.62 | MIC (%) Bacteria: 0.5 MIC (%) Fungi: 1 | 15.3 | 16.2 |
| 77-5 | Fruits | | | 0.34 | MIC (%) Bacteria: 1 MIC (%) Fungi: 0.25 | 11.8 | 13.6 |
| 77-6 | Flowers | | | 0.07 | MIC (%) Bacteria: 0.06 MIC (%) Fungi: 0.13 | 25.4 | 27.4 |

Example 78

Leopard Plant

TABLE 150

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 78 | Leopard plant | | *Farfugium japonicum* (L.) Kitam. | Leopard plant | | | | |
| 78-1 | Whole plant | 2 | | | 37.02 | 17.49 | 24.96 | 381.68 |
| | | 10 | | | 31.43 | 25.66 | 28.41 | 449.98 |
| | | 50 | | | 23.44 | 29.02 | 33.29 | 530.61 |
| 78-2 | Roots | 2 | | | 39.65 | 10.71 | 22.53 | 213.51 |
| | | 10 | | | 29.48 | 26.00 | 31.81 | 425.37 |
| | | 50 | | | 24.20 | 39.45 | 36.67 | 653.00 |
| 78-3 | Stems | 2 | | | 36.68 | 19.39 | 24.79 | 304.91 |
| | | 10 | | | 28.39 | 25.17 | 32.37 | 403.42 |
| | | 50 | | | 20.37 | 37.80 | 36.68 | 603.67 |
| 78-4 | Leaves | 2 | | | 38.43 | 16.88 | 25.17 | 217.55 |
| | | 10 | | | 19.63 | 24.29 | 31.88 | 507.84 |
| | | 50 | | | 10.16 | 39.11 | 42.41 | 730.68 |
| 78-5 | Fruits | 2 | | | 37.46 | 12.23 | 20.48 | 271.20 |
| | | 10 | | | 28.86 | 21.41 | 28.30 | 540.80 |
| | | 50 | | | 23.14 | 28.98 | 37.67 | 695.19 |
| 78-6 | Flowers | 2 | | | 34.49 | 10.43 | 12.89 | 215.10 |
| | | 10 | | | 26.09 | 29.71 | 20.46 | 465.45 |
| | | 50 | | | 21.14 | 34.95 | 29.30 | 587.74 |

TABLE 151

| No. | Sample | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|
| | Control group | | | Vitamin C 7.5 ppm | Hexanediol Bacteria: *P. aeruginosa* 2% Fungi: *A. niger* 1% | Untreated 0 mm | Untreated 0 mm |

TABLE 151-continued

| No. | Sample | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|
| 78 | Leopard plant | *Farfugium japonicum* (L.) Kitam. | Leopard plant | | | | |
| 78-1 | Whole plant | | | 0.97 | MIC (%) Bacteria: 1 MIC (%) Fungi: 2 | 19.7 | 17.2 |
| 78-2 | Roots | | | 0.91 | MIC (%) Bacteria: 1 MIC (%) Fungi: 1 | 11.6 | 27.1 |
| 78-3 | Stems | | | 0.47 | MIC (%) Bacteria: 0.13 MIC (%) Fungi: 0.5 | 14.3 | 13.8 |
| 78-4 | Leaves | | | 0.22 | MIC (%) Bacteria: 0.06 MIC (%) Fungi: 0.13 | 21.6 | 19.2 |
| 78-5 | Fruits | | | 0.53 | MIC (%) Bacteria: 0.25 MIC (%) Fungi: 0.5 | 18.8 | 9.4 |
| 78-6 | Flowers | | | 0.98 | MIC (%) Bacteria: 0.5 MIC (%) Fungi: 1 | 17.8 | 23.2 |

20

Example 79

Oriental Yellowhead

TABLE 152

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 79 | Oriental yellowhead | | *Inula britannica* var. *japonica* (Thunb.) Franch. & Sav. | Oriental yellowhead | | | | |
| Comparative Example | Elecampane | 50 | *Inula Helenium* | | 78.85 | 6.33 | 2.85 | 26.04 |
| Comparative Example | Oriental yellowhead (other area) | 50 | *Inula britannica* var. *japonica* | | 62.83 | 15.61 | 11.90 | 207.35 |
| 79-1 | Whole plant | 2 | | | 39.40 | 16.42 | 23.58 | 316.64 |
| | | 10 | | | 30.94 | 25.94 | 29.08 | 449.47 |
| | | 50 | | | 20.99 | 38.51 | 34.86 | 708.12 |
| 79-2 | Roots | 2 | | | 38.95 | 19.56 | 23.68 | 388.83 |
| | | 10 | | | 32.66 | 21.69 | 27.59 | 467.49 |
| | | 50 | | | 24.95 | 35.26 | 38.62 | 665.58 |
| 79-3 | Stems | 2 | | | 39.53 | 18.43 | 24.32 | 287.87 |
| | | 10 | | | 27.35 | 22.20 | 31.71 | 452.08 |
| | | 50 | | | 20.65 | 35.13 | 37.34 | 651.19 |
| 79-4 | Leaves | 2 | | | 35.83 | 17.58 | 22.12 | 300.59 |
| | | 10 | | | 28.16 | 23.22 | 28.78 | 554.62 |
| | | 50 | | | 21.77 | 35.32 | 34.07 | 762.71 |
| 79-5 | Fruits | 2 | | | 38.69 | 14.95 | 24.40 | 375.27 |
| | | 10 | | | 28.60 | 24.78 | 27.74 | 502.59 |
| | | 50 | | | 21.08 | 31.95 | 34.00 | 597.14 |
| 79-6 | Flowers | 2 | | | 38.45 | 18.83 | 22.02 | 253.82 |
| | | 10 | | | 22.67 | 23.66 | 27.83 | 403.15 |
| | | 50 | | | 10.09 | 32.24 | 35.17 | 617.58 |

TABLE 153

| No. | Sample | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|
| | Control group | | | Vitamin C 7.5 ppm | Hexanediol Bacteria: *P. aeruginosa* 2% Fungi: *A. niger* 1% | Untreated 0 mm | Untreated 0 mm |
| 79 | Oriental yellowhead | *Inula britannica* var. *japonica* (Thunb.) Franch. & Sav. | Oriental yellowhead | | | | |
| Comparative Example | Elecampane | *Inula Helenium* | | 2.17 | MIC (%) Bacteria: 2 MIC (%) Fungi: 2 | 15.7 | 15.7 |
| Comparative Example | Oriental yellowhead (other area) | *Inula britannica* var. *japonica* | | 1.02 | MIC (%) Bacteria: 1 MIC (%) Fungi: 1 | 12.6 | 16.3 |
| 79-1 | Whole plant | | | 0.51 | MIC (%) Bacteria: 0.25 MIC (%) Fungi: 0.25 | 26.3 | 27.7 |
| 79-2 | Roots | | | 0.96 | MIC (%) Bacteria: 0.5 MIC (%) Fungi: 1 | 26.5 | 21.5 |
| 79-3 | Stems | | | 0.14 | MIC (%) Bacteria: 0.25 MIC (%) Fungi: 0.5 | 12.6 | 16.3 |
| 79-4 | Leaves | | | 0.59 | MIC (%) Bacteria: 0.13 MIC (%) Fungi: 0.25 | 16.5 | 13.6 |
| 79-5 | Fruits | | | 0.20 | MIC (%) Bacteria: 1 MIC (%) Fungi: 1 | 11.9 | 18.7 |
| 79-6 | Flowers | | | 0.29 | MIC (%) Bacteria: 0.06 MIC (%) Fungi: 0.13 | 11.6 | 12.7 |

Example 80

Giant Butterbur

TABLE 154

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 80 | Giant butterbur | | *Petasites japonicus* (Siebold & Zucc.) Maxim. | Giant butterbur | | | | |
| Comparative Example | Reddish butterbur | 50 | *Petasites rubellus* | | 70.31 | 11.69 | 7.15 | 48.65 |
| Comparative Example | Giant butterbur (other area) | 50 | *Petasites japonicus* (Siebold & Zucc.) Maxim. | | 52.26 | 21.84 | 10.48 | 241.46 |
| 80-1 | Whole plant | 2 | | | 36.16 | 18.60 | 25.76 | 344.43 |
| | | 10 | | | 22.43 | 28.11 | 27.66 | 581.22 |
| | | 50 | | | 15.90 | 31.93 | 37.86 | 765.16 |
| 80-2 | Roots | 2 | | | 36.11 | 14.10 | 24.58 | 218.91 |
| | | 10 | | | 29.10 | 27.85 | 28.23 | 600.95 |
| | | 50 | | | 22.11 | 31.10 | 35.83 | 723.47 |
| 80-3 | Stems | 2 | | | 36.63 | 13.71 | 24.18 | 381.93 |
| | | 10 | | | 31.09 | 20.07 | 27.38 | 407.96 |
| | | 50 | | | 20.04 | 38.56 | 37.08 | 600.61 |
| 80-4 | Leaves | 2 | | | 34.53 | 16.26 | 23.31 | 285.92 |
| | | 10 | | | 21.08 | 27.64 | 33.28 | 487.43 |
| | | 50 | | | 18.00 | 38.41 | 38.35 | 736.70 |
| 80-5 | Fruits | 2 | | | 39.97 | 15.99 | 21.06 | 244.23 |
| | | 10 | | | 32.19 | 24.57 | 31.53 | 554.10 |
| | | 50 | | | 23.85 | 34.47 | 38.93 | 610.36 |
| 80-6 | Flowers | 2 | | | 39.28 | 10.11 | 20.54 | 287.29 |
| | | 10 | | | 28.11 | 24.08 | 27.91 | 448.04 |
| | | 50 | | | 25.47 | 37.65 | 34.46 | 661.44 |

TABLE 155

| No. | Sample | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|
| | Control group | | | Vitamin C 7.5 ppm | Hexanediol Bacteria: *P. aeruginosa* 2% Fungi: *A. niger* 1% | Untreated 0 mm | Untreated 0 mm |
| 80 | Giant butterbur | *Petasites japonicus* (Siebold & Zucc.) Maxim. | Giant butterbur | | | | |
| Comparative Example | Reddish butterbur | *Petasites rubellus* | | 2.99 | MIC (%) Bacteria: >2 MIC (%) Fungi: >2 | 12.0 | 10.3 |
| Comparative Example | Giant butterbur (other area) | *Petasites japonicus* (Siebold & Zucc.) Maxim. | | 1.87 | MIC (%) Bacteria: 2 MIC (%) Fungi: 1 | 10.2 | 18.9 |
| 80-1 | Whole plant | | | 0.38 | MIC (%) Bacteria: 0.25 MIC (%) Fungi: 0.5 | 25.1 | 25.0 |
| 80-2 | Roots | | | 0.80 | MIC (%) Bacteria: 0.06 MIC (%) Fungi: 0.13 | 16.2 | 15.3 |
| 80-3 | Stems | | | 0.90 | MIC (%) Bacteria: 0.25 MIC (%) Fungi: 0.13 | 19.3 | 23.1 |
| 80-4 | Leaves | | | 0.45 | MIC (%) Bacteria: 0.5 MIC (%) Fungi: 0.25 | 12.7 | 15.0 |
| 80-5 | Fruits | | | 0.68 | MIC (%) Bacteria: 0.25 MIC (%) Fungi: 0.5 | 8.6 | 16.1 |
| 80-6 | Flowers | | | 0.10 | MIC (%) Bacteria: 1 MIC (%) Fungi: 0.5 | 22.5 | 21.1 |

Example 81

Ciliated-Fruit Sedge

TABLE 156

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 81 | Ciliated-fruit sedge | | *Carex blepharicarpa* Franch. | Ciliated-fruit sedge | | | | |
| Comparative Example | Asiatic sand sedge | 50 | *Carex Kobomugi* | | 93.17 | 4.27 | 8.86 | 28.11 |
| 81-1 | Whole plant | 2 | | | 37.52 | 10.62 | 26.95 | 350.96 |
| | | 10 | | | 28.47 | 23.08 | 28.69 | 437.36 |
| | | 50 | | | 23.20 | 30.50 | 34.01 | 639.16 |
| 81-2 | Roots | 2 | | | 39.53 | 16.95 | 23.45 | 195.81 |
| | | 10 | | | 33.05 | 23.10 | 32.63 | 288.51 |
| | | 50 | | | 20.37 | 36.96 | 37.09 | 581.18 |
| 81-3 | Stems | 2 | | | 35.42 | 10.32 | 26.54 | 213.12 |
| | | 10 | | | 27.51 | 22.22 | 28.64 | 536.16 |
| | | 50 | | | 22.77 | 37.98 | 37.07 | 691.36 |
| 81-4 | Leaves | 2 | | | 28.34 | 14.55 | 23.74 | 374.75 |
| | | 10 | | | 19.31 | 23.74 | 33.17 | 504.99 |
| | | 50 | | | 13.28 | 45.65 | 37.12 | 771.58 |
| 81-5 | Fruits | 2 | | | 37.07 | 15.03 | 26.86 | 298.06 |
| | | 10 | | | 32.63 | 23.51 | 30.93 | 556.21 |
| | | 50 | | | 23.14 | 33.20 | 38.25 | 718.52 |
| 81-6 | Flowers | 2 | | | 35.40 | 11.78 | 23.45 | 225.83 |
| | | 10 | | | 33.82 | 20.03 | 31.87 | 453.83 |
| | | 50 | | | 22.17 | 30.70 | 36.25 | 619.43 |

TABLE 157

| No. | Sample | Scientific name | English name | Anti-oxidation IC50 (%) | Anti-bacteria MIC (%) | Anti-bacteria (S. mutans) Size of growth inhibition ring (mm) | Anti-bacteria (P. gingivalis) Size of growth inhibition ring (mm) |
|---|---|---|---|---|---|---|---|
| | Control group | | | Vitamin C 7.5 ppm | Hexanediol Bacteria: P. aeruginosa 2% Fungi: A. niger 1% | Untreated 0 mm | Untreated 0 mm |
| 81 | Ciliated-fruit sedge | Carex blepharicarpa Franch. | Ciliated-fruit sedge | | | | |
| Comparative Example | Asiatic sand sedge | Carex Kobomugi | | 1.98 | MIC (%) Bacteria: >2 MIC (%) Fungi: >2 | 8.5 | 12.2 |
| 81-1 | Whole plant | | | 0.47 | MIC (%) Bacteria: 1 MIC (%) Fungi: 1 | 21.6 | 25.0 |
| 81-2 | Roots | | | 0.23 | MIC (%) Bacteria: 0.5 MIC (%) Fungi: 1 | 8.4 | 15.3 |
| 81-3 | Stems | | | 0.76 | MIC (%) Bacteria: 0.5 MIC (%) Fungi: 1 | 15.0 | 13.2 |
| 81-4 | Leaves | | | 0.13 | MIC (%) Bacteria: 0.25 MIC (%) Fungi: 0.5 | 25.9 | 19.8 |
| 81-5 | Fruits | | | 0.83 | MIC (%) Bacteria: 0.5 MIC (%) Fungi: 1 | 21.8 | 17.9 |
| 81-6 | Flowers | | | 0.46 | MIC (%) Bacteria: 0.25 MIC (%) Fungi: 0.5 | 18.6 | 8.2 |

Example 82

Short-Stem Sedge

TABLE 158

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 82 | Short-stem sedge | | Carex breviculmis R. Br. | Short-stem sedge | | | | |
| Comparative Example | Low sedge | 50 | Carex Humilis | | 89.34 | 13.25 | 5.25 | 45.34 |
| 82-1 | Whole plant | 2 | | | 38.61 | 17.53 | 25.30 | 257.94 |
| | | 10 | | | 29.86 | 21.83 | 31.63 | 498.46 |
| | | 50 | | | 20.03 | 33.36 | 37.98 | 714.51 |
| 82-2 | Roots | 2 | | | 35.41 | 11.17 | 23.44 | 349.59 |
| | | 10 | | | 27.16 | 23.62 | 28.01 | 468.27 |
| | | 50 | | | 26.05 | 32.20 | 38.67 | 629.88 |
| 82-3 | Stems | 2 | | | 35.33 | 19.04 | 23.59 | 223.74 |
| | | 10 | | | 30.11 | 20.79 | 30.03 | 578.94 |
| | | 50 | | | 23.08 | 35.70 | 36.30 | 670.06 |
| 82-4 | Leaves | 2 | | | 37.71 | 18.70 | 24.91 | 338.20 |
| | | 10 | | | 28.03 | 26.08 | 33.93 | 567.39 |
| | | 50 | | | 20.86 | 39.86 | 35.51 | 629.76 |
| 82-5 | Fruits | 2 | | | 39.94 | 16.19 | 20.21 | 360.14 |
| | | 10 | | | 28.84 | 21.13 | 31.49 | 510.49 |
| | | 50 | | | 23.33 | 30.57 | 38.76 | 614.23 |
| 82-6 | Flowers | 2 | | | 36.86 | 10.45 | 23.48 | 386.61 |
| | | 10 | | | 29.72 | 27.79 | 29.95 | 508.71 |
| | | 50 | | | 23.40 | 35.01 | 37.71 | 665.17 |

TABLE 159

| No. | Sample | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|
| | Control group | | | Vitamin C 7.5 ppm | Hexanediol Bacteria: *P. aeruginosa* 2% Fungi: *A. niger* 1% | Untreated 0 mm | Untreated 0 mm |
| 82 | Short-stem sedge | *Carex breviculmis* R. Br. | Short-stem sedge | | | | |
| Comparative Example | Low sedge | *Carex Humilis* | | 2.88 | MIC (%) Bacteria: 1, Fungi: 2 | 10.6 | 11.8 |
| 82-1 | Whole plant | | | 0.01 | MIC (%) Bacteria: 0.5, Fungi: 0.5 | 27.5 | 23.7 |
| 82-2 | Roots | | | 0.73 | MIC (%) Bacteria: 0.5, Fungi: 1 | 14.7 | 27.3 |
| 82-3 | Stems | | | 0.29 | MIC (%) Bacteria: 0.5, Fungi: 1 | 21.8 | 15.9 |
| 82-4 | Leaves | | | 0.58 | MIC (%) Bacteria: 0.5, Fungi: 1 | 16.5 | 22.7 |
| 82-5 | Fruits | | | 0.32 | MIC (%) Bacteria: 1, Fungi: 1 | 11.9 | 21.1 |
| 82-6 | Flowers | | | 0.18 | MIC (%) Bacteria: 1, Fungi: 1 | 23.7 | 22.2 |

Example 83

Purple Maiden Silvergrass

TABLE 160

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 83 | Purple maiden silvergrass | | *Miscanthus sinensis* var. purpurascens (Andersson) Rendle | Purple maiden silvergrass | | | | |
| 83-1 | Whole plant | 2 | | | 39.03 | 11.88 | 22.02 | 208.66 |
| | | 10 | | | 29.36 | 28.64 | 32.40 | 512.44 |
| | | 50 | | | 22.65 | 38.06 | 39.89 | 782.07 |
| 83-2 | Roots | 2 | | | 36.63 | 15.46 | 26.33 | 376.90 |
| | | 10 | | | 31.76 | 20.58 | 29.54 | 507.23 |
| | | 50 | | | 20.90 | 33.93 | 39.74 | 757.79 |
| 83-3 | Stems | 2 | | | 38.13 | 11.53 | 25.93 | 237.31 |
| | | 10 | | | 33.89 | 23.82 | 32.66 | 548.94 |
| | | 50 | | | 23.01 | 34.08 | 35.08 | 708.87 |
| 83-4 | Leaves | 2 | | | 37.56 | 15.46 | 26.08 | 311.02 |
| | | 10 | | | 29.54 | 21.06 | 27.09 | 436.41 |
| | | 50 | | | 22.68 | 36.47 | 34.38 | 649.40 |
| 83-5 | Fruits | 2 | | | 34.90 | 19.32 | 25.15 | 337.01 |
| | | 10 | | | 28.59 | 27.84 | 31.26 | 445.49 |
| | | 50 | | | 26.34 | 36.54 | 39.28 | 716.12 |
| 83-6 | Flowers | 2 | | | 40.02 | 13.06 | 24.29 | 346.16 |
| | | 10 | | | 31.66 | 27.16 | 30.76 | 538.04 |
| | | 50 | | | 33.58 | 39.27 | 39.06 | 643.95 |
| 83-7 | Shoots | 2 | | | 36.46 | 15.94 | 24.75 | 396.58 |
| | | 10 | | | 31.84 | 28.06 | 28.49 | 543.09 |
| | | 50 | | | 25.99 | 38.37 | 37.96 | 763.88 |

TABLE 161

| No. | Sample | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|
| | Control group | | | Vitamin C 7.5 ppm | Hexanediol Bacteria: *P. aeruginosa* 2% Fungi: *A. niger* 1% | Untreated 0 mm | Untreated 0 mm |
| 83 | Purple maiden silvergrass | *Miscanthus sinensis* var. purpurascens (Andersson) Rendle | Purple maiden silvergrass | | | | |
| 83-1 | Whole plant | | | 0.13 | MIC (%) Bacteria: 0.25, Fungi: 0.5 | 8.5 | 11.5 |
| 83-2 | Roots | | | 0.87 | MIC (%) Bacteria: 0.25, Fungi: 1 | 20.4 | 22.8 |
| 83-3 | Stems | | | 1.00 | MIC (%) Bacteria: 0.5, Fungi: 1 | 15.3 | 14.0 |
| 83-4 | Leaves | | | 0.53 | MIC (%) Bacteria: 0.25, Fungi: 1 | 13.7 | 25.6 |
| 83-5 | Fruits | | | 0.43 | MIC (%) Bacteria: 0.5, Fungi: 1 | 10.2 | 18.3 |
| 83-6 | Flowers | | | 1.00 | MIC (%) Bacteria: 0.5, Fungi: 1 | 16.8 | 10.6 |
| 83-7 | Shoots | | | 0.31 | MIC (%) Bacteria: 1, Fungi: 1 | 15.6 | 10.2 |

Example 84

20

Foxtail Fountaingrass

TABLE 162

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 84 | Foxtail fountaingrass | | *Pennisetum alopecuroides* (L.) Spreng. | Foxtail fountaingrass | | | | |
| 84-1 | Whole plant | 2 | | | 35.76 | 15.10 | 25.60 | 297.20 |
| | | 10 | | | 33.30 | 20.69 | 32.93 | 580.00 |
| | | 50 | | | 25.09 | 38.83 | 39.08 | 768.17 |
| 84-2 | Roots | 2 | | | 36.01 | 13.59 | 22.23 | 382.22 |
| | | 10 | | | 30.89 | 28.08 | 31.75 | 511.86 |
| | | 50 | | | 25.71 | 36.15 | 34.00 | 784.58 |
| 84-3 | Stems | 2 | | | 35.63 | 10.03 | 23.51 | 210.50 |
| | | 10 | | | 28.18 | 26.17 | 32.33 | 435.07 |
| | | 50 | | | 22.99 | 30.63 | 38.16 | 677.66 |
| 84-4 | Leaves | 2 | | | 36.35 | 17.10 | 20.69 | 250.56 |
| | | 10 | | | 27.02 | 25.27 | 31.15 | 432.31 |
| | | 50 | | | 25.57 | 30.78 | 39.43 | 615.15 |
| 84-5 | Fruits | 2 | | | 38.55 | 12.38 | 20.60 | 395.00 |
| | | 10 | | | 30.40 | 26.52 | 32.43 | 484.93 |
| | | 50 | | | 21.20 | 33.61 | 35.32 | 765.38 |
| 84-6 | Flowers | 2 | | | 34.10 | 13.62 | 21.64 | 334.94 |
| | | 10 | | | 33.70 | 25.06 | 27.64 | 550.19 |
| | | 50 | | | 20.91 | 38.10 | 39.99 | 696.47 |

50

TABLE 163

| No. | Sample | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|
| | Control group | | | Vitamin C 7.5 ppm | Hexanediol Bacteria: *P. aeruginosa* 2% Fungi: *A. niger* 1% | Untreated 0 mm | Untreated 0 mm |
| 84 | Foxtail fountaingrass | *Pennisetum alopecuroides* (L.) Spreng. | Foxtail fountaingrass | | | | |
| 84-1 | Whole plant | | | 0.46 | MIC (%) Bacteria: 0.25, Fungi: 0.5 | 20.8 | 10.5 |
| 84-2 | Roots | | | 0.30 | MIC (%) Bacteria: 0.25, Fungi: 0.25 | 18.1 | 12.9 |
| 84-3 | Stems | | | 0.14 | MIC (%) Bacteria: 0.25, Fungi: 0.5 | 8.7 | 10.6 |

TABLE 163-continued

| No. | Sample | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|
| 84-4 | Leaves | | | 0.59 | MIC (%) Bacteria: 0.125, Fungi: 0.5 | 19.0 | 17.3 |
| 84-5 | Fruits | | | 0.41 | MIC (%) Bacteria: 0.5, Fungi: 1 | 23.8 | 18.9 |
| 84-6 | Flowers | | | 0.80 | MIC (%) Bacteria: 0.5, Fungi: 0.5 | 24.5 | 21.6 |

Example 85

Arrow Bamboo

TABLE 164

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 85 | Arrow bamboo | | *Pseudosasa japonica* (Siebold & Zucc. ex Steud.) Makino ex Nakai | Arrow bamboo | | | | |
| 85-1 | Whole plant | 2 | | | 34.10 | 10.38 | 23.30 | 383.43 |
| | | 10 | | | 27.82 | 22.15 | 29.26 | 487.01 |
| | | 50 | | | 21.14 | 37.72 | 37.60 | 670.70 |
| 85-2 | Roots | 2 | | | 39.91 | 18.59 | 25.36 | 291.57 |
| | | 10 | | | 32.18 | 22.18 | 32.33 | 514.92 |
| | | 50 | | | 25.95 | 30.55 | 39.69 | 760.62 |
| 85-3 | Stems | 2 | | | 37.19 | 13.84 | 22.84 | 334.32 |
| | | 10 | | | 29.91 | 26.16 | 28.35 | 428.80 |
| | | 50 | | | 24.21 | 37.62 | 37.92 | 682.60 |
| 85-4 | Leaves | 2 | | | 37.79 | 18.70 | 21.19 | 327.69 |
| | | 10 | | | 28.85 | 20.88 | 33.08 | 427.86 |
| | | 50 | | | 23.31 | 35.18 | 35.00 | 688.70 |
| 85-5 | Fruits | 2 | | | 38.82 | 19.23 | 21.75 | 280.47 |
| | | 10 | | | 28.73 | 25.12 | 29.53 | 451.83 |
| | | 50 | | | 26.27 | 37.74 | 38.96 | 659.56 |
| 85-6 | Flowers | 2 | | | 36.34 | 11.94 | 25.48 | 338.69 |
| | | 10 | | | 32.61 | 20.20 | 32.44 | 522.43 |
| | | 50 | | | 20.70 | 39.85 | 35.43 | 676.44 |

TABLE 165

| No. | Sample | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|
| | Control group | | | Vitamin C 7.5 ppm | Hexanediol Bacteria: *P. aeruginosa* 2% Fungi: *A. niger* 1% | Untreated 0 mm | Untreated 0 mm |
| 85 | Arrow bamboo | *Pseudosasa japonica* (Siebold & Zucc. ex Steud.) Makino ex Nakai | Arrow bamboo | | | | |
| 85-1 | Whole plant | | | 0.05 | MIC (%) Bacteria: 1, Fungi: 0.5 | 9.2 | 8.2 |
| 85-2 | Roots | | | 0.62 | MIC (%) Bacteria: 1, Fungi: 1 | 15.3 | 21.0 |
| 85-3 | Stems | | | 0.29 | MIC (%) Bacteria: 1, Fungi: 1 | 17.2 | 11.6 |
| 85-4 | Leaves | | | 0.77 | MIC (%) Bacteria: 1, Fungi: 2 | 13.3 | 13.6 |
| 85-5 | Fruits | | | 0.81 | MIC (%) Bacteria: 1, Fungi: 2 | 25.4 | 16.7 |
| 85-6 | Flowers | | | 0.89 | MIC (%) Bacteria: 2, Fungi: 2 | 13.1 | 25.2 |

Example 86

Kuril Bamboo

TABLE 166

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 86 | Kuril bamboo | | Sasa kurilensis (Rupr.) Makino & Shibata | Kuril bamboo | | | | |
| Comparative Example | Broad-leaf bamboo | 50 | Sasa Quelpaertensis | | 79.24 | 10.16 | 2.63 | 54.12 |
| 86-1 | Whole plant | 2 | | | 36.69 | 11.30 | 23.45 | 218.11 |
| | | 10 | | | 33.30 | 20.52 | 27.47 | 502.12 |
| | | 50 | | | 23.80 | 39.83 | 35.59 | 784.92 |
| 86-2 | Roots | 2 | | | 35.95 | 17.65 | 26.43 | 383.82 |
| | | 10 | | | 28.02 | 25.94 | 30.14 | 444.50 |
| | | 50 | | | 25.04 | 38.57 | 36.98 | 620.66 |
| 86-3 | Stems | 2 | | | 36.09 | 17.40 | 25.43 | 231.46 |
| | | 10 | | | 32.47 | 22.22 | 27.83 | 402.96 |
| | | 50 | | | 22.22 | 37.04 | 37.63 | 632.78 |
| 86-4 | Leaves | 2 | | | 40.02 | 11.89 | 19.26 | 244.93 |
| | | 10 | | | 31.66 | 20.62 | 22.95 | 414.63 |
| | | 50 | | | 33.58 | 27.27 | 28.13 | 522.10 |
| 86-5 | Fruits | 2 | | | 35.01 | 16.49 | 26.46 | 321.37 |
| | | 10 | | | 30.26 | 21.44 | 27.34 | 407.73 |
| | | 50 | | | 24.00 | 35.02 | 39.62 | 755.24 |
| 86-6 | Flowers | 2 | | | 38.28 | 12.18 | 23.83 | 293.99 |
| | | 10 | | | 27.01 | 20.78 | 31.10 | 493.78 |
| | | 50 | | | 22.72 | 34.21 | 34.81 | 760.55 |

TABLE 167

| No. | Sample | Scientific name | English name | Anti-oxidation IC50 (%) | Anti-bacteria MIC (%) | Anti-bacteria (S. mutans) Size of growth inhibition ring (mm) | Anti-bacteria (P. gingivalis) Size of growth inhibition ring (mm) |
|---|---|---|---|---|---|---|---|
| | Control group | | | Vitamin C 7.5 ppm | Hexanediol Bacteria: P. aeruginosa 2% Fungi: A. niger 1% | Untreated 0 mm | Untreated 0 mm |
| 86 | Kuril bamboo | Sasa kurilensis (Rupr.) Makino & Shibata | Kuril bamboo | | | | |
| Comparative Example | Broad-leaf bamboo | Sasa Quelpaertensis | | 1.99 | MIC (%) Bacteria: 1, Fungi: >2 | 11.0 | 11.5 |
| 86-1 | Whole plant | | | 0.25 | MIC (%) Bacteria: 0.25, Fungi: 0.25 | 26.3 | 27.6 |
| 86-2 | Roots | | | 0.29 | MIC (%) Bacteria: 0.25, Fungi: 0.25 | 26.3 | 24.9 |
| 86-3 | Stems | | | 0.43 | MIC (%) Bacteria: 0.25, Fungi: 0.5 | 26.3 | 16.2 |
| 86-4 | Leaves | | | 0.73 | MIC (%) Bacteria: 1, Fungi: 1 | 11.8 | 22.6 |
| 86-5 | Fruits | | | 0.35 | MIC (%) Bacteria: 0.5, Fungi: 0.5 | 13.2 | 11.3 |
| 86-6 | Flowers | | | 0.03 | MIC (%) Bacteria: 1, Fungi: 0.5 | 21.0 | 22.8 |

Example 87

Shrubby *Sophora*

TABLE 168

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 87 | Shrubby sophora | | *Sophora flavescens* Alton | Shrubby sophora | | | | |
| Comparative Example | Locust tree | 50 | *Sophora Japonica* | | 84.16 | 2.36 | 5.74 | 58.32 |
| Comparative Example | Shrubby sophora (other area) | 50 | | | 78.69 | 9.98 | 8.21 | 187.81 |
| 87-1 | Whole plant | 2 | | | 35.71 | 16.45 | 24.31 | 266.69 |
| | | 10 | | | 27.05 | 21.57 | 31.83 | 407.30 |
| | | 50 | | | 24.04 | 32.75 | 35.76 | 769.95 |
| 87-2 | Roots | 2 | | | 37.62 | 7.36 | 18.60 | 283.58 |
| | | 10 | | | 34.58 | 20.31 | 22.54 | 392.98 |
| | | 50 | | | 31.63 | 29.93 | 30.24 | 620.84 |
| 87-3 | Stems | 2 | | | 36.67 | 14.36 | 23.01 | 273.46 |
| | | 10 | | | 27.59 | 24.18 | 33.42 | 594.25 |
| | | 50 | | | 24.30 | 32.64 | 34.29 | 620.55 |
| 87-4 | Leaves | 2 | | | 36.18 | 17.46 | 25.26 | 347.28 |
| | | 10 | | | 32.57 | 21.19 | 33.49 | 525.14 |
| | | 50 | | | 22.22 | 33.51 | 38.68 | 686.58 |
| 87-5 | Fruits | 2 | | | 34.42 | 16.78 | 23.62 | 320.67 |
| | | 10 | | | 28.15 | 26.13 | 31.56 | 471.56 |
| | | 50 | | | 24.51 | 32.79 | 39.76 | 699.91 |
| 87-6 | Flowers | 2 | | | 36.80 | 11.41 | 22.50 | 312.28 |
| | | 10 | | | 29.38 | 23.60 | 28.09 | 435.20 |
| | | 50 | | | 20.98 | 37.10 | 37.72 | 763.64 |

TABLE 169

| No. | Sample | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|
| | Control group | | | Vitamin C 7.5 ppm | Hexanediol Bacteria: *P. aeruginosa* 2% Fungi: *A. niger* 1% | Untreated 0 mm | Untreated 0 mm |
| 87 | Shrubby sophora | *Sophora flavescens* Alton | Shrubby sophora | | | | |
| Comparative Example | Locust tree | *Sophora Japonica* | | 3.84 | MIC (%) Bacteria: >2, Fungi: >2 | 8.4 | 10.0 |
| Comparative Example | Shrubby sophora (other area) | | | 2.77 | MIC (%) Bacteria: >2, Fungi: 2 | 13.3 | 14.3 |
| 87-1 | Whole plant | | | 0.24 | MIC (%) Bacteria: 2, Fungi: 1 | 24.6 | 25.6 |
| 87-2 | Roots | | | 0.64 | MIC (%) Bacteria: 1, Fungi: 1 | 13.3 | 14.3 |
| 87-3 | Stems | | | 0.25 | MIC (%) Bacteria: 1, Fungi: 1 | 10.4 | 16.5 |
| 87-4 | Leaves | | | 0.22 | MIC (%) Bacteria: 1, Fungi: 1 | 14.7 | 19.3 |
| 87-5 | Fruits | | | 0.38 | MIC (%) Bacteria: 2, Fungi: 1 | 24.3 | 21.5 |
| 87-6 | Flowers | | | 0.17 | MIC (%) Bacteria: 2, Fungi: 1 | 15.7 | 14.8 |

Example 88

Orange Daylily

TABLE 170

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 88 | Orange Daylily | | *Hemerocallis fulva* (L.) L. | Orange Daylily | | | | |
| 88-1 | Whole plant | 2 | | | 37.98 | 13.04 | 20.78 | 320.33 |
| | | 10 | | | 28.74 | 21.75 | 28.83 | 527.62 |
| | | 50 | | | 24.73 | 30.10 | 36.08 | 684.39 |
| 88-2 | Roots | 2 | | | 39.51 | 11.81 | 25.71 | 271.10 |
| | | 10 | | | 33.78 | 20.80 | 28.00 | 548.53 |
| | | 50 | | | 20.02 | 37.07 | 39.09 | 775.77 |
| 88-3 | Stems | 2 | | | 36.89 | 11.44 | 23.02 | 251.80 |
| | | 10 | | | 28.32 | 22.77 | 33.82 | 481.36 |
| | | 50 | | | 23.54 | 31.80 | 39.77 | 707.59 |
| 88-4 | Leaves | 2 | | | 36.53 | 15.14 | 21.79 | 235.29 |
| | | 10 | | | 31.61 | 21.43 | 32.98 | 451.04 |
| | | 50 | | | 22.27 | 37.44 | 38.24 | 717.18 |
| 88-5 | Fruits | 2 | | | 39.44 | 10.83 | 24.71 | 389.37 |
| | | 10 | | | 30.76 | 25.35 | 28.14 | 534.34 |
| | | 50 | | | 20.69 | 37.78 | 38.18 | 707.43 |
| 88-6 | Flowers | 2 | | | 36.56 | 19.96 | 24.00 | 377.30 |
| | | 10 | | | 30.27 | 21.01 | 33.66 | 530.00 |
| | | 50 | | | 26.94 | 34.60 | 37.84 | 643.38 |

TABLE 171

| No. | Sample | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|
| | Control group | | | Vitamin C 7.5 ppm | Hexanediol Bacteria: *P. aeruginosa* 2% Fungi: *A. niger* 1% | Untreated 0 mm | Untreated 0 mm |
| 88 | Orange Daylily | *Hemerocallis fulva* (L.) L. | Orange Daylily | | | | |
| 88-1 | Whole plant | | | 0.66 | MIC (%) Bacteria: 0.5 MIC (%) Fungi: 0.5 | 14.0 17.0 | 22.4 20.1 |
| 88-2 | Roots | | | 0.58 | MIC (%) Bacteria: 0.125 MIC (%) Fungi: 0.5 | 24.1 | 14.5 |
| 88-3 | Stems | | | 0.77 | MIC (%) Bacteria: 0.25 MIC (%) Fungi: 0.25 | 9.1 | 18.2 |
| 88-4 | Leaves | | | 0.33 | MIC (%) Bacteria: 0.25 MIC (%) Fungi: 0.25 | 22.8 | 11.9 |
| 88-5 | Fruits | | | 0.31 | MIC (%) Bacteria: 0.25 MIC (%) Fungi: 0.5 | 22.8 | 16.7 |
| 88-6 | Flowers | | | 0.90 | MIC (%) Bacteria: 0.5 MIC (%) Fungi: 0.5 | 25.4 | 27.4 |

Example 89

Tiger Lily

TABLE 172

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 89 | Tiger lily | | *Lilium lancifolium* Thunb. | Tiger lily | | | | |
| Comparative Example | Madonna lily | 50 | *Lilium Candidum* | | 91.19 | 9.96 | 3.61 | 47.97 |
| 89-1 | Whole plant | 2 | | | 39.52 | 13.32 | 24.32 | 235.37 |
| | | 10 | | | 29.17 | 22.48 | 30.99 | 483.99 |
| | | 50 | | | 21.63 | 30.01 | 35.52 | 630.93 |
| 89-2 | Roots | 2 | | | 37.97 | 12.02 | 25.41 | 350.39 |
| | | 10 | | | 30.41 | 22.20 | 33.79 | 596.41 |
| | | 50 | | | 20.11 | 30.76 | 37.90 | 702.51 |
| 89-3 | Stems | 2 | | | 37.99 | 15.57 | 20.64 | 349.00 |
| | | 10 | | | 29.24 | 21.67 | 33.58 | 499.76 |
| | | 50 | | | 20.10 | 34.32 | 37.25 | 685.50 |
| 89-4 | Leaves | 2 | | | 38.52 | 15.67 | 22.66 | 336.67 |
| | | 10 | | | 33.02 | 21.75 | 32.58 | 494.37 |
| | | 50 | | | 21.60 | 35.88 | 37.64 | 768.26 |
| 89-5 | Flowers | 2 | | | 34.53 | 17.41 | 22.86 | 358.56 |
| | | 10 | | | 29.14 | 29.79 | 28.38 | 446.04 |
| | | 50 | | | 22.38 | 30.41 | 36.03 | 656.42 |
| 89-6 | Bulbils | 2 | | | 39.71 | 12.13 | 22.84 | 246.72 |
| | | 10 | | | 32.18 | 21.37 | 31.65 | 481.46 |
| | | 50 | | | 20.16 | 31.03 | 37.85 | 769.88 |

TABLE 173

| No. | Sample | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|
| | Control group | | | Vitamin C 7.5 ppm | Hexanediol Bacteria: *P. aeruginosa* 2% Fungi: *A. niger* 1% | Untreated 0 mm | Untreated 0 mm |
| 89 | Tiger lily | *Lilium lancifolium* Thunb. | Tiger lily | | | | |
| Comparative Example | Madonna lily | *Lilium Candidum* | | 2.79 | MIC (%) Bacteria: 1 MIC (%) Fungi: 1 | 8.1 | 8.5 |
| 89-1 | Whole plant | | | 0.90 | MIC (%) Bacteria: 0.25 MIC (%) Fungi: 0.125 | 19.7 | 15.5 |
| 89-2 | Roots | | | 0.16 | MIC (%) Bacteria: 0.0625 MIC (%) Fungi: 0.125 | 17.0 | 10.1 |
| 89-3 | Stems | | | 0.84 | MIC (%) Bacteria: 0.125 MIC (%) Fungi: 0.125 | 9.8 | 8.1 |
| 89-4 | Leaves | | | 0.20 | MIC (%) Bacteria: 0.125 MIC (%) Fungi: 0.125 | 11.4 | 8.5 |
| 89-5 | Flowers | | | 0.96 | MIC (%) Bacteria: 0.25 MIC (%) Fungi: 0.25 | 19.5 | 22.7 |
| 89-6 | Bulbils | | | 0.12 | MIC (%) Bacteria: 0.25 MIC (%) Fungi: 0.25 | 26.5 | 26.7 |

Example 90

Big Blue Lilyturf

TABLE 174

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 90 | Big blue lilyturf | | Liriope platyphylla F. T. Wang & T. Tang | Big blue lilyturf | | | | |
| Comparative Example | Creeping lilyturf | 50 | Liriope Spicata | | 79.02 | 11.65 | 3.77 | 22.75 |
| 90-1 | Whole plant | 2 | | | 36.28 | 15.62 | 21.68 | 218.04 |
| | | 10 | | | 33.12 | 26.66 | 33.28 | 538.92 |
| | | 50 | | | 20.99 | 30.59 | 34.15 | 666.45 |
| 90-2 | Roots | 2 | | | 37.06 | 12.96 | 25.91 | 235.68 |
| | | 10 | | | 29.27 | 25.34 | 27.61 | 535.22 |
| | | 50 | | | 24.37 | 35.75 | 37.30 | 654.28 |
| 90-3 | Stems | 2 | | | 36.28 | 15.80 | 25.75 | 333.69 |
| | | 10 | | | 33.12 | 21.84 | 32.63 | 453.20 |
| | | 50 | | | 20.99 | 39.11 | 39.29 | 800.22 |
| 90-4 | Leaves | 2 | | | 36.53 | 12.80 | 23.78 | 267.73 |
| | | 10 | | | 31.21 | 28.79 | 29.63 | 513.82 |
| | | 50 | | | 21.89 | 32.55 | 39.02 | 741.53 |
| 90-5 | Fruits | 2 | | | 38.19 | 19.02 | 20.59 | 274.84 |
| | | 10 | | | 33.42 | 23.29 | 30.95 | 516.84 |
| | | 50 | | | 23.14 | 35.83 | 35.38 | 689.71 |
| 90-6 | Flowers | 2 | | | 34.45 | 14.98 | 23.07 | 220.38 |
| | | 10 | | | 30.70 | 25.54 | 30.03 | 465.53 |
| | | 50 | | | 23.21 | 37.18 | 38.36 | 790.45 |

TABLE 175

| No. | Sample | Scientific name | English name | Anti-oxidation IC50 (%) | Anti-bacteria MIC (%) | Anti-bacteria (S. mutans) Size of growth inhibition ring (mm) | Anti-bacteria (P. gingivalis) Size of growth inhibition ring (mm) |
|---|---|---|---|---|---|---|---|
| | Control group | | | Vitamin C 7.5 ppm | Hexanediol Bacteria: P. aeruginosa 2% Fungi: A. niger 1% | Untreated 0 mm | Untreated 0 mm |
| 90 | Big blue lilyturf | Liriope platyphylla F. T. Wang & T. Tang | Big blue lilyturf | | | | |
| Comparative Example | Creeping lilyturf | Liriope Spicata | | 1.06 | MIC (%) Bacteria: >2 MIC (%) Fungi: 1 | 7.5 | 9.4 |
| 90-1 | Whole plant | | | 0.20 | MIC (%) Bacteria: 0.5 MIC (%) Fungi: 0.5 | 20.4 | 18.4 |
| 90-2 | Roots | | | 0.65 | MIC (%) Bacteria: 0.5 MIC (%) Fungi: 0.5 | 15.3 | 11.5 |
| 90-3 | Stems | | | 0.02 | MIC (%) Bacteria: 0.125 MIC (%) Fungi: 0.25 | 20.2 | 10.0 |
| 90-4 | Leaves | | | 0.53 | MIC (%) Bacteria: 0.5 MIC (%) Fungi: 0.5 | 14.8 | 8.7 |
| 90-5 | Fruits | | | 0.92 | MIC (%) Bacteria: 0.5 MIC (%) Fungi: 0.5 | 11.8 | 26.9 |
| 90-6 | Flowers | | | 0.52 | MIC (%) Bacteria: 0.5 MIC (%) Fungi: 0.5 | 18.2 | 20.9 |

Example 91

False Lily of the Valley

TABLE 176

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 91 | False lily of the valley | | Maianthemum dilatatum (A.W. Wood) A. Nelson & J. F. Macbr. | False lily of the valley | | | | |
| Comparative Example | Two leaf beadruby | 50 | Maianthemum Japonicum | | 68.47 | 15.36 | 2.03 | 63.06 |
| 91-1 | Whole plant | 2 | | | 39.69 | 11.91 | 24.67 | 280.91 |
| | | 10 | | | 31.08 | 29.05 | 29.35 | 547.20 |
| | | 50 | | | 24.36 | 38.76 | 34.63 | 737.43 |
| 91-2 | Roots | 2 | | | 39.29 | 13.13 | 23.81 | 352.54 |
| | | 10 | | | 30.16 | 29.89 | 27.70 | 528.31 |
| | | 50 | | | 22.96 | 34.60 | 38.86 | 679.29 |
| 91-3 | Stems | 2 | | | 36.63 | 13.78 | 25.15 | 213.50 |
| | | 10 | | | 30.18 | 27.28 | 31.66 | 462.46 |
| | | 50 | | | 22.69 | 33.82 | 34.62 | 651.68 |
| 91-4 | Leaves | 2 | | | 36.92 | 18.88 | 24.81 | 287.61 |
| | | 10 | | | 32.91 | 24.61 | 28.83 | 515.62 |
| | | 50 | | | 21.78 | 34.96 | 34.70 | 744.82 |
| 91-5 | Fruits | 2 | | | 35.29 | 14.00 | 26.00 | 200.58 |
| | | 10 | | | 30.08 | 22.85 | 27.38 | 517.51 |
| | | 50 | | | 24.36 | 35.25 | 34.24 | 797.02 |
| 91-6 | Flowers | 2 | | | 38.31 | 12.23 | 23.07 | 215.65 |
| | | 10 | | | 31.99 | 22.10 | 33.41 | 433.02 |
| | | 50 | | | 25.87 | 35.92 | 38.31 | 667.41 |

TABLE 177

| No. | Sample | Scientific name | English name | Anti-oxidation IC50 (%) | Anti-bacteria MIC (%) | Anti-bacteria (S. mutans) Size of growth inhibition ring (mm) | Anti-bacteria (P. gingivalis) Size of growth inhibition ring (mm) |
|---|---|---|---|---|---|---|---|
| | Control group | | | Vitamin C 7.5 ppm | Hexanediol Bacteria: P. aeruginosa 2% Fungi: A. niger 1% | Untreated 0 mm | Untreated 0 mm |
| 91 | False lily of the valley | Maianthemum dilatatum (A. W. Wood) A. Nelson & J. F. Macbr. | False lily of the valley | | | | |
| Comparative Example | Two leaf beadruby | Maianthemum Japonicum | | 2.62 | MIC (%) Bacteria: >2 MIC (%) Fungi: >2 | 8.8 | 13.8 |
| 91-1 | Whole plant | | | 0.75 | MIC (%) Bacteria: 0.25 MIC (%) Fungi: 0.5 | 26.1 | 25.6 |
| 91-2 | Roots | | | 0.83 | MIC (%) Bacteria: 0.25 MIC (%) Fungi: 0.5 | 8.4 | 12.1 |
| 91-3 | Stems | | | 0.83 | MIC (%) Bacteria: 0.5 MIC (%) Fungi: 0.5 | 11.1 | 12.0 |
| 91-4 | Leaves | | | 0.07 | MIC (%) Bacteria: 0.5 MIC (%) Fungi: 0.5 | 21.7 | 11.4 |
| 91-5 | Fruits | | | 0.12 | MIC (%) Bacteria: 0.5 MIC (%) Fungi: 0.5 | 17.6 | 13.0 |
| 91-6 | Flowers | | | 0.40 | MIC (%) Bacteria: 0.125 MIC (%) Fungi: 0.5 | 22.2 | 15.6 |

Example 92

Japanese Cedar

TABLE 178

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 92 | Japanese Cedar | | *Cryptomeria japonica* (Thunb. ex L. f.) D. Don | Japanese Cedar | | | | |
| 92-1 | Whole plant | 2 | | | 36.30 | 15.02 | 23.78 | 354.26 |
| | | 10 | | | 30.84 | 21.01 | 28.02 | 503.21 |
| | | 50 | | | 24.40 | 34.55 | 37.62 | 728.82 |
| 92-2 | Roots | 2 | | | 35.79 | 19.46 | 26.90 | 301.93 |
| | | 10 | | | 30.33 | 20.37 | 32.60 | 417.33 |
| | | 50 | | | 22.32 | 39.71 | 35.33 | 623.10 |
| 92-3 | Stems | 2 | | | 38.14 | 12.06 | 25.08 | 329.44 |
| | | 10 | | | 31.14 | 24.50 | 29.49 | 492.00 |
| | | 50 | | | 26.34 | 36.67 | 35.22 | 718.87 |
| 92-4 | Leaves | 2 | | | 39.48 | 16.24 | 21.41 | 220.60 |
| | | 10 | | | 32.69 | 26.50 | 30.03 | 514.35 |
| | | 50 | | | 25.82 | 34.88 | 36.60 | 631.17 |
| 92-5 | Fruits | 2 | | | 39.66 | 17.94 | 23.30 | 361.41 |
| | | 10 | | | 32.75 | 29.78 | 29.76 | 529.77 |
| | | 50 | | | 20.62 | 36.77 | 39.47 | 749.19 |
| 92-6 | Flowers | 2 | | | 39.26 | 19.46 | 24.57 | 250.21 |
| | | 10 | | | 32.60 | 20.37 | 32.70 | 514.83 |
| | | 50 | | | 21.44 | 39.71 | 39.94 | 795.60 |

TABLE 179

| No. | Sample | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|
| | Control group | | | Vitamin C 7.5 ppm | Hexanediol Bacteria: *P. aeruginosa* 2% Fungi: *A. niger* 1% | Untreated 0 mm | Untreated 0 mm |
| 92 | Japanese Cedar | *Cryptomeria japonica* (Thunb. ex L. f.) D. Don | Japanese Cedar | | | | |
| 92-1 | Whole plant | | | 0.73 | MIC (%) Bacteria: 0.25 MIC (%) Fungi: 0.125 | 22.0 | 14.8 |
| 92-2 | Roots | | | 0.85 | MIC (%) Bacteria: 1 MIC (%) Fungi: 0.5 | 22.4 | 18.1 |
| 92-3 | Stems | | | 0.88 | MIC (%) Bacteria: 0.25 MIC (%) Fungi: 0.125 | 26.4 | 15.4 |
| 92-4 | Leaves | | | 0.44 | MIC (%) Bacteria: 0.125 MIC (%) Fungi: 0.125 | 20.0 | 20.0 |
| 92-5 | Fruits | | | 0.20 | MIC (%) Bacteria: 0.125 MIC (%) Fungi: 0.125 | 14.5 | 21.8 |
| 92-6 | Flowers | | | 0.11 | MIC (%) Bacteria: 0.0625 MIC (%) Fungi: 0.125 | 9.6 | 17.3 |

Example 93

Thunberg's Bay-Tree

TABLE 180

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 93 | Thunberg's bay-tree | | *Machilus thunbergii* Siebold & Zucc. | Thunberg's bay-tree | | | | |
| Comparative Example | Long-leaf bay-tree | 50 | *Machilus Japonica* | | 72.02 | 15.14 | 3.48 | 52.02 |
| 93-1 | Whole plant | 2 | | | 35.10 | 15.72 | 22.14 | 379.32 |
| | | 10 | | | 30.25 | 22.38 | 27.45 | 526.57 |
| | | 50 | | | 25.92 | 33.30 | 37.72 | 558.70 |
| 93-2 | Roots | 2 | | | 34.41 | 17.68 | 26.71 | 378.76 |
| | | 10 | | | 29.43 | 24.14 | 28.32 | 474.32 |
| | | 50 | | | 20.79 | 39.91 | 39.34 | 730.56 |
| 93-3 | Stems | 2 | | | 39.83 | 19.84 | 25.68 | 390.29 |
| | | 10 | | | 27.37 | 20.42 | 27.16 | 526.15 |
| | | 50 | | | 25.05 | 34.21 | 35.82 | 610.22 |
| 93-4 | Leaves | 2 | | | 38.38 | 19.72 | 25.63 | 394.02 |
| | | 10 | | | 33.14 | 25.16 | 28.62 | 509.90 |
| | | 50 | | | 24.39 | 35.19 | 34.16 | 688.03 |
| 93-5 | Fruits | 2 | | | 37.44 | 17.07 | 23.55 | 316.07 |
| | | 10 | | | 33.88 | 22.85 | 32.91 | 415.77 |
| | | 50 | | | 22.37 | 33.58 | 37.72 | 726.90 |
| 93-6 | Flowers | 2 | | | 36.00 | 11.82 | 24.25 | 295.86 |
| | | 10 | | | 33.60 | 23.98 | 28.94 | 454.25 |
| | | 50 | | | 21.13 | 38.66 | 39.13 | 741.08 |

TABLE 181

| No. | Sample | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|
| | Control group | | | Vitamin C 7.5 ppm | Hexanediol Bacteria: *P. aeruginosa* 2% Fungi: *A. niger* 1% | Untreated 0 mm | Untreated 0 mm |
| 93 | Thunbergs's bay-tree | *Machilus thunbergii* Siebold & Zucc. | Thunberg's bay-tree | | | | |
| Comparative Example | Long-leaf bay-tree | *Machilus Japonica* | | 3.83 | MIC (%) Bacteria: 1 MIC (%) Fungi: 1 | 10.6 | 8.8 |
| 93-1 | Whole plant | | | 0.38 | MIC (%) Bacteria: 0.125 MIC (%) Fungi: 0.25 | 19.6 | 23.8 |
| 93-2 | Roots | | | 0.19 | MIC (%) Bacteria: 0.0625 MIC (%) Fungi: 0.125 | 10.9 | 10.7 |
| 93-3 | Stems | | | 0.56 | MIC (%) Bacteria: 0.125 MIC (%) Fungi: 0.25 | 25.4 | 19.2 |
| 93-4 | Leaves | | | 0.99 | MIC (%) Bacteria: 0.25 MIC (%) Fungi: 0.25 | 20.8 | 16.0 |
| 93-5 | Fruits | | | 0.15 | MIC (%) Bacteria: 0.25 MIC (%) Fungi: 0.25 | 18.9 | 13.6 |
| 93-6 | Flowers | | | 0.16 | MIC (%) Bacteria: 0.0625 MIC (%) Fungi: 0.125 | 21.4 | 20.5 |

Example 94

Ulleungdo White Pine

TABLE 182

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 94 | Ulleungdo white pine | | *Pinus parviflora* Siebold & Zucc. | Ulleungdo white pine | | | | |
| Comparative Example | Pine | 50 | *Pinus Densiflora* | | 87.79 | 13.37 | 3.97 | 31.05 |
| 94-1 | Whole plant | 2 | | | 38.93 | 11.25 | 25.19 | 273.52 |
| | | 10 | | | 31.66 | 28.42 | 32.73 | 500.18 |
| | | 50 | | | 26.31 | 34.60 | 37.76 | 721.72 |
| 94-2 | Roots | 2 | | | 34.39 | 18.43 | 22.42 | 346.78 |
| | | 10 | | | 28.45 | 27.11 | 32.16 | 580.48 |
| | | 50 | | | 25.61 | 35.25 | 39.65 | 638.27 |
| 94-3 | Stems | 2 | | | 37.91 | 12.94 | 22.82 | 226.97 |
| | | 10 | | | 32.08 | 25.55 | 27.32 | 511.27 |
| | | 50 | | | 23.50 | 34.55 | 36.02 | 784.68 |
| 94-4 | Leaves | 2 | | | 35.80 | 12.34 | 23.15 | 345.49 |
| | | 10 | | | 27.95 | 24.12 | 27.39 | 489.33 |
| | | 50 | | | 23.86 | 34.03 | 37.89 | 661.08 |
| 94-5 | Fruits | 2 | | | 37.44 | 13.47 | 21.85 | 359.25 |
| | | 10 | | | 29.42 | 29.91 | 29.66 | 479.81 |
| | | 50 | | | 25.52 | 34.13 | 35.39 | 693.26 |
| 94-6 | Flowers | 2 | | | 37.53 | 11.83 | 23.19 | 338.99 |
| | | 10 | | | 31.26 | 25.13 | 33.00 | 410.46 |
| | | 50 | | | 23.39 | 36.39 | 37.04 | 740.36 |

TABLE 183

| No. | Sample | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|
| | Control group | | | Vitamin C 7.5 ppm | Hexanediol Bacteria: *P. aeruginosa* 2% Fungi: *A. niger* 1% | Untreated 0 mm | Untreated 0 mm |
| 94 | Ulleungdo white pine | *Pinus parviflora* Siebold & Zucc. | Ulleungdo white pine | | | | |
| Comparative Example | Pine | *Pinus Densiflora* | | 2.17 | MIC (%) Bacteria: 2, Fungi: 1 | 12.1 | 8.5 |
| 94-1 | Whole plant | | | 0.19 | MIC (%) Bacteria: 0.25, Fungi: 0.125 | 21.2 | 20.4 |
| 94-2 | Roots | | | 0.52 | MIC (%) Bacteria: 0.5, Fungi: 0.125 | 10.4 | 8.0 |
| 94-3 | Stems | | | 0.51 | MIC (%) Bacteria: 1, Fungi: 0.5 | 15.6 | 21.4 |
| 94-4 | Leaves | | | 0.03 | MIC (%) Bacteria: 1, Fungi: 0.5 | 9.2 | 10.1 |
| 94-5 | Fruits | | | 1.64 | MIC (%) Bacteria: 1, Fungi: 0.5 | 25.7 | 22.8 |
| 94-6 | Flowers | | | 0.76 | MIC (%) Bacteria: 1, Fungi: 0.25 | 14.8 | 8.7 |

Example 95

Ulleungdo Hemlock

TABLE 184

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |

TABLE 184-continued

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| 95 | Ulleungdo hemlock | | *Tsuga sieboldii* Carriere | Ulleungdo hemlock | | | | |
| Comparative Example | Hemlock Canada | 50 | *Tsuga canadensis* | Hemlock Canada | 74.82 | 8.41 | 2.28 | 16.30 |
| 95-1 | Whole plant | 2 | | | 39.19 | 14.51 | 24.36 | 207.94 |
| | | 10 | | | 29.65 | 29.09 | 30.11 | 479.80 |
| | | 50 | | | 23.79 | 38.83 | 39.71 | 731.43 |
| 95-2 | Roots | 2 | | | 35.35 | 19.28 | 25.52 | 388.94 |
| | | 10 | | | 29.73 | 26.19 | 33.31 | 573.58 |
| | | 50 | | | 21.62 | 33.62 | 38.45 | 783.42 |
| 95-3 | Stems | 2 | | | 36.22 | 17.32 | 23.21 | 385.12 |
| | | 10 | | | 31.88 | 22.92 | 32.87 | 427.78 |
| | | 50 | | | 26.93 | 34.43 | 36.41 | 768.26 |
| 95-4 | Leaves | 2 | | | 34.76 | 19.68 | 22.47 | 288.96 |
| | | 10 | | | 32.14 | 25.87 | 33.83 | 553.28 |
| | | 50 | | | 22.23 | 30.28 | 38.86 | 712.88 |
| 95-5 | Fruits | 2 | | | 36.55 | 15.64 | 23.12 | 388.88 |
| | | 10 | | | 30.46 | 27.53 | 32.29 | 454.38 |
| | | 50 | | | 25.79 | 31.31 | 38.77 | 775.92 |
| 95-6 | Flowers | 2 | | | 39.06 | 17.33 | 21.53 | 349.44 |
| | | 10 | | | 30.90 | 27.00 | 33.63 | 593.31 |
| | | 50 | | | 21.29 | 31.70 | 34.12 | 605.01 |

TABLE 185

| No. | Sample | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|
| | Control group | | | Vitamin C 7.5 ppm | Hexanediol Bacteria: *P. aeruginosa* 2% Fungi: *A. niger* 1% | Untreated 0 mm | Untreated 0 mm |
| 95 | Ulleungdo hemlock | *Tsuga sieboldii* Carriere | Ulleungdo hemlock | | | | |
| Comparative Example | Hemlock Canada | *Tsuga canadensis* | Hemlock Canada | 5.27 | MIC (%) Bacteria: 1, Fungi: 1 | 10.4 | 12.5 |
| 95-1 | Whole plant | | | 0.95 | MIC (%) Bacteria: 0.25, Fungi: 0.125 | 22.8 | 23.3 |
| 95-2 | Roots | | | 0.47 | MIC (%) Bacteria: 0.5, Fungi: 0.125 | 17.8 | 13.3 |
| 95-3 | Stems | | | 0.49 | MIC (%) Bacteria: 0.5, Fungi: 0.25 | 11.6 | 27.7 |
| 95-4 | Leaves | | | 0.97 | MIC (%) Bacteria: 0.5, Fungi: 0.5 | 21.1 | 19.2 |
| 95-5 | Fruits | | | 0.09 | MIC (%) Bacteria: 0.25, Fungi: 0.5 | 21.6 | 18.5 |
| 95-6 | Flowers | | | 0.65 | MIC (%) Bacteria: 0.25, Fungi: 0.25 | 16.1 | 19.3 |

Example 96

Sericeous Newlitsea

TABLE 186

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 96 | Sericeous newlitsea | | *Neolitsea sericea* (Blume) Koidz. | Sericeous newlitsea | | | | |
| Comparative Example | Irregular-streak newlitse | 50 | *Neolitsea Aciculata* | | 88.42 | 13.32 | 5.19 | 48.14 |
| Comparative Example | Sericeous newlitsea (other area) | 50 | | | 51.97 | 28.04 | 12.61 | 128.55 |

TABLE 186-continued

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| 96-1 | Whole plant | 2 | | | 39.34 | 18.54 | 26.82 | 304.91 |
| | | 10 | | | 29.28 | 29.33 | 31.15 | 517.54 |
| | | 50 | | | 24.34 | 32.39 | 34.67 | 682.31 |
| 96-2 | Roots | 2 | | | 38.83 | 19.79 | 21.57 | 279.62 |
| | | 10 | | | 33.91 | 22.95 | 27.06 | 451.86 |
| | | 50 | | | 23.58 | 31.59 | 37.23 | 786.36 |
| 96-3 | Stems | 2 | | | 34.98 | 15.11 | 25.78 | 336.77 |
| | | 10 | | | 27.45 | 22.46 | 28.84 | 593.32 |
| | | 50 | | | 25.89 | 39.98 | 36.34 | 608.09 |
| 96-4 | Leaves | 2 | | | 36.39 | 16.78 | 23.05 | 348.61 |
| | | 10 | | | 28.44 | 29.58 | 28.56 | 404.71 |
| | | 50 | | | 20.67 | 32.68 | 35.96 | 740.33 |
| 96-5 | Fruits | 2 | | | 36.34 | 15.63 | 24.29 | 246.28 |
| | | 10 | | | 30.18 | 22.47 | 32.07 | 526.73 |
| | | 50 | | | 23.31 | 37.91 | 38.53 | 745.39 |
| 96-6 | Flowers | 2 | | | 34.67 | 12.94 | 24.72 | 368.41 |
| | | 10 | | | 28.46 | 27.60 | 30.41 | 519.83 |
| | | 50 | | | 20.06 | 35.61 | 39.32 | 638.49 |

TABLE 187

| No. | Sample | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|
| | Control group | | | Vitamin C 7.5 ppm | Hexanediol Bacteria: *P. aeruginosa* 2% Fungi: *A. niger* 1% | Untreated 0 mm | Untreated 0 mm |
| 96 | Sericeous newlitsea | *Neolitsea sericea* (Blume) Koidz. | Sericeous newlitsea | | | | |
| Comparative Example | Irregular-streak newlitse | *Neolitsea Aciculata* | | 3.34 | MIC (%) Bacteria: 1, Fungi: 1 | 9.9 | 12.5 |
| Comparative Example | Sericeous newlitsea (other area) | | | 2.20 | MIC (%) Bacteria: 0.5, Fungi: 0.5 | 12.8 | 10.5 |
| 96-1 | Whole plant | | | 0.55 | MIC (%) Bacteria: 0.25, Fungi: 0.125 | 25.7 | 20.2 |
| 96-2 | Roots | | | 0.25 | MIC (%) Bacteria: 0.25, Fungi: 0.125 | 9.1 | 14.7 |
| 96-3 | Stems | | | 0.53 | MIC (%) Bacteria: 0.5, Fungi: 0.125 | 11.8 | 14.9 |
| 96-4 | Leaves | | | 0.53 | MIC (%) Bacteria: 0.125, Fungi: | 18.9 | 24.7 |
| 96-5 | Fruits | | | 0.66 | MIC (%) Bacteria: 0.25, Fungi: 0.125 | 11.1 | 8.8 |
| 96-6 | Flowers | | | 0.79 | MIC (%) Bacteria: 0.125, Fungi: | 11.1 | 9.2 |

Example 97

Macropodous *Daphniphyllum*

TABLE 188

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 97 | Macropodous daphniphyllum | | *Daphniphyllum macropodum* Miq. | Macropodous daphniphyllum | | | | |
| Comparative Example | Macropodous daphniphyllum (other area) | 50 | | | 86.33 | 20.09 | 12.68 | 200.48 |

TABLE 188-continued

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| 97-1 | Whole plant | 2 | | | 36.03 | 12.81 | 21.30 | 315.68 |
| | | 10 | | | 33.64 | 26.96 | 27.97 | 471.27 |
| | | 50 | | | 23.97 | 33.97 | 38.75 | 669.01 |
| 97-2 | Roots | 2 | | | 37.35 | 19.39 | 25.46 | 294.80 |
| | | 10 | | | 33.92 | 23.04 | 30.49 | 594.31 |
| | | 50 | | | 23.00 | 34.53 | 36.01 | 644.03 |
| 97-3 | Stems | 2 | | | 35.13 | 17.65 | 23.22 | 324.16 |
| | | 10 | | | 29.16 | 22.15 | 30.17 | 561.48 |
| | | 50 | | | 25.48 | 36.50 | 38.96 | 685.10 |
| 97-4 | Leaves | 2 | | | 37.96 | 17.87 | 20.26 | 291.97 |
| | | 10 | | | 31.75 | 28.92 | 33.05 | 448.11 |
| | | 50 | | | 23.80 | 35.85 | 38.30 | 759.30 |
| 97-5 | Fruits | 2 | | | 38.26 | 14.07 | 23.66 | 224.42 |
| | | 10 | | | 32.05 | 21.70 | 28.96 | 497.40 |
| | | 50 | | | 24.61 | 34.91 | 38.80 | 616.34 |
| 97-6 | Flowers | 2 | | | 34.69 | 12.81 | 22.34 | 351.72 |
| | | 10 | | | 27.42 | 28.15 | 30.37 | 442.03 |
| | | 50 | | | 24.74 | 38.75 | 38.48 | 737.36 |

TABLE 189

| No. | Sample | Scientific name | English name | Anti-oxidation IC50 (%) | Anti-bacteria MIC (%) | Anti-bacteria (S. mutans) Size of growth inhibition ring (mm) | Anti-bacteria (P. gingivalis) Size of growth inhibition ring (mm) |
|---|---|---|---|---|---|---|---|
| | Control group | | | Vitamin C 7.5 ppm | Hexanediol Bacteria: P. aeruginosa 2% Fungi: A. niger 1% | Untreated 0 mm | Untreated 0 mm |
| 97 | Macropodous daphniphyllum | Daphniphyllum macropodum Miq. | Macropodous daphniphyllum | | | | |
| Comparative Example | Macropodous daphniphyllum (other area) | | | 2.93 | MIC (%) Bacteria: 2, Fungi: >2 | 9.2 | 10.9 |
| 97-1 | Whole plant | | | 0.11 | MIC (%) Bacteria: 0.25, Fungi: 0.25 | 22.3 | 18.2 |
| 97-2 | Roots | | | 0.59 | MIC (%) Bacteria: 1, Fungi: 1 | 16.7 | 17.3 |
| 97-3 | Stems | | | 0.46 | MIC (%) Bacteria: 1, Fungi: 0.5 | 11.4 | 12.9 |
| 97-4 | Leaves | | | 0.78 | MIC (%) Bacteria: 1, Fungi: 1 | 11.7 | 14.0 |
| 97-5 | Fruits | | | 0.84 | MIC (%) Bacteria: 1, Fungi: 0.125 | 22.8 | 26.5 |
| 97-6 | Flowers | | | 0.20 | MIC (%) Bacteria: 2, Fungi: 0.25 | 11.7 | 14.0 |

45

Example 98

Scabrous *Aphananthe*

TABLE 190

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 98 | Scabrous aphananthe | | Aphananthe aspera (Thuhb.) Planch. | Scabrous aphananthe | | | | |
| 98-1 | Whole plant | 2 | | | 37.27 | 10.19 | 25.96 | 397.89 |
| | | 10 | | | 33.68 | 22.01 | 29.15 | 489.62 |
| | | 50 | | | 23.98 | 31.31 | 34.20 | 780.90 |
| 98-2 | Roots | 2 | | | 39.54 | 12.09 | 23.63 | 319.91 |
| | | 10 | | | 32.19 | 24.55 | 33.61 | 558.41 |
| | | 50 | | | 26.26 | 36.26 | 37.69 | 662.14 |

TABLE 190-continued

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| 98-3 | Stems | 2 | | | 39.80 | 13.26 | 25.11 | 220.23 |
| | | 10 | | | 32.14 | 26.11 | 28.71 | 418.84 |
| | | 50 | | | 25.72 | 36.21 | 35.19 | 709.86 |
| 98-4 | Leaves | 2 | | | 34.55 | 12.53 | 24.37 | 346.40 |
| | | 10 | | | 27.50 | 21.68 | 31.81 | 425.57 |
| | | 50 | | | 24.01 | 32.27 | 39.71 | 692.42 |
| 98-5 | Fruits | 2 | | | 37.52 | 19.31 | 26.97 | 281.53 |
| | | 10 | | | 28.16 | 28.25 | 33.39 | 492.77 |
| | | 50 | | | 23.23 | 37.27 | 34.12 | 719.27 |
| 98-6 | Flowers | 2 | | | 35.43 | 15.61 | 26.44 | 202.59 |
| | | 10 | | | 32.70 | 21.69 | 28.29 | 575.13 |
| | | 50 | | | 20.96 | 38.78 | 35.77 | 643.11 |

TABLE 191

| No. | Sample | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|
| | Control group | | | Vitamin C 7.5 ppm | Hexanediol Bacteria: *P. aeruginosa* 2% Fungi: *A. niger* 1% | Untreated 0 mm | Untreated 0 mm |
| 98 | Scabrous aphananthe | *Aphananthe aspera* (Thunb.) Planch. | Scabrous aphananthe | | | | |
| 98-1 | Whole plant | | | 0.98 | MIC (%) Bacteria: 0.25, Fungi: 0.5 | 9.6 | 15.4 |
| 98-2 | Roots | | | 0.50 | MIC (%) Bacteria: 1, Fungi: 0.5 | 11.9 | 23.6 |
| 98-3 | Stems | | | 0.55 | MIC (%) Bacteria: 1, Fungi: 1 | 18.6 | 24.8 |
| 98-4 | Leaves | | | 0.71 | MIC (%) Bacteria: 2, Fungi: 0.5 | 8.1 | 23.2 |
| 98-5 | Fruits | | | 0.08 | MIC (%) Bacteria: 2, Fungi: 0.5 | 25.8 | 8.1 |
| 98-6 | Flowers | | | 0.93 | MIC (%) Bacteria: 1, Fungi: 1 | 23.2 | 26.7 |

Example 99

Caudate-Leaf Hackberry

TABLE 192

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 99 | Caudate-leaf hackberry | *Celtis jessoensis* Koidz. | Caudate-leaf hackberry | | | | | |
| 99-1 | Whole plant | 2 | | | 38.27 | 12.93 | 22.01 | 260.48 |
| | | 10 | | | 29.82 | 25.32 | 27.30 | 442.13 |
| | | 50 | | | 23.54 | 37.22 | 35.10 | 689.05 |
| 99-2 | Roots | 2 | | | 38.72 | 12.15 | 26.89 | 360.54 |
| | | 10 | | | 28.36 | 29.21 | 33.03 | 481.15 |
| | | 50 | | | 26.85 | 32.44 | 37.67 | 721.53 |
| 99-3 | Stems | 2 | | | 36.34 | 14.04 | 24.10 | 267.66 |
| | | 10 | | | 30.97 | 29.47 | 28.18 | 452.55 |
| | | 50 | | | 20.99 | 39.53 | 36.45 | 617.98 |
| 99-4 | Leaves | 2 | | | 34.43 | 13.73 | 21.01 | 249.50 |
| | | 10 | | | 32.92 | 29.62 | 26.49 | 592.59 |
| | | 50 | | | 22.34 | 33.36 | 27.10 | 670.09 |
| 99-5 | Fruits | 2 | | | 36.17 | 11.91 | 24.72 | 329.09 |
| | | 10 | | | 32.29 | 21.27 | 27.46 | 471.02 |
| | | 50 | | | 26.61 | 35.51 | 36.19 | 773.26 |

TABLE 192-continued

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| 99-6 | Flowers | 2 | | | 38.00 | 10.02 | 22.64 | 285.34 |
| | | 10 | | | 31.73 | 25.07 | 31.70 | 526.82 |
| | | 50 | | | 22.83 | 30.45 | 34.72 | 697.25 |

TABLE 193

| No. | Sample | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|
| | Control group | | | Vitamin C 7.5 ppm | Hexanediol Bacteria: *P. aeruginosa* 2% Fungi: *A. niger* 1% | Untreated 0 mm | Untreated 0 mm |
| 99 | Caudate-leaf hackberry | *Celtis jessoensis* Koidz. | Caudate-leaf hackberry | | | | |
| 99-1 | Whole plant | | | 0.61 | MIC (%) Bacteria: 0.25, Fungi: 0.25 | 16.9 | 11.2 |
| 99-2 | Roots | | | 0.32 | MIC (%) Bacteria: 1, Fungi: 0.125 | 17.0 | 23.5 |
| 99-3 | Stems | | | 0.50 | MIC (%) Bacteria: 1, Fungi: 0.5 | 19.6 | 23.4 |
| 99-4 | Leaves | | | 0.65 | MIC (%) Bacteria: 0.5, Fungi: 1 | 22.3 | 20.7 |
| 99-5 | Fruits | | | 0.67 | MIC (%) Bacteria: 2, Fungi: 0.5 | 20.5 | 8.1 |
| 99-6 | Flowers | | | 0.95 | MIC (%) Bacteria: 1, Fungi: 0.5 | 21.0 | 23.7 |

30

Example 100

Manchurian Elm

TABLE 194

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 100 | Manchurian Elm | *Ulmus laciniata* (Trautv.) Mayr | Manchurian Elm | | | | | |
| Comparative Example | Elm | 50 | *Ulmus Davidiana* | | 74.42 | 8.50 | 3.79 | 36.63 |
| 100-1 | Whole plant | 2 | | | 37.40 | 11.79 | 21.92 | 342.07 |
| | | 10 | | | 28.92 | 28.70 | 28.60 | 565.22 |
| | | 50 | | | 22.42 | 34.08 | 34.19 | 795.70 |
| 100-2 | Roots | 2 | | | 35.68 | 15.00 | 21.66 | 332.08 |
| | | 10 | | | 29.42 | 24.87 | 32.67 | 497.75 |
| | | 50 | | | 22.23 | 35.45 | 37.28 | 761.52 |
| 100-3 | Bark | 2 | | | 34.22 | 19.98 | 22.29 | 271.65 |
| | | 10 | | | 28.40 | 28.81 | 32.32 | 512.88 |
| | | 50 | | | 21.34 | 36.18 | 38.12 | 786.49 |
| 100-4 | Leaves | 2 | | | 36.24 | 15.16 | 25.81 | 394.22 |
| | | 10 | | | 28.34 | 22.60 | 32.84 | 594.80 |
| | | 50 | | | 26.80 | 38.40 | 38.31 | 666.24 |
| 100-5 | Fruits | 2 | | | 35.39 | 12.36 | 20.30 | 311.67 |
| | | 10 | | | 28.50 | 25.61 | 28.00 | 538.32 |
| | | 50 | | | 26.18 | 35.49 | 35.37 | 686.63 |
| 100-6 | Flowers | 2 | | | 39.51 | 17.14 | 20.21 | 283.76 |
| | | 10 | | | 31.72 | 27.85 | 31.28 | 571.33 |
| | | 50 | | | 24.67 | 36.93 | 39.89 | 663.11 |

TABLE 195

| No. | Sample | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|
| | Control group | | | Vitamin C 7.5 ppm | Hexanediol Bacteria: *P. aeruginosa* 2% Fungi: *A. niger* 1% | Untreated 0 mm | Untreated 0 mm |
| 100 | Manchurian Elm | *Ulmus laciniata* (Trautv.) Mayr | Manchurian Elm | | | | |
| Comparative Example | Elm | *Ulmus Davidiana* | | 3.36 | MIC (%) Bacteria: 2/Fungi: 2 | 10.0 | 12.5 |
| 100-1 | Whole plant | | | 0.13 | MIC (%) Bacteria: 1/Fungi: 0.25 | 23.9 | 22.4 |
| 100-2 | Roots | | | 0.57 | MIC (%) Bacteria: 0.5, Fungi: 1 | 24.6 | 10.3 |
| 100-3 | Bark | | | 0.11 | MIC (%) Bacteria: 0.25, Fungi: 0.5 | 27.2 | 14.4 |
| 100-4 | Leaves | | | 0.31 | MIC (%) Bacteria: 0.125, Fungi: 0.5 | 24.3 | 9.7 |
| 100-5 | Fruits | | | 0.47 | MIC (%) Bacteria: 0.5, Fungi: 1 | 13.6 | 25.9 |
| 100-6 | Flowers | | | 0.23 | MIC (%) Bacteria: 0.5, Fungi: 0.5 | 10.8 | 9.0 |

Example 101

Montane Alder

TABLE 196

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 101 | Montane alder | | *Alnus maximowiczii* Callier | Montane alder | | | | |
| Comparative Example | Alder | 50 | *Alnus Japonica* | | 86.85 | 11.44 | 1.53 | 99.99 |
| 101-1 | Whole plant | 2 | | | 36.15 | 11.81 | 25.13 | 201.20 |
| | | 10 | | | 30.78 | 29.09 | 28.00 | 527.79 |
| | | 50 | | | 25.54 | 33.02 | 39.73 | 756.51 |
| 101-2 | Roots | 2 | | | 38.09 | 17.18 | 26.93 | 232.85 |
| | | 10 | | | 27.85 | 27.66 | 33.03 | 416.76 |
| | | 50 | | | 21.05 | 36.10 | 38.13 | 729.55 |
| 101-3 | Bark | 2 | | | 38.06 | 17.62 | 26.99 | 293.96 |
| | | 10 | | | 30.18 | 21.05 | 27.89 | 535.42 |
| | | 50 | | | 23.57 | 34.65 | 35.46 | 714.95 |
| 101-4 | Leaves | 2 | | | 35.60 | 18.66 | 23.31 | 373.69 |
| | | 10 | | | 27.17 | 24.03 | 32.07 | 444.84 |
| | | 50 | | | 25.40 | 36.27 | 39.45 | 794.32 |
| 101-5 | Fruits | 2 | | | 34.03 | 12.16 | 20.45 | 213.74 |
| | | 10 | | | 28.74 | 29.98 | 31.39 | 494.44 |
| | | 50 | | | 24.57 | 31.60 | 38.89 | 697.06 |
| 101-6 | Flowers | 2 | | | 37.63 | 17.92 | 21.49 | 392.35 |
| | | 10 | | | 28.07 | 22.45 | 30.62 | 576.90 |
| | | 50 | | | 24.77 | 33.12 | 35.26 | 776.92 |

TABLE 197

| No. | Sample | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|
| | Control group | | | Vitamin C 7.5 ppm | Hexanediol Bacteria: *P. aeruginosa* 2% Fungi: *A. niger* 1% | Untreated 0 mm | Untreated 0 mm |
| 101 | Montane alder | *Alnus maximowiczii* Callier | Montane alder | | | | |

TABLE 197-continued

| No. | Sample | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|
| Comparative Example | Alder | *Alnus Japonica* | | 5.45 | MIC (%) Bacteria: 2/Fungi: >2 | 9.7 | 9.0 |
| 101-1 | Whole plant | | | 0.42 | MIC (%) Bacteria: 1/Fungi: >1 | 21.3 | 21.1 |
| 101-2 | Roots | | | 0.56 | MIC (%) Bacteria: 1, Fungi: 2 | 22.3 | 17.3 |
| 101-3 | Bark | | | 0.11 | MIC (%) Bacteria: 0.5, Fungi: 0.5 | 14.5 | 12.6 |
| 101-4 | Leaves | | | 0.93 | MIC (%) Bacteria: 0.5, Fungi: 0.5 | 9.0 | 15.6 |
| 101-5 | Fruits | | | 0.27 | MIC (%) Bacteria: 0.5, Fungi: 0.5 | 19.2 | 13.7 |
| 101-6 | Flowers | | | 0.98 | MIC (%) Bacteria: 0.5, Fungi: 0.5 | 9.2 | 13.8 |

15

Example 102

Ulleungdo Linden

TABLE 198

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 102 | Ulleungdo linden | | *Tilia insularis* Nakai | Ulleungdo linden | | | | |
| Comparative Example | *Tilia platyphyllos* | 50 | *Tilia Platyphyllos* | | 88.59 | 10.96 | 1.39 | 67.41 |
| 102-1 | Whole plant | 2 | | | 39.10 | 11.25 | 24.49 | 398.99 |
| | | 10 | | | 30.96 | 23.70 | 31.39 | 453.96 |
| | | 50 | | | 25.10 | 37.13 | 36.31 | 721.43 |
| 102-2 | Roots | 2 | | | 39.69 | 10.55 | 23.25 | 210.52 |
| | | 10 | | | 30.50 | 23.83 | 29.14 | 564.69 |
| | | 50 | | | 20.89 | 31.77 | 34.57 | 634.88 |
| 102-3 | Bark | 2 | | | 39.99 | 16.33 | 20.41 | 352.24 |
| | | 10 | | | 28.37 | 20.27 | 28.64 | 600.03 |
| | | 50 | | | 24.21 | 36.56 | 37.75 | 773.90 |
| 102-4 | Leaves | 2 | | | 37.89 | 18.59 | 23.35 | 314.05 |
| | | 10 | | | 33.19 | 24.28 | 29.92 | 544.36 |
| | | 50 | | | 20.21 | 37.37 | 35.80 | 706.82 |
| 102-5 | Fruits | 2 | | | 37.84 | 14.98 | 26.22 | 318.06 |
| | | 10 | | | 28.67 | 29.62 | 32.02 | 524.65 |
| | | 50 | | | 21.74 | 35.14 | 38.14 | 651.34 |
| 102-6 | Flowers | 2 | | | 39.95 | 13.32 | 26.32 | 237.92 |
| | | 10 | | | 31.13 | 25.30 | 32.67 | 406.62 |
| | | 50 | | | 20.39 | 39.28 | 36.28 | 695.66 |

TABLE 199

| No. | Sample | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|
| | Control group | | | Vitamin C 7.5 ppm | Hexanediol Bacteria: *P. aeruginosa* 2% Fungi: *A. niger* 1% | Untreated 0 mm | Untreated 0 mm |
| 102 | Ulleungdo linden | *Tilia insularis* Nakai | Ulleungdo linden | | | | |
| Comparative Example | *Tilia platyphyllos* | *Tilia Platyphyllos* | | 6.89 | MIC (%) Bacteria: >2/Fungi: >2 | 9.1 | 9.1 |
| 102-1 | Whole plant | | | 0.38 | MIC (%) Bacteria: 1/Fungi: 0.1 | 24.2 | 17.1 |
| 102-2 | Roots | | | 0.99 | MIC (%) Bacteria: 0.5, Fungi: 0.5 | 20.6 | 15.0 |
| 102-3 | Bark | | | 0.11 | MIC (%) Bacteria: 0.25, Fungi: 0.25 | 27.8 | 16.2 |
| 102-4 | Leaves | | | 0.61 | MIC (%) Bacteria: 2, Fungi: 1 | 22.1 | 15.2 |

TABLE 199-continued

| No. | Sample | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|
| 102-5 | Fruits | | | 0.44 | MIC (%) Bacteria: 1, Fungi: 1 | 10.1 | 20.8 |
| 102-6 | Flowers | | | 0.64 | MIC (%) Bacteria: 1, Fungi: 0.5 | 11.0 | 16.2 |

Example 103

Fragrant Snowbell

TABLE 200

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 103 | Fragrant snowbell | | *Styrax obassia* Siebold & Zucc. | Fragrant snowbell | | | | |
| Comparative Example | Snowbell | 50 | *Styrax Japonicus* | | 79.41 | 7.60 | 2.53 | 49.00 |
| 103-1 | Whole plant | 2 | | | 37.01 | 15.55 | 22.12 | 288.43 |
| | | 10 | | | 31.11 | 21.88 | 31.11 | 414.74 |
| | | 50 | | | 25.80 | 39.66 | 35.98 | 682.20 |
| 103-2 | Roots | 2 | | | 39.75 | 17.72 | 25.19 | 252.28 |
| | | 10 | | | 29.85 | 20.81 | 28.73 | 537.45 |
| | | 50 | | | 22.85 | 35.06 | 34.12 | 776.64 |
| 103-3 | Bark | 2 | | | 34.89 | 11.61 | 22.20 | 225.88 |
| | | 10 | | | 28.74 | 24.52 | 27.15 | 445.90 |
| | | 50 | | | 21.30 | 30.36 | 38.71 | 712.19 |
| 103-4 | Leaves | 2 | | | 34.34 | 15.44 | 25.62 | 209.60 |
| | | 10 | | | 27.26 | 21.02 | 29.95 | 408.02 |
| | | 50 | | | 26.06 | 38.74 | 36.41 | 660.65 |
| 103-5 | Fruits | 2 | | | 34.09 | 18.90 | 26.84 | 323.54 |
| | | 10 | | | 32.38 | 25.94 | 27.10 | 428.97 |
| | | 50 | | | 23.06 | 35.56 | 35.85 | 700.60 |
| 103-6 | Flowers | 2 | | | 36.76 | 17.54 | 25.95 | 215.69 |
| | | 10 | | | 29.39 | 21.67 | 32.73 | 540.52 |
| | | 50 | | | 22.29 | 37.53 | 38.29 | 614.62 |

TABLE 201

| No. | Sample | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|
| | Control group | | | Vitamin C 7.5 ppm | Hexanediol Bacteria: *P. aeruginosa* 2% Fungi: *A. niger* 1% | Untreated 0 mm | Untreated 0 mm |
| 103 | Fragrant snowbell | *Styrax obassia* Siebold & Zucc. | Fragrant snowbell | | | | |
| Comparative Example | Snowbell | *Styrax Japonicus* | | 4.75 | MIC (%) Bacteria: >2/Fungi: 2 | 9.9 | 8.1 |
| 103-1 | Whole plant | | | 0.49 | MIC (%) Bacteria: 0.5/Fungi: 0.25 | 26.4 | 22.2 |
| 103-2 | Roots | | | 0.28 | MIC (%) Bacteria: 1, Fungi: 0.5 | 14.5 | 17.7 |
| 103-3 | Bark | | | 0.13 | MIC (%) Bacteria: 0.25, Fungi: 0.25 | 13.2 | 26.0 |
| 103-4 | Leaves | | | 0.08 | MIC (%) Bacteria: 1, Fungi: 1 | 13.6 | 19.4 |
| 103-5 | Fruits | | | 0.28 | MIC (%) Bacteria: 0.5, Fungi: 1 | 21.1 | 20.1 |
| 103-6 | Flowers | | | 0.27 | MIC (%) Bacteria: 0.25, Fungi: 0.5 | 19.3 | 8.1 |

Example 104

Ulleungdo Flowering Cherry

TABLE 202

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 104 | Ulleungdo flowering cherry | | *Prunus takesimensis* Nakai | Ulleungdo flowering cherry | | | | |
| Comparative Example | Cherry | 50 | *Prunus Serrulata* | | 99.63 | 10.15 | 5.39 | 18.71 |
| 104-1 | Whole plant | 2 | | | 35.79 | 11.44 | 23.61 | 207.78 |
| | | 10 | | | 32.33 | 28.52 | 30.76 | 509.66 |
| | | 50 | | | 26.35 | 38.60 | 37.11 | 718.73 |
| 104-2 | Roots | 2 | | | 36.59 | 19.56 | 23.06 | 380.77 |
| | | 10 | | | 27.29 | 29.11 | 27.41 | 576.88 |
| | | 50 | | | 25.88 | 36.94 | 39.25 | 763.51 |
| 104-3 | Bark | 2 | | | 38.49 | 12.70 | 22.00 | 284.99 |
| | | 10 | | | 27.98 | 25.29 | 31.49 | 474.81 |
| | | 50 | | | 24.42 | 35.17 | 38.09 | 749.06 |
| 104-4 | Leaves | 2 | | | 35.30 | 16.76 | 24.78 | 296.96 |
| | | 10 | | | 28.54 | 21.58 | 29.62 | 463.07 |
| | | 50 | | | 25.05 | 30.71 | 37.94 | 603.53 |
| 104-5 | Fruits | 2 | | | 35.26 | 10.24 | 22.71 | 346.40 |
| | | 10 | | | 32.64 | 28.83 | 27.84 | 504.72 |
| | | 50 | | | 25.05 | 31.19 | 38.51 | 609.45 |
| 104-6 | Flowers | 2 | | | 37.00 | 19.84 | 26.65 | 242.91 |
| | | 10 | | | 32.67 | 29.00 | 29.93 | 404.07 |
| | | 50 | | | 25.62 | 37.97 | 39.46 | 618.80 |

TABLE 203

| No. | Sample | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|
| | Control group | | | Vitamin C 7.5 ppm | Hexanediol Bacteria: *P. aeruginosa* 2% Fungi: *A. niger* 1% | Untreated 0 mm | Untreated 0 mm |
| 104 | Ulleungdo flowering cherry | *Prunus takesimensis* Nakai | Ulleungdo flowering cherry | | | | |
| Comparative Example | Cherry | *Prunus Serrulata* | | 3.84 | MIC (%) Bacteria: >2/Fungi: 2 | 7.5 | 8.1 |
| 104-1 | Whole plant | | | 0.33 | MIC (%) Bacteria: 2/Fungi: 1 | 17.7 | 20.3 |
| 104-2 | Roots | | | 0.47 | MIC (%) Bacteria: 1, Fungi: 0.5 | 11.1 | 23.2 |
| 104-3 | Bark | | | 0.29 | MIC (%) Bacteria: 0.5, Fungi: 1 | 27.8 | 27.5 |
| 104-4 | Leaves | | | 0.55 | MIC (%) Bacteria: 0.5, Fungi: 0.5 | 18.2 | 12.6 |
| 104-5 | Fruits | | | 0.81 | MIC (%) Bacteria: 0.5, Fungi: 1 | 9.3 | 17.9 |
| 104-6 | Flowers | | | 0.81 | MIC (%) Bacteria: 1, Fungi: 1 | 22.8 | 19.7 |

Example 105

Spotted Laurel

TABLE 204

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 105 | Spotted laurel | | *Aucuba japonica* Thuhb. | Spotted laurel | | | | |
| 105-1 | Whole plant | 2 | | | 39.64 | 15.21 | 22.34 | 273.76 |
| | | 10 | | | 31.64 | 23.72 | 30.09 | 410.28 |
| | | 50 | | | 24.40 | 32.38 | 37.77 | 789.10 |
| 105-2 | Roots | 2 | | | 37.16 | 13.30 | 20.63 | 376.67 |
| | | 10 | | | 31.48 | 20.44 | 33.14 | 598.31 |
| | | 50 | | | 23.66 | 33.89 | 35.43 | 712.28 |
| 105-3 | Branches | 2 | | | 38.57 | 10.31 | 26.62 | 388.96 |
| | | 10 | | | 29.95 | 22.80 | 33.16 | 439.07 |
| | | 50 | | | 26.72 | 39.65 | 39.80 | 640.36 |
| 105-4 | Leaves | 2 | | | 35.68 | 12.87 | 24.13 | 212.51 |
| | | 10 | | | 33.35 | 22.21 | 29.26 | 417.65 |
| | | 50 | | | 30.67 | 29.95 | 30.31 | 497.93 |
| 105-5 | Fruits | 2 | | | 35.68 | 18.86 | 23.26 | 269.96 |
| | | 10 | | | 28.89 | 28.44 | 28.51 | 581.54 |
| | | 50 | | | 24.57 | 31.93 | 39.97 | 713.21 |
| 105-6 | Flowers | 2 | | | 36.10 | 19.67 | 24.71 | 288.20 |
| | | 10 | | | 31.88 | 24.37 | 31.40 | 412.19 |
| | | 50 | | | 22.71 | 33.17 | 38.22 | 695.99 |
| 105-7 | Bark | 2 | | | 36.59 | 13.12 | 20.94 | 336.04 |
| | | 10 | | | 28.13 | 27.91 | 30.47 | 400.45 |
| | | 50 | | | 24.45 | 35.35 | 36.99 | 632.79 |

TABLE 205

| No. | Sample | Scientific name | English name | Anti-oxidation IC50 (%) | Anti-bacteria MIC (%) | | Anti-bacteria (*S. mutans*) Size of growth inhibition ring (mm) | Anti-bacteria (*P. gingivalis*) Size of growth inhibition ring (mm) |
|---|---|---|---|---|---|---|---|---|
| | Control group | | | Vitamin C 7.5 ppm | Hexanediol Bacteria: *P. aeruginosa* 2% Fungi: *A. niger* 1% | | Untreated 0 mm | Untreated 0 mm |
| 105 | Spotted laurel | *Aucuba japonica* Thunb. | Spotted laurel | | | | | |
| 105-1 | Whole plant | | | 0.11 | MIC (%) Bacteria, Fungi: 1 | | 13.6 | 18.0 |
| 105-2 | Roots | | | 0.93 | MIC (%) Bacteria: 0.125 MIC (%) Fungi: 0.25 | | 9.1 | 14.2 |
| 105-3 | Branches | | | 0.48 | MIC (%) Bacteria: 0.5 MIC (%) Fungi: 1 | | 26.0 | 19.8 |
| 105-4 | Leaves | | | 0.46 | MIC (%) Bacteria: 0.5 MIC (%) Fungi: 0.25 | | 14.1 | 13.6 |
| 105-5 | Fruits | | | 0.35 | MIC (%) Bacteria: 0.25 MIC (%) Fungi: 0.5 | | 20.4 | 17.4 |
| 105-6 | Flowers | | | 0.49 | MIC (%) Bacteria: 0.25 MIC (%) Fungi: 0.5 | | 25.6 | 24.3 |
| 105-7 | Bark | | | 0.98 | MIC (%) Bacteria: 0.25 MIC (%) Fungi: 0.25 | | 12.3 | 13.9 |

Example 106

Ulleungdo Maple

TABLE 206

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 106 | Ulleungdo maple | | *Acer takesimense* Nakai | Ulleungdo maple | | | | |
| Comparative Example | Sugar maple | 50 | *Acer Saccharum* | | 71.27 | 12.68 | 2.19 | 19.05 |
| 106-1 | Whole plant | 2 | | | 38.99 | 11.59 | 21.36 | 298.74 |
| | | 10 | | | 31.52 | 26.39 | 28.12 | 547.10 |
| | | 50 | | | 20.19 | 32.75 | 37.03 | 732.59 |
| 106-2 | Roots | 2 | | | 34.18 | 19.32 | 24.03 | 351.47 |
| | | 10 | | | 28.21 | 22.74 | 30.26 | 455.80 |
| | | 50 | | | 25.99 | 33.55 | 35.24 | 639.76 |
| 106-3 | Branches | 2 | | | 36.35 | 12.68 | 24.34 | 227.74 |
| | | 10 | | | 33.94 | 24.85 | 29.90 | 330.35 |
| | | 50 | | | 29.72 | 28.21 | 31.91 | 408.04 |
| 106-4 | Leaves | 2 | | | 39.02 | 19.15 | 22.26 | 300.30 |
| | | 10 | | | 31.01 | 25.33 | 29.01 | 349.48 |
| | | 50 | | | 29.58 | 29.26 | 31.54 | 416.72 |
| 106-5 | Fruits | 2 | | | 34.59 | 14.63 | 21.29 | 320.67 |
| | | 10 | | | 28.37 | 24.03 | 31.29 | 406.24 |
| | | 50 | | | 23.57 | 36.54 | 39.14 | 624.71 |
| 106-6 | Flowers | 2 | | | 35.29 | 13.06 | 21.50 | 341.37 |
| | | 10 | | | 29.64 | 25.31 | 30.62 | 491.50 |
| | | 50 | | | 22.21 | 33.26 | 38.36 | 773.46 |

TABLE 207

| No. | Sample | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|
| | Control group | | | Vitamin C 7.5 ppm | Hexanediol Bacteria: *P. aeruginosa* 2% Fungi: *A. niger* 1% | Untreated 0 mm | Untreated 0 mm |
| 106 | Ulleungdo maple | *Acer takesimense* Nakai | Ulleungdo maple | | | | |
| Comparative Example | Sugar maple | *Acer Saccharum* | | 5.31 | MIC (%) Bacteria, Fungi: 2 | 9.3 | 8.0 |
| 106-1 | Whole plant | | | 0.82 | MIC (%) Bacteria, Fungi: 1 | 26.2 | 24.1 |
| 106-2 | Roots | | | 1.00 | MIC (%) Bacteria: 0.25 MIC (%) Fungi: 0.5 | 12.7 | 26.1 |
| 106-3 | Branches | | | 1.83 | MIC (%) Bacteria, Fungi: 1 | 27.4 | 22.8 |
| 106-4 | Leaves | | | 1.27 | MIC (%) Bacteria: 0.5 MIC (%) Fungi: 0.5 | 17.7 | 24.9 |
| 106-5 | Fruits | | | 0.95 | MIC (%) Bacteria: 0.25 MIC (%) Fungi: 0.5 | 25.3 | 11.7 |
| 106-6 | Flowers | | | 0.72 | MIC (%) Bacteria: 0.0625 MIC (%) Fungi: 0.25 | 12.2 | 28.0 |

Example 107

Ulleungdo Amur Corktree

TABLE 208

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 107 | Ulleungdo amur corktree | | *Phellodendron insulare Nakai* | Ulleungdo amur corktree | | | | |
| Comparative Example | Amur corktree | 50 | *Phellodendron Amurense* | | 95.46 | 7.52 | 4.90 | 12.35 |
| 107-1 | Whole plant | 2 | | | 36.21 | 11.26 | 25.61 | 213.48 |
| | | 10 | | | 32.22 | 26.42 | 29.32 | 542.64 |
| | | 50 | | | 24.09 | 33.58 | 36.06 | 790.98 |
| 107-2 | Roots | 2 | | | 37.81 | 18.08 | 21.10 | 256.00 |
| | | 10 | | | 27.35 | 23.32 | 33.18 | 493.63 |
| | | 50 | | | 23.36 | 30.76 | 35.89 | 686.78 |
| 107-3 | Branches | 2 | | | 34.52 | 12.55 | 21.36 | 379.64 |
| | | 10 | | | 29.00 | 21.94 | 32.63 | 549.60 |
| | | 50 | | | 26.37 | 39.14 | 39.79 | 768.09 |
| 107-4 | Leaves | 2 | | | 36.18 | 13.72 | 22.95 | 363.10 |
| | | 10 | | | 33.04 | 24.56 | 27.87 | 407.06 |
| | | 50 | | | 26.91 | 32.02 | 39.84 | 740.31 |
| 107-5 | Fruits | 2 | | | 36.43 | 12.55 | 24.92 | 314.53 |
| | | 10 | | | 31.37 | 24.49 | 30.14 | 561.29 |
| | | 50 | | | 23.32 | 38.13 | 38.13 | 605.19 |
| 107-6 | Flowers | 2 | | | 36.70 | 12.52 | 24.48 | 222.05 |
| | | 10 | | | 28.53 | 20.07 | 33.08 | 439.11 |
| | | 50 | | | 21.96 | 39.45 | 39.83 | 629.91 |
| 107-7 | Bark | 2 | | | 35.19 | 19.92 | 21.68 | 346.36 |
| | | 10 | | | 28.75 | 22.89 | 32.02 | 450.53 |
| | | 50 | | | 25.68 | 38.69 | 37.92 | 641.66 |

TABLE 209

| No. | Sample | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|
| | Control group | | | Vitamin C 7.5 ppm | Hexanediol Bacteria: *P. aeruginosa* 2% Fungi: *A. niger* 1% | Untreated 0 mm | Untreated 0 mm |
| 107 | Ulleungdo amur corktree | *Phellodendron insulare Nakai* | Ulleungdo amur corktree | | | | |
| Comparative Example | Amur corktree | *Phellodendron Amurense* | | 9.49 | MIC (%) Bacteria, Fungi: >2 | 8.8 | 14.1 |
| 107-1 | Whole plant | | | 0.40 | MIC (%) Bacteria, Fungi: 1 | 25.2 | 26.2 |
| 107-2 | Roots | | | 0.85 | MIC (%) Bacteria: 1 MIC (%) Fungi: 0.5 | 18.4 | 15.0 |
| 107-3 | Branches | | | 0.50 | MIC (%) Bacteria, Fungi: 0.25 | 13.9 | 18.7 |
| 107-4 | Leaves | | | 0.91 | MIC (%) Bacteria: 1 MIC (%) Fungi: 0.25 | 10.8 | 10.3 |
| 107-5 | Fruits | | | 0.19 | MIC (%) Bacteria: 0.5 MIC (%) Fungi: 0.5 | 22.3 | 24.2 |
| 107-6 | Flowers | | | 0.66 | MIC (%) Bacteria: 0.25 MIC (%) Fungi: 0.125 | 12.4 | 15.8 |
| 107-7 | Bark | | | 0.36 | MIC (%) Bacteria: 0.125 MIC (%) Fungi: 0.125 | 24.7 | 17.6 |

Example 108

Alianthus-Like Prickly-Ash

TABLE 210

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 108 | Alianthus-like prickly-ash | | *Zanthoxylum ailanthoides* Siebold & Zucc. | Alianthus-like prickly-ash | | | | |
| Comparative Example | Cho-phi | 50 | *Zanthoxylum Piperitum* | | 86.23 | 10.33 | 6.74 | 92.82 |
| 108-1 | Whole plant | 2 | | | 34.07 | 18.82 | 20.14 | 229.40 |
| | | 10 | | | 28.11 | 20.82 | 29.93 | 514.20 |
| | | 50 | | | 25.24 | 36.35 | 36.16 | 615.72 |
| 108-2 | Roots | 2 | | | 36.14 | 10.71 | 20.25 | 298.23 |
| | | 10 | | | 33.81 | 27.12 | 30.62 | 539.30 |
| | | 50 | | | 25.19 | 36.45 | 34.48 | 769.41 |
| 108-3 | Branches | 2 | | | 37.88 | 14.41 | 26.97 | 287.35 |
| | | 10 | | | 30.19 | 22.34 | 28.86 | 520.68 |
| | | 50 | | | 29.15 | 30.56 | 31.56 | 604.11 |
| 108-4 | Leaves | 2 | | | 35.53 | 17.55 | 23.49 | 292.04 |
| | | 10 | | | 33.87 | 24.79 | 25.86 | 454.73 |
| | | 50 | | | 31.35 | 28.61 | 29.12 | 633.49 |
| 108-5 | Fruits | 2 | | | 39.88 | 17.82 | 20.34 | 297.85 |
| | | 10 | | | 28.33 | 23.87 | 29.42 | 576.34 |
| | | 50 | | | 23.29 | 33.08 | 35.91 | 773.14 |
| 108-6 | Flowers | 2 | | | 39.93 | 13.44 | 26.07 | 355.02 |
| | | 10 | | | 29.54 | 25.50 | 32.43 | 521.58 |
| | | 50 | | | 26.55 | 38.51 | 36.94 | 677.79 |
| 108-7 | Seeds | 2 | | | 35.64 | 19.94 | 23.94 | 268.99 |
| | | 10 | | | 33.03 | 21.34 | 28.26 | 472.02 |
| | | 50 | | | 24.05 | 39.59 | 36.72 | 781.94 |
| 108-8 | Bark | 2 | | | 36.33 | 11.04 | 20.18 | 207.81 |
| | | 10 | | | 33.37 | 27.91 | 30.02 | 445.54 |
| | | 50 | | | 27.00 | 37.35 | 34.79 | 654.11 |

TABLE 211

| No. | Sample | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|
| | Control group | | | Vitamin C 7.5 ppm | Hexanediol Bacteria: *P. aeruginosa* 2% Fungi: *A. niger* 1% | Untreated 0 mm | Untreated 0 mm |
| 108 | Alianthus-like prickly-ash | *Zanthoxylum ailanthoides* Siebold & Zucc. | Alianthus-like prickly-ash | | | | |
| Comparative Example | Cho-phi | *Zanthoxylum Piperitum* | | 7.29 | MIC (%) Bacteria, Fungi: 2 | 7.9 | 16.7 |
| 108-1 | Whole plant | | | 0.76 | MIC (%) Bacteria, Fungi: 1 | 18.4 | 26.0 |
| 108-2 | Roots | | | 0.39 | MIC (%) Bacteria, Fungi: 0.5 | 27.1 | 16.4 |
| 108-3 | Branches | | | 1.75 | MIC (%) Bacteria, Fungi: 1 | 10.8 | 14.2 |
| 108-4 | Leaves | | | 2.44 | MIC (%) Bacteria: 1 MIC (%) Fungi: 0.5 | 14.7 | 10.1 |
| 108-5 | Fruits | | | 0.84 | MIC (%) Bacteria: 0.25 MIC (%) Fungi: 1 | 22.3 | 14.0 |
| 108-6 | Flowers | | | 0.68 | MIC (%) Bacteria: 1 MIC (%) Fungi: 1 | 14.9 | 22.8 |

TABLE 211-continued

| No. | Sample | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|
| 108-7 | Seeds | | | 0.20 | MIC (%) Bacteria, Fungi: 0.25 | 13.6 | 21.6 |
| 108-8 | Bark | | | 0.95 | MIC (%) Bacteria: 0.5 MIC (%) Fungi: 1 | 18.0 | 10.7 |

Example 109

Wax-Leaf Privet 15

TABLE 212

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 109 | Wax-leaf privet | | *Ligustrum japonicum* Thunb. | Wax-leaf privet | | | | |
| Comparative Example | Glossy privet | 50 | *Ligustrum Lucidum* | | 75.54 | 9.32 | 2.08 | 146.89 |
| 109-1 | Whole plant | 2 | | | 39.15 | 16.98 | 26.34 | 252.56 |
| | | 10 | | | 28.36 | 21.48 | 31.84 | 473.52 |
| | | 50 | | | 25.35 | 35.16 | 38.39 | 698.45 |
| 109-2 | Roots | 2 | | | 35.28 | 10.69 | 24.53 | 385.25 |
| | | 10 | | | 31.46 | 20.51 | 32.66 | 599.04 |
| | | 50 | | | 22.21 | 39.76 | 39.22 | 701.91 |
| 109-3 | Branches | 2 | | | 36.02 | 17.04 | 25.00 | 286.29 |
| | | 10 | | | 32.02 | 28.13 | 27.89 | 362.60 |
| | | 50 | | | 29.32 | 31.05 | 30.86 | 367.03 |
| 109-4 | Leaves | 2 | | | 39.73 | 18.07 | 20.27 | 248.62 |
| | | 10 | | | 29.35 | 21.77 | 28.79 | 368.58 |
| | | 50 | | | 27.07 | 33.98 | 31.17 | 400.16 |
| 109-5 | Fruits | 2 | | | 35.82 | 11.47 | 23.06 | 222.74 |
| | | 10 | | | 30.04 | 29.77 | 28.51 | 381.79 |
| | | 50 | | | 28.18 | 34.53 | 29.66 | 499.06 |
| 109-6 | Flowers | 2 | | | 37.69 | 11.78 | 21.85 | 297.17 |
| | | 10 | | | 30.13 | 22.99 | 32.02 | 517.25 |
| | | 50 | | | 26.89 | 32.74 | 36.31 | 671.19 |
| 109-7 | Bark | 2 | | | 39.21 | 16.32 | 22.70 | 223.82 |
| | | 10 | | | 31.71 | 27.19 | 32.03 | 463.23 |
| | | 50 | | | 24.35 | 39.40 | 38.74 | 772.54 |

TABLE 213

| No. | Sample | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|
| | Control group | | | Vitamin C 7.5 ppm | Hexanediol Bacteria: *P. aeruginosa* 2% Fungi: *A. niger* 1% | Untreated 0 mm | Untreated 0 mm |
| 109 | Wax-leaf privet | *Ligustrum japonicum* Thunb. | Wax-leaf privet | | | | |
| Comparative Example | Glossy privet | *Ligustrum Lucidum* | | 9.93 | MIC (%) Bacteria, Fungi: 2 | 12.4 | 12.4 |
| 109-1 | Whole plant | | | 0.95 | MIC (%) Bacteria, Fungi: 0.25 | 27.4 | 20.5 |
| 109-2 | Roots | | | 0.18 | MIC (%) Bacteria, Fungi: 0.5 | 13.1 | 24.0 |
| 109-3 | Branches | | | 1.61 | MIC (%) Bacteria, Fungi: 0.5 | 24.3 | 26.1 |
| 109-4 | Leaves | | | 3.25 | MIC (%) Bacteria: 1 MIC (%) Fungi: 0.5 | 15.8 | 10.2 |

TABLE 213-continued

| No. | Sample | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|
| 109-5 | Fruits | | | 2.97 | MIC (%) Bacteria: 0.5 MIC (%) Fungi: 1 | 13.6 | 16.2 |
| 109-6 | Flowers | | | 0.80 | MIC (%) Bacteria: 0.25 MIC (%) Fungi: 0.5 | 19.0 | 10.7 |
| 109-7 | Bark | | | 0.72 | MIC (%) Bacteria: 0.5 MIC (%) Fungi: 0.5 | 12.4 | 13.8 |

Example 110

Ulleungdo Honeysuckle

15

TABLE 214

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 110 | Ulleungdo honeysuckle | | *Lonicera insularis* Nakai | Ulleungdo honeysuckle | | | | |
| Comparative Example | Honeysuckle | 50 | *Lonicera Japonica* | | 75.89 | 11.16 | 3.22 | 160.43 |
| 110-1 | Whole plant | 2 | | | 39.45 | 19.66 | 22.49 | 203.11 |
| | | 10 | | | 30.32 | 27.20 | 29.15 | 458.35 |
| | | 50 | | | 21.23 | 38.68 | 38.75 | 791.32 |
| 110-2 | Roots | 2 | | | 38.29 | 15.41 | 24.93 | 329.43 |
| | | 10 | | | 30.53 | 23.61 | 29.61 | 563.95 |
| | | 50 | | | 26.48 | 30.08 | 38.64 | 663.80 |
| 110-3 | Stems | 2 | | | 34.56 | 18.25 | 20.92 | 298.21 |
| | | 10 | | | 30.62 | 27.04 | 23.00 | 582.05 |
| | | 50 | | | 24.07 | 31.43 | 28.76 | 790.17 |
| 110-4 | Leaves | 2 | | | 36.54 | 10.66 | 20.24 | 237.84 |
| | | 10 | | | 30.81 | 25.12 | 23.78 | 540.34 |
| | | 50 | | | 23.46 | 30.54 | 25.99 | 630.55 |
| 110-5 | Fruits | 2 | | | 36.97 | 10.00 | 24.92 | 387.60 |
| | | 10 | | | 27.55 | 28.91 | 28.74 | 580.23 |
| | | 50 | | | 22.45 | 31.51 | 38.59 | 730.80 |
| 110-6 | Flowers | 2 | | | 37.13 | 14.80 | 25.70 | 200.96 |
| | | 10 | | | 31.71 | 27.18 | 28.66 | 550.48 |
| | | 50 | | | 26.18 | 35.05 | 35.65 | 610.62 |

TABLE 215

| No. | Sample | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|
| | Control group | | | Vitamin C 7.5 ppm | Hexanediol Bacteria: *P. aeruginosa* 2% Fungi: *A. niger* 1% | Untreated 0 mm | Untreated 0 mm |
| 110 | Ulleungdo honevsuckle | *Lonicera insularis* Nakai | Ulleungdo honeysuckle | | | | |
| Comparative Example | Honeysuckle | *Lonicera Japonica* | | 7.46 | MIC (%) Bacteria: 2, Fungi: >2 | 12.6 | 9.9 |
| 110-1 | Whole plant | | | 0.14 | MIC (%) Bacteria, Fungi: 1 | 21.5 | 24.1 |
| 110-2 | Roots | | | 0.94 | MIC (%) Bacteria, Fungi: 0.5 | 14.9 | 14.2 |
| 110-3 | Stems | | | 0.70 | MIC (%) Bacteria, Fungi: 1 | 16.0 | 16.9 |
| 110-4 | Leaves | | | 0.76 | MIC (%) Bacteria: 0.5 MIC (%) Fungi: 0.25 | 21.3 | 13.7 |

TABLE 215-continued

| No. | Sample | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|
| 110-5 | Fruits | | | 0.67 | MIC (%) Bacteria: 0.25 MIC (%) Fungi: 0.25 | 22.1 | 11.0 |
| 110-6 | Flowers | | | 0.22 | MIC (%) Bacteria: 0.125 MIC (%) Fungi: 0.125 | 26.9 | 25.3 |

Example 111

Silk Tree                                    15

TABLE 216

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 111 Comparative Example | Silk tree Kalkora mimosa | 50 | *Albizia julibrissin* *Albizia Kalkora* | Silk tree | 44.21 | 17.03 | 18.50 | 154.13 |
| 111-1 | Whole plant | 2 | | | 37.84 | 14.95 | 21.43 | 299.79 |
| | | 10 | | | 28.10 | 24.41 | 31.87 | 489.87 |
| | | 50 | | | 24.22 | 31.72 | 36.88 | 571.19 |
| 111-2 | Bark | 2 | | | 36.86 | 14.07 | 25.96 | 323.19 |
| | | 10 | | | 29.37 | 26.71 | 29.75 | 559.16 |
| | | 50 | | | 21.52 | 37.31 | 38.13 | 781.23 |
| 111-3 | Roots | 2 | | | 37.39 | 12.04 | 24.08 | 172.51 |
| | | 10 | | | 27.19 | 29.77 | 27.88 | 304.79 |
| | | 50 | | | 21.36 | 34.10 | 34.17 | 529.62 |
| 111-4 | Branches | 2 | | | 36.73 | 17.61 | 23.95 | 359.01 |
| | | 10 | | | 29.89 | 22.79 | 29.04 | 448.22 |
| | | 50 | | | 23.17 | 37.59 | 36.89 | 639.13 |
| 111-5 | Leaves | 2 | | | 38.97 | 11.87 | 22.80 | 272.97 |
| | | 10 | | | 31.85 | 26.07 | 28.66 | 438.82 |
| | | 50 | | | 26.92 | 39.68 | 34.15 | 531.88 |
| 111-6 | Fruits | 2 | | | 34.22 | 11.30 | 20.14 | 293.65 |
| | | 10 | | | 27.95 | 26.45 | 30.04 | 377.80 |
| | | 50 | | | 25.25 | 32.53 | 36.09 | 556.30 |
| 111-7 | Flowers | 2 | | | 37.28 | 14.98 | 22.81 | 313.98 |
| | | 10 | | | 29.21 | 22.13 | 30.34 | 452.83 |
| | | 50 | | | 23.28 | 32.85 | 35.80 | 610.68 |

TABLE 217

| No. | Sample | Conc. (ppm) | Scientific name | English name | Anti-oxidation IC50 (%) | Anti-bacteria MIC (%) | Anti-bacteria (*S. mutans*) Size of growth inhibition ring (mm) | Anti-bacteria (*P. gingivalis*) Size of growth inhibition ring (mm) |
|---|---|---|---|---|---|---|---|---|
| | Control group | | | | Vitamin C 7.5 ppm | Hexanediol Bacteria: *P. aeruginosa* 2% Fungi: *A. niger* 1% | Untreated 0 mm | Untreated 0 mm |
| 111 Comparative Example | Silk tree Kalkora mimosa | 50 | *Albizia julibrissin* *Albizia Kalkora* | Silk tree | 1.41 | MIC (%) Bacteria: 2 MIC (%) Fungi: 2 | 3.5 | 2.5 |
| 111-1 | Whole plant | 2 | | | 0.70 | MIC (%) Bacteria: 0.5 MIC (%) Fungi: 0.5 | 11.8 | 12.4 |
| | | 10 | | | | | | |
| | | 50 | | | | | | |
| 111-2 | Bark | 2 | | | 0.11 | MIC (%) Bacteria: 0.125 MIC (%) Fungi: 0.125 | 24.3 | 15.0 |
| | | 10 | | | | | | |
| | | 50 | | | | | | |

TABLE 217-continued

| No. | Sample | Conc. (ppm) | Scientific name | English name | Anti-oxidation IC50 (%) | Anti-bacteria MIC (%) | | Anti-bacteria (*S. mutans*) Size of growth inhibition ring (mm) | Anti-bacteria (*P. gingivalis*) Size of growth inhibition ring (mm) |
|---|---|---|---|---|---|---|---|---|---|
| 111-3 | Roots | 2 10 50 | | | 0.91 | MIC (%) Bacteria: 0.5 | MIC (%) Fungi: 0.5 | 2.7 | 7.1 |
| 111-4 | Branches | 2 10 50 | | | 0.83 | MIC (%) Bacteria: 0.25 | MIC (%) Fungi: 0.25 | 12.7 | 8.3 |
| 111-5 | Leaves | 2 10 50 | | | 0.56 | MIC (%) Bacteria: 0.5 | MIC (%) Fungi: 0.5 | 2.3 | 1.3 |
| 111-6 | Fruits | 2 10 50 | | | 0.23 | MIC (%) Bacteria: 0.5 | MIC (%) Fungi: 0.5 | 1.8 | 7.4 |
| 111-7 | Flowers | 2 10 50 | | | 0.03 | MIC (%) Bacteria: 0.125 | MIC (%) Fungi: 0.125 | 14.6 | 10.1 |

Example 112

False Daisy

TABLE 218

| No. | Sample | Conc. (ppm) | Scientific name | English name | Whitening Melanin content (%) | Anti-wrinkle Collagen synthesis (% of control) | Anti-inflammation Inhibition of NO production (%) | Moisturizing HA synthesis (%) |
|---|---|---|---|---|---|---|---|---|
| | Control group | | | | Arbutin (200 ppm) 35% | TGFb (10 ppb) 25% | L-NMMA (5 ppm) 28% | EGF (10 ppb) 320% |
| 112 Comparative Example | False daisy Fine-leaf false daisy | 50 | *Eclipta prostrata* *Eclipta alba* | False daisy | 46.81 | 11.72 | 4.23 | 251.26 |
| 112-1 | Whole plant | 2 10 50 | | | 39.38 33.95 25.45 | 18.50 21.62 37.67 | 23.27 29.69 38.31 | 238.97 507.30 759.48 |
| 112-2 | Roots | 2 10 50 | | | 34.77 31.99 24.79 | 15.67 26.87 35.72 | 24.38 29.45 36.18 | 231.64 342.45 348.54 |
| 112-3 | Stems | 2 10 50 | | | 35.32 31.00 21.57 | 19.67 28.08 33.85 | 25.11 33.32 36.97 | 192.98 264.29 369.80 |
| 112-4 | Leaves | 2 10 50 | | | 37.40 30.94 20.55 | 12.60 27.11 31.82 | 21.76 32.47 38.45 | 250.14 257.05 319.48 |
| 112-5 | Fruits | 2 10 50 | | | 34.68 30.40 20.16 | 12.36 26.89 34.15 | 24.31 32.84 34.99 | 151.18 207.81 285.57 |
| 112-6 | Flowers | 2 10 50 | | | 39.65 33.64 22.37 | 11.97 29.37 30.00 | 26.69 29.90 34.02 | 198.64 314.58 559.51 |

TABLE 219

| No. | Sample | Conc. (ppm) | Scientific name | English name | Anti-oxidation IC50 (%) | Anti-bacteria MIC (%) | | Anti-bacteria (*S. mutans*) Size of growth inhibition ring (mm) | Anti-bacteria (*P. gingivalis*) Size of growth inhibition ring (mm) |
|---|---|---|---|---|---|---|---|---|---|
| | Control group | | | | Vitamin C 7.5 ppm | Hexanediol Bacteria: *P. aeruginosa* 2% | Fungi: *A. niger* 1% | Untreated 0 mm | Untreated 0 mm |

TABLE 219-continued

| No. | Sample | Conc. (ppm) | Scientific name | English name | Anti-oxidation IC50 (%) | Anti-bacteria MIC (%) | | Anti-bacteria (S. mutans) Size of growth inhibition ring (mm) | Anti-bacteria (P. gingivalis) Size of growth inhibition ring (mm) |
|---|---|---|---|---|---|---|---|---|---|
| 112 Comparative Example | False daisy Fine-leaf false daisy | 50 | *Eclipta prostrata* *Eclipta alba* | False daisy | 1.85 | MIC (%) Bacteria: 1 MIC (%) Fungi: 2 | | 1.9 | 2.3 |
| 112-1 | Whole plant | 2 10 50 | | | 0.17 | MIC (%) Bacteria: 0.125 MIC (%) Fungi: 0.125 | | 18.0 | 24.7 |
| 112-2 | Roots | 2 10 50 | | | 0.69 | MIC (%) Bacteria: 1 MIC (%) Fungi: 1 | | 6.2 | 3.3 |
| 112-3 | Stems | 2 10 50 | | | 0.73 | MIC (%) Bacteria: 1 MIC (%) Fungi: 1 | | 7.4 | 2.0 |
| 112-4 | Leaves | 2 10 50 | | | 0.99 | MIC (%) Bacteria: 0.25 MIC (%) Fungi: 0.5 | | 3.9 | 7.8 |
| 112-5 | Fruits | 2 10 50 | | | 0.24 | MIC (%) Bacteria: 0.5 MIC (%) Fungi: 0.5 | | 4.4 | 3.2 |
| 112-6 | Flowers | 2 10 50 | | | 0.09 | MIC (%) Bacteria: 0.25 MIC (%) Fungi: 0.25 | | 14.1 | 10.3 |

Formulation Example 1

Preparation of Pharmaceutical Preparations

1. Preparation of Powder 0.001 g of plant extracts 1 g of lactose

The above ingredients were mixed, and a sealable bag was filled with the mixed ingredients to prepare powder.

2. Preparation of Tablets 0.2 mg of plant extracts 100 mg of corn starch 100 mg of lactose 2 mg of magnesium stearate After mixing the above ingredients, tableting was performed according to a conventional tablet preparation method to prepare tablets.

3. Preparation of Capsules 0.2 mg of plant extracts 100 mg of corn starch 100 mg of lactose 2 mg of magnesium stearate After mixing the above ingredients, gelatin capsules were filled with the mixed ingredients according to a conventional capsule preparation method to prepare capsules.

4. Preparation of Pills 0.003 g of plant extracts 1.5 g of lactose 1 g of glycerin 0.5 g of xylitol After mixing the above ingredients, according to a conventional method, pills were prepared so that the weight of one pill was 4 g.

5. Preparation of Granules 2 mg of plant extracts 50 mg of soybean extracts 200 mg of glucose 600 mg of starch After mixing the above ingredients, 100 mg of 30% ethanol was added thereto, and drying was performed at 60° C. to form granules. Then, a capsule was filled with the granules.

Formulation Example 2

Preparation of Cosmetics

1. Preparation of Softening Lotion (Skin Lotion)

According to the following composition, a softening lotion containing plant extracts as active ingredients was prepared according to a conventional method.

0.1% by weight of plant extracts 1.0% by weight of beta-1,3-glucan 2.0% by weight of butylene glycol 2.0% by weight of propylene glycol 0.1% by weight of a carboxyvinyl polymer 0.2% by weight of PEG-12 nonylphenyl ether 0.4% by weight of polysorbate 80

10.0% by weight of ethanol 0.1% by weight of triethanolamine 0.05% by weight of a preservative 0.05% by weight of a pigment 0.05% by weight of a perfume Purified water: Up to 100% by weight 2. Preparation of Nourishing Lotion (Milk Lotion)

According to the following composition, a nourishing lotion containing plant extracts as active ingredients was prepared according to a conventional method.

0.1% by weight of plant extracts 1.0% by weight of beta-1,3-glucan 4.0% by weight of beeswax 1.5% by weight of polysorbate 60

1.5% by weight of sorbitan sesquioleate 0.5% by weight of liquid paraffin 5.0% by weight of caprylic/capric triglyceride 3.0% by weight of glycerin 3.0% by weight of butylene glycol 3.0% by weight of propylene glycol 0.1% by weight of a carboxyvinyl polymer 0.2% by weight of triethanolamine
0.05% by weight of a preservative
0.05% by weight of a pigment
0.05% by weight of a perfume
Purified water: Up to 100% by weight 3. Preparation of Nourishing Cream According to the following composition, a nourishing cream containing plant extracts as active ingredients was prepared according to a conventional method.

0.2% by weight of plant extracts
5.0% by weight of beta-1,3-glucan
10.0% by weight of beeswax
1.5% by weight of polysorbate 60
2.0% by weight of PEG 60 hydrogenated castor oil
0.5% by weight of sorbitan sesquioleate
10.0% by weight of liquid paraffin
5.0% by weight of squalene
5.0% by weight of caprylic/capric triglyceride
5.0% by weight of glycerin
3.0% by weight of butylene glycol
3.0% by weight of propylene glycol
0.2% by weight of triethanolamine
0.05% by weight of a preservative
0.05% by weight of a pigment
0.05% by weight of a perfume
Purified water: Up to 100% by weight 4. Preparation of Massage Cream According to the following composition, a massage cream containing plant extracts as active ingredients was prepared according to a conventional method.

0.1% by weight of plant extracts
3.0% by weight of beta-1,3-glucan
10.0% by weight of beeswax
1.5% by weight of polysorbate 60
2.0% by weight of PEG 60 hydrogenated castor oil
0.8% by weight of sorbitan sesquioleate
40.0% by weight of liquid paraffin
5.0% by weight of squalene
4.0% by weight of caprylic/capric triglyceride
5.0% by weight of glycerin
3.0% by weight of butylene glycol
3.0% by weight of propylene glycol
0.2% by weight of triethanolamine
0.05% by weight of a preservative
0.05% by weight of a pigment
0.05% by weight of a perfume
Purified water: Up to 100% by weight 5. Preparation of Pack According to the following composition, a pack containing plant extracts as active ingredients was prepared according to a conventional method.

0.2% by weight of plant extracts
1.0% by weight of beta-1,3-glucan
13.0% by weight of polyvinyl alcohol
0.2% by weight of sodium carboxymethyl cellulose
5.0% by weight of glycerin
0.1% by weight of allantoin
6.0% by weight of ethanol
0.3% by weight of PEG-12 nonylphenyl ether
0.3% by weight of polysorbate 60
0.05% by weight of a preservative
0.05% by weight of a pigment
0.05% by weight of a perfume
Purified water: Up to 100% by weight Formulation Example 3

Preparation of Skin External Preparation

1. Preparation of Gel

According to the following composition, a gel containing plant extracts as active ingredients was prepared according to a conventional method.

0.1% by weight of plant extracts
0.1% by weight of beta-1,3-glucan
0.05% by weight of sodium ethylenediamine acetate
5.0% by weight of glycerin
0.3% by weight of a carboxyvinyl polymer
5.0% by weight of ethanol
0.5% by weight of PEG-60 hydrogenated castor oil
0.3% by weight of triethanolamine
0.05% by weight of a preservative
0.05% by weight of a pigment
0.05% by weight of a perfume
Purified water: Up to 100% by weight 2. Preparation of Ointment According to the following composition, an ointment containing plant extracts as active ingredients was prepared according to a conventional method.

0.5% by weight of plant extracts
10.0% by weight of beta-1,3-glucan
10.0% by weight of beeswax
5.0% by weight of polysorbate 60
2.0% by weight of PEG 60 hydrogenated castor oil
0.5% by weight of sorbitan sesquioleate
5.0% by weight of Vaseline
10.0% by weight of liquid paraffin
5.0% by weight of squalene
3.0% by weight of shea butter
5.0% by weight of caprylic/capric triglyceride
10.0% by weight of glycerin
10.2% by weight of propylene glycol
0.2% by weight of triethanolamine
0.05% by weight of a preservative
0.05% by weight of a pigment
0.05% by weight of a perfume
water: Up to 100% by weight 3. Preparation of Drug for Topical Administration (Gel Ointment)

According to the following composition, a gel ointment containing plant extracts as active ingredients was prepared according to a conventional method.

0.5% by weight of plant extracts
10.0% by weight of beta-1,3-glucan
1.5% by weight of polyacrylic acid (Carbopol 940)
5.0% by weight of isopropanol
25.0% by weight of hexylene glycol
1.7% by weight of triethanolamine
Deionized water: Up to 100% by weight 4. Preparation of Drug for Topical Administration (Patch)

According to the following composition, a patch containing plant extracts as active ingredients was prepared according to a conventional method.

0.5% by weight of plant extracts
3.0% by weight of beta-1,3-glucan
20.0% by weight of hexylene glycol
0.7% by weight of diethylamine
1.0% by weight of polyacrylic acid (Carbopol 934P)
0.1% by weight of sodium sulfite
1.0% by weight of polyoxyethylene lauryl ether (E.O=9)
1.0% by weight of polyhydroxyethylene cetyl stearyl ether (Cetomacrogol 1000)

2.5% by weight of viscous paraffin oil 2.5% by weight of caprylic acid ester/capric acid ester (Cetiol LC)

3.0% by weight of polyethylene glycol 400

Deionized water: Up to 100% by weight

Formulation Example 4

Manufacture of Food

Foods containing the plant extracts of the present invention were prepared as follows.

1. Manufacture of Flour Food 0.05 to 1.0 part by weight of the plant extracts was added to flour to prepare a mixture. This mixture was used to manufacture health foods such as breads, cakes, cookies, crackers, and noodles.

2. Manufacture of Dairy Products 0.2 parts by weight of the plant extracts was added to milk, and various dairy products such as butter and ice cream were manufactured using the milk.

3. Manufacture of Mixed Grain Powder

Brown rice, barley, glutinous rice, and adlay were dried through pregelatinization by a known method, and then the dried grains were roasted and pulverized using a grinder to obtain powder having a particle size of 60 mesh. In addition, black beans, black sesame, and perilla were steamed and dried according to a known method. Then, the dried grains were roasted and pulverized using a grinder to obtain powder having a particle size of 60 mesh. The plant extracts were concentrated under reduced pressure using a vacuum concentrator and dried through spraying and hot air drying to obtain a dried product. The dried product was pulverized using a grinder to obtain powder having a particle size of 60 mesh.

Based on 100 parts by weight of the mixed powder, the dry powder of grains, seeds, and plant extracts prepared above was blended in the following ratios.

Grains (30 parts by weight of brown rice, 15 parts by weight of adlay, and 20 parts by weight of barley), Seeds (7 parts by weight of perilla, 8 parts by weight of black beans, and 7 parts by weight of black sesame), 0.1 parts by weight of plant extracts, 0.5 parts by weight of lingzhi mushroom, 0.5 parts by weight of adhesive rehmannia Formulation Example 5

Manufacture of Beverages

1. Manufacture of Health Drinks 0.1 mg of plant extracts 1.000 mg of citric acid 100 g of oligosaccharide 2 g of plum concentrate 1 g of taurine Adjusting the total volume to 900 mL with purified water After mixing the above ingredients according to a conventional health drink manufacturing method, the mixture was stirred and heated at 85° C. for about 1 hour to obtain a solution. The solution was placed in a filtered and sterilized 2 L container, sealed, and sterilized. Thereafter, the filtered solution was refrigerated. Then, the solution was used in preparation of the health drink composition of the present invention.

As a preferred embodiment, the composition ratio is determined based on ingredients suitable for favorite drinks. However, the composition ratio may be arbitrarily changed according to regional and ethnic preferences such as demand class, demand country, and use purpose.

2. Manufacture of Vegetable Juice 1 g of the plant extracts of the present invention was added to 1,000 mL of tomato or carrot juice to prepare vegetable juice for health promotion.

3. Manufacture of Fruit Juice 1 g of the plant extracts of the present invention was added to 1,000 mL of apple or grape juice to prepare fruit juice for health promotion.

INDUSTRIAL APPLICABILITY

A composition comprising plant extracts according to the present invention has a skin whitening effect by reducing the total amount of melanin and tyrosinase activity in melanocytes of the skin, promotes skin regeneration and increases skin elasticity or reduces skin wrinkles by promoting collagen synthesis and inhibiting collagenase activity in fibroblasts of the skin, has an anti-inflammatory or a skin soothing effect by suppressing NO generation, increases the amount of moisture in the skin and has a moisturizing effect by promoting generation of hyaluronic acid in fibroblasts, and has an antioxidant effect by scavenging free radicals. In addition, since the composition of the present invention has a broad antibacterial effect against various bacteria, the composition can be used as a cosmetic composition, a pharmaceutical composition, a skin external preparation, or a food composition.

The invention claimed is:

1. A method of skin-moisturizing, which comprises applying a composition for moisturizing skin to the skin of a patient in need of treatment of a dry skin disease, wherein the composition comprises an effective amount of a plant extract comprising *Cirsium nipponicum* as an active ingredient.

2. The method according to claim 1, wherein the plant extract comprises substances extracted from the plant using water, an organic solvent, or a mixture thereof.

3. The method according to claim 2, wherein the organic solvent is a low-grade alcohol having 1 to 6 carbon atoms, a polyhydric alcohol, a hydrocarbon-based solvent, or a mixture thereof.

4. The method according to claim 1, wherein, based on 100 parts by weight of the composition, the plant extract is comprised in an amount of 0.0001 to 10 parts by weight.

5. The method according to claim 1, wherein the composition is a cosmetic composition.

6. The method according to claim 1, wherein the composition is a pharmaceutical composition.

7. The method according to claim 1, wherein the composition is a skin external preparation.

8. The method according to claim 1, wherein the plant extract comprises a combination of *Cirsium nipponicum* and *Anthriscus sylvestris*.

9. The method according to claim 1, wherein the dry skin disease is one or more of atopic dermatitis or psoriasis.

* * * * *